US011142586B2

(12) United States Patent
Garcia et al.

(10) Patent No.: US 11,142,586 B2
(45) Date of Patent: Oct. 12, 2021

(54) ANTI-HUMAN NICOTINAMIDE PHOSPHORIBOSYLTRANSFERASE (NAMPT) ANTIBODIES

(71) Applicant: AQUALUNG THERAPEUTICS, Tucson, AZ (US)

(72) Inventors: Joe G. N. Garcia, Tucson, AZ (US); Darragh MacCann, County Derry (IE)

(73) Assignee: Aqualung Therapeutics, Tucson, AZ (US)

(*) Notice: Subject to any disclaimer, the term of this patent is extended or adjusted under 35 U.S.C. 154(b) by 0 days.

(21) Appl. No.: 16/988,383

(22) Filed: Aug. 7, 2020

(65) Prior Publication Data

US 2021/0070883 A1 Mar. 11, 2021

Related U.S. Application Data

(60) Provisional application No. 62/883,952, filed on Aug. 7, 2019.

(51) Int. Cl.

| | |
|---|---|
| ***C07K 16/40*** | (2006.01) |
| ***A61K 39/00*** | (2006.01) |
| ***A61P 31/14*** | (2006.01) |
| ***A61P 11/00*** | (2006.01) |

(52) U.S. Cl.

CPC .............. *C07K 16/40* (2013.01); *A61P 11/00* (2018.01); *A61P 31/14* (2018.01); *A61K 2039/505* (2013.01); *C07K 2317/24* (2013.01); *C07K 2317/34* (2013.01); *C07K 2317/565* (2013.01); *C07K 2317/76* (2013.01)

(58) Field of Classification Search

CPC ................ C07K 16/40; C07K 2317/24; C07K 2317/34; C07K 2317/565; C07K 2317/76; A61P 11/00; A61P 31/14; A61K 2039/505

See application file for complete search history.

(56) References Cited

U.S. PATENT DOCUMENTS

| | | | |
|---|---|---|---|
| 2017/0340704 | A1 | 11/2017 | Pulé et al. |
| 2018/0094065 | A1 | 4/2018 | Bowers et al. |

FOREIGN PATENT DOCUMENTS

| | | |
|---|---|---|
| WO | WO 2003/080675 | 10/2003 |
| WO | WO 2004/050708 | 6/2004 |
| WO | WO 2009/058346 | 5/2009 |
| WO | WO 2016/090337 | 6/2016 |
| WO | WO 2016/102965 | 6/2016 |
| WO | WO 2016/168542 | 10/2016 |
| WO | WO 2018/191751 | 10/2018 |
| WO | WO 2019/133512 | 7/2019 |

OTHER PUBLICATIONS

International Search Report dated Jan. 12, 2021 issued in PCT/US2020/045511.

Written Opinion dated Jan. 12, 2021 issued in PCT/US2020/045511.

*Primary Examiner* — Robert S Landsman

(74) *Attorney, Agent, or Firm* — Womble Bond Dickinson (US) LLP

(57) ABSTRACT

Anti-nicotinamide phosphoribosyltransferase (NAMPT) antibodies, or antigen binding fragments thereof, are described, as well as methods for treating a subject having a (NAMPT)-associated local and/or systemic inflammatory disorder.

17 Claims, 21 Drawing Sheets

Specification includes a Sequence Listing.

LPS/VILI

LPS/VILI + anti-NAMPT mAb

ANTI-HUMAN NICOTINAMIDE PHOSPHORIBOSYLTRANSFERASE (NAMPT) ANTIBODIES

RELATED APPLICATION

This application claims priority to U.S. Provisional Application No. 62/883,952, filed on Aug. 7, 2019. The entire content of the foregoing priority application is incorporated herein by reference.

FEDERALLY-SPONSORED RESEARCH OR DEVELOPMENT

This invention was made with U.S. government support under grant number R41 HL110707 STTR and R42 HL152888 by National Institutes of Health (NIH). The U.S. government has certain rights in the invention.

SEQUENCE LISTING

The instant application contains a Sequence Listing which has been submitted electronically in ASCII format and is hereby incorporated by reference in its entirety. Said ASCII copy, created on Aug. 7, 2020, is named A105818_1020US.1_SL.txt and is 53,769 bytes in size.

BACKGROUND

The Nicotinamide phosphoribosyltransferase (NAMPT) gene encodes a protein that catalyzes the condensation of nicotinamide with 5-phosphoribosyl-1-pyrophosphate to yield nicotinamide mononucleotide. The protein belongs to the nicotinic acid phosphoribosyltransferase (NAPRTase) family and is thought to be involved in many important biological processes, including metabolism, stress response and aging.

Nicotinamide phosphoribosyltransferase (NAMPT) exists as both intracellular NAMPT and extracellular NAMPT (eNAMPT) proteins. eNAMPT is secreted into the blood and functions as a cytokine/enzyme (cytozyme) that activates NF-κB signaling via ligation of Toll-like receptor 4 (TLR4), further serving as a biomarker for inflammatory lung disorders such as acute respiratory distress syndrome.

SUMMARY OF THE INVENTION

Provided herein are anti-NAMPT antibodies, including humanized antibodies useful for therapeutic purposes. Currently known therapies for clinical treatment of acute and chronic inflammatory lung disorders (e.g., ARDS, VILI) are merely supportive. Thus, there is an unmet need to in the art for effective prophylactic and therapeutic agents to reduce the morbidity and mortality of inflammatory disorders and observed in patients, particularly in critically ill patients, suffering from these disorders.

Also provided are methods of treating a subject having Coronavirus disease 2019 (COVID-19) by administering to the subject an effective amount of an isolated antibody or an antigen-binding fragment thereof that binds to human nicotinamide phosphoribosyltransferase (NAMPT).

In some embodiments of the above aspect, the antibody or antigen-binding fragment thereof comprises: (i) a heavy chain variable region comprising a CDR1 domain having an amino acid sequence as set forth in SEQ ID NO: 3; a CDR2 domain having an amino acid sequence as set forth in SEQ ID NOs: 4 or 29; and a CDR3 domain having an amino acid sequence as set forth in SEQ ID NO: 5; and (ii) a light chain variable region comprising a CDR1 domain having an amino acid sequence as set forth in SEQ ID NO: 6 or 11; a CDR2 domain having an amino acid sequence as set forth in SEQ ID NO: 7, 12, 14, 33, 35 or 37; and a CDR3 domain having an amino acid sequence as set forth in SEQ ID NO: 8.

In some embodiments of the aforementioned aspect, the isolated antibody or antigen-binding fragment thereof comprises a light chain variable region having an amino acid sequence as set forth in SEQ ID NO: 2, 10, 13, 30, 31, 32, 34 or 36; and/or a heavy chain variable region having an amino acid sequence as set forth in SEQ ID NO: 1, 9, 15, 16 or 28.

In some embodiments of the above aspect, the subject shows one or more symptoms of COVID-19 and/or is diagnosed with COVID-19.

In some embodiments of the above aspect, the subject is a human.

Also provided are isolated antibodies, or an antigen-binding fragments thereof, that specifically binds to human nicotinamide phosphoribosyltransferase (NAMPT), said antibody or antigen-binding fragment thereof comprising: (i) a heavy chain variable region comprising a CDR1 domain having an amino acid sequence as set forth in SEQ ID NO: 3; a CDR2 domain having an amino acid sequence as set forth in SEQ ID NOs: 4 or 29; and a CDR3 domain having an amino acid sequence as set forth in SEQ ID NO: 5; and (ii) a light chain variable region comprising a CDR1 domain having an amino acid sequence as set forth in SEQ ID NO: 6 or 11; a CDR2 domain having an amino acid sequence as set forth in SEQ ID NO: 7, 12, 14, 33, 35 or 37; and a CDR3 domain having an amino acid sequence as set forth in SEQ ID NO: 8.

In some embodiments of the above aspect, the heavy chain variable region of the isolated antibody, or antigen-binding fragment thereof comprises: (a) a CDR1 domain having an amino acid sequence as set forth in SEQ ID NO: 3, a CDR2 domain having an amino acid sequence as set forth in SEQ ID NO: 4, and a CDR3 domain having an amino acid sequence as set forth in SEQ ID NO: 5; or (b) a CDR1 domain having an amino acid sequence as set forth in SEQ ID NO: 3, a CDR2 domain having an amino acid sequence as set forth in SEQ ID NO: 29, and a CDR3 domain having an amino acid sequence as set forth in SEQ ID NO: 5.

In some embodiments, the light chain variable region of the isolated antibody or antigen-binding fragment thereof comprises: (a) a CDR1 domain having an amino acid sequence as set forth in SEQ ID NO: 6, a CDR2 domain having an amino acid sequence as set forth in SEQ ID NO: 7, and a CDR3 domain having an amino acid sequence as set forth in SEQ ID NO: 8; (b) a CDR1 domain having an amino acid sequence as set forth in SEQ ID NO: 6, a CDR2 domain having an amino acid sequence as set forth in SEQ ID NO: 12, and a CDR3 domain having an amino acid sequence as set forth in SEQ ID NO: 8; (c) a CDR1 domain having an amino acid sequence as set forth in SEQ ID NO: 6, a CDR2 domain having an amino acid sequence as set forth in SEQ ID NO: 14, and a CDR3 domain having an amino acid sequence as set forth in SEQ ID NO: 8; (d) a CDR1 domain having an amino acid sequence as set forth in SEQ ID NO: 6, a CDR2 domain having an amino acid sequence as set forth in SEQ ID NO: 33, and a CDR3 domain having an amino acid sequence as set forth in SEQ ID NO: 8; (e) a CDR1 domain having an amino acid sequence as set forth in SEQ ID NO: 6, a CDR2 domain having an amino acid sequence as set forth in SEQ ID NO: 35, and a CDR3 domain having an amino acid sequence as set forth in SEQ ID NO: 8; (f) a CDR1 domain having an amino acid sequence as set forth in SEQ ID NO: 6, a CDR2 domain having an amino acid sequence as set forth in SEQ ID NO: 37, and a CDR3 domain having an amino acid sequence as set forth in SEQ ID NO: 8; (g) a CDR1 domain having an amino acid sequence as set forth in SEQ ID NO: 11, a CDR2 domain having an amino acid sequence as set forth in SEQ ID NO: 7, and a CDR3 domain having an amino acid sequence as set forth in SEQ ID NO: 8; (h) a CDR1 domain having an amino acid sequence as set forth in SEQ ID NO: 11, a CDR2 domain having an amino acid sequence as set forth in SEQ ID NO: 12, and a CDR3 domain having an amino acid sequence as set forth in SEQ ID NO: 8; (i) a CDR1 domain having an amino acid sequence as set forth in SEQ ID NO: 11; a CDR2 domain having an amino acid sequence as set forth in SEQ ID NO: 14; and a CDR3 domain having an amino acid sequence as set forth in SEQ ID NO: 8; (j) a CDR1 domain having an amino acid sequence as set forth in SEQ ID NO: 11; a CDR2 domain having an amino acid sequence as set forth in SEQ ID NO: 33; and a CDR3 domain having an amino acid sequence as set forth in SEQ ID NO: 8; (k) a CDR1 domain having an amino acid sequence as set forth in SEQ ID NO: 11; a CDR2 domain having an amino acid sequence as set forth in SEQ ID NO: 35; and a CDR3 domain having an amino acid sequence as set forth in SEQ ID NO: 8; or (1) a CDR1 domain having an amino acid sequence as set forth in SEQ ID NO: 11; a CDR2 domain having an amino acid sequence as set forth in SEQ ID NO: 37; and a CDR3 domain having an amino acid sequence as set forth in SEQ ID NO: 8.

In some embodiments, the antibody or antigen-binding fragment thereof comprises: (a) a heavy chain variable region comprising a CDR1 domain having an amino acid sequence as set forth in SEQ ID NO: 3, a CDR2 domain having an amino acid sequence as set forth in SEQ ID NO: 4, and a CDR3 domain having an amino acid sequence as set forth in SEQ ID NO: 5; and a light chain variable region comprising a CDR1 domain having an amino acid sequence as set forth in SEQ ID NO: 6, a CDR2 domain having an amino acid sequence as set forth in SEQ ID NO: 7, and a CDR3 domain having an amino acid sequence as set forth in SEQ ID NO: 8; (b) a heavy chain variable region comprising a CDR1 domain having an amino acid sequence as set forth in SEQ ID NO: 3, a CDR2 domain having an amino acid sequence as set forth in SEQ ID NO: 4, and a CDR3 domain having an amino acid sequence as set forth in SEQ ID NO: 5; and a light chain variable region comprising a CDR1 domain having an amino acid sequence as set forth in SEQ ID NO: 11, a CDR2 domain having an amino acid sequence as set forth in SEQ ID NO: 12, and a CDR3 domain having an amino acid sequence as set forth in SEQ ID NO: 8; (c) a heavy chain variable region comprising a CDR1 domain having an amino acid sequence as set forth in SEQ ID NO: 3, a CDR2 domain having an amino acid sequence as set forth in SEQ ID NO: 4, and a CDR3 domain having an amino acid sequence as set forth in SEQ ID NO: 5; and a light chain variable region comprising a CDR1 domain having an amino acid sequence as set forth in SEQ ID NO: 11, a CDR2 domain having an amino acid sequence as set forth in SEQ ID NO: 14, and a CDR3 domain having an amino acid sequence as set forth in SEQ ID NO: 8; (d) a heavy chain variable region comprising a CDR1 domain having an amino acid sequence as set forth in SEQ ID NO: 3, a CDR2 domain having an amino acid sequence as set forth in SEQ ID NO: 29, and a CDR3 domain having an amino acid sequence as set forth in SEQ ID NO: 5; and a light chain variable region comprising a CDR1 domain having an amino acid sequence as set forth in SEQ ID NO: 11, a CDR2 domain having an amino acid sequence as set forth in SEQ ID NO: 14, and a CDR3 domain having an amino acid sequence as set forth in SEQ ID NO: 8; (e) a heavy chain variable region comprising a CDR1 domain having an amino acid sequence as set forth in SEQ ID NO: 3, a CDR2 domain having an amino acid sequence as set forth in SEQ ID NO: 29, and a CDR3 domain having an amino acid sequence as set forth in SEQ ID NO: 5; and a light chain variable region comprising a CDR1 domain having an amino acid sequence as set forth in SEQ ID NO: 11, a CDR2 domain having an amino acid sequence as set forth in SEQ ID NO: 33, and a CDR3 domain having an amino acid sequence as set forth in SEQ ID NO: 8; (f) a heavy chain variable region comprising a CDR1 domain having an amino acid sequence as set forth in SEQ ID NO: 3, a CDR2 domain having an amino acid sequence as set forth in SEQ ID NO: 29, and a CDR3 domain having an amino acid sequence as set forth in SEQ ID NO: 5; and a light chain variable region comprising a CDR1 domain having an amino acid sequence as set forth in SEQ ID NO: 11, a CDR2 domain having an amino acid sequence as set forth in SEQ ID NO: 35, and a CDR3 domain having an amino acid sequence as set forth in SEQ ID NO: 8; (g) a heavy chain variable region comprising a CDR1 domain having an amino acid sequence as set forth in SEQ ID NO: 3, a CDR2 domain having an amino acid sequence as set forth in SEQ ID NO: 29, and a CDR3 domain having an amino acid sequence as set forth in SEQ ID NO: 5; and a light chain variable region comprising a CDR1 domain having an amino acid sequence as set forth in SEQ ID NO: 11, a CDR2 domain having an amino acid sequence as set forth in SEQ ID NO: 37, and a CDR3 domain having an amino acid sequence as set forth in SEQ ID NO: 8; (h) a heavy chain variable region comprising a CDR1 domain having an amino acid sequence as set forth in SEQ ID NO: 3, a CDR2 domain having an amino acid sequence as set forth in SEQ ID NO: 4, and a CDR3 domain having an amino acid sequence as set forth in SEQ ID NO: 5; and a light chain variable region comprising a CDR1 domain having an amino acid sequence as set forth in SEQ ID NO: 11, a CDR2 domain having an amino acid sequence as set forth in SEQ ID NO: 33, and a CDR3 domain having an amino acid sequence as set forth in SEQ ID NO: 8; (i) a heavy chain variable region comprising a CDR1 domain having an amino acid sequence as set forth in SEQ ID NO: 3, a CDR2 domain having an amino acid sequence as set forth in SEQ ID NO: 4, and a CDR3 domain having an amino acid sequence as set forth in SEQ ID NO: 5; and a light chain variable region comprising a CDR1 domain having an amino acid sequence as set forth in SEQ ID NO: 11; a CDR2 domain having an amino acid sequence as set forth in SEQ ID NO: 35; and a CDR3 domain having an amino acid sequence as set forth in SEQ ID NO: 8; or (j) a heavy chain variable region comprising a CDR1 domain having an amino acid sequence as set forth in SEQ ID NO: 3, a CDR2 domain having an amino acid sequence as set forth in SEQ ID NO: 4, and a CDR3 domain having an amino acid sequence as set forth in SEQ ID NO: 5; and a light chain variable region comprising a CDR1 domain having an amino acid sequence as set forth in SEQ ID NO: 11; a CDR2 domain having an amino acid sequence as set forth in SEQ ID NO: 37; and a CDR3 domain having an amino acid sequence as set forth in SEQ ID NO: 8.

In some embodiments, the isolated antibody or antigen-binding fragment thereof is humanized.

In some embodiments, the isolated antibody or antigen-binding fragment thereof comprises a light chain variable region having an amino acid sequence as set forth in SEQ ID NO: 2, 10, 13, 30, 31, 32, 34 or 36. In some embodiments, the isolated antibody, or antigen-binding fragment thereof comprises a heavy chain variable region having an amino acid sequence as set forth in SEQ ID NO: 1, 9, 15, 16 or 28.

In some embodiments, the isolated antibody or the antigen-binding fragment thereof comprises a heavy chain comprising a variable region comprising the amino acid sequence as set forth in SEQ ID NO: 15, and a light chain comprising a variable region comprising the amino acid sequence as set forth in SEQ ID NO: 13.

In some embodiments, the isolated antibody or the antigen-binding fragment thereof comprises a heavy chain comprising a variable region comprising the amino acid sequence as set forth in SEQ ID NO: 26, and a light chain comprising a variable region comprising the amino acid sequence as set forth in SEQ ID NO: 18.

In some embodiments, the isolated antibody or the antigen-binding fragment thereof comprises a heavy chain comprising a variable region as described in Table 17, and a light chain comprising a variable region as described in Table 17.

In some embodiments, the antibody or the antigen-binding fragment thereof comprises a heavy chain comprising a heavy chain CDR1, CDR2, and CDR3 as described in Table 17, and a light chain comprising a light chain CDR1, CDR2, and CDR3 as described in Table 17.

Some embodiments comprise an isolated anti-NAMPT antibody which comprises a heavy chain variable region and a light chain variable region of antibody AL-303.

Some embodiments comprise an isolated anti-NAMPT antibody which comprises a heavy chain variable region and a light chain variable region of antibody AL-310.

In some embodiments, the isolated antibody or the antigen-binding fragment thereof is an isolated humanized anti-NAMPT antibody comprising a humanized heavy chain variable region derived from murine antibody AL-303 or AL-310, and a humanized light chain variable region derived from murine antibody AL-303 or AL-310.

In some embodiments, the isolated antibody or the antigen-binding fragment thereof is an isolated anti-NAMPT antibody that specifically binds to human NAMPT in a homodimeric conformation, wherein the antibody binds an epitope on human NAMPT comprising either:(a) an epitope on human NAMPT comprising at least one amino acid in amino acid residues 17-44 of SEQ ID NO: 60; at least one amino acid in amino acid residues 117-127 of SEQ ID NO: 60; at least one amino acid in amino acid residues 162-170 of SEQ ID NO: 60; at least one amino acid in amino acid residues 242-261 of SEQ ID NO: 60; at least one amino acid in amino acid residues 262-273 of SEQ ID NO: 60; at least one amino acid in amino acid residues 289-305 of SEQ ID NO: 60; at least one amino acid in amino acid residues 332-342 of SEQ ID NO: 60; at least one amino acid in amino acid residues 374-389 of SEQ ID NO: 60; at least one amino acid in amino acid residues 418-425 of SEQ ID NO: 60; at least one amino acid in amino acid residues 453-466 of SEQ ID NO: 60; and at least one amino acid in amino acid residues 408-416 of SEQ ID NO: 60; or (b) an epitope on human NAMPT comprising at least one amino acid in amino acid residues 29-51 of SEQ ID NO: 60; at least one amino acid in amino acid residues 61-72 of SEQ ID NO: 60; at least one amino acid in amino acid residues 156-170 of SEQ ID NO: 60; at least one amino acid in amino acid residues 216-234 of SEQ ID NO: 60; at least one amino acid in amino acid residues 316-331 of SEQ ID NO: 60; at least one amino acid in amino acid residues 332-342 of SEQ ID NO: 60; at least one amino acid in amino acid residues 373-389 of SEQ ID NO: 60; at least one amino acid in amino acid residues 417-431 of SEQ ID NO: 60; at least one amino acid in amino acid residues 454-469 of SEQ ID NO: 60; and at least one amino acid in amino acid residues 470-478 of SEQ ID NO: 60.

In some embodiments, the isolated antibody or the antigen-binding fragment thereof comprises an Fc domain.

In some embodiments, the isolated antibody or antigen-binding fragment thereof is a monoclonal antibody.

In some embodiments, the isolated antibody or antigen-binding fragment thereof is an IgG antibody. In some embodiments, the isolated antibody or antigen-binding fragment thereof is an IgG1 antibody. In some embodiments, the isolated antibody or antigen-binding fragment thereof is an IgG4 antibody.

Also provided are nucleic acids encoding any of the isolated antibodies or antigen-binding fragments featured herein, a vector comprising the nucleic acid, and/or a host cell comprising the nucleic acid or the vector.

Also provided are pharmaceutical compositions comprising any of the isolated antibodies or antigen-binding fragments, and a pharmaceutically acceptable carrier.

Also provided are methods of treating a disorder associated with detrimental NAMPT activity in a subject in need thereof by administering to the subject an effective amount of any of the isolated antibodies or antigen-binding fragments featured herein.

Also provided are methods of treating a subject having an inflammatory condition, said method comprising administering to the subject an effective amount of an isolated antibody or antigen-binding fragment described herein. In some embodiments, the inflammatory condition is pulmonary fibrosis (IPF), pulmonary hypertension, acute lung injury (ALI), acute respiratory distress syndrome (ARDS), ventilator-induced lung injury (VILI), ARDS/VILI-induced ALI, trauma-induced acute lung injury (TIALI) and brain injury, or radiation-induced lung injury (e.g., radiation-induced lung injury that is caused by radiation associated with cancer therapy).

Also provided are methods for treating prostate cancer (PCa) in a subject in need thereof, said method comprising administering to the subject an effective amount of any of the isolated antibodies or antigen-binding fragments described herein. In some embodiments, the subject has recurrent PCa. In some embodiments, the subject is at a risk of developing metastatic PCa. In certain embodiments, the PCa is resistant to androgen deprivation therapy (ADT). In some embodiments, the method further includes administering ADT to the subject.

BRIEF DESCRIPTION OF THE DRAWINGS

FIG. 4A is a graph showing the effect of the murine anti-NAMPT antibodies on NAMPT-induced bronchoalveolar lavage (BAL) protein levels, and FIG. 4B is a graph showing the effect of the murine anti-NAMPT antibodies on NAMPT-induced BAL-expressing polymorphonuclear neutrophil (PMN) count (n=3-6 mice,*P<0.05).

FIG. 7A is a graphical representation of the effect of humanized 1076 and 1093 anti-hNAMPT antibodies on hNAMPT-induced NFκB phosphorylation. FIG. 7B is a graphical representation of the effect of humanized 1076 and 1093 anti-hNAMPT antibodies on hNAMPT-induced decline in endothelial cell (EC) barrier integrity.

FIG. 8A is a graphical representation of the effect of 1076 anti-hNAMPT antibodies V-1076, N-1076, K-1076, and P-1076 on BAL protein levels (FIG. 8A, left panel) and BAL PMN count (FIG. 8A, right panel) in a mouse model of lung injury. FIG. 8B is a graphical representation of the effect of 1093 anti-hNAMPT antibodies SS-1093, CC-1093, XX-1093, and UU-1093 on BAL protein levels (FIG. 8B, left panel) and BAL PMN count (FIG. 8B, right panel) in a mouse model of lung injury. FIG. 8C is a graphical representation of the effect of 1076 anti-hNAMPT antibody P-1076 on BAL protein levels (FIG. 8C, left panel) and BAL PMN count (FIG. 8C, right panel) in a rat model of lung injury. FIG. 8D depicts H&E stained micrographs showing the effect of 1093 anti-hNAMPT antibody UU-1093 on cell infiltration and edema in a mouse model of lung injury.

FIG. 9A is a micrograph showing extremely low NAMPT expression in normal prostatic gland tissue. FIG. 9B is a micrograph showing significantly increased albeit moderate NAMPT expression in gland-confined prostatic adenocarcinoma. FIG. 9C is a micrograph showing strong NAMPT expression within tumor cells in three separate prostatic adenocarcinomas with smooth muscle capsular penetration and invasion into periprostatic adipose tissue. FIG. 9D is a graph showing cumulative analysis of NAMPT expression in 26 PCa patients with organ-confined (n=12) and capsule invasive disease (n=14).

FIG. 10A provides micrographs of H&E staining showing evidence of inflammation and injury of murine lung tissue at 1-week post radiation exposure (FIG. 10A, lower panel), and prior to exposure to a single dose of thoracic radiation (FIG. 10A, upper panel). FIG. 10B provides micrographs of IHC staining showing NAMPT expression in murine lung tissue at 1-week post radiation exposure (FIG. 10B, lower panel), and prior to exposure to radiation (FIG. 10B, upper panel). FIG. 10C is a high magnification image of a micrograph showing NAMPT expression in alveolar macrophages (long arrow) and pneumocytes (short arrow). FIG. 10D depicts micrographs showing NAMPT expression in normal, post-surgical human tonsillar epithelial tissue that were either exposed to 8 Gy radiation for 24 hrs ("Irradiated") (FIG. 10D, lower panel), or not exposed to radiation ("Unirradiated") (FIG. 10D, upper panel).

FIG. 11A is a graph showing the number of invading DU-145 PCa cells in absence ("Media Only") or presence ("NAMPT") of NAMPT; medium with no PCa cells ("No PCa Cells") served as negative control. FIG. 11B provides micrographs of wells with PCa cells that were cultured in absence ("Media Only") or presence ("NAMPT") of NAMPT; wells with no PCa cells ("No PCa Cells") served as negative control.

FIG. 12A is a graph showing the effect of the humanized anti-hNAMPT antibodies on lung injury score in the LPS-induced "one hit" lung injury model. FIG. 12B is a graph showing the effect of the humanized anti-hNAMPT antibodies on lung injury score in the LPS/VILI-induced "two hit" lung injury model. FIG. 12C provides micrographs showing the histological indices of the effect of humanized anti-hNAMPT antibody P-1076 on lung injury in the LPS-induced "one hit" lung injury model (FIG. 12C, upper panel) and LPS/VILI-induced "two hit" lung injury model (FIG. 12C, lower panel).

FIG. 13A is a micrograph showing severe studding of the peritoneum with invasion through the smooth muscle layer in SCID mice, 6 weeks after intraperitoneal (IP) injection of PC3, a highly metastatic human PCa cell; an enlarged image of the micrograph is provided in FIG. 13A, lower panel. FIG. 13B is a micrograph showing inhibition of PC3 cell invasion in PC3-injected mice that received a humanized anti-hNAMPT antibody, P-1076; an enlarged image of the micrograph is provided in FIG. 13B, lower panel. FIG. 13C is a graph showing the percent of PC3 cells invading the diaphragm in mice that were treated with the anti-hNAMPT antibody P-1076, or vehicle alone.

FIG. 14A provides representative micrographs showing H&E staining in lung tissues of non-irradiated control mice (inset of FIG. 14A, left panel) or irradiated RILI mice that were injected with vehicle control (FIG. 14A, left panel), an anti-NAMPT polyclonal antibody (pAb) (FIG. 14A, middle panel), or an anti-NAMPT monoclonal antibody (mAb) (FIG. 14A, right panel) post radiation exposure. FIG. 14B is a graphical depiction of H&E staining (% area) in lung tissue of non-irradiated control mice or irradiated RILI mice that were injected with vehicle control, anti-NAMPT pAb, or anti-NAMPT mAb. FIG. 14C is a graphical representation of BAL protein levels (μg/ml) in lung tissues of non-irradiated control mice or irradiated RILI mice that were injected with vehicle control, anti-NAMPT pAb, or anti-NAMPT mAb. FIG. 14D is a graphical representation of number of BAL-expressing cells in lung tissues of non-irradiated control mice or irradiated RILI mice that were injected with vehicle control, anti-NAMPT pAb, or anti-NAMPT mAb. FIG. 14E is a graphical representation of ALI severity score of non-irradiated control mice or irradiated RILI mice that were injected with vehicle control, anti-NAMPT pAb, or anti-NAMPT mAb.*indicates $p<0.05$ FIG. 15A provides representative autoradiograph images depicting detection of NAMPT expression by the $^{99m}$Tc-labeled anti-NAMPT mAb probe in a non-irradiated control mouse (FIG. 15A, left panel) or in an irradiated (RILI) mouse exposed to 8Gy partial body irradiation (PBI) (FIG. 15A, right panel). FIG. 15B provides representative autoradiograph images depicting detection of NAMPT expression by the $^{99m}$Tc-labeled anti-NAMPT mAb probe in a non-irradiated control mouse (FIG. 15B, top panel) or in an irradiated (RILI) mouse (FIG. 15B, bottom panel). FIG. 15C is a graphical representation of ratio of lung activity over tissue background from left and right lungs of non-irradiated control mice or irradiated (RILI) mice. FIG. 15D is a graphical representation of radioactivity (% ID/g) in lung tissues of non-irradiated control mice or irradiated (RILI) mice.*indicates $p<0.05$ FIG. 16A is a graph depicting number of BAL-expressing cells in lung tissues of irradiated RILI mice that were intraperitoneally injected with anti-NAMPT mAb or vehicle control. FIG. 16B provides representative images from western blot analyses showing expression of SMA in lung tissue homogenate of irradiated RILI mice that were intraperitoneally injected with anti-NAMPT mAb or vehicle control. FIG. 16C provides representative micrographs showing collagen deposition, as detected by Trichrome staining, in lung tissue of irradiated RILI mice that were intraperitoneally injected with anti-NAMPT mAb or vehicle control.*indicates $p<0.05$.

FIG. 17A provides representative images and micrographs showing lung or lung tissue section of trauma/VILI challenged rats that were injected with vehicle control. The left panel of FIG. 17A provides representative image of lung from trauma/VILI challenged rats injected with vehicle control. The middle and right panels of FIG. 17A provides representative micrographs showing inflammatory cell infiltration and edema, as assessed by H&E staining, in trauma/VILI challenged rats injected with vehicle control. The inset of the rightmost panel of FIG. 17A provides representative micrograph showing H&E staining in lung tissue of rats not challenged with trauma/VILI. FIG. 17B provides representative images and micrographs showing lung or lung tissue section of trauma/VILI challenged rats that were injected with anti-NAMPT mAb. The left panel of FIG. 17B provides representative image of lung from trauma/VILI challenged rats injected with anti-NAMPT mAb. The middle and right panels of FIG. 17B provides representative micrographs showing inflammatory cell infiltration and edema, as assessed by H&E staining, in trauma/VILI challenged rat injected with anti-NAMPT mAb. FIG. 17C is a graph depicting lung injury score of trauma/VILI challenged rats that were injected with either anti-NAMPT mAb or vehicle control.

FIG. 18A provides a representative micrograph showing inflammatory cell infiltration and edema, as assessed by H&E staining, in LPS/VILI challenged mouse injected with vehicle control. The inset of FIG. 18A provides representative a micrograph showing H&E staining in lung tissue from mouse not challenged with LPS/VILI. FIG. 18B provides a representative micrograph showing inflammatory cell infiltration and edema, as assessed by H&E staining, in LPS/VILI challenged mouse injected with anti-NAMPT mAb. FIG. 18C is a graph depicting ALI severity score as assessed in LPS/VILI challenged mice that were injected with anti-NAMPT mAb, anti-NAMPT pAb or vehicle control (PBS). The graph in FIG. 18C also depicts ALI severity score of control mice that were not challenged with LPS/VILI.*indicates $p<0.05$;***indicates $p<0.001$.

FIG. 19A provides representative autoradiograph images depicting detection of NAMPT expression by the $^{99m}$Tc-labeled anti-NAMPT mAb probe (PRONAMPTOR) (FIG. 19A, right panel) or a radiolabeled IgG control Ab (FIG. 19A, left panel) in mice that were exposed to 20Gy total lung irradiation (WTLI). FIG. 19B provides representative autoradiograph images depicting detection of NAMPT expression by the $^{99m}$Tc-labeled anti-NAMPT mAb probe in LPS challenged mouse 3 hours after LPS challenge (FIG. 19B, right panel) or in a non-challenged control mouse (FIG. 19B, left panel). FIG. 19C provides representative autoradiograph images depicting detection of NAMPT expression by the $^{99m}$Tc-labeled anti-NAMPT mAb probe in lung of LPS challenged mouse 3 hours after LPS challenge (FIG. 19C, bottom panel) or in lung of a non-challenged control mouse (FIG. 18C, top panel). FIG. 19D is a graphical representation of uptake of the radiolabeled anti-NAMPT mAb probe, as assessed by radioactivity (% ID/g), in lung tissues of LPS challenged mouse at 3 hours and 18 hours post LPS challenge or in lung tissues of non-challenged control mice.*indicates $p<0.05$.

FIG. 20A is a graphical representation of RVSP in MCT-challenged rats that were injected with either anti-NAMPT mAb or vehicle control (control MCT mice). FIG. 20B provides representative micrographs showing pulmonary artery thickness, as assessed by H&E staining, in MCT-challenged rats that were injected with either anti-NAMPT mAb (FIG. 20B, right panel) or vehicle control (FIG. 20B, left panel).*indicates $p<0.05$.

DETAILED DESCRIPTION OF THE INVENTION

Figure 1:
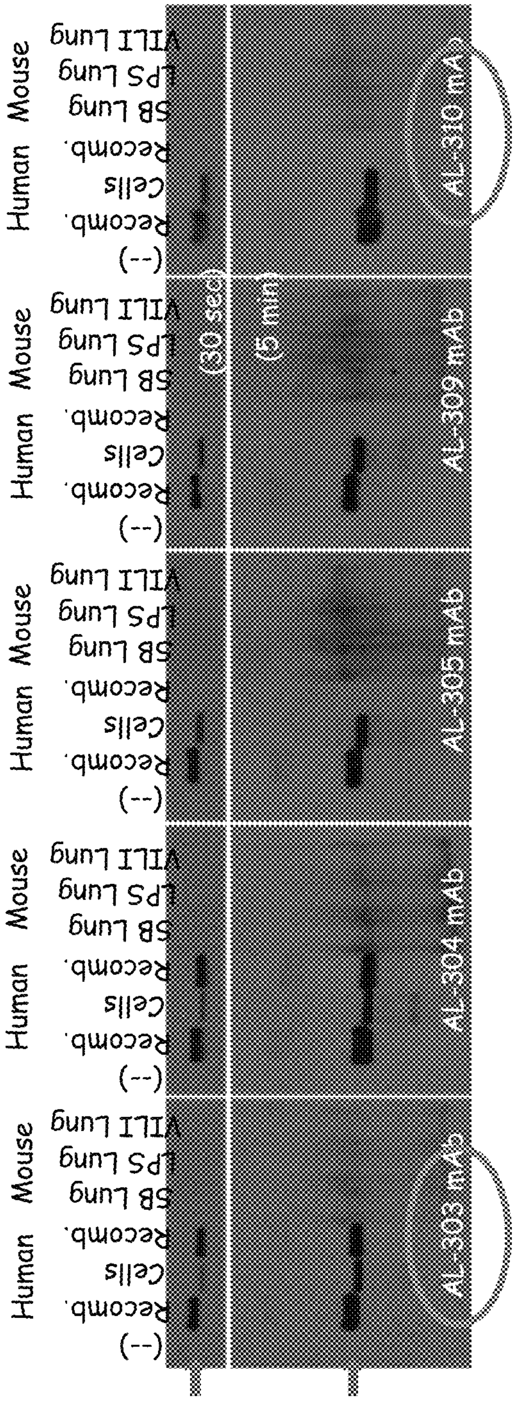
FIG. 1 is a Western blot assay depicting the detection of human and mouse NAMPT by murine anti-NAMPT antibodies AL-303, AL-304, AL-305, AL-309, and AL-310.

The invention may be embodied in many different forms. Disclosed herein are non-limiting, illustrative embodiments of the invention that exemplify the principles thereof. Any section headings used herein are for organizational purposes only and are not to be construed as limiting the subject matter described. For the purposes of the instant disclosure all identifying sequence accession numbers may be found in the NCBI Reference Sequence (REFSEQ) database and/or the NCBI GenBank® archival sequence database unless otherwise noted.

Various aspects of the invention relate to anti-NAMPT antibodies and antibody fragments, and pharmaceutical compositions thereof, as well as nucleic acids, recombinant expression vectors and host cells for making such antibodies and fragments. Methods of using the antibodies described herein to detect human NAMPT, to inhibit human NAMPT activity (in vitro or in vivo), and to treat NAMPT-related disease, including, but not limited to, pulmonary fibrosis (IPF), pulmonary hypertension, acute lung injury (ALI), acute respiratory distress syndrome (ARDS), ventilator-induced lung injury (VILI), ARDS/VILI-induced ALI, trauma-induced acute lung injury (TIALI) and brain injury, radiation-induced lung injury, and cancer (e.g., prostate cancer (PCa)), which are also encompassed by the invention.

Definitions

In order that the invention may be more readily understood, certain terms are first defined. In addition, it should be noted that whenever a value or range of values of a parameter are recited, it is intended that values and ranges intermediate to the recited values are also intended to be part of this invention.

The term "NAMPT" or "eNAMPT", used interchangeably herein, refers to the secreted form of nicotinamide phosphoribosyltransferase unless specifically mentioned to relate to a non-secreted form (e.g., intracellular NAMPT or NAMPT nucleic acids). The amino acid sequence of secreted human NAMPT (also referred to as human eNAMPT) is provided below as SEQ ID NO: 60 (see also NCBI Gene Ref. No. NC_000007.14 and Protein Ref. No. NP_005737.1).

```
                                        (SEQ ID NO: 60)
MNPAAEAEFN ILLATDSYKV THYKQYPPNT SKVYSYFECR

EKKTENSKLR KVKYEETVFY GLQYILNKYL KGKVVTKEKI

QEAKDVYKEH FQDDVFNEKG WNYILEKYDG HLPIEIKAVP

EGFVIPRGNV LFTVENTDPE CYWLTNWIET ILVQSWYPIT

VATNSREQKK ILAKYLLETS GNLDGLEYKL HDFGYRGVSS

QETAGIGASA HLVNFKGTDT VAGLALIKKY YGTKDPVPGY

SVPAAEHSTI TAWGKDHEKD AFEHIVTQFS SVPVSVVSDS

YDIYNACEKI WGEDLRHLIV SRSTQAPLII RPDSGNPLDT

VLKVLEILGK KFPVTENSKG YKLLPPYLRV IQGDGVDINT

LQEIVEGMKQ KMWSIENIAF GSGGGLLQKL TRDLLNCSFK

CSYVVTNGLG INVFKDPVAD PNKRSKKGRL SLHRTPAGNF

VTLEEGKGDL EEYGQDLLHT VFKNGKVTKS YSFDEIRKNA

QLNIELEAAHH
```

NAMPT is also referred to as pre-B cell colony enhancing factor (PBEF) or visfatin.

The terms "NAMPT antibody" or "anti-NAMPT antibody", used interchangeably herein, refer to an antibody that specifically binds to the secreted form of NAMPT (also referred to herein as eNAMPT). An antibody "which binds" an antigen of interest, i.e., NAMPT, is one capable of binding that antigen with sufficient affinity such that the antibody is useful in targeting a cell expressing the antigen. In a preferred embodiment, the antibody specifically binds to human NAMPT (hNAMPT), particularly extracellular human NAMPT (human eNAMPT). Examples of anti-eNAMPT antibodies are disclosed in the examples and in the Sequence Table provided below.

"Biological activity of NAMPT" as used herein, refers to all inherent biological properties of NAMPT, including, but not limited to, binding to TLR4.

The term "specifically binds," or "binds specifically to", or the like, means that an antibody or antigen-binding fragment thereof forms a complex with an antigen, e.g., NAMPT, that is relatively stable under physiologic conditions. Specific binding can be characterized by an equilibrium dissociation constant of at least about $1\times10^{-8}$M or less (e.g., a smaller $K_D$ denotes a tighter binding). Methods for determining whether two molecules specifically bind are well known in the art and include, for example, equilibrium dialysis, surface plasmon resonance, and the like.

The term "antibody" broadly refers to an immunoglobulin (Ig) molecule, generally comprised of four polypeptide chains, two heavy (H) chains and two light (L) chains, or any functional fragment, mutant, variant, or derivative thereof, that retains the essential target binding features of an Ig molecule. Such mutant, variant, or derivative antibody formats are known in the art. Non-limiting embodiments of which are discussed below.

In a full-length antibody, each heavy chain is comprised of a heavy chain variable region (abbreviated herein as HCVR or VH) and a heavy chain constant region.

Both the light and heavy chains are divided into regions of structural and functional homology. The terms "constant" and "variable" are used functionally. In this regard, it will be appreciated that the variable domains of both the variable light (VL) and variable heavy (VH) chain portions determine antigen recognition and specificity. Conversely, the constant domains of the light chain (CL) and the heavy chain (CH1, CH2 or CH3) confer biological properties such as secretion, transplacental mobility, Fc receptor binding, complement binding, and the like. By convention the numbering of the constant region domains increases as they become more distal from the antigen binding site or amino-terminus of the antibody. The N-terminal portion is a variable region and at the C-terminal portion is a constant region; the CH3 (or CH4 in the case of IgM) and CL domains actually comprise the carboxy-terminus of the heavy and light chain, respectively.

The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. Immunoglobulin molecules can be of any class (e.g., IgG, IgE, IgM, IgD, IgA and IgY) and isotype (e.g., IgG1, IgG2, IgG3, IgG4, IgA1 and IgA2) or subclass. Light chains are classified as either kappa or lambda (κ, λ).

The "complementarity determining regions" or "CDRs" present in an antibody antigen-binding domain are each short, non-contiguous sequences of amino acids that are specifically positioned to form the binding domain as the antibody assumes its three dimensional configuration in an aqueous environment. The remainder of the amino acids in the binding domain of an antibody, referred to as "framework" or "FW" regions, show less inter-molecular variability. The binding domain formed by the positioned CDRs defines a surface complementary to the epitope on the immunoreactive antigen. This complementary surface promotes the non-covalent binding of the antibody to its cognate epitope. The amino acids that make up the CDRs and the framework regions, respectively, can be readily identified for any given heavy or light chain variable region by one of ordinary skill in the art, since they have been defined in various different ways as described below. Exemplary CDRs are provided herein. However, CDRs can also be defined according to Kabat, Chothia, Martin, PyIgClassify, or IMGT. Exemplary CDR definitions are described in Chiu et al, "Antibody Structure and Function: The Basis for Engineering Therapeutics," Antibodies, 8(55): 1-80 (2019), which is incorporated herein by reference in its entirety.

For heavy chain constant region amino acid positions discussed in the invention, numbering is according to the EU index first described in Edelman et al., 1969, *Proc. Natl. Acad. Sci. USA* 63(1): 78-85 describing the amino acid sequence of the myeloma protein Eu, which reportedly was the first human IgG1 sequenced. The EU index of Edelman is also set forth in Kabat et al., 1991 (supra.). Thus, the terms "EU index as set forth in Kabat" or "EU index of Kabat" or "EU index" or "EU numbering" in the context of the heavy chain refers to the residue numbering system based on the human IgG1 Eu antibody of Edelman et al. as set forth in Kabat et al., 1991 (supra.) The numbering system used for the light chain constant region amino acid sequence is similarly set forth in Kabat et al., (supra.) An exemplary kappa light chain constant region amino acid sequence compatible with the present disclosure is set forth immediately below:

```
                                      (SEQ ID NO: 59)
RTVAAPSVFIFPPSDEQLKSGTASVVCLLNNFYPREAKVQWK

VDNALQSGNSQESVTEQDSKDSTYSLSSTLTLSKADYEKHKV

YACEVTHQGLSSPVTKSFNRGEC
```

Similarly, an exemplary IgG1 heavy chain constant region amino acid sequence compatible with the present invention is set forth immediately below:

```
                                      (SEQ ID NO: 58)
ASTKGPSVFPLAPSSKSTSGGTAALGCLVKDYFPEPVTVSWNS

GALTSGVHTFPAVLQSSGLYSLSSVVTVPSSSLGTQTYICNVN

HKPSNTKVDKKVEPKSCDKTHTCPPCPAPELLGGPSVFLFPPK

PKDTLMISRTPEVTCVVVDVSHEDPEVKFNWYVDGVEVHNAKT

KPREEQYNSTYRVVSVLTVLHQDWLNGKEYKCKVSNKALPAPI

EKTISKAKGQPREPQVYTLPPSRDELTKNQVSLTCLVKGFYPS

DIAVEWESNGQPENNYKTTPPVLDSDGSFFLYSKLTVDKSRWQ

QGNVFSCSVMHEALHNHYTQKSLSLSPGK
```

The term "antigen binding portion" or "binding fragment" of an antibody, as used herein, refers to one or more fragments of an antibody that retain the ability to specifically bind to an antigen (e.g., hNAMPT). It has been shown that the antigen binding function of an antibody can be performed by fragments of a full-length antibody. Such antibody embodiments may also be bispecific, dual specific, or multi-specific formats; specifically binding to two or more different antigens. Examples of binding fragments encompassed within the term "antigen binding portion" of an antibody include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546, Winter et al., PCT publication WO 90/05144 A1 herein incorporated by reference), which comprises a single variable domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen binding portion" of an antibody. In certain embodiments of the invention, scFv molecules may be incorporated into a fusion protein. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) *Proc. Natl. Acad. Sci. USA* 90:6444-6448; Poljak, R. J., et al. (1994) *Structure* 2:1121-1123). Such antibody binding portions are known in the art (Kontermann and Dubel eds., Antibody Engineering (2001) Springer-Verlag. New York. 790 pp. (ISBN 3-540-41354-5).

A "fully human" antibody comprises an antibody variable domain that has a sequence derived from a human immunoglobulin (e.g., obtained from a human immunoglobulin coding sequence). The term "human antibody" includes, for example, antibodies having variable and constant regions (if present) derived from human germline immunoglobulin sequences. The term "human" as applied herein to an antibody or to a fragment such as a variable domain does not encompass an antibody from another species, e.g., mouse, that has been "humanized" through grafting of human constant region sequences onto an antibody polypeptide (i.e., replacing non-human constant regions with human constant regions) or through grafting of human V region framework sequences onto an immunoglobulin variable domain from a non-human mammal (i.e., replacing non-human framework regions of a V domain with human framework regions). Methods of humanizing immunoglobulin variable regions through rational modification of complementarity determining residues have been described (US 2006/0258852).

The term "humanized antibody" designates antibodies from a non-human species having one or more complementarity determining regions (CDRs) from said non-human species and a framework region from a human immunoglobulin molecule. Humanized antibodies may optionally further comprise one or more framework residues derived from the non-human species from which the CDRs were derived. Such framework sequences can be obtained from public DNA database covering germline antibody gene sequences or from published references. For example, germline DNA sequences of human heavy and light chain variable region genes can be found in "VBase" human germline sequence database (available on the world wide web (www) at mrccpe.com.ac.uk/vbase), as well as can be found in Kabat, E A, et al, 1991 Sequences of Proteins of Immunological Interest, 5th Ed. To avoid the decrease in the activity during immunogenicity reduction, the variable region frame sequence of the human antibody is subjected to a minimum back mutation to maintain the activity.

The humanized antibody can be selected from any class of immunoglobulins, including IgM, IgG, IgD, IgA and IgE, and any isotype, including without limitation IgG1, IgG2, IgG3 and IgG4. The humanized antibody may comprise sequences from more than one class or isotype, and particular constant domains may be selected to optimize desired effector functions using techniques well-known in the art.

The term "multispecific" antibody refers to an antibody that has binding domains for two or more different epitopes within a single antibody molecule. Other binding molecules in addition to the canonical antibody structure can be constructed with two binding specificities. Epitope binding by bispecific or multispecific antibodies can be simultaneous or sequential. Triomas and hybrid hybridomas are two examples of cell lines that can secrete bispecific antibodies. Bispecific antibodies can also be constructed by recombinant means. (Strohlein and Heiss, *Future Oncol.* 6:1387-94 (2010); Mabry and Snavely, IDrugs. 13:543-9 (2010)). A bispecific antibody can also be a diabody.

The term "labeled antibody" as used herein, refers to an antibody, or an antigen binding portion thereof, with a label incorporated that provides for the identification of the binding protein, e.g., an antibody. Preferably, the label is a detectable marker, e.g., incorporation of a radiolabeled amino acid or attachment to a polypeptide of biotinyl moieties that can be detected by marked avidin (e.g., streptavidin containing a fluorescent marker or enzymatic activity that can be detected by optical or colorimetric methods). Examples of labels for polypeptides include, but are not limited to, the following: radioisotopes or radionuclides (e.g., $^{3}H$, $^{14}C$, $^{35}S$, $^{90}Y$, $^{99}Tc$, $^{111}In$, $^{125}I$, $^{131}I$, $^{177}Lu$, $^{166}Ho$, or $^{153}Sm$); fluorescent labels (e.g., FITC, rhodamine, lanthanide phosphors), enzymatic labels (e.g., horseradish peroxidase, luciferase, alkaline phosphatase); chemiluminescent markers; biotinyl groups; predetermined polypeptide epitopes recognized by a secondary reporter (e.g., leucine zipper pair sequences, binding sites for secondary antibodies, metal binding domains, epitope tags); and magnetic agents, such as gadolinium chelates.

A "conservative amino acid substitution" is one in which one amino acid is replaced with another amino acid having a similar side chain. Families of amino acids having similar side chains have been defined in the art, including basic side chains (e.g., lysine, arginine, histidine), acidic side chains (e.g., aspartic acid, glutamic acid), uncharged polar side chains (e.g., asparagine, glutamine, serine, threonine, tyrosine, cysteine), nonpolar side chains (e.g., glycine, alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). For example, substitution of a phenylalanine for a tyrosine is a conservative substitution. In certain embodiments, conservative substitutions in the sequences of the polypeptides and antibodies of the present disclosure do not abrogate the binding of the polypeptide or antibody containing the amino acid sequence to the antigen to which the binding molecule binds. Methods of identifying nucleotide and amino acid conservative substitutions which do not eliminate antigen-binding are well-known in the art (see, e.g., Brummell et al., *Biochem.* 32: 1180-1 187 (1993); Kobayashi et al., *Protein Eng.* 12(10): 879-884 (1999); and Burks et al., *Proc. Natl. Acad. Sci. USA* 94:412-417 (1997)).

The term "polynucleotide" is intended to encompass a singular nucleic acid as well as plurality of nucleic acids, and refers to an isolated nucleic acid molecule or construct, e.g., messenger RNA (mRNA), cDNA, or plasmid DNA (pDNA). A polynucleotide can comprise a conventional phosphodiester bond or a non-conventional bond (e.g., an amide bond, such as found in peptide nucleic acids (PNA)). The terms "nucleic acid" or "nucleic acid sequence" refer to any one or more nucleic acid segments, e.g., DNA or RNA fragments, present in a polynucleotide.

By an "isolated" nucleic acid or polynucleotide is intended any form of the nucleic acid or polynucleotide that is separated from its native environment. For example, gel-purified polynucleotide, or a recombinant polynucleotide encoding a polypeptide contained in a vector would be considered to be "isolated." Also, a polynucleotide segment, e.g., a PCR product, which has been engineered to have restriction sites for cloning is considered to be "isolated." Further examples of an isolated polynucleotide include recombinant polynucleotides maintained in heterologous host cells or purified (partially or substantially) polynucleotides in a non-native solution such as a buffer or saline. Isolated RNA molecules include in vivo or in vitro RNA transcripts of polynucleotides, where the transcript is not one that would be found in nature. Isolated polynucleotides or nucleic acids further include such molecules produced synthetically. In addition, polynucleotide or a nucleic acid can be or can include a regulatory element such as a promoter, ribosome binding site, or a transcription terminator.

The term "expression" as used herein refers to a process by which a gene produces a biochemical, for example, a polypeptide. The process includes any manifestation of the functional presence of the gene within the cell including, without limitation, gene knockdown as well as both transient expression and stable expression. It includes without limitation transcription of the gene into messenger RNA (mRNA), and the translation of such mRNA into polypeptide(s). If the final desired product is a biochemical, expression includes the creation of that biochemical and any precursors. Expression of a gene produces a "gene product." As used herein, a gene product can be either a nucleic acid, e.g., a messenger RNA produced by transcription of a gene, or a polypeptide which is translated from a transcript. Gene products described herein further include nucleic acids with post transcriptional modifications, e.g., polyadenylation, or polypeptides with post translational modifications, e.g., methylation, glycosylation, the addition of lipids, association with other protein subunits, proteolytic cleavage, and the like.

As used herein, a "neutralizing antibody", (e.g., an "antibody that inhibits NAMPT activity"), is intended to include to an antibody whose binding to NAMPT results in inhibition of the biological activity of NAMPT. A neutralizing antibody will substantially inhibit binding of NAMPT to its ligand or substrate when an excess of antibody reduces the quantity of binding partner bound to the determinant by at least about 20%, 30%, 40%, 50%, 60%, 70%, 80%, 85%, 90%, 95%, 97%, 99% or more as measured, for example, by target molecule activity or in an in vitro competitive binding assay. It will be appreciated that the modified activity may be measured directly using art recognized techniques or may be measured by the impact the altered activity has downstream. This inhibition of the biological activity of NAMPT, or its ligands, can be assessed by measuring one or more indicators of NAMPT biological activity, such as quantities of extracellular NAMPT (either in vitro or in vivo), NAMPT-induced cellular activation (e.g., NFkB phosphorylation) and NAMPT binding to NAMPT ligands. These indicators of NAMPT biological activity can be assessed by one or more of several standard in vitro or in vivo assays known in the art (see Examples). For example, in some embodiments, the ability of an antibody to inhibit NAMPT activity is assessed by inhibition of NAMPT-induced activation of endothelial cells. As an additional or alternative parameter of NAMPT activity, the ability of an antibody to inhibit NAMPT-induced transcription activities via NFκB as a measure of NAMPT-induced cellular activation, can be assessed.

Terms such as "treating" or "treatment" or "to treat" or "alleviating" or "to alleviate" refer to therapeutic measures that cure, slow down, lessen symptoms of, and/or halt or slow the progression of an existing diagnosed pathologic condition or disorder. Such treatment can include, but does not require, a total elimination of all symptoms or a cure of the disease. Terms such as "prevent," "prevention," "avoid," "deterrence" and the like refer to prophylactic or preventative measures that prevent the development of an undiagnosed targeted pathologic condition or disorder. Thus, "those in need of treatment" can include those already with the disorder; those prone to have the disorder; those at risk of developing the disorder; and those in whom the disorder is to be prevented.

By "subject" or "individual" or "animal" or "patient" or "mammal," is meant any subject, particularly a mammalian subject, for whom diagnosis, prognosis, or therapy is desired. Mammalian subjects include humans, domestic animals, farm animals, and zoo, sports, or pet animals such as dogs, cats, guinea pigs, rabbits, rats, mice, horses, swine, cows, bears, and so on.

As used herein, phrases such as "a subject that would benefit from therapy" and "an animal in need of treatment" includes subjects, such as mammalian subjects, that would benefit from administration of an anti-NAMPT antibody (e.g., a humanized anti-NAMPT antibody). Such antibodies, can be used, e.g., for a diagnostic procedure and/or for treatment or prevention of a disease, e.g., inflammatory lung disorder or cancer (e.g., prostate cancer).

The terms "effective amount" and "therapeutically effective amount" are used interchangeably herein, and refer to an amount of a compound, formulation, material, or composition, as described herein effective to achieve a particular biological result. Such results may include, but are not limited to, the inhibition of NAMPT expression or activity, or the expression or activity of signaling molecules which are downstream of NAMPT as determined by any means suitable in the art. For example, NAMPT activity includes but is not limited to cytokine activity, nicotinamide phosphoribosyltransferase activity, chemotactic factor, NF-κB signaling activity, redox signaling activity, and/or a role in mitochondrial function and apoptosis. It is emphasized that a therapeutically effective amount will not always be effective in treating a condition, even though such dosage is deemed to be a therapeutically effective amount by those of skill in the art. For convenience only, exemplary dosages, drug delivery amounts, therapeutically effective amounts and therapeutic levels are provided herein with reference to adult human subjects. Those skilled in the art can adjust such amounts in accordance with standard practices as needed to treat a specific subject and/or condition.

Anti-NAMPT Antibodies

As provided herein, the present disclosure relates to anti-nicotinamide phosphoribosyltransferase (NAMPT) antibodies, or antigen binding fragments thereof, including compositions, methods, and articles of manufacture (e.g., kits, systems) comprising the same for prophylactic and therapeutic uses in patients suffering from NAMPT-associated local and systemic inflammatory disorders. Also described are nucleic acids including polynucleotide sequences that encode such antibodies. In particular embodiments, the monoclonal antibodies provided herein bind to extracellular NAMPT (eNAMPT), and prevent Toll-like receptor 4 (TLR4) activation, thereby reducing or blocking one or more downstream signal transduction pathways and the consequent systemic and lung inflammation in specific respiratory disorders.

The NAMPT gene product is the rate-limiting enzyme in the nicotinamide adenine dinucleotide (NAD+) salvage pathway that converts nicotinamide to nicotinamide mononucleotide in mammals to enable NAD+ biosynthesis. The mature form of the extracellular NAMPT protein is a homodimer of approximately 120 kDa (Takahashi, et al., *J. Biochem.* 147: 95-107 (2010)). It has been established that mutations which reduce or inhibit the function of the NAMPT enzyme can reduce the pathophysiological processes that give rise to disorders such as leukemia and pulmonary arterial hypertension (PAH).

The human NAMPT gene (NAMPT) is located at chromosome 7, (segment 7q22.3; base pairs 106,248,285 to 106,286,326). Nucleic acid sequences for the human NAMPT gene product are known in the art. See, for example, NCBI Reference Sequence: NM 005746.2, *Homo sapiens* nicotinamide phosphoribosyltransferase (NAMPT), mRNA (see also Samal, et al., Mol. Cell. Biol. 14 (2), 1431-1437 (1994)). Amino acid sequences of the human NAMPT enzyme are known in the art. See, for example, GenBank® Accession No. NP 005737.1. NAMPT has been shown to increase the production of IL-6, TNF-α, and IL-Iβ in $CD14^+$ monocyctes, macrophages, and dendritic cells, enhance the effectiveness of T cells, and be involved in the development of both B and T lymphocytes (Sun, et al., *Cytokine & Growth Factor Reviews* 24(5):433-442 (2013)). A NAMPT enzyme crystal structure is described in detail in Kim, et al. J. Mol. Biol.; 362:66-77 (2006).

The receptor for NAMPT is the Toll-like receptor 4 (TLR4), a protein that in humans is encoded by the TLR4 gene. TLR4 is a transmembrane protein and a member of the toll-like receptor family, which belongs to the pattern recognition receptor (PRR) family. Its activation leads to an intracellular NF-κB signaling pathway and inflammatory cytokine production which is responsible for activating the innate immune system. It is most well-known for recognizing lipopolysaccharide (LPS), a component present in many Gram-negative bacteria (e.g. *Neisseria* spp.) and select Gram-positive bacteria. Its ligands also include several viral proteins, polysaccharide, and a variety of endogenous proteins such as low-density lipoprotein, beta-defensins, and heat shock protein. The human TLR4 gene (TLR4) is located at chromosome 9, (segment 9q32-q33) (Georgel, et al., *PLoS ONE* 4(11): e7803 (2009)). Nucleic acid sequences for the human TLR4 gene product are known in the art. See, for example, NCBI Reference Sequence: AAY82268.1, *Homo sapiens* toll-like receptor 4 (TLR4), mRNA. Amino acid sequences of the human TLR4 are known in the art. See, for example, GenBank® Accession No. AAY82268.

In certain aspects, the present disclosure provides a humanized 1076 anti-hNAMPT antibody or antigen-binding fragment thereof. Examples of anti-NAMPT antibodies are provided below.

Anti-NAMPT antibody D-1076:D-1076 has (i) a heavy chain variable region with an amino acid sequence as set forth in SEQ ID NO: 1, containing a CDR1 domain with an amino acid sequence as set forth in SEQ ID NO: 3, a CDR2 domain with an amino acid sequence as set forth in SEQ ID NO: 4, and a CDR3 domain with an amino acid sequence as set forth in SEQ ID NO: 5; and (ii) a light chain variable region with an amino acid sequence as set forth in SEQ ID NO: 2, containing a CDR1 domain with an amino acid sequence as set forth in SEQ ID NO: 6, a CDR2 domain with an amino acid sequence as set forth in SEQ ID NO: 7, and a CDR3 domain with an amino acid sequence as set forth in SEQ ID NO: 8.

Anti-NAMPT antibody G-1076: G-1076 has (i) a heavy chain variable region with an amino acid sequence as set forth in SEQ ID NO: 9, containing a CDR1 domain with an amino acid sequence as set forth in SEQ ID NO: 3, a CDR2 domain with an amino acid sequence as set forth in SEQ ID NO: 4, and a CDR3 domain with an amino acid sequence as set forth in SEQ ID NO: 5; and (ii) a light chain variable region with an amino acid sequence as set forth in SEQ ID NO: 10, containing a CDR1 domain with an amino acid sequence as set forth in SEQ ID NO: 11, a CDR2 domain with an amino acid sequence as set forth in SEQ ID NO: 12, and a CDR3 domain with an amino acid sequence as set forth in SEQ ID NO: 8.

Anti-NAMPT antibody K-1076: K-1076 has (i) a heavy chain variable region with an amino acid sequence as set forth in SEQ ID NO: 9, containing a CDR1 domain with an amino acid sequence as set forth in SEQ ID NO: 3, a CDR2 domain with an amino acid sequence as set forth in SEQ ID NO: 4, and a CDR3 domain with an amino acid sequence as set forth in SEQ ID NO: 5; and (ii) a light chain variable region with an amino acid sequence as set forth in SEQ ID NO: 13, containing a CDR1 domain with an amino acid sequence as set forth in SEQ ID NO: 11, a CDR2 domain with an amino acid sequence as set forth in SEQ ID NO: 14, and a CDR3 domain with an amino acid sequence as set forth in SEQ ID NO: 8.

Anti-NAMPT antibody N-1076: N-1076 has (i) a heavy chain variable region with an amino acid sequence as set forth in SEQ ID NO: 15, containing a CDR1 domain with an amino acid sequence as set forth in SEQ ID NO: 3, a CDR2 domain with an amino acid sequence as set forth in SEQ ID NO: 4, and a CDR3 domain with an amino acid sequence as set forth in SEQ ID NO: 5; and (ii) a light chain variable region with an amino acid sequence as set forth in SEQ ID NO: 2, containing a CDR1 domain with an amino acid sequence as set forth in SEQ ID NO: 6, a CDR2 domain with an amino acid sequence as set forth in SEQ ID NO: 7, and a CDR3 domain with an amino acid sequence as set forth in SEQ ID NO: 8;

Anti-NAMPT antibody P-1076: P-1076 has (i) a heavy chain variable region with an amino acid sequence as set forth in SEQ ID NO: 15, containing a CDR1 domain with an amino acid sequence as set forth in SEQ ID NO: 3, a CDR2 domain with an amino acid sequence as set forth in SEQ ID NO: 4, and a CDR3 domain with an amino acid sequence as set forth in SEQ ID NO: 5; and (ii) a light chain variable region with an amino acid sequence as set forth in SEQ ID NO: 13, containing a CDR1 domain with an amino acid sequence as set forth in SEQ ID NO: 11, a CDR2 domain with an amino acid sequence as set forth in SEQ ID NO: 14, and a CDR3 domain with an amino acid sequence as set forth in SEQ ID NO: 8;

Anti-NAMPT antibody V-1076: V-1076 has (i) a heavy chain variable region with an amino acid sequence as set forth in SEQ ID NO: 16, containing a CDR1 domain with an amino acid sequence as set forth in SEQ ID NO: 3, a CDR2 domain with an amino acid sequence as set forth in SEQ ID NO: 4, and a CDR3 domain with an amino acid sequence as set forth in SEQ ID NO: 5; and (ii) a light chain variable region with an amino acid sequence as set forth in SEQ ID NO: 10, containing a CDR1 domain with an amino acid sequence as set forth in SEQ ID NO: 11, a CDR2 domain with an amino acid sequence as set forth in SEQ ID NO: 12, and a CDR3 domain with an amino acid sequence as set forth in SEQ ID NO: 8.

Anti-NAMPT antibody X-1076: X-1076 has (i) a heavy chain variable region with an amino acid sequence as set forth in SEQ ID NO: 16, containing a CDR1 domain with an amino acid sequence as set forth in SEQ ID NO: 3, a CDR2 domain with an amino acid sequence as set forth in SEQ ID NO: 4, and a CDR3 domain with an amino acid sequence as set forth in SEQ ID NO: 5; and (ii) a light chain variable region with an amino acid sequence as set forth in SEQ ID NO: 2, containing a CDR1 domain with an amino acid sequence as set forth in SEQ ID NO: 6, a CDR2 domain with an amino acid sequence as set forth in SEQ ID NO: 7, and a CDR3 domain with an amino acid sequence as set forth in SEQ ID NO: 8.

Anti-NAMPT antibody P-1076-mod1: P-1076-mod1 has (i) a heavy chain variable region with an amino acid sequence as set forth in SEQ ID NO: 28, containing a CDR1 domain with an amino acid sequence as set forth in SEQ ID NO: 3, a CDR2 domain with an amino acid sequence as set forth in SEQ ID NO: 29, and a CDR3 domain with an amino acid sequence as set forth in SEQ ID NO: 5; and (ii) a light chain variable region with an amino acid sequence as set forth in SEQ ID NO: 30, containing a CDR1 domain with an amino acid sequence as set forth in SEQ ID NO: 11, a CDR2 domain with an amino acid sequence as set forth in SEQ ID NO: 14, and a CDR3 domain with an amino acid sequence as set forth in SEQ ID NO: 8.

Anti-NAMPT antibody P-1076-mod2: P-1076-mod2 has (i) a heavy chain variable region with an amino acid sequence as set forth in SEQ ID NO: 28, containing a CDR1 domain with an amino acid sequence as set forth in SEQ ID NO: 3, a CDR2 domain with an amino acid sequence as set forth in SEQ ID NO: 29, and a CDR3 domain with an amino acid sequence as set forth in SEQ ID NO: 5; and (ii) a light chain variable region with an amino acid sequence as set forth in SEQ ID NO: 31, containing a CDR1 domain with an amino acid sequence as set forth in SEQ ID NO: 11, a CDR2 domain with an amino acid sequence as set forth in SEQ ID NO: 14, and a CDR3 domain with an amino acid sequence as set forth in SEQ ID NO: 8.

Anti-NAMPT antibody P-1076-mod3: P-1076-mod3 has (i) a heavy chain variable region with an amino acid sequence as set forth in SEQ ID NO: 28, containing a CDR1 domain with an amino acid sequence as set forth in SEQ ID NO: 3, a CDR2 domain with an amino acid sequence as set forth in SEQ ID NO: 29, and a CDR3 domain with an amino acid sequence as set forth in SEQ ID NO: 5; and (ii) a light chain variable region with an amino acid sequence as set forth in SEQ ID NO: 32, containing a CDR1 domain with an amino acid sequence as set forth in SEQ ID NO: 11, a CDR2 domain with an amino acid sequence as set forth in SEQ ID NO: 33, and a CDR3 domain with an amino acid sequence as set forth in SEQ ID NO: 8.

Anti-NAMPT antibody P-1076-mod4: P-1076-mod4 has (i) a heavy chain variable region with an amino acid sequence as set forth in SEQ ID NO: 28, containing a CDR1 domain with an amino acid sequence as set forth in SEQ ID NO: 3, a CDR2 domain with an amino acid sequence as set forth in SEQ ID NO: 29, and a CDR3 domain with an amino acid sequence as set forth in SEQ ID NO: 5; and (ii) a light chain variable region with an amino acid sequence as set forth in SEQ ID NO: 34, containing a CDR1 domain with an amino acid sequence as set forth in SEQ ID NO: 11, a CDR2 domain with an amino acid sequence as set forth in SEQ ID NO: 35, and a CDR3 domain with an amino acid sequence as set forth in SEQ ID NO: 8.

Anti-NAMPT antibody P-1076-mod5: P-1076-mod5 has (i) a heavy chain variable region with an amino acid sequence as set forth in SEQ ID NO: 28, containing a CDR1 domain with an amino acid sequence as set forth in SEQ ID NO: 3, a CDR2 domain with an amino acid sequence as set forth in SEQ ID NO: 29, and a CDR3 domain with an amino acid sequence as set forth in SEQ ID NO: 5; and (ii) a light chain variable region with an amino acid sequence as set forth in SEQ ID NO: 36, containing a CDR1 domain with an amino acid sequence as set forth in SEQ ID NO: 11, a CDR2 domain with an amino acid sequence as set forth in SEQ ID NO: 37, and a CDR3 domain with an amino acid sequence as set forth in SEQ ID NO: 8.

Anti-NAMPT antibody P-1076-mod6: P-1076-mod6 has (i) a heavy chain variable region with an amino acid sequence as set forth in SEQ ID NO: 15, containing a CDR1 domain with an amino acid sequence as set forth in SEQ ID NO: 3, a CDR2 domain with an amino acid sequence as set forth in SEQ ID NO: 4, and a CDR3 domain with an amino acid sequence as set forth in SEQ ID NO: 5; and (ii) a light chain variable region with an amino acid sequence as set forth in SEQ ID NO: 30, containing a CDR1 domain with an amino acid sequence as set forth in SEQ ID NO: 11, a CDR2 domain with an amino acid sequence as set forth in SEQ ID NO: 14, and a CDR3 domain with an amino acid sequence as set forth in SEQ ID NO: 8.

Anti-NAMPT antibody P-1076-mod7: P-1076-mod7 has (i) a heavy chain variable region with an amino acid sequence as set forth in SEQ ID NO: 15, containing a CDR1 domain with an amino acid sequence as set forth in SEQ ID NO: 3, a CDR2 domain with an amino acid sequence as set forth in SEQ ID NO: 4, and a CDR3 domain with an amino acid sequence as set forth in SEQ ID NO: 5; and (ii) a light chain variable region with an amino acid sequence as set forth in SEQ ID NO: 31, containing a CDR1 domain with an amino acid sequence as set forth in SEQ ID NO: 11, a CDR2 domain with an amino acid sequence as set forth in SEQ ID NO: 14, and a CDR3 domain with an amino acid sequence as set forth in SEQ ID NO: 8.

Anti-NAMPT antibody P-1076-mod8: P-1076-mod8 has (i) a heavy chain variable region with an amino acid sequence as set forth in SEQ ID NO: 15, containing a CDR1 domain with an amino acid sequence as set forth in SEQ ID NO: 3, a CDR2 domain with an amino acid sequence as set forth in SEQ ID NO: 4, and a CDR3 domain with an amino acid sequence as set forth in SEQ ID NO: 5; and (ii) a light chain variable region with an amino acid sequence as set forth in SEQ ID NO: 32, containing a CDR1 domain with an amino acid sequence as set forth in SEQ ID NO: 11, a CDR2 domain with an amino acid sequence as set forth in SEQ ID NO: 33, and a CDR3 domain with an amino acid sequence as set forth in SEQ ID NO: 8.

Anti-NAMPT antibody P-1076-mod9: P-1076-mod9 has (i) a heavy chain variable region with an amino acid sequence as set forth in SEQ ID NO: 15, containing a CDR1 domain with an amino acid sequence as set forth in SEQ ID NO: 3, a CDR2 domain with an amino acid sequence as set forth in SEQ ID NO: 4, and a CDR3 domain with an amino acid sequence as set forth in SEQ ID NO: 5; and (ii) a light chain variable region with an amino acid sequence as set forth in SEQ ID NO: 34, containing a CDR1 domain with an amino acid sequence as set forth in SEQ ID NO: 11, a CDR2 domain with an amino acid sequence as set forth in SEQ ID NO: 35, and a CDR3 domain with an amino acid sequence as set forth in SEQ ID NO: 8.

Anti-NAMPT antibody P-1076-mod10: P-1076-mod10 has (i) a heavy chain variable region with an amino acid sequence as set forth in SEQ ID NO: 15, containing a CDR1 domain with an amino acid sequence as set forth in SEQ ID NO: 3, a CDR2 domain with an amino acid sequence as set forth in SEQ ID NO: 4, and a CDR3 domain with an amino acid sequence as set forth in SEQ ID NO: 5; and (ii) a light chain variable region with an amino acid sequence as set forth in SEQ ID NO: 36, containing a CDR1 domain with an amino acid sequence as set forth in SEQ ID NO: 11, a CDR2 domain with an amino acid sequence as set forth in SEQ ID NO: 37, and a CDR3 domain with an amino acid sequence as set forth in SEQ ID NO: 8.

Anti-NAMPT antibody P-1076-mod11: P-1076-mod11 has (i) a heavy chain variable region with an amino acid sequence as set forth in SEQ ID NO: 28, containing a CDR1 domain with an amino acid sequence as set forth in SEQ ID NO: 3, a CDR2 domain with an amino acid sequence as set forth in SEQ ID NO: 29, and a CDR3 domain with an amino acid sequence as set forth in SEQ ID NO: 5; and (ii) a light chain variable region with an amino acid sequence as set forth in SEQ ID NO: 13, containing a CDR1 domain with an amino acid sequence as set forth in SEQ ID NO: 11, a CDR2 domain with an amino acid sequence as set forth in SEQ ID NO: 14, and a CDR3 domain with an amino acid sequence as set forth in SEQ ID NO: 8.

In certain aspects, the present disclosure provides a humanized 1093 anti-hNAMPT antibody or antigen-binding fragment thereof. Examples of a 1093 anti-NAMPT antibodies are provided below.

Anti-NAMPT antibody FF-1093:FF-1093 has (i) a heavy chain variable region with an amino acid sequence as set forth in SEQ ID NO: 17, containing a CDR1 domain with an amino acid sequence as set forth in SEQ ID NO: 19, a CDR2 domain with an amino acid sequence as set forth in SEQ ID NO: 20, and a CDR3 domain with an amino acid sequence as set forth in SEQ ID NO: 21; and (ii) a light chain variable region with an amino acid sequence as set forth in SEQ ID NO: 18, containing a CDR1 domain with an amino acid sequence as set forth in SEQ ID NO: 6, a CDR2 domain with an amino acid sequence as set forth in SEQ ID NO: 7, and a CDR3 domain with an amino acid sequence as set forth in SEQ ID NO: 22.

Anti-NAMPT antibody II-1093: 11-1093 has (i) a heavy chain variable region with an amino acid sequence as set forth in SEQ ID NO: 23, containing a CDR1 domain with an amino acid sequence as set forth in SEQ ID NO: 19, a CDR2 domain with an amino acid sequence as set forth in SEQ ID NO: 20, and a CDR3 domain with an amino acid sequence as set forth in SEQ ID NO: 21; and (ii) a light chain variable region with an amino acid sequence as set forth in SEQ ID NO: 24, containing a CDR1 domain with an amino acid sequence as set forth in SEQ ID NO: 6, a CDR2 domain with an amino acid sequence as set forth in SEQ ID NO: 7, and a CDR3 domain with an amino acid sequence as set forth in SEQ ID NO: 22.

Anti-NAMPT antibody NN-1093: NN-1093 has (i) a heavy chain variable region with an amino acid sequence as set forth in SEQ ID NO: 25, containing a CDR1 domain with an amino acid sequence as set forth in SEQ ID NO: 19, a CDR2 domain with an amino acid sequence as set forth in SEQ ID NO: 20, and a CDR3 domain with an amino acid sequence as set forth in SEQ ID NO: 21; and (ii) a light chain variable region with an amino acid sequence as set forth in SEQ ID NO: 24, containing a CDR1 domain with an amino acid sequence as set forth in SEQ ID NO: 6, a CDR2 domain with an amino acid sequence as set forth in SEQ ID NO: 7, and a CDR3 domain with an amino acid sequence as set forth in SEQ ID NO: 22.

Anti-NAMPT antibody PP-1093: PP-1093 has (i) a heavy chain variable region with an amino acid sequence as set forth in SEQ ID NO: 25, containing a CDR1 domain with an amino acid sequence as set forth in SEQ ID NO: 19, a CDR2 domain with an amino acid sequence as set forth in SEQ ID NO: 20, and a CDR3 domain with an amino acid sequence as set forth in SEQ ID NO: 21; and (ii) a light chain variable region with an amino acid sequence as set forth in SEQ ID NO: 18, containing a CDR1 domain with an amino acid sequence as set forth in SEQ ID NO: 6, a CDR2 domain with an amino acid sequence as set forth in SEQ ID NO: 7, and a CDR3 domain with an amino acid sequence as set forth in SEQ ID NO: 22.

Anti-NAMPT antibody SS-1093: SS-1093 has (i) a heavy chain variable region with an amino acid sequence as set forth in SEQ ID NO: 26, containing a CDR1 domain with an amino acid sequence as set forth in SEQ ID NO: 19, a CDR2 domain with an amino acid sequence as set forth in SEQ ID NO: 20, and a CDR3 domain with an amino acid sequence as set forth in SEQ ID NO: 21; and (ii) a light chain variable region with an amino acid sequence as set forth in SEQ ID NO: 24, containing a CDR1 domain with an amino acid sequence as set forth in SEQ ID NO: 6, a CDR2 domain with an amino acid sequence as set forth in SEQ ID NO: 7, and a CDR3 domain with an amino acid sequence as set forth in SEQ ID NO: 22.

Anti-NAMPT antibody UU-1093: UU-1093 has (i) a heavy chain variable region with an amino acid sequence as set forth in SEQ ID NO: 26, containing a CDR1 domain with an amino acid sequence as set forth in SEQ ID NO: 19, a CDR2 domain with an amino acid sequence as set forth in SEQ ID NO: 20, and a CDR3 domain with an amino acid sequence as set forth in SEQ ID NO: 21; and (ii) a light chain variable region with an amino acid sequence as set forth in SEQ ID NO: 18, containing a CDR1 domain with an amino acid sequence as set forth in SEQ ID NO: 6, a CDR2 domain with an amino acid sequence as set forth in SEQ ID NO: 7, and a CDR3 domain with an amino acid sequence as set forth in SEQ ID NO: 22.

Anti-NAMPT antibody XX-1093: XX-1093 has (i) a heavy chain variable region with an amino acid sequence as set forth in SEQ ID NO: 27, containing a CDR1 domain with an amino acid sequence as set forth in SEQ ID NO: 19, a CDR2 domain with an amino acid sequence as set forth in SEQ ID NO: 20, and a CDR3 domain with an amino acid sequence as set forth in SEQ ID NO: 21; and (ii) a light chain variable region with an amino acid sequence as set forth in SEQ ID NO: 24, containing a CDR1 domain with an amino acid sequence as set forth in SEQ ID NO: 6, a CDR2 domain with an amino acid sequence as set forth in SEQ ID NO: 7, and a CDR3 domain with an amino acid sequence as set forth in SEQ ID NO: 22.

Anti-NAMPT antibody ZZ-1093: ZZ-1093 has (i) a heavy chain variable region with an amino acid sequence as set forth in SEQ ID NO: 27, containing a CDR1 domain with an amino acid sequence as set forth in SEQ ID NO: 19, a CDR2 domain with an amino acid sequence as set forth in SEQ ID NO: 20, and a CDR3 domain with an amino acid sequence as set forth in SEQ ID NO: 21; and (ii) a light chain variable region with an amino acid sequence as set forth in SEQ ID NO: 18, containing a CDR1 domain with an amino acid sequence as set forth in SEQ ID NO: 6, a CDR2 domain with an amino acid sequence as set forth in SEQ ID NO: 7, and a CDR3 domain with an amino acid sequence as set forth in SEQ ID NO: 22.

Anti-NAMPT antibody UU-1093-mod1: UU-1093-mod1 has (i) a heavy chain variable region with an amino acid sequence as set forth in SEQ ID NO: 38, containing a CDR1 domain with an amino acid sequence as set forth in SEQ ID NO: 19, a CDR2 domain with an amino acid sequence as set forth in SEQ ID NO: 39, and a CDR3 domain with an amino acid sequence as set forth in SEQ ID NO: 21; and (ii) a light chain variable region with an amino acid sequence as set forth in SEQ ID NO: 47, containing a CDR1 domain with an amino acid sequence as set forth in SEQ ID NO: 11, a CDR2 domain with an amino acid sequence as set forth in SEQ ID NO: 7, and a CDR3 domain with an amino acid sequence as set forth in SEQ ID NO: 22.

Anti-NAMPT antibody UU-1093-mod2: UU-1093-mod2 has (i) a heavy chain variable region with an amino acid sequence as set forth in SEQ ID NO: 40, containing a CDR1 domain with an amino acid sequence as set forth in SEQ ID NO: 19, a CDR2 domain with an amino acid sequence as set forth in SEQ ID NO: 39, and a CDR3 domain with an amino acid sequence as set forth in SEQ ID NO: 41; and (ii) a light chain variable region with an amino acid sequence as set forth in SEQ ID NO: 47, containing a CDR1 domain with an amino acid sequence as set forth in SEQ ID NO: 11, a CDR2 domain with an amino acid sequence as set forth in SEQ ID NO: 7, and a CDR3 domain with an amino acid sequence as set forth in SEQ ID NO: 22.

Anti-NAMPT antibody UU-1093-mod3: UU-1093-mod3 has (i) a heavy chain variable region with an amino acid sequence as set forth in SEQ ID NO: 42, containing a CDR1 domain with an amino acid sequence as set forth in SEQ ID NO: 43, a CDR2 domain with an amino acid sequence as set forth in SEQ ID NO: 39, and a CDR3 domain with an amino acid sequence as set forth in SEQ ID NO: 44; and (ii) a light chain variable region with an amino acid sequence as set forth in SEQ ID NO: 47, containing a CDR1 domain with an amino acid sequence as set forth in SEQ ID NO: 11, a CDR2 domain with an amino acid sequence as set forth in SEQ ID NO: 7, and a CDR3 domain with an amino acid sequence as set forth in SEQ ID NO: 22.

Anti-NAMPT antibody UU-1093-mod4: UU-1093-mod4 has (i) a heavy chain variable region with an amino acid sequence as set forth in SEQ ID NO: 45, containing a CDR1 domain with an amino acid sequence as set forth in SEQ ID NO: 46, a CDR2 domain with an amino acid sequence as set forth in SEQ ID NO: 39, and a CDR3 domain with an amino acid sequence as set forth in SEQ ID NO: 41; and (ii) a light chain variable region with an amino acid sequence as set forth in SEQ ID NO: 47, containing a CDR1 domain with an amino acid sequence as set forth in SEQ ID NO: 11, a CDR2 domain with an amino acid sequence as set forth in SEQ ID NO: 7, and a CDR3 domain with an amino acid sequence as set forth in SEQ ID NO: 22.

Anti-NAMPT antibody UU-1093-mod5: UU-1093-mod5 has (i) a heavy chain variable region with an amino acid sequence as set forth in SEQ ID NO: 38, containing a CDR1 domain with an amino acid sequence as set forth in SEQ ID NO: 19, a CDR2 domain with an amino acid sequence as set forth in SEQ ID NO: 39, and a CDR3 domain with an amino acid sequence as set forth in SEQ ID NO: 21; and (ii) a light chain variable region with an amino acid sequence as set forth in SEQ ID NO: 48, containing a CDR1 domain with an amino acid sequence as set forth in SEQ ID NO: 49, a CDR2 domain with an amino acid sequence as set forth in SEQ ID NO: 50, and a CDR3 domain with an amino acid sequence as set forth in SEQ ID NO: 22.

Anti-NAMPT antibody UU-1093-mod6: UU-1093-mod6 has (i) a heavy chain variable region with an amino acid sequence as set forth in SEQ ID NO: 40, containing a CDR1 domain with an amino acid sequence as set forth in SEQ ID NO: 19, a CDR2 domain with an amino acid sequence as set forth in SEQ ID NO: 39, and a CDR3 domain with an amino acid sequence as set forth in SEQ ID NO: 41; and (ii) a light chain variable region with an amino acid sequence as set forth in SEQ ID NO: 48, containing a CDR1 domain with an amino acid sequence as set forth in SEQ ID NO: 49, a CDR2 domain with an amino acid sequence as set forth in SEQ ID NO: 50, and a CDR3 domain with an amino acid sequence as set forth in SEQ ID NO: 22.

Anti-NAMPT antibody UU-1093-mod7: UU-1093-mod7 has (i) a heavy chain variable region with an amino acid sequence as set forth in SEQ ID NO: 42, containing a CDR1 domain with an amino acid sequence as set forth in SEQ ID NO: 43, a CDR2 domain with an amino acid sequence as set forth in SEQ ID NO: 39, and a CDR3 domain with an amino acid sequence as set forth in SEQ ID NO: 44; and (ii) a light chain variable region with an amino acid sequence as set forth in SEQ ID NO: 48, containing a CDR1 domain with an amino acid sequence as set forth in SEQ ID NO: 49, a CDR2 domain with an amino acid sequence as set forth in SEQ ID NO: 50, and a CDR3 domain with an amino acid sequence as set forth in SEQ ID NO: 22.

Anti-NAMPT antibody UU-1093-mod8: UU-1093-mod8 has (i) a heavy chain variable region with an amino acid sequence as set forth in SEQ ID NO: 45, containing a CDR1 domain with an amino acid sequence as set forth in SEQ ID NO: 46, a CDR2 domain with an amino acid sequence as set forth in SEQ ID NO: 39, and a CDR3 domain with an amino acid sequence as set forth in SEQ ID NO: 41; and (ii) a light chain variable region with an amino acid sequence as set forth in SEQ ID NO: 48, containing a CDR1 domain with an amino acid sequence as set forth in SEQ ID NO: 49, a CDR2 domain with an amino acid sequence as set forth in SEQ ID NO: 50, and a CDR3 domain with an amino acid sequence as set forth in SEQ ID NO: 22.

Anti-NAMPT antibody UU-1093-mod9: UU-1093-mod9 has (i) a heavy chain variable region with an amino acid sequence as set forth in SEQ ID NO: 38, containing a CDR1 domain with an amino acid sequence as set forth in SEQ ID NO: 19, a CDR2 domain with an amino acid sequence as set forth in SEQ ID NO: 39, and a CDR3 domain with an amino acid sequence as set forth in SEQ ID NO: 21; and (ii) a light chain variable region with an amino acid sequence as set forth in SEQ ID NO: 51, containing a CDR1 domain with an amino acid sequence as set forth in SEQ ID NO: 11, a CDR2 domain with an amino acid sequence as set forth in SEQ ID NO: 52, and a CDR3 domain with an amino acid sequence as set forth in SEQ ID NO: 53.

Anti-NAMPT antibody UU-1093-mod10: UU-1093-mod10 has (i) a heavy chain variable region with an amino acid sequence as set forth in SEQ ID NO: 40, containing a CDR1 domain with an amino acid sequence as set forth in SEQ ID NO: 19, a CDR2 domain with an amino acid sequence as set forth in SEQ ID NO: 39, and a CDR3 domain with an amino acid sequence as set forth in SEQ ID NO: 41; and (ii) a light chain variable region with an amino acid sequence as set forth in SEQ ID NO: 51, containing a CDR1 domain with an amino acid sequence as set forth in SEQ ID NO: 11, a CDR2 domain with an amino acid sequence as set forth in SEQ ID NO: 52, and a CDR3 domain with an amino acid sequence as set forth in SEQ ID NO: 53.

Anti-NAMPT antibody UU-1093-mod11: UU-1093-mod11 has (i) a heavy chain variable region with an amino acid sequence as set forth in SEQ ID NO: 42, containing a CDR1 domain with an amino acid sequence as set forth in SEQ ID NO: 43, a CDR2 domain with an amino acid sequence as set forth in SEQ ID NO: 39, and a CDR3 domain with an amino acid sequence as set forth in SEQ ID NO: 44; and (ii) a light chain variable region with an amino acid sequence as set forth in SEQ ID NO: 51, containing a CDR1 domain with an amino acid sequence as set forth in SEQ ID NO: 11, a CDR2 domain with an amino acid sequence as set forth in SEQ ID NO: 52, and a CDR3 domain with an amino acid sequence as set forth in SEQ ID NO: 53.

Anti-NAMPT antibody UU-1093-mod12: UU-1093-mod12 has (i) a heavy chain variable region with an amino acid sequence as set forth in SEQ ID NO: 45, containing a CDR1 domain with an amino acid sequence as set forth in SEQ ID NO: 46, a CDR2 domain with an amino acid sequence as set forth in SEQ ID NO: 39, and a CDR3 domain with an amino acid sequence as set forth in SEQ ID NO: 41; and (ii) a light chain variable region with an amino acid sequence as set forth in SEQ ID NO: 51, containing a CDR1 domain with an amino acid sequence as set forth in SEQ ID NO: 11, a CDR2 domain with an amino acid sequence as set forth in SEQ ID NO: 52, and a CDR3 domain with an amino acid sequence as set forth in SEQ ID NO: 53.

Anti-NAMPT antibody UU-1093-mod13: UU-1093-mod13 has (i) a heavy chain variable region with an amino acid sequence as set forth in SEQ ID NO: 38, containing a CDR1 domain with an amino acid sequence as set forth in SEQ ID NO: 19, a CDR2 domain with an amino acid sequence as set forth in SEQ ID NO: 39, and a CDR3 domain with an amino acid sequence as set forth in SEQ ID NO: 21; and (ii) a light chain variable region with an amino acid sequence as set forth in SEQ ID NO: 18, containing a CDR1 domain with an amino acid sequence as set forth in SEQ ID NO: 6, a CDR2 domain with an amino acid sequence as set forth in SEQ ID NO: 7, and a CDR3 domain with an amino acid sequence as set forth in SEQ ID NO: 22.

Anti-NAMPT antibody UU-1093-mod14: UU-1093-mod14 has (i) a heavy chain variable region with an amino acid sequence as set forth in SEQ ID NO: 40, containing a CDR1 domain with an amino acid sequence as set forth in SEQ ID NO: 19, a CDR2 domain with an amino acid sequence as set forth in SEQ ID NO: 39, and a CDR3 domain with an amino acid sequence as set forth in SEQ ID NO: 41; and (ii) a light chain variable region with an amino acid sequence as set forth in SEQ ID NO: 18, containing a CDR1 domain with an amino acid sequence as set forth in SEQ ID NO: 6, a CDR2 domain with an amino acid sequence as set forth in SEQ ID NO: 7, and a CDR3 domain with an amino acid sequence as set forth in SEQ ID NO: 22.

Anti-NAMPT antibody UU-1093-mod15: UU-1093-mod15 has (i) a heavy chain variable region with an amino acid sequence as set forth in SEQ ID NO: 42, containing a CDR1 domain with an amino acid sequence as set forth in SEQ ID NO: 43, a CDR2 domain with an amino acid sequence as set forth in SEQ ID NO: 39, and a CDR3 domain with an amino acid sequence as set forth in SEQ ID NO: 44; and (ii) a light chain variable region with an amino acid sequence as set forth in SEQ ID NO: 18, containing a CDR1 domain with an amino acid sequence as set forth in SEQ ID NO: 6, a CDR2 domain with an amino acid sequence as set forth in SEQ ID NO: 7, and a CDR3 domain with an amino acid sequence as set forth in SEQ ID NO: 22.

Anti-NAMPT antibody UU-1093-mod16: UU-1093-mod16 has (i) a heavy chain variable region with an amino acid sequence as set forth in SEQ ID NO: 45, containing a CDR1 domain with an amino acid sequence as set forth in SEQ ID NO: 46, a CDR2 domain with an amino acid sequence as set forth in SEQ ID NO: 39, and a CDR3 domain with an amino acid sequence as set forth in SEQ ID NO: 41; and (ii) a light chain variable region with an amino acid sequence as set forth in SEQ ID NO: 18, containing a CDR1 domain with an amino acid sequence as set forth in SEQ ID NO: 6, a CDR2 domain with an amino acid sequence as set forth in SEQ ID NO: 7, and a CDR3 domain with an amino acid sequence as set forth in SEQ ID NO: 22.

Anti-NAMPT antibody UU-1093-mod17: UU-1093-mod17 has (i) a heavy chain variable region with an amino acid sequence as set forth in SEQ ID NO: 26, containing a CDR1 domain with an amino acid sequence as set forth in SEQ ID NO: 19, a CDR2 domain with an amino acid sequence as set forth in SEQ ID NO: 20, and a CDR3 domain with an amino acid sequence as set forth in SEQ ID NO: 21; and (ii) a light chain variable region with an amino acid sequence as set forth in SEQ ID NO: 47, containing a CDR1 domain with an amino acid sequence as set forth in SEQ ID NO: 11, a CDR2 domain with an amino acid sequence as set forth in SEQ ID NO: 7, and a CDR3 domain with an amino acid sequence as set forth in SEQ ID NO: 22.

Anti-NAMPT antibody UU-1093-mod18: UU-1093-mod18 has (i) a heavy chain variable region with an amino acid sequence as set forth in SEQ ID NO: 26, containing a CDR1 domain with an amino acid sequence as set forth in SEQ ID NO: 19, a CDR2 domain with an amino acid sequence as set forth in SEQ ID NO: 20, and a CDR3 domain with an amino acid sequence as set forth in SEQ ID NO: 21; and (ii) a light chain variable region with an amino acid sequence as set forth in SEQ ID NO: 48, containing a CDR1 domain with an amino acid sequence as set forth in SEQ ID NO: 49, a CDR2 domain with an amino acid sequence as set forth in SEQ ID NO: 50, and a CDR3 domain with an amino acid sequence as set forth in SEQ ID NO: 22.

Anti-NAMPT antibody UU-1093-mod19: UU-1093-mod19 has (i) a heavy chain variable region with an amino acid sequence as set forth in SEQ ID NO: 26, containing a CDR1 domain with an amino acid sequence as set forth in SEQ ID NO: 19, a CDR2 domain with an amino acid sequence as set forth in SEQ ID NO: 20, and a CDR3 domain with an amino acid sequence as set forth in SEQ ID NO: 21; and (ii) a light chain variable region with an amino acid sequence as set forth in SEQ ID NO: 51, containing a CDR1 domain with an amino acid sequence as set forth in SEQ ID NO: 11, a CDR2 domain with an amino acid sequence as set forth in SEQ ID NO: 52, and a CDR3 domain with an amino acid sequence as set forth in SEQ ID NO: 53.

In some embodiments, the invention includes an anti-NAMPT antibody that binds to human NAMPT in the NAMPT homodimeric conformation to a discontinuous epitope on human NAMPT. In some embodiments, the antibody, or antigen-binding portion thereof, binds to an epitope on human NAMPT comprising at least one amino acid in amino acid residues 17-44 of SEQ ID NO: 60; at least one amino acid in amino acid residues 117-127 of SEQ ID NO: 60; at least one amino acid in amino acid residues 162-170 of SEQ ID NO: 60; at least one amino acid in amino acid residues 242-261 of SEQ ID NO: 60; at least one amino acid in amino acid residues 262-273 of SEQ ID NO: 60; at least one amino acid in amino acid residues 289-305 of SEQ ID NO: 60; at least one amino acid in amino acid residues 332-342 of SEQ ID NO: 60; at least one amino acid in amino acid residues 374-389 of SEQ ID NO: 60; at least one amino acid in amino acid residues 418-425 of SEQ ID NO: 60; at least one amino acid in amino acid residues 453-466 of SEQ ID NO: 60; and/or at least one amino acid in amino acid residues 408-416 of SEQ ID NO: 60. In some embodiments, the antibody, or antigen-binding portion thereof, binds to an epitope on human NAMPT comprising at least one amino acid in amino acid residues 29-51 of SEQ ID NO: 60; at least one amino acid in amino acid residues 61-72 of SEQ ID NO: 60; at least one amino acid in amino acid residues 156-170 of SEQ ID NO: 60; at least one amino acid in amino acid residues 216-234 of SEQ ID NO: 60; at least one amino acid in amino acid residues 316-331 of SEQ ID NO: 60; at least one amino acid in amino acid residues 332-342 of SEQ ID NO: 60; at least one amino acid in amino acid residues 373-389 of SEQ ID NO: 60; at least one amino acid in amino acid residues 417-431 of SEQ ID NO: 60; at least one amino acid in amino acid residues 454-469 of SEQ ID NO: 60; and/or at least one amino acid in amino acid residues 470-478 of SEQ ID NO: 60.

In certain aspects, the provided antibody or fragment thereof can have a binding affinity ($K_D$) for human NAMPT expressed on human cells of about 3 nM to approximately 20 nM as measured by surface plasmon resonance.

In certain embodiments, an antibody, or antigen binding fragment thereof, described herein binds NAMPT, e.g., human NAMPT, with an off rate ($k_{(off)}$) of less than or equal to, e.g., $5\times10^{-2}$ $sec^{-1}$, $10^{-2}$ $sec^{-1}$, $5\times10^{-3}$ $sec^{-1}$, $10^{-3}$ $sec^{-1}$, $5\times10^{-4}$ $sec^{-1}$, $10^{-4}$ $sec^{-1}$, $5\times10^{-5}$ $sec^{-1}$, or $10^{-5}$ $sec^{-1}$ $5\times10^{-6}$ $sec^{-1}$, $10^{-6}$ $sec^{-1}$, $5\times10^{-7}$ $sec^{-1}$ or $10^{-7}$ $sec^{-1}$.

In certain embodiments, an antibody, or antigen binding fragment thereof, described herein binds NAMPT, e.g., human NAMPT, with an on rate ($k_{(on)}$) of greater than or equal to, e.g., $10^3$ $M^{-1}$ $sec^{-1}$, $5\times10^3$ $M^{-1}$ $sec^{-1}$, $10^4M^{-1}$ $sec^{-1}$, $5\times10^4$ $M^{-1}$ $sec^{-1}$, $10^5M^{-1}$ $sec^{-1}$, $5\times10^5$ $M^{-1}$ $sec^{-1}$, $10^6M^{-1}$ $sec^{-1}$, or $5\times10^6$ $M^{-1}$ $sec^{-1}$ or $10^7M^{-1}$ $sec^{-1}$.

In certain embodiments, an antibody, or antigen binding fragment thereof, described herein binds NAMPT, e.g., human NAMPT, with a dissociation constant or $K_D$ equal to or greater than, e.g., $5\times10^{-7}$ M, $10^{-7}$ M, $5\times10^{-8}$ M, $10^{-8}$M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$M, or $5\times10^{-13}$ M. Binding affinity may be determined using various techniques known in the art, for example, surface plasmon resonance (SPR), bio-layer interferometry, dual polarization interferometry, static light scattering, dynamic light scattering, isothermal titration calorimetry, ELISA, analytical ultracentrifugation, and flow cytometry.

In certain aspects, an anti-NAMPT antibody or antigen-binding fragment thereof as provided herein can further include a heterologous agent, e.g., a stabilizing agent, an immune response modifier, or a detectable agent. In certain aspects the heterologous agent comprises one or more additional polypeptide sequences fused to the polypeptide subunit via a peptide bond, such as a signal sequence (e.g., a secretory signal sequence), a linker sequence, an amino acid tag or label, or a peptide or polypeptide sequence that facilitates purification. In certain aspects, the heterologous polypeptide can be fused to the N-terminus or the C-terminus of either a heavy chain or light chain antibody subunit, or fragment thereof, as long as the functional characteristics of the domains are maintained.

In certain aspects, the heterologous agent can be chemically conjugated to an anti-NAMPT antibody or antigen-binding fragment thereof as provided herein. Exemplary heterologous agents that can be chemically conjugated to the polypeptide subunit include, without limitation, linkers, drugs, toxins, imaging agents, radioactive compounds, organic and inorganic polymers, and any other compositions which can provide a desired activity that is not provided by the polypeptide subunit itself. Specific agents include, without limitation, polyethylene glycol (PEG), a cytotoxic agent, a radionuclide, an imaging agent, biotin.

In some embodiments, an anti-NAMPT antibody, or fragment, is labeled with a radiolabel for use in in vitro or in vivo detection. Examples of radioactive isotopes which may be used to label the antibodies disclosed herein include, but are not limited to $At^{211}$, $I^{131}$, $I^{125}$, $Y^{90}$, $Re^{186}$, $Re^{188}$, $Sm^{153}$, $Bi^{212}$, $P^{32}$, $Pb^{212}$ or radioactive isotopes of Lu. In some embodiments, the invention includes an anti-NAMPT antibody as described herein conjugated to a radioactive atom to form a radioconjugate. A variety of radioactive isotopes are available for the production of radioconjugates. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the radioconjugate is used for detection, it may comprise a radioactive atom for scintigraphic studies, for example tc99m or I123, or a spin label for nuclear magnetic resonance (NMR) imaging (also known as magnetic resonance imaging, MRI), such as iodine-123 again, iodine-131, indium-111, fluorine-19, carbon-13, nitrogen-15, oxygen-17, gadolinium, manganese or iron.

In certain embodiments, any of the anti-NAMPT antibodies provided herein is useful for detecting the presence of NAMPT in a biological sample. The term "detecting" as used herein encompasses quantitative or qualitative detection. In certain embodiments, a biological sample comprises a cell or tissue, such as cerebrospinal fluid, a cell or tissue of the lung, or blood.

In some embodiments, an anti-NAMPT antibody for use in a method of diagnosis or detection is provided. In a further aspect, a method of detecting the presence of NAMPT in a biological sample is provided. In certain embodiments, the method comprises contacting the biological sample with an anti-NAMPT antibody as described herein under conditions permissive for binding of the anti-NAMPT antibody to NAMPT, and detecting whether a complex is formed between the anti-NAMPT antibody and NAMPT. Such method may be an in vitro or in vivo method. Further, the complex formed between the anti-NAMPT antibody and NAMPT in a test biological sample can be compared to the complex formed in a control biological sample (e.g., a biological sample from a healthy subject or subjects). The amount of the complex formed between the anti-NAMPT antibody and NAMPT in a test biological sample can also be quantified and compared to the amount of the complex formed in a control biological sample (e.g., a biological sample from a healthy subject or subjects) or to the average amount of the complex known to be formed in healthy subjects.

Anti-NAMPT antibodies and fragments disclosed herein can also be used as reagents for detection of human NAMPT, and, in some embodiments, murine NAMPT. For example, anti-NAMPT antibodies described herein may be used in ELISA assays. Detection of the presence of NAMPT may be accomplished in a number of ways using the antibodies and fragments disclosed herein, such as by Western blotting (with or without immunoprecipitation), immunoprecipitation, fluorescence activated cell sorting (FACS), flow cytometry, and ELISA procedures for assaying a wide variety of tissues and samples, including plasma or serum. A wide range of immunoassay techniques using such an assay format are available which can include the antibodies disclosed herein, see, e.g., U.S. Pat. Nos. 4,016,043, 4,424,279, and 4,018,653. These include both single-site and two-site or "sandwich" assays of the non-competitive types, as well as in the traditional competitive binding assays. These assays also include direct binding of a labeled anti-NAMPT antibody to a target biomarker.

Sandwich assays are among the most useful and commonly used assays. A number of variations of the sandwich assay technique exist, and all are intended to be encompassed by the present invention. Briefly, in a typical forward assay, an unlabeled antibody is immobilized on a solid substrate, and the sample to be tested brought into contact with the bound molecule. After incubation for a period of time sufficient to allow formation of an antibody-antigen complex, a second antibody specific to the antigen, labeled with a reporter molecule capable of producing a detectable signal is then added and incubated, allowing time sufficient for the formation of another complex of antibody-antigen-labeled antibody. Any unreacted material is washed away, and the presence of the antigen is determined by observation of a signal produced by the reporter molecule. The results may either be qualitative, by simple observation of the visible signal, or may be quantitated by comparing with a control sample containing known amounts of biomarker.

For recombinant production of an anti-NAMPT antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, Methods in Molecular Biology, Vol. 248 (B. K. C. Lo, ed., Humana Press, Totowa, N.J., 2003), pp. 245-254, describing expression of antibody fragments in *E. coli*.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, Nat. Biotech. 22:1409-1414 (2004), and Li et al., Nat. Biotech. 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., J. Gen Virol. 36:59 (1977)); baby hamster kidney cells (BHK); mouse sertoli cells (TM4 cells as described, e.g., in Mather, Biol. Reprod. 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., Annals N.Y. Acad. Sci. 383:44-68 (1982); MRC 5 cells; and FS4 cells. Other useful mammalian host cell lines include Chinese hamster ovary (CHO) cells, including DHFR-CHO cells (Urlaub et al., Proc. Natl. Acad. Sci. USA 77:4216 (1980)); and myeloma cell lines such as Y0, NS0 and Sp2/0. For a review of certain mammalian host cell lines suitable for antibody production, see, e.g., Yazaki and Wu, Methods in Molecular Biology, Vol. 248 (B. K. C. Lo, ed., Humana Press, Totowa, N.J.), pp. 255-268 (2003).

Anti-NAMTP Antibody Pharmaceutical Compositions and Therapeutic Uses

Also provided are methods of treating a condition associated with inflammation. Some embodiments comprise reducing inflammation, injury, the amount of proteins in BAL fluid, and/or BAL PMNs in a dose-dependent manner via administration of an anti-NAMPT antibody or antigen-binding fragment thereof. Some embodiments comprise reducing eNAMPT-, lipopolysaccharide-, and/or ventilator-induced lung injury. Conditions treatable with an anti-NAMPT antibody, or binding fragment thereof, include without limitation inflammatory conditions, such as pulmonary fibrosis (IPF), pulmonary hypertension, acute lung injury (ALI), acute respiratory distress syndrome (ARDS), ventilator-induced lung injury (VILI), ARDS/VILI-induced ALI, trauma-induced acute lung injury (TIALI), brain injury (including traumatic brain injury), or radiation-induced lung injury (RILI)); prostate cancer; lung cancer; cancer associated with inflammation; expectant mothers with chorioamnionitis (e.g., subjects at risk for premature births and maternal/neonatal complications); non-alcoholic steatohepatitis (NASH); hepatic fibrosis; cardiac ischemia; and cardiac fibrosis.

Also provided are compositions (e.g., a pharmaceutical composition) comprising an anti-NAMPT antibody or an antigen binding fragment thereof, optionally further comprising one or more carriers, diluents, excipients, or other additives. Some embodiments comprise compositions (e.g., a pharmaceutical composition) comprising a polynucleotide or vector, optionally further comprising one or more carriers, diluents, excipients, or other additives.

Also provided are methods of preparing and administering an anti-NAMPT antibody or an antigen-binding fragment thereof to a subject in need thereof, e.g., to attenuate and/or treat the symptoms, morbidity, or mortality associated with NAMPT-associated acute and chronic inflammatory disorders (e.g., ARDS, VILI, and trauma-induced inflammatory lung injury), are well known to or can be readily determined by those skilled in the art. The anti-NAMPT antibody or an antigen-binding fragment thereof can be administered to the subject, for example, intravenously, intraarterially, intraperitoneally, intrapleurally, intratracheally, topically, subcutaneously, mucosally, intrapericardially, orally, locally, by inhalation, by injection, by infusion, by continuous infusion, by localized perfusion bathing target cells directly, via a catheter, via aerosol, via nebulizer, and/or via a lavage. In some embodiments, the composition comprising an anti-NAMPT antibody or an antigen-binding fragment thereof is administered directly to a tissue or organ that is inflamed or shows signs of inflammation. Usually, a suitable pharmaceutical composition can comprise, without limitation, a buffer (e.g. acetate, phosphate or citrate buffer), a surfactant (e.g. polysorbate), a stabilizer agent (e.g. human albumin), etc.

Certain pharmaceutical compositions provided herein can be orally administered in an acceptable dosage form including, e.g., capsules, tablets, aqueous suspensions or solutions. Certain pharmaceutical compositions also can be administered by nasal aerosol or inhalation. Such compositions can be prepared as solutions in saline, employing benzyl alcohol or other suitable preservatives, absorption promoters to enhance bioavailability, and/or other conventional solubilizing or dispersing agents.

The amount of an anti-NAMPT antibody or an antigen-binding fragment thereof that can be combined with carrier materials to produce a single dosage form will vary depending upon the subject treated and the particular mode of administration. The composition can be administered as a single dose, multiple doses or over an established period of time in an infusion. Dosage regimens also can be adjusted to provide the optimum desired response (e.g., a therapeutic or prophylactic response). By way of example, an antibody may be intravenously administered/administrable to a patient in an amount from approximately 0.1 mg/kg to about 20 mg/kg at a frequency from approximately weekly to monthly.

In some embodiments, the intended goal is to prevent or treat an inflammatory condition or disease, which means an effective amount is that amount expected to achieve some prevention or treatment of the inflammatory condition or disease. In some embodiments it refers to preventing or alleviating symptoms and/or cellular processes associated with a particular disease or condition, including but not limited to VILI, ALI or ARDS; such symptoms may be vascular permeability or elevated BAL protein secretion). An inflammatory disease or condition refers to a disease or condition that is characterized by inflammation. The inflammation may affect any of the following tissues or organs: heart, lung, kidney, liver, bone marrow, pancreas, brain, skin, bone, vein, artery, cornea, ear, eye, nasopharyngeal tissue, stomach, joints, cartilage, vascular tissue or cells, blood, small intestine, large intestine, larynx, brain, spinal cord, smooth muscle, nerves, skeletal muscle, breast, ovary, testis, uterus, and umbilical cord. Moreover, the tissue can contain one or more of the following cell types: platelet, myelocyte, erythrocyte, lymphocyte, adipocyte, fibroblast, epithelial cell, endothelial cell, smooth muscle cell, skeletal muscle cell, endocrine cell, glial cell, neuron, secretory cell, barrier function cell, contractile cell, absorptive cell, mucosal cell, limbus cell (from cornea), stem cell (totipotent, pluripotent or multipotent), unfertilized or fertilized oocyte, or sperm.

In some aspects, one or more agents may have been administered, is/are concurrently administered/administrable, or will later be administered/is subsequently administrable to the patient. Exemplary agents include azathioprine, bortezomib, carfilzomib, cyclophosphamide, dexamethasone, doxorubicin, lenalidomide, melphalan, pomalidomide, prednisolone, thalidomide, and vincristine. Exemplary agents also include antibiotics. Exemplary agents may also be administered/administrable as part of a therapeutic regimen.

This disclosure further provides pharmaceutical packs and kits comprising one or more containers, wherein a container can comprise one or more doses of an anti-NAMPT antibody or antigen binding fragment, including compositions that can be used to perform the methods described herein. In certain embodiments, a kit comprises at least one purified anti-NAMPT antibody or an antigen-binding fragment thereof. One skilled in the art will readily recognize that the disclosed anti-NAMPT antibody can be readily incorporated into one of the established kit formats that are well known in the art.

In certain aspects, the disclosure provides prophylactic and/or therapeutic methods for preventing, reducing and/or reversing the pathophysiological processes that lead to the onset and progression of NAMPT-associated acute and chronic inflammatory in a subject in need thereof, the method comprising administering an effective amount of anti-NAMPT antibody or an antigen-binding fragment thereof (including compositions and pharmaceutical compositions provided herein). As used herein, an "NAMPT-associated acute and chronic inflammatory disorder or condition," includes any inflammatory condition or biological process which results in inflammation involving NAMPT, e.g., an elevated expression and/or activity of NAMPT (e.g., eNAMPT), including downstream signaling molecules such as inflammatory cytokines. In particular embodiments, the composition comprises a neutralizing humanized anti-NAMPT antibody. In particular embodiments, the subject is a mammal, including but not limited to humans. Methods of treatment and corresponding uses in accordance with the teachings herein may retard, halt or reverse one or more symptoms associated with disorder, and thereby improve the subject's quality of life and/or extend the patient's lifespan.

In some embodiments, anti-NAMPT antibodies, or fragments thereof, described herein are used to treat a patient having symptoms of an acute or a chronic inflammatory condition or disease (e.g., an inflammatory lung condition or disease) or is at risk for developing an acute or a chronic inflammatory condition or disease (e.g., an inflammatory lung condition or disease).

A subject in need thereof who would benefit from the methods provided by the disclosure, includes but is not limited to a critically-ill subject; a critically-ill subject with respiratory failure; a critically-ill subject exposed to infection, trauma, and/or sepsis; a subject with radiation exposure; a subject with diagnosis of pulmonary fibrosis (IPF); a subject with pulmonary hypertension; a subject suffering from acute respiratory distress syndrome (ARDS); a subject with a ventilator-induced lung injury (VILI); an intensive care unit (ICU) subject with respiratory failure or at risk for VILI, and/or ARDS/VILI-induced ALI; a subject with pancreatitis; a subject with a smoke inhalation injury, blast injury, and/or trauma-induced acute lung injury (TIALI); a subject with a traumatic brain injury; a subject with hemorrhagic shock and resuscitation; a subject with radiation-induced lung injury (including cancer treatment associated radiation-induced lung injury); pregnant subjects with chorioamnionitis (e.g., who are at risk for premature births and maternal/neonatal complications, or complications of prematurity); and subjects with primary and metastatic cancers. Also provided are subjects at risk of developing any of the conditions disclosed herein.

In certain aspects, the disclosure provides a method for treating a patient suffering from or at risk for inflammatory lung condition or disease, comprising administering to the patient an effective amount of an anti-NAMPT antibody or an antigen-binding fragment thereof (including compositions and pharmaceutical compositions provided herein). This may be based on the patient's symptoms, medical history, or the results of one or more tests. In some cases, a patient has already been diagnosed with an inflammatory condition or disease of the lungs when the patient is administered the anti-NAMPT antibody or antigen binding fragment thereof (including compositions and pharmaceutical compositions provided herein). In other cases, the patient has not been diagnosed with an inflammatory condition or disease of the lungs but the patient is at risk for such a disease or condition. Such a patient includes one who has been placed or will be placed on a ventilator, someone with pneumonia, someone who has experienced bodily trauma, someone with severe bleeding, someone who has aspirated vomit, someone who has inhaled chemicals, someone who has smoked heavily, and/or someone who drinks heavily. For instance, the patient may be placed on a ventilator or have been on a ventilator within 1, 2, 3, 4, 5, 6, 7, 8, 9, 10, 11, 12, 13, 14, 15, 16, 17, 18, 19, 20, 21, 22, 23, 24, 30, 36, 42, 48, 54, 60, 66, 72, 78, 84, 90, 96, 102, 108, 114, or 120 hours (or any range derivable therein) and/or 1, 2, 3, 4, 5, 6, or 7 days (or any range derivable therein).

In certain aspects, the disclosure provides a method for treating a patient suffering from or at risk for acute lung injury (ALI), ventilator-induced lung injury (VILI), or acute respiratory distress syndrome (ARDS) comprising administering to the patient an effective amount of an anti-NAMPT antibody or an antigen-binding fragment thereof (including compositions and pharmaceutical compositions provided herein). At risk patients include, but are not limited to, patients with sepsis or symptoms of sepsis, patients with pneumonia or symptoms of pneumonia, patients with severe bleeding because of an injury to the body, patients who have a severe injury to the chest or head, patients who have breathed harmful fumes or smoke, patients who have inhaled vomit, patients who have had multiple or massive blood transfusions, patients who have fractured long bones (such as the femur), patients who have nearly drowned, patients who have had an adverse reaction to cancer drugs or other medications, patients who have had a drug overdose, patients with pancreatitis, patients who smoke heavily, patients who drink heavily, patients with inflammatory bowel disease, patients with rheumatoid arthritis, patients with colorectal cancer, and patients with obesity-related insulin resistance, or any combination thereof.

In certain aspects, the disclosure provides a method for preventing ventilator-induced lung injury (VILI) in a patient, the method comprising administering an effective amount of anti-NAMPT antibody or an antigen-binding fragment thereof (including compositions and pharmaceutical compositions provided herein). In particular embodiments, the anti-NAMPT antibody is a neutralizing antibody. In particular embodiments the administration occurs before the patient is placed on a ventilator. In particular embodiments the administration occurs after the patient is placed on a ventilator.

In certain aspects, the disclosure provides a method of reducing levels or one or more cytokines (e.g., IL-6, TNF-α, IL-1β, IL-8) in a subject at risk of suffering from or suffering from an NAMPT-associated acute and/or chronic inflammatory disorder.

In certain aspects, the disclosure provides a method for reducing eNAMPT levels in a subject at risk of suffering from or suffering from an NAMPT-associated acute and/or chronic inflammatory disorder.

In some embodiments, anti-NAMPT antibodies disclosed herein can be used to treat cancer. In some embodiments, the cancer is prostate cancer (PCa). In particular aspects, the disclosure provides a method for treating PCa in a subject in need thereof by administering to the subject a therapeutically effective amount of an anti-NAMPT antibody or antigen-binding fragment described herein. In some embodiments, the subject having prostate cancer has recurrent PCa, aggressive PCa, or metastatic PCa. In some embodiments, the subject has aggressive PCa that is resistant to androgen deprivation therapy (ADT).

Alternatively, in some instances, an anti-NAMPT antibody or antigen-binding fragment, can be administered to a subject in combination with ADT. ADT can be administered to the subject prior to, concurrently with, or subsequent to administering an anti-NAMPT antibody or antigen-binding fragment.

ADT that can be administered to a subject in combination with an anti-NAMPT antibody or antigen-binding fragment, may include one or more of a luteinizing hormone-releasing hormone (LHRH) agonist; a LHRH antagonist; a CYP17 inhibitor; an anti-androgen; and/or an androgen-suppressing drug. In particular embodiments, the LHRH agonist can be Leuprolide (e.g., LUPRONI™, ELIGARD™, etc.), Goserelin (e.g., ZOLADEX™), Triptorelin (e.g., TRELSTAR™), and/or Histrelin (e.g., VANTAS™); the LHRH antagonist can be Degarelix (e.g., FIRMAGON™); the CYP17 inhibitor can be Abiraterone (e.g., ZYTIGA™); the anti-androgen can be Flutamide (e.g., EULEXIN™), Bicalutamide (e.g., CASODEX™), Nilutamide (e.g., NILANDRON™), Enzalutamide (e.g., XTANDI™), and/or Apalutamide (e.g., ERLEADA™); and/or the androgen-suppressing drug can be Estrogen and/or Ketoconazole (e.g., NIZORAL™).

Some embodiments comprise treating Coronavirus disease 2019 (COVID-19) with one or more NAMPT antibodies. COVID-19 is a severe acute respiratory syndrome caused by coronavirus 2 (SARS-CoV-2). SARS-CoV-2 has a diameter of 60 nm to 140 nm and distinctive spikes, ranging from 9 nm to 12 nm, giving the virions the appearance of a solar corona. Through genetic recombination and variation, coronaviruses can adapt to and infect new hosts. SARS-CoV-2 infection may be asymptomatic or it may cause a wide spectrum of symptoms. Exemplary symptoms include fever, cough, shortness of breath, weakness, fatigue, nausea, vomiting, and changes to taste and smell. Adverse outcomes include diffuse intravascular coagulation; inflamed lung tissues and pulmonary endothelial cells; deep venous thrombosis; pulmonary embolism; thrombotic arterial complications (e.g., limb ischemia; ischemic stroke; myocardial infarction); sepsis; and multi-organ failure. SARS-CoV-2 infection is discussed in greater detail in Wiersinga et al., "Pathophysiology, Transmission, Diagnosis, and Treatment of Coronavirus Disease 2019 (COVID-2019): A Review," *JAMA*, doi:10.1001/jama.2020.12839 (published online Jul. 10, 2020), which is incorporated herein by reference in its entirety. In some embodiments, the present disclosure provides methods for treating a subject having COVID-19 (e.g., a subject diagnosed with COVID-19 and/or a subject showing one or more symptoms of COVID-19) by administering to the subject an effective amount of an anti-NAMPT antibody or an antigen-binding fragment thereof.

EXAMPLES

The following examples are included for purpose of illustration only and are not intended to be limiting.

Example 1. Generation of Anti-Human NAMPT Monoclonal Antibodies

Anti-NAMPT neutralizing murine antibodies were developed by immunizing three mice with recombinant extracellular human NAMPT (hNAMPT; MBL International). Mouse 4C6 and mouse 589 yielded 52 parental clone anti-NAMPT antibodies collectively. Binding of the murine antibodies to hNAMPT was assessed by ELISA. The murine antibodies were also tested for in vitro neutralization by analyzing the effect of the antibodies on hNAMPT-induced phosphorylation of NFκB. Anti-hNAMPT antibodies AL-303 and AL-310 were selected for their ability to bind recombinant hNAMPT, as well as hNAMPT in lysate from human pulmonary artery endothelial cells (HPAEC). Both AL-303 and AL-310 were also able to inhibit hNAMPT-induced phosphorylation of NFκB. AL-303 was further able to cross react with recombinant mouse NAMPT (mNAMPT), while AL-310 was not. Furthermore, these antibodies were subjected to in vivo testing, as described below in Examples 4 and 5.

AL-303

Murine anti-hNAMPT antibody AL-303 has a heavy chain variable region with an amino acid sequence as set forth in SEQ ID NO: 54, and a light chain variable region with an amino acid sequence as set forth in SEQ ID NO: 55. The heavy chain variable region of AL-303 contains a CDR1 domain with an amino acid sequence as set forth in SEQ ID NO: 3, a CDR2 domain with an amino acid sequence as set forth in SEQ ID NO: 4, and a CDR3 domain with an amino acid sequence as set forth in SEQ ID NO: 5. The light chain variable region of AL-303 contains a CDR1 domain with an amino acid sequence as set forth in SEQ ID NO: 6, a CDR2 domain with an amino acid sequence as set forth in SEQ ID NO: 7, and a CDR3 domain with an amino acid sequence as set forth in SEQ ID NO: 8.

AL-310

Murine anti-NAMPT antibody AL-310 has a heavy chain variable region with an amino acid sequence as set forth in SEQ ID NO: 56, and a light chain variable region with an amino acid sequence as set forth in SEQ ID NO: 57. The heavy chain variable region of AL-310 contains a CDR1 domain with an amino acid sequence as set forth in SEQ ID NO: 19, a CDR2 domain with an amino acid sequence as set forth in SEQ ID NO: 20, and a CDR3 domain with an amino acid sequence as set forth in SEQ ID NO: 21. The light chain variable region of AL-310 contains a CDR1 domain with an amino acid sequence as set forth in SEQ ID NO: 6, a CDR2 domain with an amino acid sequence as set forth in SEQ ID NO: 7, and a CDR3 domain with an amino acid sequence as set forth in SEQ ID NO: 22.

The amino acid sequences of the heavy and light chain variable regions, as well as the CDRs, of AL-303 and AL-310 is provided in Table 1.

TABLE 1

Sequence of murine anti-NAMPT antibodies

| Antibody | Description | Amino Acid Sequence | Sequence Identifier |
|---|---|---|---|
| AL-303 | AL-303 heavy chain variable region (VH) (CDRs underlined) | QVQLQQPGADLVKPGASVKLSCK ASGYTFTSYWMQWVKQRPGQGL EWIGEIDPSNSYTNYNQKFRGKAT LTVDPSSSTAYMQLSSLTSEDSAV YYCARGGYWGQGTTLTVSS | SEQ ID NO: 54 |
| | AL-303 light chain variable region (VL) (CDRs underlined) | DIVMTQAAFSNPVTLGTSASISCRS SKSLLHSNGITYLYWYLQKPGQSP QLLIYQMSNLASGVPDRFSSSGSG TDFTLRISRVEAEDVGVYYCVQNL ELPYTFGGGTKLEIK | SEQ ID NO: 55 |
| | AL-303 CDR-H1 | GYTFTSYWMQ | SEQ ID NO: 3 |
| | AL-303 CDR-H2 | EIDPSNSYTNYNQKFRG | SEQ ID NO: 4 |
| | AL-303 CDR-H3 | ARGGY | SEQ ID NO: 5 |
| | AL-303 CDR-L1 | RSSKSLLHSNGITYLY | SEQ ID NO: 6 |
| | AL-303 CDR-L2 | QMSNLAS | SEQ ID NO: 7 |
| | AL-303 CDR-L3 | VQNLELPYT | SEQ ID NO: 8 |
| AL-310 | AL-310 heavy chain variable region (VH) (CDRs underlined) | QVQLQQSGAESVMPGASVKLSCK ASGYTFTSYWMHWVKQRPGQGL EWIGEIDPSDSYTNYNQKFKGKST LTVDKSSSTAYMQLSSLTSEDSAV YYCAKSNYVVPWYFDVWGTGTT VTVSS | SEQ ID NO: 56 |
| | AL-310 light chain variable region (VL) (CDRs underlined) | DIVMTQAAFSNPVTLGTSASISCRS SKSLLHSNGITYLYWYLQKPGQSP QLLIYQMSNLASGVPDRFSSSGSG TDFTLRISRVEAEDVGVYYCAQNL ELPWTFGGGTKLEIK | SEQ ID NO: 57 |
| | AL-310 CDR-H1 | GYTFTSYWMH | SEQ ID NO: 19 |
| | AL-310 CDR-H2 | EIDPSDSYTNYNQKFKG | SEQ ID NO: 20 |
| | AL-310 CDR-H3 | AKSNYVVPWYFDV | SEQ ID NO: 21 |
| | AL-310 CDR-L1 | RSSKSLLHSNGITYLY | SEQ ID NO: 6 |
| | AL-310 CDR-L2 | QMSNLAS | SEQ ID NO: 7 |
| | AL-310 CDR-L3 | AQNLELPWT | SEQ ID NO: 22 |

Example 2. Detection of Human and Mouse NAMPT by Murine Anti-NAMPT Antibodies To evaluate immunoreactivity of human and mouse NAMPT by murine anti-NAMPT antibodies AL-303 and AL-310, detection of hNAMPT and mNAMPT by these antibodies was tested by Western blot analysis. Immunoreactivity of AL-303 and AL-310 with hNAMPT was also evaluated by assessing the ability of these antibodies to detect recombinant hNAMPT and hNAMPT in HPAEC cell lysate. Immunoreactivity of AL-303 AL-310 with mNAMPT was further tested by assessing the ability of these antibodies to detect recombinant mNAMPT, mNAMPT in lysate from spontaneously breathing mice ("SB"), mNAMPT in lysate from murine lung exposed to LPS, and mNAMPT in lysate from a murine ventilator-induced lung injury (VILI) model.

Results from the corresponding Western blot analyses is provided in FIG. 1. As shown, AL-303 and AL-310 were strongly immunoreactive with hNAMPT (as compared to other antibodies shown). In comparison, immunoreactivity of these antibodies with mNAMPT was substantially weaker. Of the five murine antibodies tested, only AL-303 and AL-304 (which contained the same sequence as AL-303) were immunoreactive with recombinant mNAMPT, while all of the antibodies were reactive with recombinant hNAMPT and hNAMPT in HPAEC cells.

Example 3. Effect of Murine Anti-NAMPT Antibodies on hNAMPT-Induced NFκB Phosphorylation Effect of murine anti-NAMPT antibodies AL-303, AL-304, AL-305, AL-309, and AL-310 on hNAMPT-induced NFκB phosphorylation was assessed by Western blot analysis of phospho-NFκB (p-NFκB) expression in cells that were exposed to hNAMPT in absence or presence of these antibodies.

Recombinant hNAMPT (1 μg/ml) was premixed for 30 min with vehicle, 100 μg/ml of anti-NAMPT polyclonal (pAb), or 100 μg/ml of a murine anti-NAMPT antibody (AL-303, AL-304, AL-305, AL-309, or AL-310). HPAEC cells were stimulated by exposing the cells to the hNAMPT mix for 1 hr. Unstimulated cells ("Unstim"), which were exposed to vehicle, 100 μg/ml of anti-NAMPT pAb, or 100 μg/ml of a murine anti-NAMPT antibody (AL-303, AL-304, AL-305, AL-309, or AL-310) alone, were used as a negative control. HPAEC cells, which were exposed to TNF-α, were used as a positive control. Expression of p-NFκB in lysates from the unstimulated cells, hNAMPT-stimulated cells, and TNF-α-stimulated cells was assessed by Western blot analysis using a p-NFkB specific antibody. Result from the Western blot analysis is provided in FIG. 2.

Figure 2:
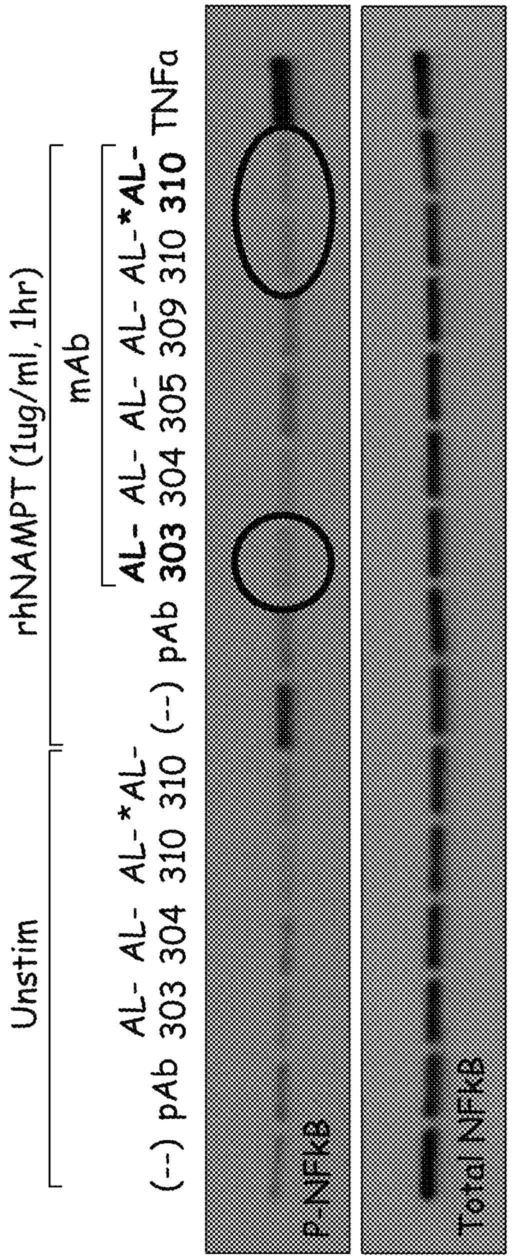
FIG. 2 is a Western blot assay depicting the capacity of murine anti-NAMPT antibodies AL-303, AL-304, AL-305, AL-309, and AL-310mAb, to reduce hNAMPT-induced phosphorylation of NFκB.

As shown in FIG. 2, hNAMPT induced phosphorylation of NFκB in the hNAMPT-stimulated cells, which was substantially attenuated in presence of AL-303, AL-304, AL-305, AL-309, or AL-310. While all of the five antibodies effectively reduced hNAMPT-induced NFκB phosphorylation, the most substantial effect was observed with AL-303 and AL-310. AL-304, AL-304, AL-305, and AL-309 were anti-hNAMPT antibodies also obtained in the initial murine screen.

Example 4. In Vivo Testing of AL-303, AL-304 and AL-305 in Lung Injury Model

Ability of murine anti-NAMPT antibodies AL-303, AL-304 and AL-305 to treat lung injury was tested in vivo, using a mouse model.

Figure 3:
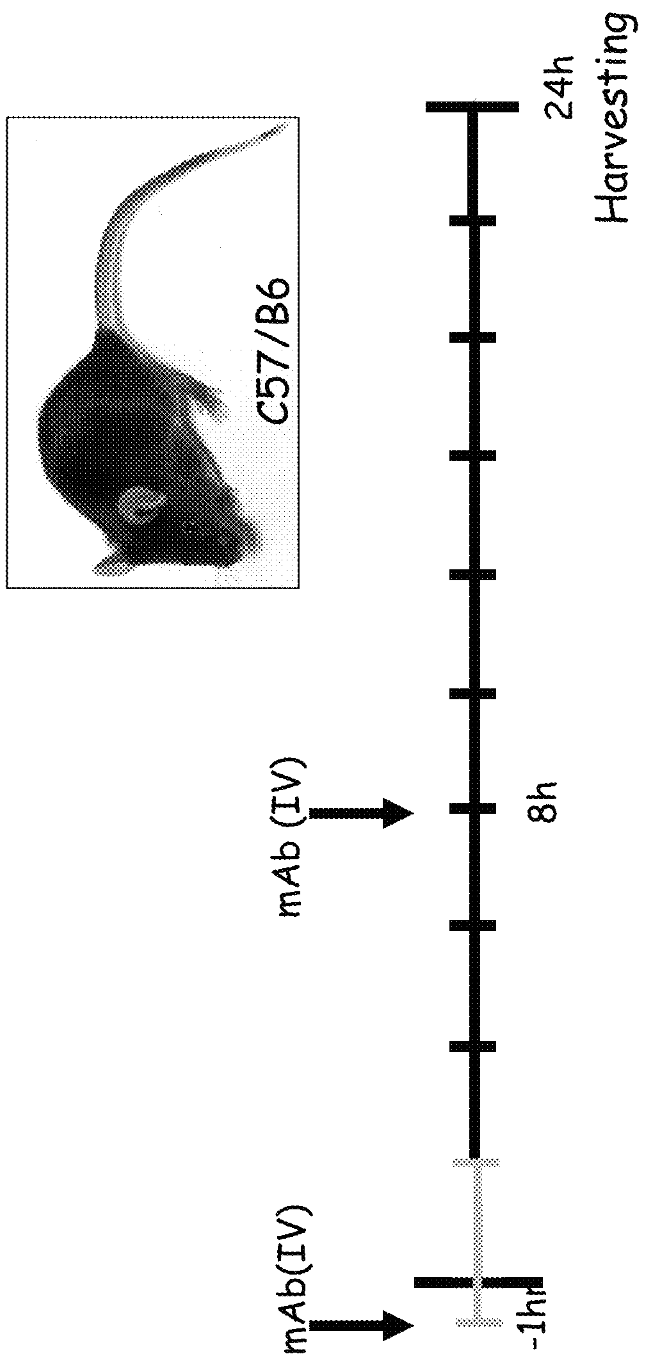
FIG. 3 is a schematic depiction of experimental protocol for in vivo studies to assess the effect of murine anti-NAMPT antibodies AL-303, AL-304, and AL-305 on NAMPT-induced murine lung injury.

As described in FIG. 3, C57/B6 mice were intravenously injected with 50 μg, 100 μg, or 200 μg of murine anti-NAMPT antibody, AL-303, AL-304, or AL-305, or with vehicle alone. One hour after the anti-NAMPT antibody injection, the mice were exposed to 40 μg/ml intratracheal hNAMPT (Peprotech). Eight hours post hNAMPT exposure, the anti-NAMPT antibodies were administered again at the same concentrations. Control mice were injected with vehicle and exposed to intratracheal hNAMPT, or injected with vehicle and not exposed to intratracheal hNAMPT. All animals were sacrificed 24 hr after hNAMPT exposure, and assessed for lung injury by analyzing the expression of bronchioalveolar lavage (BAL) protein, and count of BAL-expressing polymorphonuclear neutrophils (PMNs).

Figure 4A:
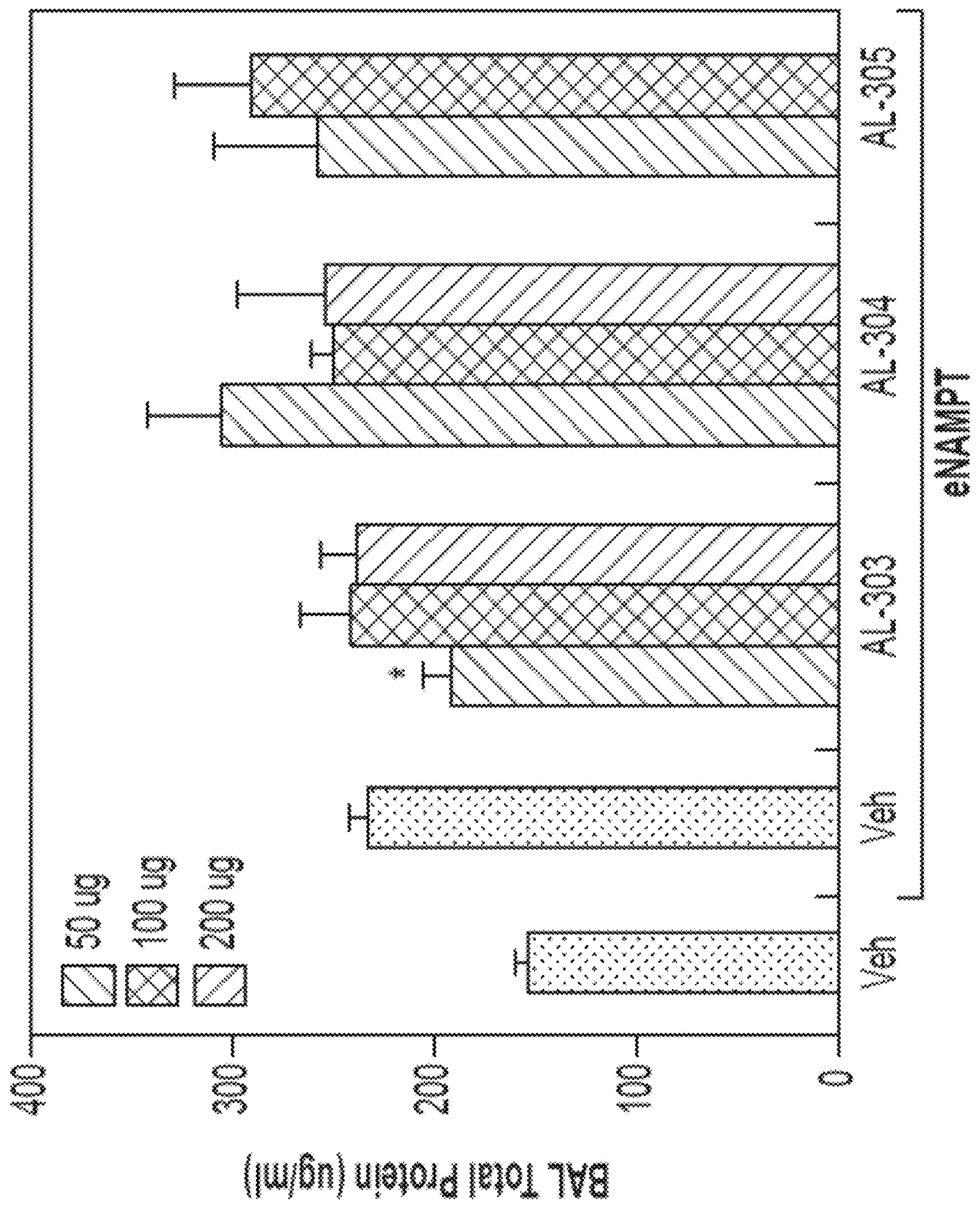
FIGS. 4A-4B are graphical representations of the effect of murine anti-NAMPT antibodies AL-303, AL-304, and AL-305 on NAMPT-induced murine lung injury.
Figure 4B:
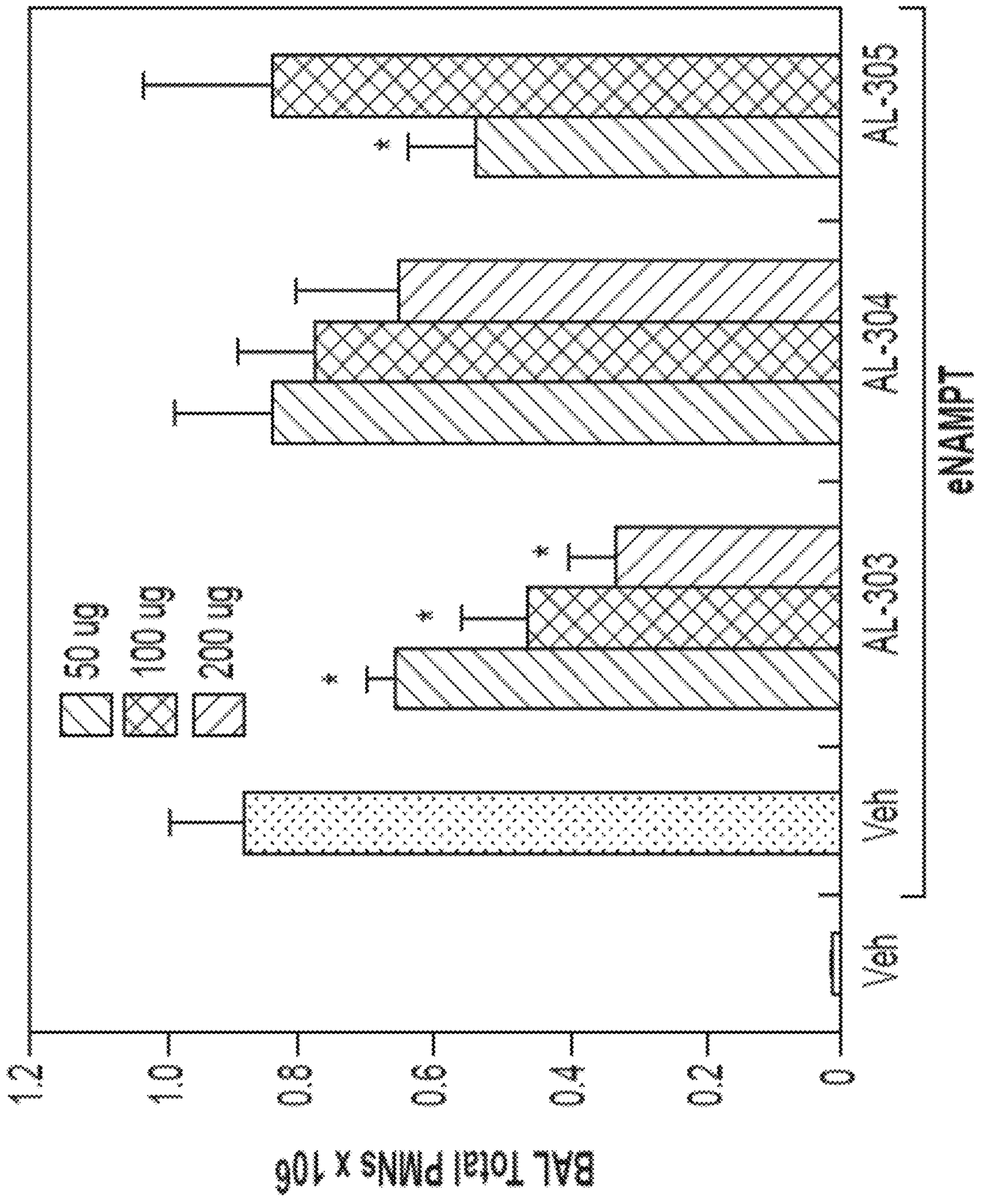

Results from the assessment is provided in FIGS. 4A-4B. As described in FIGS. 4A-4B, the expression of BAL protein (FIG. 4A) and the count of BAL-expressing PMNs (FIG. 4B) was induced in mice that were exposed to intratracheal hNAMPT. Murine anti-NAMPT antibodies AL-303, AL-304 and AL-305 effectively reduced hNAMPT-mediated induction of BAL PMN count, and hNAMPT-induced increase in BAL protein level was substantially attenuated by AL-303. Thus, as described in FIGS. 4A-4B, all of AL-303, AL-304 and AL-305 effectively reduced hNAMPT-induced murine lung injury, while the most substantial effect was observed with AL-303. Accordingly, AL-303 was selected for subsequent humanization.

Example 5. In Vivo Testing of AL-310 in Lung Injury

The ability of murine anti-NAMPT antibody AL-310 to treat lung injury was tested in vivo, using a mouse model.

Figure 5:
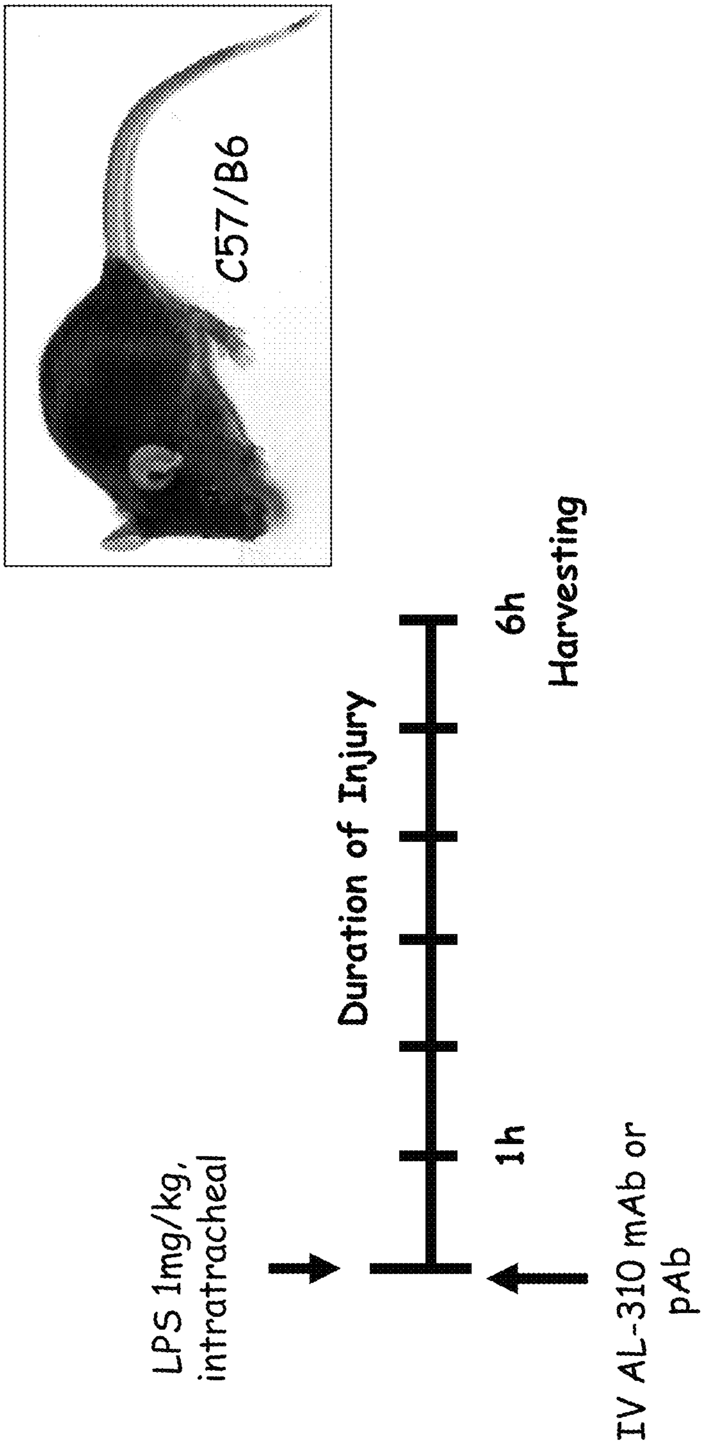
FIG. 5 is a schematic depiction of experimental protocol for in vivo studies to assess the effect of murine anti-NAMPT antibody AL-310 on LPS-induced murine lung injury.

As described in FIG. 5, C57/B6 mice were intravenously injected with 10 μg, 25 μg, 50 μg, 100 μg, or 200 μg of murine anti-NAMPT antibody AL-310, 100 μg of anti-NAMPT pAb, or vehicle alone. Concurrent with the antibody injection, the mice were exposed to 1 mg/kg intratracheal LPS. Mice, which were exposed to intratracheal LPS and injected with vehicle or pAb, were used as positive control. Mice, which were injected with vehicle and not exposed to intratracheal LPS, were used as negative control. All animals were sacrificed 6 hr after LPS exposure, and assessed for lung injury by analyzing the expression of BAL protein level.

Figure 6:
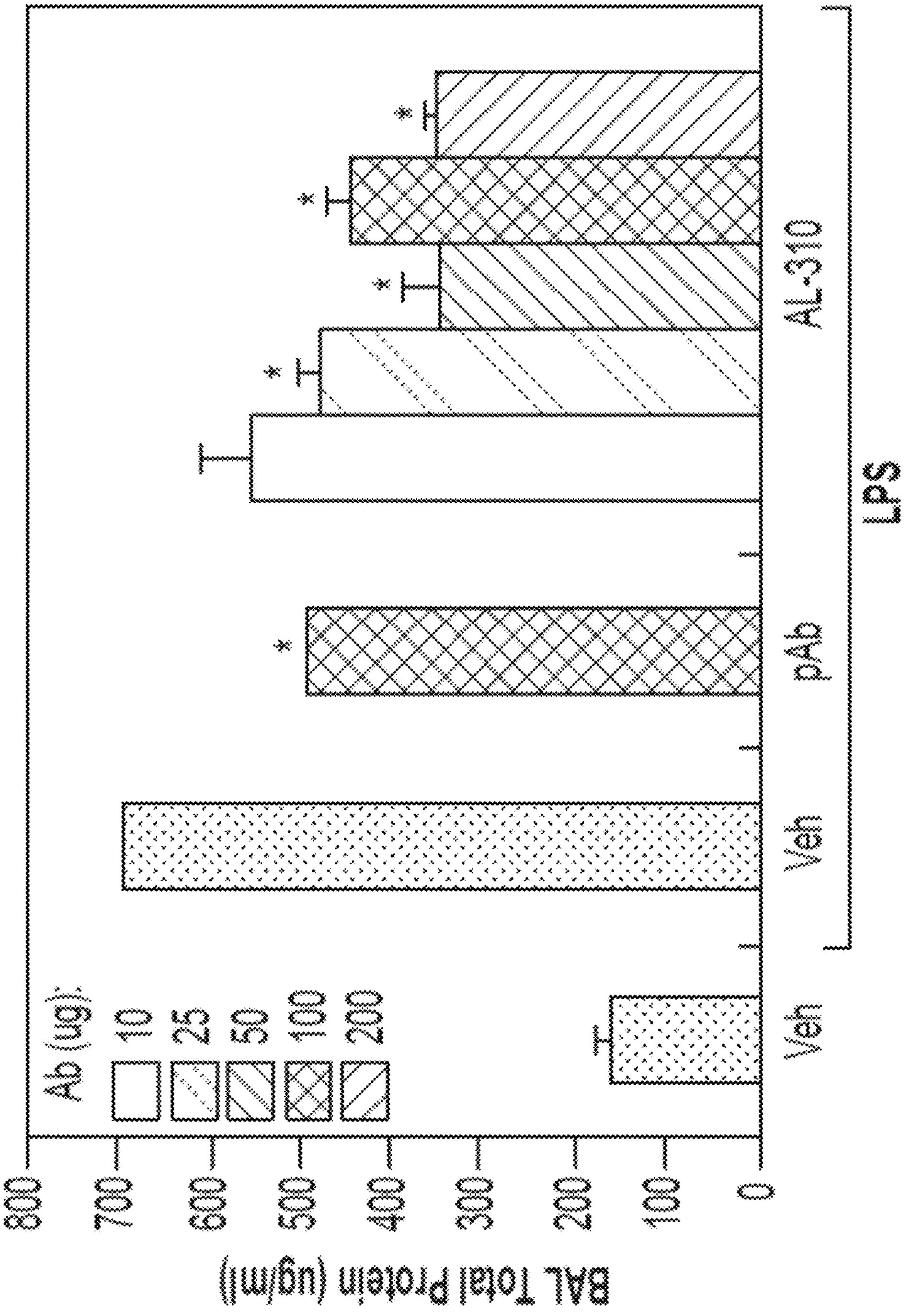
FIG. 6 is a graph showing the effect of murine anti-NAMPT antibody AL-310 on LPS-induced BAL protein levels.

Results from the assessment is provided in FIG. 6. As shown in FIG. 6, expression of BAL protein was induced in mice that were exposed to intratracheal LPS. Murine anti-NAMPT antibody AL-310 effectively reduced LPS-mediated induction of BAL protein level, and the effect was substantially more pronounced compared to the effect observed with the positive control. Thus, FIG. 6 shows that AL-310 effectively reduced LPS-induced murine lung injury. Accordingly, AL-310 was selected for subsequent humanization.

Example 6. Humanization of Anti-NAMPT Antibody AL-303

Based on the results of in vitro and in vivo testing described in Examples 2-4, murine anti-NAMPT antibody AL-303 was selected for humanization.

1076 Humanized Anti-hNAMPT Antibodies

The term "1076" collectively refers to humanized versions of anti-hNAMPT antibody AL-303. Specifically, CDRs of VH and VL chains of AL-303 were grafted onto human heavy and light chain acceptor sequences.

Following grafting, various framework back-mutations were introduced, by de nova synthesis of the variable domain, or mutagenic oligonucleotide primers and polymerase chain reactions, or both, by methods well known in the art. Different combinations of back mutations and other mutations were constructed for heavy and/or light chains of each of the CDR-grafts to generate 1076 humanized anti-hNMAPT antibodies D-1076, G-1076, K-1076, N-1076, P-1076, V-1076 and X-1076.

Amino acid sequences of the heavy and light chain variable regions of the 1076 humanized anti-hNMAPT antibodies are provided in Table 2. Table 3 provides an alignment of the amino acid sequences of the heavy chain CDRs for 1076 humanized anti-hNMAPT antibodies D-1076, G-1076, K-1076, N-1076, P-1076, V-1076 and X-1076 in comparison to the murine anti-NAMPT antibody AL-303. Table 4 provides an alignment of the amino acid sequences of the light chain CDRs for 1076 humanized anti-hNMAPT antibodies D-1076, G-1076, K-1076, N-1076, P-1076, V-1076 and X-1076 in comparison to the murine anti-NAMPT antibody AL-303. Blank spaces in Tables 3 and 4 indicate that the residue is the same as AL-303.

D-1076

1076 humanized anti-hNMAPT antibody D-1076 has a heavy chain variable region with an amino acid sequence as set forth in SEQ ID NO: 1, and a light chain variable region with an amino acid sequence as set forth in SEQ ID NO: 2. The heavy chain variable region of D-1076 contains a CDR1 domain with an amino acid sequence as set forth in SEQ ID NO: 3, a CDR2 domain with an amino acid sequence as set forth in SEQ ID NO: 4, and a CDR3 domain with an amino acid sequence as set forth in SEQ ID NO: 5. For the heavy chain of D-1076, one or more back mutations and other mutations were introduced. The light chain variable region of D-1076 contains a CDR1 domain with an amino acid sequence as set forth in SEQ ID NO: 6, a CDR2 domain with an amino acid sequence as set forth in SEQ ID NO: 7, and a CDR3 domain with an amino acid sequence as set forth in SEQ ID NO: 8.

G-1076

1076 humanized anti-hNMAPT antibody G-1076 has a heavy chain variable region with an amino acid sequence as set forth in SEQ ID NO: 9, and a light chain variable region with an amino acid sequence as set forth in SEQ ID NO: 10. The heavy chain variable region of G-1076 contains a CDR1 domain with an amino acid sequence as set forth in SEQ ID NO: 3, a CDR2 domain with an amino acid sequence as set forth in SEQ ID NO: 4, and a CDR3 domain with an amino acid sequence as set forth in SEQ ID NO: 5. For the heavy chain of G-1076, one or more back mutations and other mutations were introduced. The light chain variable region of G-1076 contains a CDR1 domain with an amino acid sequence as set forth in SEQ ID NO: 11, a CDR2 domain with an amino acid sequence as set forth in SEQ ID NO: 12, and a CDR3 domain with an amino acid sequence as set forth in SEQ ID NO: 8.

K-1076

1076 humanized anti-hNMAPT antibody K-1076 has a heavy chain variable region with an amino acid sequence as set forth in SEQ ID NO: 9, and a light chain variable region with an amino acid sequence as set forth in SEQ ID NO: 13. The heavy chain variable region of K-1076 contains a CDR1 domain with an amino acid sequence as set forth in SEQ ID NO: 3, a CDR2 domain with an amino acid sequence as set forth in SEQ ID NO: 4, and a CDR3 domain with an amino acid sequence as set forth in SEQ ID NO: 5. For the heavy chain of K-1076, one or more back mutations and other mutations were introduced. The light chain variable region of K-1076 contains a CDR1 domain with an amino acid sequence as set forth in SEQ ID NO: 11, a CDR2 domain with an amino acid sequence as set forth in SEQ ID NO: 14, and a CDR3 domain with an amino acid sequence as set forth in SEQ ID NO: 8.

N-1076

1076 humanized anti-hNMAPT antibody N-1076 has a heavy chain variable region with an amino acid sequence as set forth in SEQ ID NO: 15, and a light chain variable region with an amino acid sequence as set forth in SEQ ID NO: 2. The heavy chain variable region of N-1076 contains a CDR1 domain with an amino acid sequence as set forth in SEQ ID NO: 3, a CDR2 domain with an amino acid sequence as set forth in SEQ ID NO: 4, and a CDR3 domain with an amino acid sequence as set forth in SEQ ID NO: 5. For the heavy chain of N-1076, one or more back mutations and other mutations were introduced. The light chain variable region of N-1076 contains a CDR1 domain with an amino acid sequence as set forth in SEQ ID NO: 6, a CDR2 domain with an amino acid sequence as set forth in SEQ ID NO: 7, and a CDR3 domain with an amino acid sequence as set forth in SEQ ID NO: 8.

P-1076

1076 humanized anti-hNMAPT antibody P-1076 has a heavy chain variable region with an amino acid sequence as set forth in SEQ ID NO: 15, and a light chain variable region with an amino acid sequence as set forth in SEQ ID NO: 13. The heavy chain variable region of P-1076 contains a CDR1 domain with an amino acid sequence as set forth in SEQ ID NO: 3, a CDR2 domain with an amino acid sequence as set forth in SEQ ID NO: 4, and a CDR3 domain with an amino acid sequence as set forth in SEQ ID NO: 5. For the heavy chain of P-1076, one or more back mutations and other mutations were introduced. The light chain variable region of P-1076 contains a CDR1 domain with an amino acid sequence as set forth in SEQ ID NO: 11, a CDR2 domain with an amino acid sequence as set forth in SEQ ID NO: 14, and a CDR3 domain with an amino acid sequence as set forth in SEQ ID NO: 8.

V-1076

1076 humanized anti-hNMAPT antibody V-1076 has a heavy chain variable region with an amino acid sequence as set forth in SEQ ID NO: 16, and a light chain variable region with an amino acid sequence as set forth in SEQ ID NO: 10. The heavy chain variable region of V-1076 contains a CDR1 domain with an amino acid sequence as set forth in SEQ ID NO: 3, a CDR2 domain with an amino acid sequence as set forth in SEQ ID NO: 4, and a CDR3 domain with an amino acid sequence as set forth in SEQ ID NO: 5. For the heavy chain of V-1076, one or more back mutations and other mutations were introduced. The light chain variable region of V-1076 contains a CDR1 domain with an amino acid sequence as set forth in SEQ ID NO: 11, a CDR2 domain with an amino acid sequence as set forth in SEQ ID NO: 12, and a CDR3 domain with an amino acid sequence as set forth in SEQ ID NO: 8.

X-1076

1076 humanized anti-hNMAPT antibody X-1076 has a heavy chain variable region with an amino acid sequence as set forth in SEQ ID NO: 16, and a light chain variable region with an amino acid sequence as set forth in SEQ ID NO: 2. The heavy chain variable region of X-1076 contains a CDR1 domain with an amino acid sequence as set forth in SEQ ID NO: 3, a CDR2 domain with an amino acid sequence as set forth in SEQ ID NO: 4, and a CDR3 domain with an amino acid sequence as set forth in SEQ ID NO: 5. For the heavy chain of X-1076, one or more back mutations and other mutations were introduced. The light chain variable region of X-1076 contains a CDR1 domain with an amino acid sequence as set forth in SEQ ID NO: 6, a CDR2 domain with an amino acid sequence as set forth in SEQ ID NO: 7, and a CDR3 domain with an amino acid sequence as set forth in SEQ ID NO: 8.

TABLE 2

Sequence of 1076 humanized anti-hNAMPT antibodies

| Antibody | Description | Amino Acid Sequence | Sequence Identifier |
|---|---|---|---|
| D-1076 | D-1076 heavy chain variable region (VH) (CDRs underlined) | QVQLVESGAEVKKPGASVKLSCKASGYTFTSYWMQWVRQAPGQRLEWMGEIDPSNSYTNYNQKFRGRVTITVDKSASTAYMELSSLRSEDTAVYYCARGGYWGPGTTVTVSS | SEQ ID NO: 1 |
| | D-1076 light chain variable region (VL) (CDRs underlined) | DIVMTQTPLSLSVTPGQPASISCRSSKSLLHSNGITYLYWYLQKPGQPPQLLIYQMSNLASGVPDRFSGSGSGTDFTLKISRVEAEDVGVYYCVQNLELPYTFGPGTKVDIK | SEQ ID NO: 2 |
| | D-1076 CDR-H1 | GYTFTSYWMQ | SEQ ID NO: 3 |
| | D-1076 CDR-H2 | EIDPSNSYTNYNQKFRG | SEQ ID NO: 4 |
| | D-1076 CDR-H3 | ARGGY | SEQ ID NO: 5 |
| | D-1076 CDR-L1 | RSSKSLLHSNG1TYLY | SEQ ID NO: 6 |
| | D-1076 CDR-L2 | QMSNLAS | SEQ ID NO: 7 |
| | D-1076 CDR-L3 | VQNLELPYT | SEQ ID NO: 8 |
| G-1076 | G-1076 heavy chain variable | QVQLVQSGAEVKKPGASVKVSCKASGYTFTSYWMQWVRQAPGQGL | SEQ ID NO: 9 |

TABLE 2-continued

Sequence of 1076 humanized anti-hNAMPT antibodies

| Antibody | Description | Amino Acid Sequence | Sequence Identifier |
|---|---|---|---|
| | region (VH) (CDRs underlined) | EWMGEIDPSNSYTNYNQKFRGRVTMTTDTSTSTAYMELRSLRSDDTAVYYCARGGYWGQGTTVTVSS | |
| | G-1076 light chain variable region (VL) (CDRs underlined) | DIQLTQSPLSLPVTPGEPASISCRSSKSLLHSQG1TYLYWYLQKPGQSPQLL1YQLSNLASGVPDRFSGSGSGTDFTLKISRVEAEDVGVYYCVQNLELPYTFGGGTKLEIK | SEQ ID NO: 10 |
| | G-1076 CDR-H1 | GYTFTSYWMQ | SEQ ID NO: 3 |
| | G-1076 CDR-H2 | EIDPSNSYTNYNQKFRG | SEQ ID NO: 4 |
| | G-1076 CDR-H3 | ARGGY | SEQ ID NO: 5 |
| | G-1076 CDR-L1 | RSSKSLLHSQGITYLY | SEQ ID NO: 11 |
| | G-1076 CDR-L2 | QLSNLAS | SEQ ID NO: 12 |
| | G-1076 CDR-L3 | VQNLELPYT | SEQ ID NO: 8 |
| K-1076 | K-1076 heavy chain variable region (VH) hIgG1 backbone (CDRs underlined) | QVQLVQSGAEVKKPGASVKVSCKASGYTFTSYWMQWVRQAPGQGLEWMGEIDPSNSYTNYNQKFRGRVTMTTDTSTSTAYMELRSLRSDDTAVYYCARGGYWGQGTTVTVSS | SEQ ID NO: 9 |
| | K-1076 light chain variable region (VL) (CDRs underlined) | DIVMTQSPLSLPVTPGEPASISCRSSKSLLHSQGITYLYWYLQKPGQSPQLLIYQLSNRASGVPDRFSGSGSGTDFTLKISRVEAEDVGVYYCVQNLELPYTFGGGTKLEIK | SEQ ID NO: 13 |
| | K-1076 CDR-H1 | GYTFTSYWMQ | SEQ ID NO: 3 |
| | K-1076 CDR-H2 | EIDPSNSYTNYNQKFRG | SEQ ID NO: 4 |
| | K-1076 CDR-H3 | ARGGY | SEQ ID NO: 5 |
| | K-1076 CDR-L1 | RSSKSLLHSQGITYLY | SEQ ID NO: 11 |
| | K-1076 CDR-L2 | QLSNRAS | SEQ ID NO: 14 |
| | K-1076 CDR-L3 | VQNLELPYT | SEQ ID NO: 8 |
| N-1076 | N-1076 heavy chain variable region (VH) (CDRs underlined) | QVQLVQSGAEVTKPGASVKVSCKASGYTFTSYWMQWVRQAPGQGLEWVGEIDPSNSYTNYNQKFRGRVTLTRDTSTTTVYMELSSLRSEDTAVYYCARGGYWGQGTTVTVSS | SEQ ID NO: 15 |
| | N-1076 light chain variable region (VL) (CDRs underlined) | DIVMTQTPLSLSVTPGQPASISCRSSKSLLHSNGITYLYWYLQKPGQPPQLLIYQMSNLASGVPDRFSGSGSGTDFTLKISRVEAEDVGVYYCVQNLELPYTFGPGTKVDIK | SEQ ID NO: 2 |
| | N-1076 CDR-H1 | GYTFTSYWMQ | SEQ ID NO: 3 |
| | N-1076 CDR-H2 | EIDPSNSYTNYNQKFRG | SEQ ID NO: 4 |
| | N-1076 CDR-H3 | ARGGY | SEQ ID NO: 5 |
| | N-1076 CDR-L1 | RSSKSLLHSNGITYLY | SEQ ID NO: 6 |
| | N-1076 CDR-L2 | QMSNLAS | SEQ ID NO: 7 |
| | N-1076 CDR-L3 | VQNLELPYT | SEQ ID NO: 8 |
| P-1076 | P-1076 heavy chain variable region (VH) (CDRs underlined) | QVQLVQSGAEVTKPGASVKVSCKASGYTFTSYWMQWVRQAPGQGLEWVGEIDPSNSYTNYNQKFRGRVTLTRDTSTTTVYMELSSLRSEDTAVYYCARGGYWGQGTTVTVSS | SEQ ID NO: 15 |
| | P-1076 light chain variable region (VL) (CDRs underlined) | DIVMTQSPLSLPVTPGEPASISCRSSKSLLHSQGITYLYWYLQKPGQSPQLLIYQLSNRASGVPDRFSGSGSGTDFTLKISRVEAEDVGVYYCVQNLELPYTFGGGTKLEIK | SEQ ID NO: 13 |
| | P-1076 CDR-H1 | GYTFTSYWMQ | SEQ ID NO: 3 |
| | P-1076 CDR-H2 | EIDPSNSYTNYNQKFRG | SEQ ID NO: 4 |
| | P-1076 CDR-H3 | ARGGY | SEQ ID NO: 5 |
| | P-1076 CDR-L1 | RSSKSLLHSQGITYLY | SEQ ID NO: 11 |
| | P-1076 CDR-L2 | QLSNRAS | SEQ ID NO: 14 |
| | P-1076 CDR-L3 | VQNLELPYT | SEQ ID NO: 8 |
| V-1076 | V-1076 heavy chain variable region (VH) (CDRs underlined) | QVQLVQSGAEVKKPGASVKVSCKASGYTFTSYWMQWVRQAPGQGLEWMGEIDPSNSYTNYNQKFRGRVTMTRDTSTSTVYMELSSLRSEDTAVYYCARGGYWGQGTTVTVSS | SEQ ID NO: 16 |
| | V-1076 light chain variable region | DIQLTQSPLSLPVTPGEPASISCRSSKSLLHSQGITYLYWYLQKPGQSPQ | SEQ ID NO: 10 |

TABLE 2-continued

Sequence of 1076 humanized anti-hNAMPT antibodies

| Antibody | Description | Amino Acid Sequence | Sequence Identifier |
|---|---|---|---|
| | (VL)<br>(CDRs underlined) | LLIYQLSNLASGVPDRFSGSGSGT<br>DFTLKISRVEAEDVGVYYCVQNLE<br>LPYTFGGGTKLEIK | |
| | V-1076 CDR-H1 | GYTFTSYWMQ | SEQ ID NO 3 |
| | V-1076 CDR-H2 | EIDPSNSYTNYNQKFRG | SEQ ID NO: 4 |
| | V-1076 CDR-H3 | ARGGY | SEQ ID NO: 5 |
| | V-1076 CDR-L1 | RSSKSLLHSQGITYLY | SEQ ID NO: 11 |
| | V-1076 CDR-L2 | QLSNLAS | SEQ ID NO: 12 |
| | V-1076 CDR-L3 | VQNLELPYT | SEQ ID NO: 8 |
| X-1076 | X-1076 heavy chain variable region (VH) (CDRs underlined) | QVQLVQSGAEVKKPGASVKVSCK<br>ASGYTFTSYWMQWVRQAPGQGL<br>EWMGEIDPSNSYTNYNQKFRGRV<br>TMTRDTSTSTVYMELSSLRSEDTA<br>VYYCARGGYWGQGTTVTVSS | SEQ ID NO: 16 |
| | X-1076 light chain variable region (VL) (CDRs underlined) | DIVMTQTPLSLSVTPGQPASISCRS<br>SKSLLHSNGITYLYWYLQKPGQPP<br>QLLIYQMSNLASGVPDRFSGSGSG<br>TDFTLKISRVEAEDVGVYYCVQNL<br>ELPYTFGPGTKVDIK | SEQ ID NO: 2 |
| | X-1076 CDR-H1 | GYTFTSYWMQ | SEQ ID NO: 3 |
| | X-1076 CDR-H2 | EIDPSNSYTNYNQKFRG | SEQ ID NO: 4 |
| | X-1076 CDR-H3 | ARGGY | SEQ ID NO: 5 |
| | X-1076 CDR-L1 | RSSKSLLHSNGITYLY | SEQ ID NO: 6 |
| | X-1076 CDR-L2 | QMSNLAS | SEQ ID NO: 7 |
| | X-1076 CDR-L3 | VQNLELPYT | SEQ ID NO: 8 |

TABLE 3

Comparison of HC CDRs of 1076 anti-hNAMPT antibodies with HC CDRs of AL-303

| | Heavy Chain (HC) CDR1 | | | | | | | | | SEQ ID NO: | HC CDR2 | | | | | | |
|---|---|---|---|---|---|---|---|---|---|---|---|---|---|---|---|---|---|
| AL-303 | G | Y | T | F | T | S | Y | W | M | Q | 3 | E | I | D | P | S | N | S |
| D-1076 | | | | | | | | | | | 3 | | | | | | | |
| G-1076 | | | | | | | | | | | 3 | | | | | | | |
| K-1076 | | | | | | | | | | | 3 | | | | | | | |
| N-1076 | | | | | | | | | | | 3 | | | | | | | |
| P-1076 | | | | | | | | | | | 3 | | | | | | | |
| V-1076 | | | | | | | | | | | 3 | | | | | | | |
| X-1076 | | | | | | | | | | | 3 | | | | | | | |

| | HC CDR2 | | | | | | | | | SEQ ID NO: | HC CDR3 | | | | | SEQ ID NO: |
|---|---|---|---|---|---|---|---|---|---|---|---|---|---|---|---|---|
| AL-303 | Y | T | N | Y | N | Q | K | F | R | G | 4 | A | R | G | G | Y | 5 |
| D-1076 | | | | | | | | | | | 4 | | | | | | 5 |
| G-1076 | | | | | | | | | | | 4 | | | | | | 5 |
| K-1076 | | | | | | | | | | | 4 | | | | | | 5 |
| N-1076 | | | | | | | | | | | 4 | | | | | | 5 |
| P-1076 | | | | | | | | | | | 4 | | | | | | 5 |

TABLE 3-continued

| Comparison of HC CDRs of 1076 anti-hNAMPT antibodies with HC CDRs of AL-303 | | |
|---|---|---|
| V-1076 | 4 | 5 |
| X-1076 | 4 | 5 |

TABLE 4

Comparison of LC CDRs of 1076 anti-hNAMPT antibodies with LC CDRs of AL-303

| | Light Chain (LC) CDR1 | | | | | | | | | | | | | | | | SEQ ID NO: | LC CDR2 |
|---|---|---|---|---|---|---|---|---|---|---|---|---|---|---|---|---|---|---|
| AL-303 | R | S | S | K | S | L | L | H | S | N | G | I | T | Y | L | Y | 6 | Q |
| D-1076 | | | | | | | | | | | | | | | | | 6 | |
| G-1076 | | | | | | | | | | Q | | | | | | | 11 | |
| K-1076 | | | | | | | | | | Q | | | | | | | 11 | |
| N-1076 | | | | | | | | | | | | | | | | | 6 | |
| P-1076 | | | | | | | | | | Q | | | | | | | 11 | |
| V-1076 | | | | | | | | | | Q | | | | | | | 11 | |
| X-1076 | | | | | | | | | | | | | | | | | 6 | |

| | LC CDR2 | | | | | | SEQ ID NO: | LC CDR3 | | | | | | | | | SEQ ID NO: |
|---|---|---|---|---|---|---|---|---|---|---|---|---|---|---|---|---|---|
| AL-303 | M | S | N | L | A | S | 7 | V | Q | N | L | E | L | P | Y | T | 8 |
| D-1076 | | | | | | | 7 | | | | | | | | | | 8 |
| G-1076 | L | | | | | | 12 | | | | | | | | | | 8 |
| K-1076 | L | | | R | | | 14 | | | | | | | | | | 8 |
| N-1076 | | | | | | | 7 | | | | | | | | | | 8 |
| P-1076 | L | | | R | | | 14 | | | | | | | | | | 8 |
| V-1076 | L | | | | | | 12 | | | | | | | | | | 8 |
| X-1076 | | | | | | | 7 | | | | | | | | | | 8 |

Example 7. Humanization of Anti-NAMPT Antibody AL-310

Based on the results of in vitro and in vivo testing described in Examples 2-5, murine anti-NAMPT antibody AL-310 was selected for humanization.

"1093" refers to a group of humanized antibodies derived from murine anti-NAMPT antibody AL-310. By applying the humanization methodology, the CDR sequences of VH and VL chains of AL-310 were grafted onto different human heavy and light chain acceptor sequences.

By grafting the corresponding VH and VL CDRs of AL-310 into these acceptor sequences, CDR-grafted, humanized, and modified VH and VL sequences were prepared. To generate humanized antibody with potential framework back-mutations, mutations were identified and introduced into the CDR-grafted antibody sequences by de nova synthesis of the variable domain, or mutagenic oligonucleotide primers and polymerase chain reactions, or both, by methods well known in the art. Different combinations of back mutations and other mutations were constructed for heavy and/or light chains of each of the CDR-grafts to generate 1093 humanized anti-hNMAPT antibodies FF-1093, 11-1093, NN-1093, PP-1093, SS-1093, UU-1093, XX-1093, and ZZ-1093.

Amino acid sequences of the heavy and light chain variable regions of the 1093 humanized anti-hNMAPT antibodies are provided in Table 5. Table 6 provides an alignment of the amino acid sequences of the heavy chain CDRs for 1093 humanized anti-hNMAPT antibodies FF-1093, 11-1093, NN-1093, PP-1093, SS-1093, UU-1093, XX-1093, and ZZ-1093 in comparison to the murine anti-NAMPT antibody AL-310. Table 7 provides an alignment of the amino acid sequences of the light chain CDRs for 1093 humanized anti-hNMAPT antibodies FF-1093, 11-1093, NN-1093, PP-1093, SS-1093, UU-1093, XX-1093, and ZZ-1093 in comparison to the murine anti-NAMPT antibody AL-310. Blank spaces in Tables 6 and 7 indicate that the residue is the same as AL-310.

FF-1093

1093 humanized anti-hNMAPT antibody FF-1093 has a heavy chain variable region with an amino acid sequence as set forth in SEQ ID NO: 17, and a light chain variable region with an amino acid sequence as set forth in SEQ ID NO: 18. The heavy chain variable region of FF-1093 contains a CDR1 domain with an amino acid sequence as set forth in SEQ ID NO: 19, a CDR2 domain with an amino acid sequence as set forth in SEQ ID NO: 20, and a CDR3 domain with an amino acid sequence as set forth in SEQ ID NO: 21. For the heavy chain of FF-1093, one or more back mutations and other mutations were introduced. The light chain variable region of FF-1093 contains a CDR1 domain with an amino acid sequence as set forth in SEQ ID NO: 6, a CDR2 domain with an amino acid sequence as set forth in SEQ ID NO: 7, and a CDR3 domain with an amino acid sequence as set forth in SEQ ID NO: 22.

II-1093

1093 humanized anti-hNMAPT antibody II-1093 has a heavy chain variable region with an amino acid sequence as set forth in SEQ ID NO: 23, and a light chain variable region with an amino acid sequence as set forth in SEQ ID NO: 24. The heavy chain variable region of II-1093 contains a CDR1 domain with an amino acid sequence as set forth in SEQ ID NO: 19, a CDR2 domain with an amino acid sequence as set forth in SEQ ID NO: 20, and a CDR3 domain with an amino acid sequence as set forth in SEQ ID NO: 21. For the heavy chain of II-1093, one or more back mutations and other mutations were introduced. The light chain variable region of II-1093 contains a CDR1 domain with an amino acid sequence as set forth in SEQ ID NO: 6, a CDR2 domain with an amino acid sequence as set forth in SEQ ID NO: 7, and a CDR3 domain with an amino acid sequence as set forth in SEQ ID NO: 22.

NN-1093

1093 humanized anti-hNMAPT antibody NN-1093 has a heavy chain variable region with an amino acid sequence as set forth in SEQ ID NO: 25, and a light chain variable region with an amino acid sequence as set forth in SEQ ID NO: 24. The heavy chain variable region of NN-1093 contains a CDR1 domain with an amino acid sequence as set forth in SEQ ID NO: 19, a CDR2 domain with an amino acid sequence as set forth in SEQ ID NO: 20, and a CDR3 domain with an amino acid sequence as set forth in SEQ ID NO: 21. For the heavy chain of NN-1093, one or more back mutations and other mutations were introduced. The light chain variable region of NN-1093 contains a CDR1 domain with an amino acid sequence as set forth in SEQ ID NO: 6, a CDR2 domain with an amino acid sequence as set forth in SEQ ID NO: 7, and a CDR3 domain with an amino acid sequence as set forth in SEQ ID NO: 22.

PP-1093

1093 humanized anti-hNMAPT antibody PP-1093 has a heavy chain variable region with an amino acid sequence as set forth in SEQ ID NO: 25, and a light chain variable region with an amino acid sequence as set forth in SEQ ID NO: 18. The heavy chain variable region of PP-1093 containing a CDR1 domain with an amino acid sequence as set forth in SEQ ID NO: 19, a CDR2 domain with an amino acid sequence as set forth in SEQ ID NO: 20, and a CDR3 domain with an amino acid sequence as set forth in SEQ ID NO: 21. For the heavy chain of PP-1093, one or more back mutations and other mutations were introduced. The light chain variable region of PP-1093 contains a CDR1 domain with an amino acid sequence as set forth in SEQ ID NO: 6, a CDR2 domain with an amino acid sequence as set forth in SEQ ID NO: 7, and a CDR3 domain with an amino acid sequence as set forth in SEQ ID NO: 22.

SS-1093

1093 humanized anti-hNMAPT antibody SS-1093 has a heavy chain variable region with an amino acid sequence as set forth in SEQ ID NO: 26, and a light chain variable region with an amino acid sequence as set forth in SEQ ID NO: 24. The heavy chain variable region of SS-1093 contains a CDR1 domain with an amino acid sequence as set forth in SEQ ID NO: 19, a CDR2 domain with an amino acid sequence as set forth in SEQ ID NO: 20, and a CDR3 domain with an amino acid sequence as set forth in SEQ ID NO: 21. For the heavy chain of SS-1093, one or more back mutations and other mutations were introduced. The light chain variable region of SS-1093 contains a CDR1 domain with an amino acid sequence as set forth in SEQ ID NO: 6, a CDR2 domain with an amino acid sequence as set forth in SEQ ID NO: 7, and a CDR3 domain with an amino acid sequence as set forth in SEQ ID NO: 22.

UU-1093

1093 humanized anti-hNMAPT antibody UU-1093 has a heavy chain variable region with an amino acid sequence as set forth in SEQ ID NO: 26, and a light chain variable region with an amino acid sequence as set forth in SEQ ID NO: 18. The heavy chain variable region of UU-1093 contains a CDR1 domain with an amino acid sequence as set forth in SEQ ID NO: 19, a CDR2 domain with an amino acid sequence as set forth in SEQ ID NO: 20, and a CDR3 domain with an amino acid sequence as set forth in SEQ ID NO: 21. For the heavy chain of UU-1093, one or more back mutations and other mutations were introduced. The light chain variable region of UU-1093 contains a CDR1 domain with an amino acid sequence as set forth in SEQ ID NO: 6, a CDR2 domain with an amino acid sequence as set forth in SEQ ID NO: 7, and a CDR3 domain with an amino acid sequence as set forth in SEQ ID NO: 22.

XX-1093

1093 humanized anti-hNMAPT antibody XX-1093 has a heavy chain variable region with an amino acid sequence as set forth in SEQ ID NO: 27, and a light chain variable region with an amino acid sequence as set forth in SEQ ID NO: 24. The heavy chain variable region of XX-1093 contains a CDR1 domain with an amino acid sequence as set forth in SEQ ID NO: 19, a CDR2 domain with an amino acid sequence as set forth in SEQ ID NO: 20, and a CDR3 domain with an amino acid sequence as set forth in SEQ ID NO: 21. For the heavy chain of XX-1093, one or more back mutations and other mutations were introduced. The light chain variable region of XX-1093 contains a CDR1 domain with an amino acid sequence as set forth in SEQ ID NO: 6, a CDR2 domain with an amino acid sequence as set forth in SEQ ID NO: 7, and a CDR3 domain with an amino acid sequence as set forth in SEQ ID NO: 22.

ZZ-1093

1093 humanized anti-hNMAPT antibody ZZ-1093 has a heavy chain variable region with an amino acid sequence as set forth in SEQ ID NO: 27, and a light chain variable region with an amino acid sequence as set forth in SEQ ID NO: 18. The heavy chain variable region of ZZ-1093 contains a CDR1 domain with an amino acid sequence as set forth in SEQ ID NO: 19, a CDR2 domain with an amino acid sequence as set forth in SEQ ID NO: 20, and a CDR3 domain with an amino acid sequence as set forth in SEQ ID NO: 21. For the heavy chain of ZZ-1093, one or more back mutations and other mutations were introduced. The light chain variable region of ZZ-1093 contains a CDR1 domain with an amino acid sequence as set forth in SEQ ID NO: 6, a CDR2 domain with an amino acid sequence as set forth in SEQ ID NO: 7, and a CDR3 domain with an amino acid sequence as set forth in SEQ ID NO: 22.

TABLE 5

Sequence of 1093 humanized anti-hNAMPT antibodies

| Antibody | Description | Amino Acid Sequence | Sequence Identifier |
|---|---|---|---|
| FF-1093 | FF-1093 heavy chain variable region (VH) (CDRs underlined) | QVQLVESGAEVKKPGASVKLSCKASGYTFTSYWMHWVRQAPGQRLEWMGEIDPSDSYTNYNQKFKGRVTITVDKSASTAYMELSSLRSEDTAVYYCAKSNYVVPWYFDVWGPGTTVTVSS | SEQ ID NO: 17 |
| | FF-1093 light chain variable region (VL) (CDRs underlined) | EIVLTQSPGTLSLSPGERATLSCRSSKSLLHSNGITYLYWYQQKPGQAPRLLIYQMSNLASGIPDRFSGSGSGTDFTLTISRLEPEDFAVYYCAQNLELPWTFGGGTKLEIK | SEQ ID NO: 18 |
| | FF-1093 CDR-H1 | GYTFTSYWMH | SEQ ID NO: 19 |
| | FF-1093 CDR-H2 | E1DPSDSYTNYNQKFKG | SEQ ID NO: 20 |
| | FF-1093 CDR-H3 | AKSNYVVPWYFDV | SEQ ID NO: 21 |
| | FF-1093 CDR-L1 | RSSKSLLHSNGITYLY | SEQ ID NO: 6 |
| | FF-1093 CDR-L2 | QMSNLAS | SEQ ID NO: 7 |
| | FF-1093 CDR-L3 | AQNLELPWT | SEQ ID NO: 22 |
| II-1093 | II-1093 heavy chain variable region (VH) hlgGl backbone (CDRs underlined) | QVQLVQSGAEVRKPGASVKVSCKASGYTFTSYWMHWVRQAPGQGLEWVGEIDPSDSYTNYNQKFKGRVTITADKSTSTAYMELSSLRSEDTDVYYCAKSNYVVPWYFDVWGQGTTVTVSS | SEQ ID NO: 23 |
| | II-1093 light chain variable region (VL) (CDRs underlined) | EIVLTQSPATLSLSPGERATLSCRSSKSLLHSNGITYLYWYQQKPGQAPRLLIYQMSNLASGIPARFSGSGSGTDFTLTISSLEPEDFAVYYCAQNLELPWTFGGGTKLEIK | SEQ ID NO: 24 |
| | II-1093 CDR-H1 | GYTFTSYWMH | SEQ ID NO: 19 |
| | II-1093 CDR-H2 | EIDPSDSYTNYNQKFKG | SEQ ID NO: 20 |
| | II-1093 CDR-H3 | AKSNYVVPWYFDV | SEQ ID NO: 21 |
| | II-1093 CDR-L1 | RSSKSLLHSNGITYLY | SEQ ID NO: 6 |
| | II-1093 CDR-L2 | QMSNLAS | SEQ ID NO: 7 |
| | II-1093 CDR-L3 | AQNLELPWT | SEQ ID NO: 22 |
| NN-1093 | NN-1093 heavy chain variable region (VH) (CDRs underlined) | QVQLVQSGAEVTKPGASVKVSCKASGYTFTSYWMHWVRQAPGQGLEWVGEIDPSDSYTNYNQKFKGRVTLTRDTSTTTVYMELSSLRSEDTAVYYCAKSNYVVPWYFDVWGQGTTVTVSS | SEQ ID NO: 25 |
| | NN-1093 light chain variable region (VL) (CDRs underlined) | EIVLTQSPATLSLSPGERATLSCRSSKSLLHSNGITYLYWYQQKPGQAPRLLIYQMSNLASGIPARFSGSGSGTDFTLTISSLEPEDFAVYYCAQNLELPWTFGGGTKLEIK | SEQ ID NO: 24 |
| | NN-1093 CDR-H1 | GYTFTSYWMH | SEQ ID NO: 19 |
| | NN-1093 CDR-H2 | EIDPSDSYTNYNQKFKG | SEQ ID NO: 20 |
| | NN-1093 CDR-H3 | AKSNYVVPWYFDV | SEQ ID NO: 21 |
| | NN-1093 CDR-L1 | RSSKSLLHSNGITYLY | SEQ ID NO: 6 |
| | NN-1093 CDR-L2 | QMSNLAS | SEQ ID NO: 7 |
| | NN-1093 CDR-L3 | AQNLELPWT | SEQ ID NO: 22 |
| PP-1093 | PP-1093 heavy chain variable region (VH) (CDRs underlined) | QVQLVQSGAEVTKPGASVKVSCKASGYTFTSYWMHWVRQAPGQGLEWVGEIDPSDSYTNYNQKFKGRVTLTRDTSTTTVYMELSSLRSEDTAVYYCAKSNYVVPWYFDVWGQGTTVTVSS | SEQ ID NO: 25 |
| | PP-1093 light chain variable region (VL) (CDRs underlined) | EIVLTQSPGTLSLSPGERATLSCRSSKSLLHSNGITYLYWYQQKPGQAPRLLIYQMSNLASGIPDRFSGSGSGTDFTLTISRLEPEDFAVYYCAQNLELPWTFGGGTKLEIK | SEQ ID NO: 18 |
| | PP-1093 CDR-H1 | GYTFTSYWMH | SEQ ID NO: 19 |
| | PP-1093 CDR-H2 | EIDPSDSYTNYNQKFKG | SEQ ID NO: 20 |
| | PP-1093 CDR-H3 | AKSNYVVPWYFDV | SEQ ID NO: 21 |
| | PP-1093 CDR-L1 | RSSKSLLHSNGITYLY | SEQ ID NO: 6 |

TABLE 5 -continued

Sequence of 1093 humanized anti-hNAMPT antibodies

| Antibody | Description | Amino Acid Sequence | Sequence Identifier |
|---|---|---|---|
| | PP-1093 CDR-L2 | QMSNLAS | SEQ ID NO: 7 |
| | PP-1093 CDR-L3 | AQNLELPWT | SEQ ID NO: 22 |
| SS-1093 | SS-1093 heavy chain variable region (VH) (CDRs underlined) | EVQLVQSGAEVKKPGESLRISCKA SGYTFTSYWMHWVRQMPGKGLE WMGEIDPSDSYTNYNQKFKGHVT ISADKSISTAYLQWSSLKASDTAM YYCAKSNYVVPWYFDVWGQGTL VTVSS | SEQ ID NO: 26 |
| | SS-1093 light chain variable region (VL) (CDRs underlined) | EIVLTQSPATLSLSPGERATLSCRS SKSLLHSNGITYLYWYQQKPGQA PRLLIYQMSNLASGIPARFSGSGSG TDFTLTISSLEPEDFAVYYCAQNLE LPWTFGGGTKLEIK | SEQ ID NO: 24 |
| | SS-1093 CDR-H1 | GYTFTSYWMH | SEQ ID NO: 19 |
| | SS-1093 CDR-H2 | EIDPSDSYTNYNQKFKG | SEQ ID NO: 20 |
| | SS-1093 CDR-H3 | AKSNYVVPWYFDV | SEQ ID NO: 21 |
| | SS-1093 CDR-L1 | RSSKSLLHSNGITYLY | SEQ ID NO: 6 |
| | SS-1093 CDR-L2 | QMSNLAS | SEQ ID NO: 7 |
| | SS-1093 CDR-L3 | AQNLELPWT | SEQ ID NO: 22 |
| UU-1093 | UU-1093 heavy chain variable region (VH) (CDRs underlined) | EVQLVQSGAEVKKPGESLRISCKA SGYTFTSYWMHWVRQMPGKGLE WMGEIDPSDSYTNYNQKFKGHVT ISADKSISTAYLQWSSLKASDTAM YYCAKSNYVVPWYFDVWGQGTL VTVSS | SEQ ID NO: 26 |
| | UU-1093 light chain variable region (VL) (CDRs underlined) | EIVLTQSPGTLSLSPGERATLSCRS SKSLLHSNGITYLYWYQQKPGQA PRLLIYQMSNLASGIPDRFSGSGSG TDFTLTISRLEPEDFAVYYCAQNL ELPWTFGGGTKLEIK | SEQ ID NO: 18 |
| | UU-1093 CDR-H1 | GYTFTSYWMH | SEQ ID NO: 19 |
| | UU-1093 CDR-H2 | EIDPSDSYTNYNQKFKG | SEQ ID NO: 20 |
| | UU-1093 CDR-H3 | AKSNYVVPWYFDV | SEQ ID NO: 21 |
| | UU-1093 CDR-L1 | RSSKSLLHSNGITYLY | SEQ ID NO: 6 |
| | UU-1093 CDR-L2 | QMSNLAS | SEQ ID NO: 7 |
| | UU-1093 CDR-L3 | AQNLELPWT | SEQ ID NO: 22 |
| XX-1093 | XX-1093 heavy chain variable region (VH) (CDRs underlined) | QVQLVQSGAEVKKPGASVKVSCK ASGYTFTSYWMHWVRQAPGQGL EWMGEIDPSDSYTNYNQKFKGRV TMTRDTSTSTVYMELSSLRSEDTA VYYCAKSNYVVPWYFDVWGTGT TVTVSS | SEQ ID NO: 27 |
| | XX-1093 light chain variable region (VL) (CDRs underlined) | EIVLTQSPATLSLSPGERATLSCRS SKSLLHSNGITYLYWYQQKPGQA PRLLIYQMSNLASGIPARFSGSGSG TDFTLTISSLEPEDFAVYYCAQNLE LPWTFGGGTKLEIK | SEQ ID NO: 24 |
| | XX-1093 CDR-H1 | GYTFTSYWMH | SEQ ID NO: 19 |
| | XX-1093 CDR-H2 | EIDPSDSYTNYNQKFKG | SEQ ID NO: 20 |
| | XX-1093 CDR-H3 | AKSNYVVPWYFDV | SEQ ID NO: 21 |
| | XX-1093 CDR-L1 | RSSKSLLHSNGITYLY | SEQ ID NO: 6 |
| | XX-1093 CDR-L2 | QMSNLAS | SEQ ID NO: 7 |
| | XX-1093 CDR-L3 | AQNLELPWT | SEQ ID NO: 22 |
| ZZ-1093 | ZZ-1093 heavy chain variable region (VH) (CDRs underlined) | QVQLVQSGAEVKKPGASVKVSCK ASGYTFTSYWMHWVRQAPGQGL EWMGEIDPSDSYTNYNQKFKGRV TMTRDTSTSTVYMELSSLRSEDTA VYYCAKSNYVVPWYFDVWGTGT TVTVSS | SEQ ID NO: 27 |
| | ZZ-1093 light chain variable region (VL) (CDRs underlined) | EIVLTQSPGTLSLSPGERATLSCRS SKSLLHSNGITYLYWYQQKPGQA PRLLIYQMSNLASGIPDRFSGSGSG TDFTLTISRLEPEDFAVYYCAQNL ELPWTFGGGTKLEIK | SEQ ID NO: 18 |
| | ZZ-1093 CDR-H1 | GYTFTSYWMH | SEQ ID NO: 19 |
| | ZZ-1093 CDR-H2 | EIDPSDSYTNYNQKFKG | SEQ ID NO: 20 |
| | ZZ-1093 CDR-H3 | AKSNYVVPWYFDV | SEQ ID NO: 21 |
| | ZZ-1093 CDR-L1 | RSSKSLLHSNGITYLY | SEQ ID NO: 6 |
| | ZZ-1093 CDR-L2 | QMSNLAS | SEQ ID NO: 7 |
| | ZZ-1093 CDR-L3 | AQNLELPWT | SEQ ID NO: 22 |

TABLE 6

Comparison of HC CDRs of 1093 anti-hNAMPT antibodies with HC CDRs of AL-310

| | Heavy Chain (HC) CDR1 | | | | | | | | | | SEQ ID NO: | HC CDR2 | | | | | | | | | | |
|---|---|---|---|---|---|---|---|---|---|---|---|---|---|---|---|---|---|---|---|---|---|---|
| AL-303 | G | Y | T | F | T | S | Y | W | M | Q | 19 | E | I | D | P | S | D | S | Y | T | N | Y |
| FF-1093 | | | | | | | | | | | 19 | | | | | | | | | | | |
| II-1093 | | | | | | | | | | | 19 | | | | | | | | | | | |
| NN-1093 | | | | | | | | | | | 19 | | | | | | | | | | | |
| PP-1093 | | | | | | | | | | | 19 | | | | | | | | | | | |
| SS-1093 | | | | | | | | | | | 19 | | | | | | | | | | | |
| UU-1093 | | | | | | | | | | | 19 | | | | | | | | | | | |
| XX-1093 | | | | | | | | | | | 19 | | | | | | | | | | | |
| ZZ-1093 | | | | | | | | | | | 19 | | | | | | | | | | | |

| | HC CDR2 | | | | | | SEQ ID NO: | HC CDR3 | | | | | | | | | | | | SEQ ID NO: |
|---|---|---|---|---|---|---|---|---|---|---|---|---|---|---|---|---|---|---|---|---|
| AL-303 | N | Q | K | F | K | G | 20 | A | K | S | N | Y | V | V | P | W | Y | F | D | V | 21 |
| FF-1093 | | | | | | | 20 | | | | | | | | | | | | | | 21 |
| II-1093 | | | | | | | 20 | | | | | | | | | | | | | | 21 |
| NN-1093 | | | | | | | 20 | | | | | | | | | | | | | | 21 |
| PP-1093 | | | | | | | 20 | | | | | | | | | | | | | | 21 |
| SS-1093 | | | | | | | 20 | | | | | | | | | | | | | | 21 |
| UU-1093 | | | | | | | 20 | | | | | | | | | | | | | | 21 |
| XX-1093 | | | | | | | 20 | | | | | | | | | | | | | | 21 |
| ZZ-1093 | | | | | | | 20 | | | | | | | | | | | | | | 21 |

TABLE 7

Comparison of LC CDRs of 1093 anti-hNAMPT antibodies with LC CDRs of AL-310

| | Light Chain (LC) CDR1 | | | | | | | | | | | | | | | | SEQ ID NO: | LC CDR2 | |
|---|---|---|---|---|---|---|---|---|---|---|---|---|---|---|---|---|---|---|---|
| AL-310 | R | S | S | K | S | L | L | H | S | N | G | I | T | Y | L | Y | 6 | Q | M |
| FF-1093 | | | | | | | | | | | | | | | | | 6 | | |
| II-1093 | | | | | | | | | | | | | | | | | 6 | | |
| NN-1093 | | | | | | | | | | | | | | | | | 6 | | |
| PP-1093 | | | | | | | | | | | | | | | | | 6 | | |
| SS-1093 | | | | | | | | | | | | | | | | | 6 | | |
| UU-1093 | | | | | | | | | | | | | | | | | 6 | | |

TABLE 7-continued

Comparison of LC CDRs of 1093 anti-hNAMPT antibodies with LC CDRs of AL-310

| | SEQ ID NO: |
|---|---|
| XX-1093 | 6 |
| ZZ-1093 | 6 |

| | LC CDR2 | | | | | SEQ ID NO: | LC CDR3 | | | | | | | | | SEQ ID NO: |
|---|---|---|---|---|---|---|---|---|---|---|---|---|---|---|---|---|
| AL-310 | S | N | L | A | S | 7 | A | Q | N | L | E | L | P | W | T | 22 |
| FF-1093 | | | | | | 7 | | | | | | | | | | 22 |
| II-1093 | | | | | | 7 | | | | | | | | | | 22 |
| NN-1093 | | | | | | 7 | | | | | | | | | | 22 |
| PP-1093 | | | | | | 7 | | | | | | | | | | 22 |
| SS-1093 | | | | | | 7 | | | | | | | | | | 22 |
| UU-1093 | | | | | | 7 | | | | | | | | | | 22 |
| XX-1093 | | | | | | 7 | | | | | | | | | | 22 |
| ZZ-1093 | | | | | | 7 | | | | | | | | | | 22 |

Example 8. Mapping the Epitopes of Humanized Anti-hNAMPT Antibodies

The epitopes of humanized anti-NAMPT antibody K-1076 (described in Example 6) and humanized anti-NAMPT antibody NN-1093 (described in Example 7) were mapped using both linear and conformational epitope mapping.

A library of peptide-based peptide mimics was synthesized using Fmoc-based solid-phase peptide synthesis. To generate a library of linear peptide mimics, the amino acid sequence of human NAMPT (SEQ ID NO: 60) was split in overlapping fragments in silico, and then synthesized on a solid support. An amino functionalized polypropylene support was obtained by grafting with a proprietary hydrophilic polymer formulation, followed by reaction with t-butyloxycarbonyl-hexamethylenediamine (BocHMDA) using dicyclohexylcarbodiimide (DCC) with N-hydroxybenzotriazole (HOBt) and subsequent cleavage of the Boc-groups using trifluoroacetic acid (TFA). Standard Fmoc-peptide synthesis was used to synthesize peptides on the amino-functionalized solid support by custom modified JANUS liquid handling stations (Perkin Elmer).

Synthesis of structural mimics was done using a PEPSCAN' proprietary Chemically Linked Peptides on Scaffolds (CLIPS™) technology. CLIPS™ technology allows to structure peptides into single loops, double-loops, triple loops, sheet-like folds, helix-like folds, and combinations thereof. CLIPS™ templates are coupled to cysteine residues. The side-chains of multiple cysteines in the peptides were coupled to one or two CLIPS™ templates. For example, a 0.5 mM solution of the P2 CLIPS™ (2,6-bis(bromomethyl) pyridine) was dissolved in ammonium bicarbonate (20 mM, pH 7.8)/acetonitrile (1:3(v/v)). This solution was added onto the peptide arrays. The CLIPS™ template binds to side-chains of two cysteines as present in the solid-phase bound peptides of the peptide-arrays (455 wells plate with 3 μl wells). The peptide arrays were gently shaken in the solution for 30 to 60 minutes while completely covered in solution. Finally, the peptide arrays were washed extensively with excess of $H_2O$ and sonicated in disrupt-buffer containing 1% SDS/0.1% 2,2'-(Ethylenedioxy)diethanethiol in PBS (pH 7.2) at 70° C. for 30 minutes, followed by sonication in $H_2O$ for another 45 minutes. The T3 CLIPS™ carrying peptides were made in a similar way, but with three cysteines.

The binding of antibody to each of the synthesized peptides was tested in a PEPSCAN™-based ELISA. The peptide arrays were incubated with primary antibody solution (overnight at 4° C.). After washing, the peptide arrays were incubated with a 1/1000 dilution of an appropriate detection antibody (an antibody peroxidase conjugate (SBA)) for one hour at 25° C. A HRP-conjugated goat anti-human antibody (Southern Biotech; Catalog No: 2010-05) was used as the detection antibody. After washing, the peroxidase substrate 2,2'-azino-di-3-ethylbenzthiazoline sulfonate (ABTS) and 20 μl/ml of 3 percent $H_2O_2$ were added. After one hour, the color development was measured. The color development was quantified with a charge coupled device (CCD) camera and an image processing system.

The values obtained from the CCD camera ranged from 0 to 3000 mAU, similar to a standard 96-well plate ELISA-reader. The results were quantified and stored into the Peplab database. Occasionally a well containing an air-bubble resulted in a false-positive value; hence, the cards were manually inspected and any values caused by an air-bubble was scored as 0.

To verify the quality of the synthesized peptides, a separate set of positive and negative control peptides was synthesized in parallel. These were screened with commercial antibodies 3C9 and 57.9 (Posthumus et al. (*J Virol* 64:3304-3309, 1990)).

Data analysis and interpretation was performed using a box-and-whisker plot, linear intensity profile, and heat map analysis.

Ten different sets (Set 1-Set 10) of peptides, ranging in size from 9 to 30 amino acids, were synthesized, as described below.

Set 1 (LIN15)

Set 1 peptides, also referred to herein as LIN15 peptides, are 15 amino acid long linear peptides that were derived from the target sequence of NAMPT with an offset of one residue.

Set 2 (LIN15.AA)

Set 2 peptides, also referred to herein as LIN15.AA peptides, are 15 amino acid long linear peptides that are similar to Set 1 or LIN15 peptides, but with residues on positions 10 and 11 replaced by Ala. When a native Ala would occur on either position, it was replaced by Gly.

Set 3 (LIN30)

Set 3 peptides, also referred to herein as LIN30 peptides, are 30 amino acid long linear peptides that were derived from the target sequence of NAMPT with an offset of one residue.

Set 4 (LOOP7)

Set 4 peptides, also referred to herein as LOOP7 peptides, are 9 amino acid long constrained peptides. On positions 2-8 are 7-mer peptides derived from the target sequence of NAMPT with an offset of one residue. Cys residues were inserted on positions 1 and 9 and joined by mP2 CLIPS™ in order to create a loop mimic. Native Cys were replaced by Cys-acm (denoted "2").

Set 5 (LOOP15)

Set 5 peptides, also referred to herein as LOOP15 peptides, are 17 amino acid long constrained peptides. On positions 2 16 are 15-mer peptides derived from the target sequence of NAMPT (SEQ ID NO: 60) with an offset of one residue. Cys residues were inserted on positions 1 and 17 and joined by mP2 CLIPS™ in order to create a loop mimic. Native Cys were replaced by Cys-acm (denoted "2").

Set 6 (LOOP15.AA)

Set 6 peptides, also referred to herein as LOOP15.AA peptides, are 17 amino acid long constrained peptides that are similar to Set 5 or LOOP15 peptides, but with residues on positions 10 and 11 replaced by Ala. When a native Ala would occur on either position, it is replaced by Gly.

Set 7 (LOOP25)

Set 7 peptides, also referred to herein as LOOP25 peptides, are 27 amino acid long constrained peptides. On positions 2-26 are 25-mer peptides derived from the target sequence of NAMPT (SEQ ID NO: 60) with an offset of one residue. Cys residues were inserted on positions 1 and 27 and joined by mP2 CLIPS™ in order to create a loop mimic. Native Cys were replaced by Cys-acm (denoted "2").

Set 8 (BET)

Set 8 peptides, also referred to herein as BET peptides, are 22 amino acid long (β-turn peptide mimics. On positions 2-21 are 20-mer peptides derived from the target sequence of NAMPT (SEQ ID NO: 60) with an offset of one residue. Residues on positions 11 and 12 are replaced by "PG" motif in order to induce the β-turn formation. Cys residues were inserted on positions 1 and 22 and joined by mP2 CLIPS™ in order to stabilize the mimic. Native Cys were replaced by Cys-acm (denoted "2").

Set 9 (HEL.CC)

Set 9 peptides, also referred to herein as HEL.CC peptides, are 22 amino acid long α-helical peptide mimics derived from residues of the target sequence (NAMPT; SEQ ID NO: 60) with an offset of one residue. Cys residues were inserted on positions 1 and 5 and joined by means of mP2 CLIPS™ in order to nucleate an a-helical structure. Native Cys were replaced by Cys-acm (denoted "2").

Set 10 (HEL.IL)

Set 10 peptides, also referred to herein as HEL.IL peptides, are 26 amino acid long α-helical peptide mimics derived from residues of the target sequence (NAMPT; SEQ ID NO: 60) with an offset of one residue Leu and Ile residues were inserted in the sequence to facilitate a helical secondary structure without covalent restraints.

Screening Details

Antibody binding depends on a combination of factors, including concentration of the antibody and the amounts and nature of competing proteins in the ELISA buffer. Also, the pre-coat conditions (the specific treatment of the peptide arrays prior to incubation with the experimental sample) affect binding. These details are summed up in Table 8. For the PEPSCAN™ Buffer and Preconditioning (SQ), the numbers indicate the relative amount of competing protein (a combination of horse serum and ovalbumin).

TABLE 8

| Screening details | | | |
|---|---|---|---|
| Label | Dilution | Sample buffer | Pre-conditioning |
| K-1076 (Ab-1076-HC2-LC5) | 5 ug/mL | 10% SQ | 10% SQ |
| NN-1093 (NN-1093-HC3-LC3) | 2 ug/mL | 1% SQ | 1% SQ |

For both antibodies in this study, we observed binding signals in various different regions throughout the NAMPT sequence. This suggests that the epitope for both antibodies are discontinuous epitopes. All signals observed were specific for the antibodies as incubation with secondary antibody alone did not result in any signal on the arrays. For Ab-1076-HC2-LC5, the core sequences derived from overlapping peptide sequences seem to form a binding interface that spans both monomers within an NAMPT dimer. Especially in the plot for the LIN30 mimic a dominant putative binding site can be observed, that is surrounded in the structure by additional sequences derived from lower intensity peaks. Tentative core epitopes for the antibody are listed below. Both antibodies bound the dimeric form of NAMPT.

The identified epitope candidates for both sequences showed a significant amount of recurring sequence similarities (e.g. $_{17}$SYKVTHYKQYPPNTSKVYSYFECREKKT$_{44}$ (SEQ ID NO: 61) vs. $_{162}$ATNSREQKK$_{170}$ (SEQ ID NO: 63), $_{29}$NTSKVYSYFECREKKTENSKLRK$_{51}$ (SEQ ID NO: 72) vs. $_{332}$FPVTENSKGYK$_{342}$ (SEQ ID NO: 67), and $_{216}$KGTDTVAGLALIKKYYGTK$_{234}$ (SEQ ID NO: 75) vs. $_{316}$NPLDTVLKVLEILGKK$_{331}$ (SEQ ID NO: 76).

TABLE 9

List of main epitope candidates found in this study. Top candidates based on an intensity of at least 2x the median intensity value for the linear and conformational peptide arrays.

| Antibody | NAMPT Residue | Main epitope candidates identifier | Sequence |
|---|---|---|---|
| K-1076 | 17-44 | SYKVTHYKQYPPNT SKVYSYFECREKKT | SEQ ID NO: 61 |
| | 117-127 | KAVPEGFVIPR | SEQ ID NO: 62 |
| | 162-170 | ATNSREQKK | SEQ ID NO: 63 |
| | 242-261 | VPAAEHSTITAWGK DHEKDA | SEQ ID NO: 64 |
| | 262-273 | FEHIVTQFSSVP | SEQ ID NO: 65 |
| | 289-305 | KIWGEDLRHLI VSRSTQ | SEQ ID NO: 66 |

TABLE 9-continued

List of main epitope candidates found in this study. Top candidates based on an intensity of at least 2x the median intensity value for the linear and conformational peptide arrays.

| Antibody | NAMPT Residue | Main epitope candidates identifier | Sequence |
|---|---|---|---|
| | 332-342 | FPVTENSKGYK | SEQ ID NO: 67 |
| | 374-389 | SIENIAFGSGG GLLQK | SEQ ID NO: 68 |
| | 418-425 | VADPNKRS | SEQ ID NO: 69 |
| | 453-466 | YGQDLLHTVFKNGK | SEQ ID NO: 70 |
| | 408-417 | GLGINVFKDP | SEQ ID NO: 71 |
| NN-1093 | 29-51 | NTSKVYSYFECREK KTENSKLRK | SEQ ID NO: 72 |
| | 61-72 | GLQYILNKYLKG | SEQ ID NO: 73 |
| | 156-170 | WYPITVATN SREQKK | SEQ ID NO: 74 |
| | 216-234 | KGTDTVAGLALIK KYYGTK | SEQ ID NO: 75 |
| | 316-331 | NPLDTVLKVLEIL GKK | SEQ ID NO: 76 |
| | 332-342 | FPVTENSKGYK | SEQ ID NO: 77 |
| | 373-389 | WSIENIAFGS GGGLLQK | SEQ ID NO: 78 |
| | 417-431 | PVADPNKRSK KGRLS | SEQ ID NO: 79 |
| | 454-469 | GQDLLHTVF KNGKVTK | SEQ ID NO: 80 |
| | 470-478 | SYSFDEIRK | SEQ ID NO: 81 |

Example 9. Characterization of Humanized Anti-hNAMPT Antibodies 1076 humanized anti-hNAMPT antibodies described in Example 6, and 1093 humanized anti-hNAMPT antibodies described in Example 7 were subjected to in vitro and in vivo and testing for selection of lead humanized anti-hNAMPT antibodies.

Effect of Humanized Anti-hNAMPT Antibodies on hNAMPT-Induced Inflammatory Signaling Effect of 1093 humanized anti-hNAMPT antibodies CC-1093, KK-1093, RR-1093, UU-1093, and XX-1093 on hNAMPT-induced inflammatory signaling was assessed by evaluation of NFκB activation in cells that were exposed to hNAMPT in absence or presence of these antibodies.

Recombinant hNAMPT (1.5 μg/ml) was premixed with vehicle or 100 μg/ml of a 1093 humanized anti-hNAMPT antibody (CC-1093, KK-1093, RR-1093, UU-1093, or XX-1093). Human lung endothelial cells (EC) were stimulated by exposing the cells to the hNAMPT mix for 1 hr. Unstimulated cells, which were not exposed to the hNAMPT mix, served as negative control ("NC"). Stimulated cells, which were exposed to hNAMPT premixed with vehicle alone ("--"), served as positive control. Activation of NFκB in the cells was assessed by evaluating NFκB luciferase activity (NFκB-SecNanoLuc) (n=3-4 for each mAb). Results from the luciferase assay are provided in FIG. 7A.

Figure 7B:
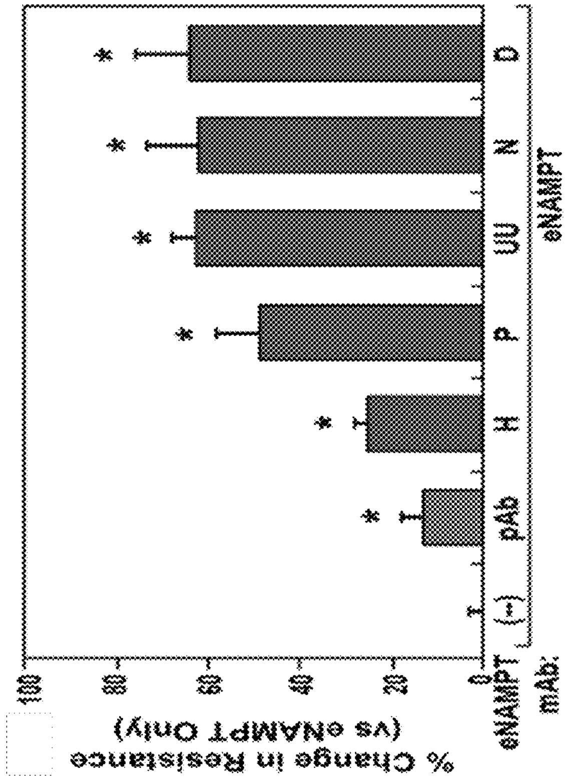
FIGS. 7A-7B are graphical representations of the effect of humanized 1076 and 1093 anti-hNAMPT antibodies.
Figure 7A:
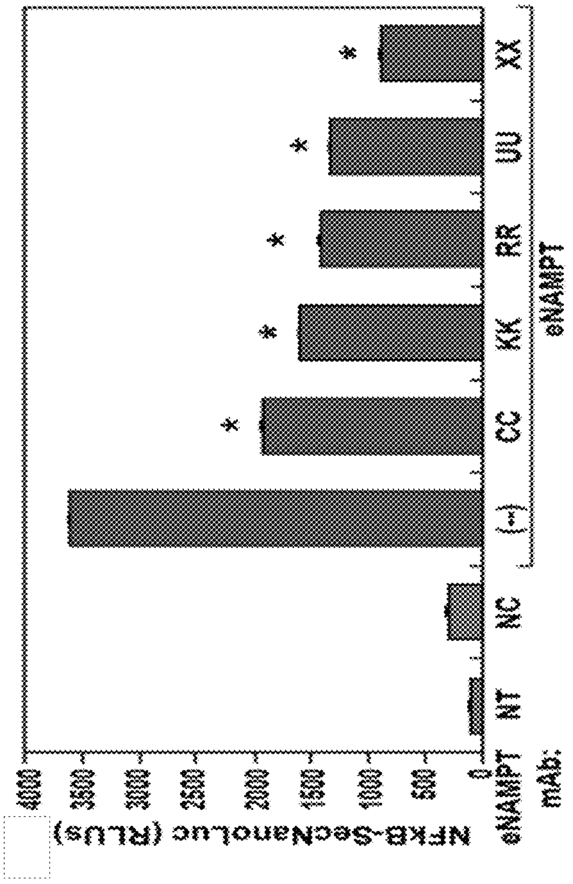

As shown in FIG. 7A, hNAMPT induced NFκB activation in the hNAMPT-stimulated cells, which was substantially attenuated in presence of humanized anti-hNAMPT antibodies CC-1093, KK-1093, RR-1093, UU-1093, or XX-1093. While all of the five antibodies effectively reduced hNAMPT-induced activation of NFκB, the most substantial effect was observed with UU-1093 and XX-1093.

Effect of Humanized Anti-hNAMPT Antibodies on hNAMPT-Induced Decline in EC Barrier Integrity EC electrical resistance is a reflection of lung EC barrier integrity. Accordingly, the effect of 1093 humanized anti-hNAMPT antibody UU-1093, and 1076 humanized anti-hNAMPT antibodies H-1076, P-1076, N-1076, and D-1076 on hNAMPT-induced decline in EC barrier integrity was assessed by evaluating electrical resistance in ECs that were exposed to hNAMPT in absence or presence of these antibodies.

Recombinant hNAMPT (1.5 μg/ml) was premixed with vehicle alone, anti-NAMPT pAb, or a humanized anti-hNAMPT antibody (UU-1093, H-1076, P-1076, N-1076, or D-1076). Human lung ECs were stimulated by exposing the cells to the hNAMPT mix for 1 hr. Stimulated cells, which were exposed to hNAMPT premixed with vehicle alone or to hNAMPT premixed with pAb, served as controls. EC electrical resistance was evaluated as a readout of EC barrier integrity. Results from the testing are provided in FIG. 7B.

As shown in FIG. 7B, ECs exposed to hNAMPT premixed with each of the humanized anti-hNAMPT antibodies showed substantial induction of EC barrier activity over the control cells. Thus, hNAMPT-mediated decline in EC barrier activity was effectively reversed in presence of 1076 and 1093 humanized anti-hNAMPT antibodies.

In Vivo Testing of Humanized Anti-hNAMPT Antibodies in Lung Injury

Ability of 1076 humanized anti-hNAMPT antibodies (V-1076, N-1076, K-1076, and P-1076) and 1093 humanized anti-hNAMPT antibodies (SS-1093, CC-1093, XX-1093, and UU-1093) to treat lung injury was tested in vivo, using mouse and rat lung injury models.

To assess the effect of humanized anti-hNAMPT antibodies on a murine model of lung injury, V-1076, N-1076, K-1076, P-1076, SS-1093, CC-1093, XX-1093, or UU-1093 were injected intravenously at a dose of 0.4 mg/kg to mice that were exposed to LPS for 8 hr and VILI for the final 4 hr. Mice injected with vehicle and exposed to hNAMPT and VILI served as controls. Lung injury in the mice was assessed by analyzing the expression of BAL protein, and count of BAL-expressing cells. Also, edema and inflammatory cell infiltration in lung tissue was assessed by H & E staining, as readout of lung injury. Results from this "two hit" model of lung injury are provided in FIGS. 8A, 8B, and 8D.

Figure 8A:
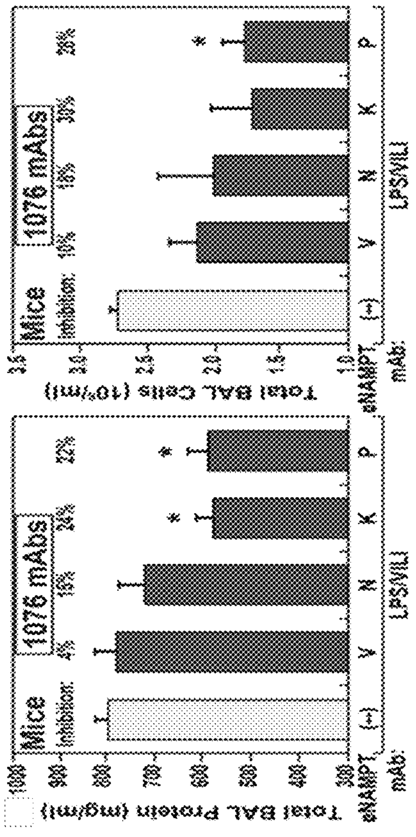
FIGS. 8A-8D depict the effect of humanized 1076 and 1093 anti-hNAMPT antibodies on murine and rat models of lung injury.

As described in FIG. 8A, compared to the control mice, BAL protein level (FIG. 8A, left panel) and count of BAL-expressing cells (FIG. 8A, right panel) was effectively reduced in mice that were injected with either of the 1076 humanized anti-hNAMPT antibodies. While all of the 1076 humanized anti-hNAMPT antibodies tested effectively reduced lung injury in this "two hit" murine model, the most substantial effect was observed with P-1076.

Figure 8B:
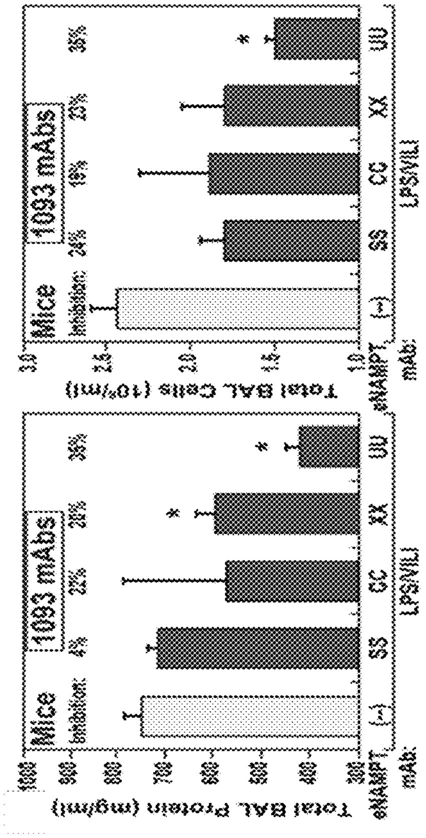

As described in FIG. 8B, compared to the control mice, BAL protein level (FIG. 8B, left panel) and count of BAL-expressing cells (FIG. 8B, right panel) was effectively reduced in mice that were injected with either of the 1093 humanized anti-hNAMPT antibodies. While all of the 1093 humanized anti-hNAMPT antibodies tested effectively reduced lung injury in this "two hit" murine model, the most substantial effect was observed with UU-1093. Moreover, as described in FIG. 8D, protective effect of UU-1093 in the two-hit lung injury model was further reflected by reduced inflammatory cell infiltration and reduced edema in lung tissue from mice that were injected with UU-1093.

To assess the effect of humanized anti-hNAMPT antibody on a rat model of lung injury, 40 mg/kg, 80 mg/kg, or 160 mg/kg of P-1076 was injected intravenously to Sprague Dawley rats that were exposed to LPS. Rats injected with vehicle and exposed to LPS served as positive controls. Rats injected with vehicle alone and not exposed to LPS served as negative controls. Lung injury in the rats was assessed by analyzing the expression of BAL protein, and count of BAL-expressing cells. Results from this rat model of lung injury are provided in FIG. 8C.

Figure 8C:
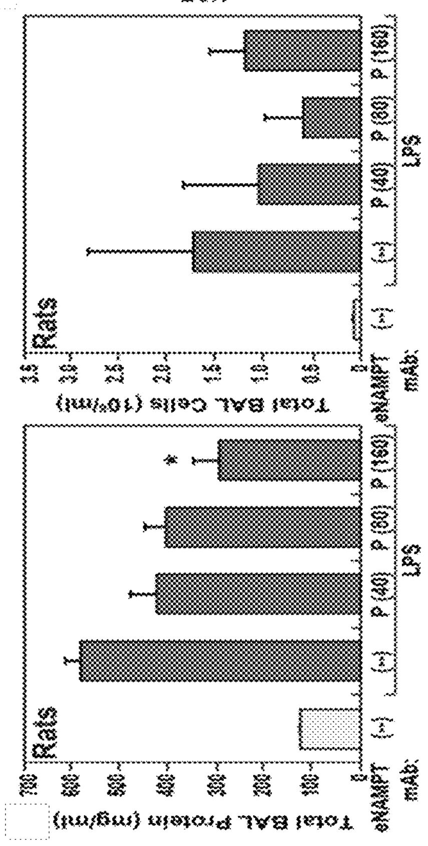
Figure 8D:
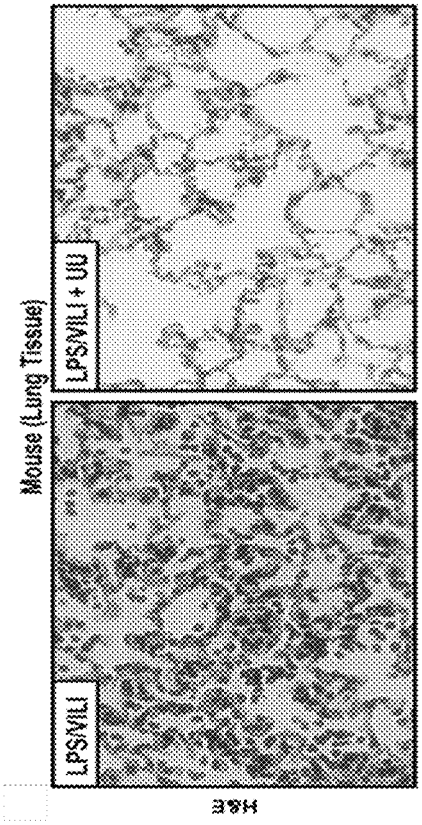

As described in FIG. 8C, compared to control mice (which were injected with vehicle and exposed to LPS), BAL protein level (FIG. 8C, left panel) and count of BAL-expressing cells (FIG. 8C, right panel) was effectively reduced in mice that were injected with humanized anti-hNAMPT antibody P-1076.

Thus, as described in FIG. 8, while all the tested humanized anti-hNAMPT antibodies effectively reduced lung injury in in vivo lung injury models, the most substantial effect was observed with P-1076 and UU-1093. Accordingly, P-1076 and UU-1093 were selected as the lead humanized and anti-hNAMPT antibodies, and were further modified to generate improved anti-hNAMPT antibodies.

Example 10. Modification of Humanized Anti-hNAMPT Antibody P-1076

Based on the results of in vitro and in vivo testing described in Example 9, anti-hNAMPT antibody P-1076 was selected for further modification to generate improved 1076 anti-hNAMPT antibodies.

P-1076-Mod Humanized Anti-hNAMPT Antibodies

P-1076-mod refers to humanized anti-hNAMPT antibodies that were generated by modifying 1076 humanized anti-hNAMPT antibody P-1076.

To generate improved P-1076-mod anti-hNAMPT antibodies, one or more mutations were introduced into the P-1076 sequence by de nova synthesis of the variable domain, or mutagenic oligonucleotide primers and polymerase chain reactions, or both, by methods well known in the art. These mutations were introduced to remove oxidation sites, to reduce or remove deamidation, to remove potential cleavage or fragmentation sites, to remove potential T-cell epitopes, and/or to reduce binding of potential T-cell epitopes. Different combinations of back mutations and other mutations were constructed for heavy and/or light chains of P-1076 to generate P-1076-mod anti-hNAMPT antibodies P-1076-mod1, P-1076-mod2, P-1076-mod3, P-1076-mod4, P-1076-mod5, P-1076-mod6, P-1076-mod7, P-1076-mod8, P-1076-mod9, P-1076-mod10, and P-1076-mod11.

Amino acid sequences of the heavy and light chain variable regions of the modified P-1076-mod anti-hNAMPT antibodies are provided in Table 10. In Table 10, mutated residues are in bold font. Table 11 provides an alignment of the amino acid sequences of the heavy chain CDRs for modified P-1076-mod anti-hNAMPT antibodies P-1076-mod1, P-1076-mod2, P-1076-mod3, P-1076-mod4, P-1076-mod5, P-1076-mod6, P-1076-mod7, P-1076-mod8, P-1076-mod9, P-1076-mod10, and P-1076-mod11 in comparison to P-1076. Table 12 provides an alignment of the amino acid sequences of the light chain CDRs for modified P-1076-mod anti-hNAMPT antibodies P-1076-mod1, P-1076-mod2, P-1076-mod3, P-1076-mod4, P-1076-mod5, P-1076-mod6, P-1076-mod7, P-1076-mod8, P-1076-mod9, P-1076-mod10, and P-1076-mod11 in comparison to P-1076. Blank spaces in Tables 11 and 12 indicate that the residue is the same as P-1076. A summary of biophysical characteristics of modified P-1076-mod anti-hNAMPT antibodies is provided in Table 13.

P-1076-Mod1

P-1076-mod anti-hNAMPT antibody P-1076-mod1 has a heavy chain variable region with an amino acid sequence as set forth in SEQ ID NO: 28, and a light chain variable region with an amino acid sequence as set forth in SEQ ID NO: 30. The heavy chain variable region of P-1076-mod1 contains a CDR1 domain with an amino acid sequence as set forth in SEQ ID NO: 3, a CDR2 domain with an amino acid sequence as set forth in SEQ ID NO: 29, and a CDR3 domain with an amino acid sequence as set forth in SEQ ID NO: 5. For the heavy chain of P-1076-mod1, a D-to-E mutation was introduced into the P-1076 VH CDR2 to remove a potential cleavage or fragmentation site. The light chain variable region of P-1076-mod1 contains a CDR1 domain with an amino acid sequence as set forth in SEQ ID NO: 11, a CDR2 domain with an amino acid sequence as set forth in SEQ ID NO: 14, and a CDR3 domain with an amino acid sequence as set forth in SEQ ID NO: 8. For the light chain of P-1076-mod1, a L-to-V mutation was introduced in the framework region of P-1076 VL to remove a potential T-cell epitope.

P-1076-Mod2

P-1076-mod anti-hNAMPT antibody P-1076-mod2 has a heavy chain variable region with an amino acid sequence as set forth in SEQ ID NO: 28, and a light chain variable region with an amino acid sequence as set forth in SEQ ID NO: 31. The heavy chain variable region of P-1076-mod2 contains a CDR1 domain with an amino acid sequence as set forth in SEQ ID NO: 3, a CDR2 domain with an amino acid sequence as set forth in SEQ ID NO: 29, and a CDR3 domain with an amino acid sequence as set forth in SEQ ID NO: 5. For the heavy chain of P-1076-mod2, a D-to-E mutation was introduced into the P-1076 VH CDR2 to remove a potential cleavage or fragmentation site. The light chain variable region of P-1076-mod2 contains a CDR1 domain with an amino acid sequence as set forth in SEQ ID NO: 11, a CDR2 domain with an amino acid sequence as set forth in SEQ ID NO: 14, and a CDR3 domain with an amino acid sequence as set forth in SEQ ID NO: 8. For the light chain of P-1076-mod2, a L-to-I mutation was introduced in the framework region of P-1076 VL to remove a potential T-cell epitope.

P-1076-Mod3

P-1076-mod anti-hNAMPT antibody P-1076-mod3 has a heavy chain variable region with an amino acid sequence as set forth in SEQ ID NO: 28, and a light chain variable region with an amino acid sequence as set forth in SEQ ID NO: 32. The heavy chain variable region of P-1076-mod3 contains a CDR1 domain with an amino acid sequence as set forth in SEQ ID NO: 3, a CDR2 domain with an amino acid sequence as set forth in SEQ ID NO: 29, and a CDR3 domain with an amino acid sequence as set forth in SEQ ID NO: 5. For the heavy chain of P-1076-mod3, a D-to-E mutation was introduced into the P-1076 VH CDR2 to remove a potential cleavage or fragmentation site. The light chain variable region of P-1076-mod3 contains a CDR1 domain with an amino acid sequence as set forth in SEQ ID NO: 11, a CDR2 domain with an amino acid sequence as set forth in SEQ ID NO: 33, and a CDR3 domain with an amino acid sequence as set forth in SEQ ID NO: 8. For the light chain of P-1076-mod3, a L-to-V mutation was introduced in the framework region of P-1076 VL and a L-to-G mutation was introduced in the P-1076 VL CDR2 to remove potential T-cell epitopes.

P-1076-Mod4

P-1076-mod anti-hNAMPT antibody P-1076-mod4 has a heavy chain variable region with an amino acid sequence as set forth in SEQ ID NO: 28, and a light chain variable region with an amino acid sequence as set forth in SEQ ID NO: 34. The heavy chain variable region of P-1076-mod4 contains a CDR1 domain with an amino acid sequence as set forth in SEQ ID NO: 3, a CDR2 domain with an amino acid sequence as set forth in SEQ ID NO: 29, and a CDR3 domain with an amino acid sequence as set forth in SEQ ID NO: 5. For the heavy chain of P-1076-mod4, a D-to-E mutation was introduced into the P-1076 VH CDR2 to remove a potential cleavage or fragmentation site. The light chain variable region of P-1076-mod4 contains a CDR1 domain with an amino acid sequence as set forth in SEQ ID NO: 11, a CDR2 domain with an amino acid sequence as set forth in SEQ ID NO: 35, and a CDR3 domain with an amino acid sequence as set forth in SEQ ID NO: 8. For the light chain of P-1076-mod4, a L-to-V mutation was introduced in the framework region of P-1076 VL and a L-to-E mutation was introduced in the P-1076 VL CDR2 to remove potential T-cell epitopes.

P-1076-Mod5

P-1076-mod anti-hNAMPT antibody P-1076-mod5 has a heavy chain variable region with an amino acid sequence as set forth in SEQ ID NO: 28, and a light chain variable region with an amino acid sequence as set forth in SEQ ID NO: 36. The heavy chain variable region of P-1076-mod5 contains a CDR1 domain with an amino acid sequence as set forth in SEQ ID NO: 3, a CDR2 domain with an amino acid sequence as set forth in SEQ ID NO: 29, and a CDR3 domain with an amino acid sequence as set forth in SEQ ID NO: 5. For the heavy chain of P-1076-mod5, a D-to-E mutation was introduced into the P-1076 VH CDR2 to remove a potential cleavage or fragmentation site. The light chain variable region of P-1076-mod5 contains a CDR1 domain with an amino acid sequence as set forth in SEQ ID NO: 11, a CDR2 domain with an amino acid sequence as set forth in SEQ ID NO: 37, and a CDR3 domain with an amino acid sequence as set forth in SEQ ID NO: 8. For the light chain of P-1076-mod5, a L-to-I mutation was introduced in the framework region of P-1076 VL to remove a potential T-cell epitope, and a L-to-E mutation was introduced in the P-1076 VL CDR2 to reduce the binding of a potential T-cell epitope.

P-1076-Mod6

P-1076-mod anti-hNAMPT antibody P-1076-mod6 has a heavy chain variable region with an amino acid sequence as set forth in SEQ ID NO: 15, and a light chain variable region with an amino acid sequence as set forth in SEQ ID NO: 30. The heavy chain variable region of P-1076-mod6 contains a CDR1 domain with an amino acid sequence as set forth in SEQ ID NO: 3, a CDR2 domain with an amino acid sequence as set forth in SEQ ID NO: 4, and a CDR3 domain with an amino acid sequence as set forth in SEQ ID NO: 5. The heavy chain of P-1076-mod6 is identical to P-1076 VH. The light chain variable region of P-1076-mod6 contains a CDR1 domain with an amino acid sequence as set forth in SEQ ID NO: 11, a CDR2 domain with an amino acid sequence as set forth in SEQ ID NO: 14, and a CDR3 domain with an amino acid sequence as set forth in SEQ ID NO: 8. For the light chain of P-1076-mod5, a L-to-V mutation was introduced in the framework region of P-1076 VL to remove a potential T-cell epitope.

P-1076-Mod7

P-1076-mod anti-hNAMPT antibody P-1076-mod7 has a heavy chain variable region with an amino acid sequence as set forth in SEQ ID NO: 15, and a light chain variable region with an amino acid sequence as set forth in SEQ ID NO: 31. The heavy chain variable region of P-1076-mod7 contains a CDR1 domain with an amino acid sequence as set forth in SEQ ID NO: 3, a CDR2 domain with an amino acid sequence as set forth in SEQ ID NO: 4, and a CDR3 domain with an amino acid sequence as set forth in SEQ ID NO: 5. The heavy chain of P-1076-mod7 is identical to P-1076 VH. The light chain variable region of P-1076-mod7 contains a CDR1 domain with an amino acid sequence as set forth in SEQ ID NO: 11, a CDR2 domain with an amino acid sequence as set forth in SEQ ID NO: 14, and a CDR3 domain with an amino acid sequence as set forth in SEQ ID NO: 8. For the light chain of P-1076-mod7, a L-to-I mutation was introduced in the framework region of P-1076 VL to remove a potential T-cell epitope.

P-1076-Mod8

P-1076-mod anti-hNAMPT antibody P-1076-mod8 has a heavy chain variable region with an amino acid sequence as set forth in SEQ ID NO: 15, and a light chain variable region with an amino acid sequence as set forth in SEQ ID NO: 32. The heavy chain variable region of P-1076-mod8 contains a CDR1 domain with an amino acid sequence as set forth in SEQ ID NO: 3, a CDR2 domain with an amino acid sequence as set forth in SEQ ID NO: 4, and a CDR3 domain with an amino acid sequence as set forth in SEQ ID NO: 5. The heavy chain of P-1076-mod8 is identical to P-1076 VH. The light chain variable region of P-1076-mod8 contains a CDR1 domain with an amino acid sequence as set forth in SEQ ID NO: 11, a CDR2 domain with an amino acid sequence as set forth in SEQ ID NO: 33, and a CDR3 domain with an amino acid sequence as set forth in SEQ ID NO: 8. For the light chain of P-1076-mod8, a L-to-V mutation was introduced in the framework region of P-1076 VL and a L-to-G mutation was introduced in the P-1076 VL CDR2 to remove potential T-cell epitopes.

P-1076-Mod9

P-1076-mod anti-hNAMPT antibody P-1076-mod9 has a heavy chain variable region with an amino acid sequence as set forth in SEQ ID NO: 15, and a light chain variable region with an amino acid sequence as set forth in SEQ ID NO: 34. The heavy chain variable region of P-1076-mod9 contains a CDR1 domain with an amino acid sequence as set forth in SEQ ID NO: 3, a CDR2 domain with an amino acid sequence as set forth in SEQ ID NO: 4, and a CDR3 domain with an amino acid sequence as set forth in SEQ ID NO: 5. The heavy chain of P-1076-mod9 is identical to P-1076 VH. The light chain variable region of P-1076-mod9 contains a CDR1 domain with an amino acid sequence as set forth in SEQ ID NO: 11, a CDR2 domain with an amino acid sequence as set forth in SEQ ID NO: 35, and a CDR3 domain with an amino acid sequence as set forth in SEQ ID NO: 8. For the light chain of P-1076-mod9, a L-to-V mutation was introduced in the framework region of P-1076 VL and a L-to-E mutation was introduced in the P-1076 VL CDR2 to remove potential T-cell epitopes.

P-1076-Mod10

P-1076-mod anti-hNAMPT antibody P-1076-mod10 has a heavy chain variable region with an amino acid sequence as set forth in SEQ ID NO: 15, and a light chain variable region with an amino acid sequence as set forth in SEQ ID NO: 36. The heavy chain variable region of P-1076-mod10 contains a CDR1 domain with an amino acid sequence as set forth in SEQ ID NO: 3, a CDR2 domain with an amino acid sequence as set forth in SEQ ID NO: 4, and a CDR3 domain with an amino acid sequence as set forth in SEQ ID NO: 5. The heavy chain of P-1076-mod10 is identical to P-1076

VH. The light chain variable region of P-1076-mod10 contains a CDR1 domain with an amino acid sequence as set forth in SEQ ID NO: 11, a CDR2 domain with an amino acid sequence as set forth in SEQ ID NO: 37, and a CDR3 domain with an amino acid sequence as set forth in SEQ ID NO: 8. For the light chain of P-1076-mod10, a L-to-I mutation was introduced in the framework region of P-1076 VL to remove a potential T-cell epitope, and a L-to-V mutation was introduced in the P-1076 VL CDR2 to reduce the binding of a potential T-cell epitope.

P-1076-Mod11

Modified P-1076-mod anti-hNAMPT antibody P-1076-mod11 has a heavy chain variable region with an amino acid sequence as set forth in SEQ ID NO: 28, and a light chain variable region with an amino acid sequence as set forth in SEQ ID NO: 13. The heavy chain variable region of P-1076-mod11 contains a CDR1 domain with an amino acid sequence as set forth in SEQ ID NO: 3, a CDR2 domain with an amino acid sequence as set forth in SEQ ID NO: 29, and a CDR3 domain with an amino acid sequence as set forth in SEQ ID NO: 5. For the heavy chain of P-1076-mod11, a D-to-E mutation was introduced into the P-1076 VH CDR2 to remove a potential cleavage or fragmentation site. The light chain variable region of P-1076-mod11 contains a CDR1 domain with an amino acid sequence as set forth in SEQ ID NO: 11, a CDR2 domain with an amino acid sequence as set forth in SEQ ID NO: 14, and a CDR3 domain with an amino acid sequence as set forth in SEQ ID NO: 8. The light chain of P-1076-mod11 is identical to P-1076 VL.

TABLE 10

Sequence of P-1076-mod anti-hNAMPT antibodies

| Antibody | Description | Amino Acid Sequence | Sequence Identifier |
|---|---|---|---|
| P-1076-mod1 | P-1076-mod1 heavy chain variable region (VH) (CDRs underlined) | QVQLVQSGAEVTKPGASVKVSCK<br>ASGYTFTSYWMQWVRQAPGQGL<br>EWVGEI**E**PSNSYTNYNQKFRGRV<br>TLTRDTSTTTVYMELSSLRSEDTA<br>VYYCARGGYWGQGTTVTVSS | SEQ ID NO: 28 |
| | P-1076-mod1 light chain variable region (VL) (CDRs underlined) | DIVMTQSPLSLPVTPGEPASISCRSS<br>KSLLHSQGITYLYWY**V**QKPGQSP<br>QLLIYQLSNRASGVPDRFSGSGSG<br>TDFTLKISRVEAEDVGVYYCVQNL<br>ELPYTFGGGTKLEIK | SEQ ID NO: 30 |
| | P-1076-mod1 CDR-H1 | GYTFTSYWMQ | SEQ ID NO: 3 |
| | P-1076-mod1 CDR-H2 | EI**E**PSNSYTNYNQKFRG | SEQ ID NO: 29 |
| | P-1076-mod1 CDR-H3 | ARGGY | SEQ ID NO: 5 |
| | P-1076-mod1 CDR-L1 | RSSKSLLHSQG1TYLY | SEQ ID NO: 11 |
| | P-1076-mod1 CDR-L2 | QLSNRAS | SEQ ID NO: 14 |
| | P-1076-mod1 CDR-L3 | VQNLELPYT | SEQ ID NO: 8 |
| P-1076-mod2 | P-1076-mod2 heavy chain variable region (VH) (CDRs underlined) | QVQLVQSGAEVTKPGASVKVSCK<br>ASGYTFTSYWMQWVRQAPGQGL<br>EWVGEI**E**PSNSYTNYNQKFRGRV<br>TLTRDTSTTTVYMELSSLRSEDTA<br>VYYCARGGYWGQGTTVTVSS | SEQ ID NO: 28 |
| | P-1076-mod2 light chain variable region (VL) (CDRs underlined) | DIVMTQSPLSLPVTPGEPASISCRSS<br>KSLLHSQGITYLYWY**I**QKPGQSPQ<br>LLIYQLSNRASGVPDRFSGSGSGT<br>DFTLKISRVEAEDVGVYYCVQNLE<br>LPYTFGGGTKLEIK | SEQ ID NO: 31 |
| | P-1076-mod2 CDR-H1 | GYTFTSYWMQ | SEQ ID NO: 3 |
| | P-1076-mod2 CDR-H2 | EI**E**PSNSYTNYNQKFRG | SEQ ID NO: 29 |
| | P-1076-mod2 CDR-H3 | ARGGY | SEQ ID NO: 5 |
| | P-1076-mod2 CDR-L1 | RSSKSLLHSQGITYLY | SEQ ID NO: 11 |
| | P-1076-mod2 CDR-L2 | QLSNRAS | SEQ ID NO: 14 |
| | P-1076-mod2 CDR-L3 | VQNLELPYT | SEQ ID NO: 8 |

TABLE 10 -continued

Sequence of P-1076-mod anti-hNAMPT antibodies

| Antibody | Description | Amino Acid Sequence | Sequence Identifier |
|---|---|---|---|
| P-1076-mod3 | P-1076-mod3 heavy chain variable region (VH) (CDRs underlined) | QVQLVQSGAEVTKPGASVKVSCKASGYTFTSYWMQWVRQAPGQGLEWVGEIEPSNSYTNYNQKFRGRVTLTRDTSTTTVYMELSSLRSEDTAVYYCARGGYWGQGTTVTVSS | SEQ ID NO: 28 |
| | P-1076-mod3 light chain variable region (VL) (CDRs underlined) | DIVMTQSPLSLPVTPGEPASISCRSSKSLLHSQGITYLYWYVQKPGQSPQLL1YQGSNRASGVPDRFSGSGSGTDFTLKISRVEAEDVGVYYCVQNLELPYTFGGGTKLEIK | SEQ ID NO: 32 |
| | P-1076-mod3 CDR-H1 | GYTFTSYWMQ | SEQ ID NO: 3 |
| | P-1076-mod3 CDR-H2 | EIEPSNSYTNYNQKFRG | SEQ ID NO: 29 |
| | P-1076-mod3 CDR-H3 | ARGGY | SEQ ID NO: 5 |
| | P-1076-mod3 CDR-L1 | RSSKSLLHSQGITYLY | SEQ ID NO: 11 |
| | P-1076-mod3 CDR-L2 | Q**G**SNRAS | SEQ ID NO: 33 |
| | P-1076-mod3 CDR-L3 | VQNLELPYT | SEQ ID NO: 8 |
| P-1076-mod4 | P-1076-mod4 heavy chain variable region (VH) (CDRs underlined) | QVQLVQSGAEVTKPGASVKVSCKASGYTFTSYWMQWVRQAPGQGLEWVGEI**E**PSNSYTNYNQKFRGRVTLTRDTSTTTVYMELSSLRSEDTAVYYCARGGYWGQGTTVTVSS | SEQ ID NO: 28 |
| | P-1076-mod4 light chain variable region (VL) (CDRs underlined) | DIVMTQSPLSLPVTPGEPASISCRSSKSLLHSQGITYLYWYVQKPGQSPQLLIYQ**E**SNRASGVPDRFSGSGSGTDFTLKISRVEAEDVGVYYCVQNLELPYTFGGGTKLEIK | SEQ ID NO: 34 |
| | P-1076-mod4 CDR-H1 | GYTFTSYWMQ | SEQ ID NO: 3 |
| | P-1076-mod4 CDR-H2 | EI**E**PSNSYTNYNQKFRG | SEQ ID NO: 29 |
| | P-1076-mod4 CDR-H3 | ARGGY | SEQ ID NO: 5 |
| | P-1076-mod4 CDR-L1 | RSSKSLLHSQGITYLY | SEQ ID NO: 11 |
| | P-1076-mod4 CDR-L2 | Q**E**SNRAS | SEQ ID NO: 35 |
| | P-1076-mod4 CDR-L3 | VQNLELPYT | SEQ ID NO: 8 |
| P-1076-mod5 | P-1076-mod5 heavy chain variable region (VH) (CDRs underlined) | QVQLVQSGAEVTKPGASVKVSCKASGYTFTSYWMQWVRQAPGQGLEWVGEI**E**PSNSYTNYNQKFRGRVTLTRDTSTTTVYMELSSLRSEDTAVYYCARGGYWGQGTTVTVSS | SEQ ID NO: 28 |
| | P-1076-mod5 light chain variable region (VL) (CDRs underlined) | DIVMTQSPLSLPVTPGEPASISCRSSKSLLHSQGITYLYWY**I**QKPGQSPQLLIYQ**V**SNRASGVPDRFSGSGSGTDFTLKISRVEAEDVGVYYCVQNLELPYTFGGGTKLEIK | SEQ ID NO: 36 |
| | P-1076-mod5 CDR-H1 | GYTFTSYWMQ | SEQ ID NO: 3 |
| | P-1076-mod5 CDR-H2 | EI**E**PSNSYTNYNQKFRG | SEQ ID NO: 29 |
| | P-1076-mod5 CDR-H3 | ARGGY | SEQ ID NO: 5 |
| | P-1076-mod5 CDR-L1 | RSSKSLLHSQGITYLY | SEQ ID NO: 11 |
| | P-1076-mod5 CDR-L2 | Q**V**SNRAS | SEQ ID NO: 37 |
| | P-1076-mod5 CDR-L3 | VQNLELPYT | SEQ ID NO: 8 |
| P-1076-mod6 | P-1076-mod6 heavy chain variable region (VH) | QVQLVQSGAEVTKPGASVKVSCKASGYTFTSYWMQWVRQAPGQGLEWVGEIDPSNSYTNYNQKFRGRVTLTRDTSTTTVYMELSSLRSEDTA | SEQ ID NO: 15 |

TABLE 10 -continued

Sequence of P-1076-mod anti-hNAMPT antibodies

| Antibody | Description | Amino Acid Sequence | Sequence Identifier |
|---|---|---|---|
| | (CDRs underlined) | VYYCARGGYWGQGTTVTVSS | |
| | P-1076-mod6 light chain variable region (VL) (CDRs underlined) | DIVMTQSPLSLPVTPGEPASISCRSS KSLLHSQGITYLYWYVQKPGQSP QLLIYQLSNRASGVPDRFSGSGSG TDFTLKISRVEAEDVGVYYCVQNL ELPYTFGGGTKLEIK | SEQ ID NO: 30 |
| | P-1076-mod6 CDR-H1 | GYTFTSYWMQ | SEQ ID NO: 3 |
| | P-1076-mod6 CDR-H2 | EIDPSNSYTNYNQKFRG | SEQ ID NO: 4 |
| | P-1076-mod6 CDR-H3 | ARGGY | SEQ ID NO: 5 |
| | P-1076-mod6 CDR-L1 | RSSKSLLHSQGITYLY | SEQ ID NO: 11 |
| | P-1076-mod6 CDR-L2 | QLSNRAS | SEQ ID NO: 14 |
| | P-1076-mod6 CDR-L3 | VQNLELPYT | SEQ ID NO: 8 |
| P-1076-mod7 | P-1076-mod7 heavy chain variable region (VH) (CDRs underlined) | QVQLVQSGAEVTKPGASVKVSCK ASGYTFTSYWMQWVRQAPGQGL EWVGEIDPSNSYTNYNQKFRGRV TLTRDTSTTTVYMELSSLRSEDTA VYYCARGGYWGQGTTVTVSS | SEQ ID NO: 15 |
| | P-1076-mod7 light chain variable region (VL) (CDRs underlined) | DIVMTQSPLSLPVTPGEPASISCRSS KSLLHSQGITYLYWYIQKPGQSPQ LLIYQLSNRASGVPDRFSGSGSGT DFTLKISRVEAEDVGVYYCVQNLE LPYTFGGGTKLEIK | SEQ ID NO: 31 |
| | P-1076-mod7 CDR-H1 | GYTFTSYWMQ | SEQ ID NO: 3 |
| | P-1076-mod7 CDR-H2 | EIDPSNSYTNYNQKFRG | SEQ ID NO: 4 |
| | P-1076-mod7 CDR-H3 | ARGGY | SEQ ID NO: 5 |
| | P-1076-mod7 CDR-L1 | RSSKSLLHSQGITYLY | SEQ ID NO: 11 |
| | P-1076-mod7 CDR-L2 | QLSNRAS | SEQ ID NO: 14 |
| | P-1076-mod7 CDR-L3 | VQNLELPYT | SEQ ID NO: 8 |
| P-1076-mod8 | P-1076-mod8 heavy chain variable region (VH) (CDRs underlined) | QVQLVQSGAEVTKPGASVKVSCK ASGYTFTSYWMQWVRQAPGQGL EWVGEIDPSNSYTNYNQKFRGRV TLTRDTSTTTVYMELSSLRSEDTA VYYCARGGYWGQGTTVTVSS | SEQ ID NO: 15 |
| | P-1076-mod8 light chain variable region (VL) (CDRs underlined) | DIVMTQSPLSLPVTPGEPASISCRSS KSLLHSQGITYLYWYIQKPGQSPQ LLIYQGSNRASGVPDRFSGSGSGT DFTLKISRVEAEDVGVYYCVQNLE LPYTFGGGTKLEIK | SEQ ID NO: 32 |
| | P-1076-mod8 CDR-H1 | GYTFTSYWMQ | SEQ ID NO: 3 |
| | P-1076-mod8 CDR-H2 | EIDPSNSYTNYNQKFRG | SEQ ID NO: 4 |
| | P-1076-mod8 CDR-H3 | ARGGY | SEQ ID NO: 5 |
| | P-1076-mod8 CDR-L1 | RSSKSLLHSQGITYLY | SEQ ID NO: 11 |
| | P-1076-mod8 CDR-L2 | QGSNRAS | SEQ ID NO: 33 |
| | P-1076-mod8 CDR-L3 | VQNLELPYT | SEQ ID NO: 8 |
| P-1076-mod9 | P-1076-mod9 heavy chain variable region (VH) (CDRs underlined) | QVQLVQSGAEVTKPGASVKVSCK ASGYTFTSYWMQWVRQAPGQGL EWVGEIDPSNSYTNYNQKFRGRV TLTRDTSTTTVYMELSSLRSEDTA VYYCARGGYWGQGTTVTVSS | SEQ ID NO: 15 |
| | P-1076-mod9 light chain variable region (VL) (CDRs underlined) | DIVMTQSPLSLPVTPGEPASISCRSS KSLLHSQGITYLYWYVQKPGQSP QLLIYQESNRASGVPDRFSGSGSG TDFTLKISRVEAEDVGVYYCVQNL ELPYTFGGGTKLEIK | SEQ ID NO: 34 |

TABLE 10 -continued

| Sequence of P-1076-mod anti-hNAMPT antibodies | | | |
|---|---|---|---|
| Antibody | Description | Amino Acid Sequence | Sequence Identifier |
| | P-1076-mod9 CDR-H1 | GYTFTSYWMQ | SEQ ID NO: 3 |
| | P-1076-mod9 CDR-H2 | EIDPSNSYTNYNQKFRG | SEQ ID NO: 4 |
| | P-1076-mod9 CDR-H3 | ARGGY | SEQ ID NO: 5 |
| | P-1076-mod9 CDR-L1 | RSSKSLLHSQGITYLY | SEQ ID NO: 11 |
| | P-1076-mod9 CDR-L2 | Q**E**SNRAS | SEQ ID NO: 35 |
| | P-1076-mod9 CDR-L3 | VQNLELPYT | SEQ ID NO: 8 |
| P-1076-mod10 | P-1076-mod10 heavy chain variable region (VH) (CDRs underlined) | QVQLVQSGAEVTKPGASVKVSCKASGYTFTSYWMQWVRQAPGQGLEWVGEIDPSNSYTNYNQKFRGRVTLTRDTSTTTVYMELSSLRSEDTAVYYCARGGYWGQGTTVTVSS | SEQ ID NO: 15 |
| | P-1076-mod10 light chain variable region (VL) (CDRs underlined) | DIVMTQSPLSLPVTPGEPASISCRSSKSLLHSQGITYLYWY**I**QKPGQSPQLLIYQ**V**SNRASGVPDRFSGSGSGTDFTLKISRVEAEDVGVYYCVQNLELPYTFGGGTKLEIK | SEQ ID NO: 36 |
| | P-1076-mod10 CDR-H1 | GYTFTSYWMQ | SEQ ID NO: 3 |
| | P-1076-mod10 CDR-H2 | EIDPSNSYTNYNQKFRG | SEQ ID NO: 4 |
| | P-1076-mod10 CDR-H3 | ARGGY | SEQ ID NO: 5 |
| | P-1076-mod10 CDR-L1 | RSSKSLLHSQGITYLY | SEQ ID NO: 11 |
| | P-1076-mod10 CDR-L2 | Q**V**SNRAS | SEQ ID NO: 37 |
| | P-1076-mod10 CDR-L3 | VQNLELPYT | SEQ ID NO: 8 |
| P-1076-mod11 | P-1076-mod11 heavy chain variable region (VH) hIgG1 backbone (CDRs underlined) | QVQLVQSGAEVTKPGASVKVSCKASGYTFTSYWMQWVRQAPGQGLEWVGEI**E**PSNSYTNYNQKFRGRVTLTRDTSTTTVYMELSSLRSEDTAVYYCARGGYWGQGTTVTVSS | SEQ ID NO: 28 |
| | P-1076-mod11 light chain variable region (VL) (CDRs underlined) | DIVMTQSPLSLPVTPGEPASISCRSSKSLLHSQGITYLYWYLQKPGQSPQLLIYQLSNRASGVPDRFSGSGSGTDFTLKISRVEAEDVGVYYCVQNLELPYTFGGGTKLEIK | SEQ ID NO: 13 |
| | P-1076-mod11 CDR-H1 | GYTFTSYWMQ | SEQ ID NO: 3 |
| | P-1076-mod11 CDR-H2 | EI**E**PSNSYTNYNQKFRG | SEQ ID NO: 29 |
| | P-1076-mod11 CDR-H3 | ARGGY | SEQ ID NO: 5 |
| | P-1076-mod11 CDR-L1 | RSSKSLLHSQGITYLY | SEQ ID NO: 11 |
| | P-1076-mod11 CDR-L2 | QLSNRAS | SEQ ID NO: 14 |
| | P-1076-mod11 CDR-L3 | VQNLELPYT | SEQ ID NO: 8 |

* In TABLE 10, mutated residues are in bold font.

TABLE 11

Comparison of HC CDRs of P-1076-mod anti-hNAMPT antibodies with HC CDRs of P-1076

| | Heavy Chain (HC) CDR1 | | | | | | | | | | SEQ ID NO: | HC CDR2 | | | | | | | | | | | | | | | | | SEQ ID NO: | HC CDR3 | | | | | SEQ ID NO: |
|---|---|---|---|---|---|---|---|---|---|---|---|---|---|---|---|---|---|---|---|---|---|---|---|---|---|---|---|---|---|---|---|---|---|---|---|
| P-1076 | G | Y | T | F | T | S | Y | W | M | Q | 3 | E | I | D | P | S | N | S | Y | T | N | Y | N | Q | K | F | R | G | 4 | A | R | G | G | Y | 5 |
| P-1076-mod1 | | | | | | | | | | | 3 | | | E | | | | | | | | | | | | | | | 29 | | | | | | 5 |
| P-1076-mod2 | | | | | | | | | | | 3 | | | E | | | | | | | | | | | | | | | 29 | | | | | | 5 |
| P-1076-mod3 | | | | | | | | | | | 3 | | | E | | | | | | | | | | | | | | | 29 | | | | | | 5 |
| P-1076-mod4 | | | | | | | | | | | 3 | | | E | | | | | | | | | | | | | | | 29 | | | | | | 5 |
| P-1076-mod5 | | | | | | | | | | | 3 | | | E | | | | | | | | | | | | | | | 29 | | | | | | 5 |
| P-1076-mod6 | | | | | | | | | | | 3 | | | | | | | | | | | | | | | | | | 4 | | | | | | 5 |
| P-1076-mod7 | | | | | | | | | | | 3 | | | | | | | | | | | | | | | | | | 4 | | | | | | 5 |
| P-1076-mod8 | | | | | | | | | | | 3 | | | | | | | | | | | | | | | | | | 4 | | | | | | 5 |
| P-1076-mod9 | | | | | | | | | | | 3 | | | | | | | | | | | | | | | | | | 4 | | | | | | 5 |
| P-1076-mod10 | | | | | | | | | | | 3 | | | | | | | | | | | | | | | | | | 4 | | | | | | 5 |
| P-1076-mod11 | | | | | | | | | | | 3 | | | E | | | | | | | | | | | | | | | 29 | | | | | | 5 |

TABLE 12

Comparison of LC CDRs of P-1076-mod anti-hNAMPT antibodies with LC CDRs of P-1076

| | Light Chain (LC) CDR1 | | | | | | | | | | | | | | | | SEQ ID NO: | LC CDR2 | | | | | | | SEQ ID NO: | LC CDR3 | | | | | | | | | SEQ ID NO: |
|---|---|---|---|---|---|---|---|---|---|---|---|---|---|---|---|---|---|---|---|---|---|---|---|---|---|---|---|---|---|---|---|---|---|---|---|
| P-1076 | R | S | S | K | S | L | L | H | S | Q | G | I | T | Y | L | Y | 11 | Q | L | S | N | R | A | S | 14 | V | Q | N | L | E | L | P | Y | T | 8 |
| P-1076-mod1 | | | | | | | | | | | | | | | | | 11 | | | | | | | | 14 | | | | | | | | | | 8 |
| P-1076-mod2 | | | | | | | | | | | | | | | | | 11 | | | | | | | | 14 | | | | | | | | | | 8 |
| P-1076-mod3 | | | | | | | | | | | | | | | | | 11 | | G | | | | | | 33 | | | | | | | | | | 8 |
| P-1076-mod4 | | | | | | | | | | | | | | | | | 11 | | E | | | | | | 35 | | | | | | | | | | 8 |
| P-1076-mod5 | | | | | | | | | | | | | | | | | 11 | | V | | | | | | 37 | | | | | | | | | | 8 |
| P-1076-mod6 | | | | | | | | | | | | | | | | | 11 | | | | | | | | 14 | | | | | | | | | | 8 |
| P-1076-mod7 | | | | | | | | | | | | | | | | | 11 | | | | | | | | 14 | | | | | | | | | | 8 |
| P-1076-mod8 | | | | | | | | | | | | | | | | | 11 | | G | | | | | | 33 | | | | | | | | | | 8 |
| P-1076-mod9 | | | | | | | | | | | | | | | | | 11 | | E | | | | | | 35 | | | | | | | | | | 8 |
| P-1076-mod10 | | | | | | | | | | | | | | | | | 11 | | V | | | | | | 37 | | | | | | | | | | 8 |
| P-1076-mod11 | | | | | | | | | | | | | | | | | 11 | | | | | | | | 14 | | | | | | | | | | 8 |

TABLE 13

| Biophysical characteristics of P-1076-mod anti-hNAMPT antibodies | | | | | |
|---|---|---|---|---|---|
| Antibody | Concentration (mg/ml) | Volume (ml) | Total (mg) | Pot. Yield (mg/L) | *Purity |
| P-1076 | 1.82 | 1.34 | 2.44 | 97.60 | >95% |
| P-1076-mod6 | 1.29 | 1.43 | 1.84 | 73.60 | >95% |
| P-1076-mod7 | 1.27 | 1.28 | 1.63 | 65.20 | >95% |
| P-1076-mod8 | 1.25 | 1.36 | 1.70 | 68.00 | >95% |
| P-1076-mod9 | 1.32 | 1.28 | 1.69 | 67.60 | >95% |
| P-1076-mod10 | 1.23 | 1.22 | 1.50 | 60.00 | >95% |
| P-1076-mod11 | 1.22 | 1.26 | 1.54 | 61.60 | >95% |
| P-1076-mod1 | 1.21 | 1.39 | 2.85 | 114.00 | >95% |
| P-1076-mod2 | 0.89 | 1.30 | 1.16 | 46.40 | >95% |
| P-1076-mod3 | 1.07 | 1.34 | 1.43 | 57.20 | >95% |
| P-1076-mod4 | 1.17 | 1.38 | 1.61 | 64.40 | >95% |
| P-1076-mod5 | 0.77 | 1.34 | 1.03 | 41.20 | >95% |

Example 11. Modification of Humanized Anti-hNAMPT Antibody UU-1093

Based on the results of in vitro and in vivo testing described in Example 9, anti-hNAMPT antibody UU-1093 was selected for further modification to generate modified 1093 anti-hNAMPT antibodies.

UU-1093-Mod Humanized Anti-hNAMPT Antibodies

UU-1093-mod refers to humanized anti-hNAMPT antibodies that were generated by modifying 1093 humanized anti-hNAMPT antibody UU-1093.

To generate improved UU-1093-mod anti-hNAMPT antibodies, one or more mutations were introduced into the UU-1093 amino acid sequence by de nova synthesis of the variable domain, or mutagenic oligonucleotide primers and polymerase chain reactions, or both, by methods well known in the art. These mutations were introduced to remove oxidation sites, to reduce or remove deamidation, to remove potential cleavage or fragmentation sites, to remove potential T-cell epitopes, and/or to reduce the binding of potential T-cell epitopes. Different combinations of back mutations and other mutations were constructed for heavy and/or light chains of UU-1093 to generate modified UU-1093-mod anti-hNAMPT antibodies UU-1093-mod1, UU-1093-mod2, UU-1093-mod3, UU-1093-mod4, UU-1093-mod5, UU-1093-mod6, UU-1093-mod7, UU-1093-mod8, UU-1093-mod9, UU-1093-mod10, UU-1093-mod11, UU-1093-mod12, UU-1093-mod13, UU-1093-mod14, UU-1093-mod15, UU-1093-mod16, UU-1093-mod17, UU-1093-mod18, and UU-1093-mod19.

Amino acid sequences of the heavy and light chain variable regions of the modified P-1076-mod anti-hNAMPT antibodies are provided in Table 14. In Table 14, mutated residues are in bold font. Table 15 provides an alignment of the amino acid sequences of the heavy chain CDRs for modified UU-1093-mod anti-hNAMPT antibodies UU-1093-mod1, UU-1093-mod2, UU-1093-mod3, UU-1093-mod4, UU-1093-mod5, UU-1093-mod6, UU-1093-mod7, UU-1093-mod8, UU-1093-mod9, UU-1093-mod10, UU-1093-mod11, UU-1093-mod12, UU-1093-mod13, UU-1093-mod14, UU-1093-mod15, UU-1093-mod16, UU-1093-mod17, UU-1093-mod18, and UU-1093-mod19 in comparison to UU-1093. Table 16 provides an alignment of the amino acid sequences of the light chain CDRs for modified UU-1093-mod anti-hNAMPT antibodies UU-1093-mod1, UU-1093-mod2, UU-1093-mod3, UU-1093-mod4, UU-1093-mod5, UU-1093-mod6, UU-1093-mod7, UU-1093-mod8, UU-1093-mod9, UU-1093-mod10, UU-1093-mod11, UU-1093-mod12, UU-1093-mod13, UU-1093-mod14, UU-1093-mod15, UU-1093-mod16, UU-1093-mod17, UU-1093-mod18, and UU-1093-mod19 in comparison to UU-1093. Blank spaces in Tables 15 and 16 indicate that the residue is the same as UU-1093.

UU-1093-Mod1

UU-1093-mod anti-hNAMPT antibody UU-1093-mod1 has a heavy chain variable region with an amino acid sequence as set forth in SEQ ID NO: 38, and a light chain variable region with an amino acid sequence as set forth in SEQ ID NO: 47. The heavy chain variable region of UU-1093-mod1 contains a CDR1 domain with an amino acid sequence as set forth in SEQ ID NO: 19, a CDR2 domain with an amino acid sequence as set forth in SEQ ID NO: 39, and a CDR3 domain with an amino acid sequence as set forth in SEQ ID NO: 21. For the heavy chain of UU-1093-mod1, a D-to-E mutation was introduced into the UU-1093 VH CDR2 to remove a potential cleavage or fragmentation site. The light chain variable region of UU-1093-mod1 contains a CDR1 domain with an amino acid sequence as set forth in SEQ ID NO: 11, a CDR2 domain with an amino acid sequence as set forth in SEQ ID NO: 7, and a CDR3 domain with an amino acid sequence as set forth in SEQ ID NO: 22. For the light chain of UU-1093-mod1, a N-to-Q mutation was introduced into the UU-1093 VL CDR1 to reduce or remove deamidation.

UU-1093-Mod2

UU-1093-mod anti-hNAMPT antibody UU-1093-mod2 has a heavy chain variable region with an amino acid sequence as set forth in SEQ ID NO: 40, and a light chain variable region with an amino acid sequence as set forth in SEQ ID NO: 47. The heavy chain variable region of UU-1093-mod2 contains a CDR1 domain with an amino acid sequence as set forth in SEQ ID NO: 19, a CDR2 domain with an amino acid sequence as set forth in SEQ ID NO: 39, and a CDR3 domain with an amino acid sequence as set forth in SEQ ID NO: 41. For the heavy chain of UU-1093-mod2, a D-to-E mutation was introduced into the UU-1093 VH CDR2 to remove a potential cleavage or fragmentation site, and a S-to-T mutation was introduced into the UU-1093 VH CDR3 to remove a potential T-cell epitope. The light chain variable region of UU-1093-mod2 contains a CDR1 domain with an amino acid sequence as set forth in SEQ ID NO: 11, a CDR2 domain with an amino acid sequence as set forth in SEQ ID NO: 7, and a CDR3 domain with an amino acid sequence as set forth in SEQ ID NO: 22. For the light chain of UU-1093-mod2, a N-to-Q mutation was introduced into the UU-1093 VL CDR1 to reduce or remove deamidation.

UU-1093-Mod3

UU-1093-mod anti-hNAMPT antibody UU-1093-mod3 has a heavy chain variable region with an amino acid sequence as set forth in SEQ ID NO: 42, and a light chain variable region with an amino acid sequence as set forth in SEQ ID NO: 47. The heavy chain variable region of UU-1093-mod3 contains a CDR1 domain with an amino acid sequence as set forth in SEQ ID NO: 43, a CDR2 domain with an amino acid sequence as set forth in SEQ ID NO: 39, and a CDR3 domain with an amino acid sequence as set forth in SEQ ID NO: 44. For the heavy chain of UU-1093-mod3, a M-to-I mutation was introduced into the UU-1093 VH CDR1 to remove an oxidation site; a M-to-V mutation was introduced into the UU-1093 VH framework region 2 to remove an oxidation site and a potential T-cell epitope; a D-to-E mutation was introduced into the UU-1093 VH CDR2 to remove a potential cleavage or fragmentation site; a M-to-V mutation was introduced into the UU-1093 VH framework region 3 to remove an oxidation site; and a K-to-R mutation was introduced into the UU-1093 VH CDR3 to reduce the binding of a potential T-cell epitope. The light chain variable region of UU-1093-mod3 contains a CDR1 domain with an amino acid sequence as set forth in SEQ ID NO: 11, a CDR2 domain with an amino acid sequence as set forth in SEQ ID NO: 7, and a CDR3 domain with an amino acid sequence as set forth in SEQ ID NO: 22. For the light chain of UU-1093-mod3, a N-to-Q mutation was introduced into the UU-1093 VL CDR1 to reduce or remove deamidation.

UU-1093-Mod4

UU-1093-mod anti-hNAMPT antibody UU-1093-mod4 has a heavy chain variable region with an amino acid sequence as set forth in SEQ ID NO: 45, and a light chain variable region with an amino acid sequence as set forth in SEQ ID NO: 47. The heavy chain variable region of UU-1093-mod4 contains a CDR1 domain with an amino acid sequence as set forth in SEQ ID NO: 46, a CDR2 domain with an amino acid sequence as set forth in SEQ ID NO: 39, and a CDR3 domain with an amino acid sequence as set forth in SEQ ID NO: 41. For the heavy chain of UU-1093-mod4, a W-to-F mutation and a M-to-I mutation were introduced into the UU-1093 VH CDR1 to remove an oxidation site; a M-to-V mutation was introduced into the UU-1093 VH framework region 2 to remove an oxidation site and a potential T-cell epitope; a D-to-E mutation was introduced into the UU-1093 VH CDR2 to remove a potential cleavage or fragmentation site; a M-to-V mutation was introduced into the UU-1093 VH framework region 3 to remove an oxidation site; and a S-to-T mutation was introduced into the UU-1093 VH CDR3 to remove a potential T-cell epitope. The light chain variable region of UU-1093-mod4 contains a CDR1 domain with an amino acid sequence as set forth in SEQ ID NO: 11, a CDR2 domain with an amino acid sequence as set forth in SEQ ID NO: 7, and a CDR3 domain with an amino acid sequence as set forth in SEQ ID NO: 22. For the light chain of UU-1093-mod4, a N-to-Q mutation was introduced into the UU-1093 VL CDR1 to reduce or remove deamidation.

UU-1093-Mod5

UU-1093-mod anti-hNAMPT antibody UU-1093-mod5 has a heavy chain variable region with an amino acid sequence as set forth in SEQ ID NO: 38, and a light chain variable region with an amino acid sequence as set forth in SEQ ID NO: 48. The heavy chain variable region of UU-1093-mod5 contains a CDR1 domain with an amino acid sequence as set forth in SEQ ID NO: 19, a CDR2 domain with an amino acid sequence as set forth in SEQ ID NO: 39, and a CDR3 domain with an amino acid sequence as set forth in SEQ ID NO: 21. For the heavy chain of UU-1093-mod5, a D-to-E mutation was introduced into the UU-1093 VH CDR2 to remove a potential cleavage or fragmentation site. The light chain variable region of UU-1093-mod5 contains a CDR1 domain with an amino acid sequence as set forth in SEQ ID NO: 49, a CDR2 domain with an amino acid sequence as set forth in SEQ ID NO: 50, and a CDR3 domain with an amino acid sequence as set forth in SEQ ID NO: 22. For the light chain of UU-1093-mod5, a G-to-A mutation was introduced into the UU-1093 VL CDR1 to reduce or remove deamidation; a I-to-V mutation was introduced into the UU-1093 VL framework region 2 to reduce the binding of a potential T-cell epitope; a M-to-V mutation was introduced into the UU-1093 VL CDR2 to reduce the binding of a potential T-cell epitope and to remove an oxidation site; and a I-to-V mutation was introduced into the UU-1093 VH framework region 3 to reduce the binding of a potential T-cell epitope.

UU-1093-Mod6

UU-1093-mod anti-hNAMPT antibody UU-1093-mod6 has a heavy chain variable region with an amino acid sequence as set forth in SEQ ID NO: 40, and a light chain variable region with an amino acid sequence as set forth in SEQ ID NO: 48. The heavy chain variable region of UU-1093-mod6 contains a CDR1 domain with an amino acid sequence as set forth in SEQ ID NO: 19, a CDR2 domain with an amino acid sequence as set forth in SEQ ID NO: 39, and a CDR3 domain with an amino acid sequence as set forth in SEQ ID NO: 41. For the heavy chain of UU-1093-mod6, a D-to-E mutation was introduced into the UU-1093 VH CDR2 to remove a potential cleavage or fragmentation site, and a S-to-T mutation was introduced into the UU-1093 VH CDR3 to remove a potential T-cell epitope. The light chain variable region of UU-1093-mod6 contains a CDR1 domain with an amino acid sequence as set forth in SEQ ID NO: 49, a CDR2 domain with an amino acid sequence as set forth in SEQ ID NO: 50, and a CDR3 domain with an amino acid sequence as set forth in SEQ ID NO: 22. For the light chain of UU-1093-mod6, a G-to-A mutation was introduced into the UU-1093 VL CDR1 to reduce or remove deamidation; a I-to-V mutation was introduced into the UU-1093 VL framework region 2 to reduce the binding of a potential T-cell epitope; a M-to-V mutation was introduced into the UU-1093 VL CDR2 to reduce the binding of a potential T-cell epitope and to remove an oxidation site; and a I-to-V mutation was introduced into the UU-1093 VH framework region 3 to reduce the binding of a potential T-cell epitope.

UU-1093-Mod7

UU-1093-mod anti-hNAMPT antibody UU-1093-mod7 has a heavy chain variable region with an amino acid sequence as set forth in SEQ ID NO: 42, and a light chain variable region with an amino acid sequence as set forth in SEQ ID NO: 48. The heavy chain variable region of UU-1093-mod7 contains a CDR1 domain with an amino acid sequence as set forth in SEQ ID NO: 43, a CDR2 domain with an amino acid sequence as set forth in SEQ ID NO: 39, and a CDR3 domain with an amino acid sequence as set forth in SEQ ID NO: 44. For the heavy chain of UU-1093-mod7, a M-to-I mutation was introduced into the UU-1093 VH CDR1 to remove an oxidation site; a M-to-V mutation was introduced into the UU-1093 VH framework region 2 to remove an oxidation site and a potential T-cell epitope; a D-to-E mutation was introduced into the UU-1093 VH CDR2 to remove a potential cleavage or fragmentation site; a M-to-V mutation was introduced into the UU-1093 VH framework region 3 to remove an oxidation site; and a K-to-R mutation was introduced into the UU-1093 VH CDR3 to reduce the binding of a potential T-cell epitope. The light chain variable region of UU-1093-mod7 contains a CDR1 domain with an amino acid sequence as set forth in SEQ ID NO: 49, a CDR2 domain with an amino acid sequence as set forth in SEQ ID NO: 50, and a CDR3 domain with an amino acid sequence as set forth in SEQ ID NO: 22. For the light chain of UU-1093-mod7, a G-to-A mutation was introduced into the UU-1093 VL CDR1 to reduce or remove deamidation; a I-to-V mutation was introduced into the UU-1093 VL framework region 2 to reduce the binding of a potential T-cell epitope; a M-to-V mutation was introduced into the UU-1093 VL CDR2 to reduce the binding of a potential T-cell epitope and to remove an oxidation site; and a I-to-V mutation was introduced into the UU-1093 VH framework region 3 to reduce the binding of a potential T-cell epitope.

UU-1093-Mod8

UU-1093-mod anti-hNAMPT antibody UU-1093-mod8 has a heavy chain variable region with an amino acid sequence as set forth in SEQ ID NO: 45, and a light chain variable region with an amino acid sequence as set forth in SEQ ID NO: 48. The heavy chain variable region of UU-1093-mod8 contains a CDR1 domain with an amino acid sequence as set forth in SEQ ID NO: 46, a CDR2 domain with an amino acid sequence as set forth in SEQ ID NO: 39, and a CDR3 domain with an amino acid sequence as set forth in SEQ ID NO: 41. For the heavy chain of UU-1093-mod8, a W-to-F mutation and a M-to-I mutation were introduced into the UU-1093 VH CDR1 to remove an oxidation site; a M-to-V mutation was introduced into the UU-1093 VH framework region 2 to remove an oxidation site and a potential T-cell epitope; a D-to-E mutation was introduced into the UU-1093 VH CDR2 to remove a potential cleavage or fragmentation site; a M-to-V mutation was introduced into the UU-1093 VH framework region 3 to remove an oxidation site; and a S-to-T mutation was introduced into the UU-1093 VH CDR3 to remove a potential T-cell epitope. The light chain variable region of UU-1093-mod8 contains a CDR1 domain with an amino acid sequence as set forth in SEQ ID NO: 49, a CDR2 domain with an amino acid sequence as set forth in SEQ ID NO: 50, and a CDR3 domain with an amino acid sequence as set forth in SEQ ID NO: 22. For the light chain of UU-1093-mod8, a G-to-A mutation was introduced into the UU-1093 VL CDR1 to reduce or remove deamidation; a I-to-V mutation was introduced into the UU-1093 VL framework region 2 to reduce the binding of a potential T-cell epitope; a M-to-V mutation was introduced into the UU-1093 VL CDR2 to reduce the binding of a potential T-cell epitope and to remove an oxidation site; and a I-to-V mutation was introduced into the UU-1093 VH framework region 3 to reduce the binding of a potential T-cell epitope.

UU-1093-Mod9

UU-1093-mod anti-hNAMPT antibody UU-1093-mod9 has a heavy chain variable region with an amino acid sequence as set forth in SEQ ID NO: 38, and a light chain variable region with an amino acid sequence as set forth in SEQ ID NO: 51. The heavy chain variable region of UU-1093-mod9 contains a CDR1 domain with an amino acid sequence as set forth in SEQ ID NO: 19, a CDR2 domain with an amino acid sequence as set forth in SEQ ID NO: 39, and a CDR3 domain with an amino acid sequence as set forth in SEQ ID NO: 21. For the heavy chain of UU-1093-mod9, a D-to-E mutation was introduced into the UU-1093 VH CDR2 to remove a potential cleavage or fragmentation site. The light chain variable region of UU-1093-mod9 contains a CDR1 domain with an amino acid sequence as set forth in SEQ ID NO: 11, a CDR2 domain with an amino acid sequence as set forth in SEQ ID NO: 52, and a CDR3 domain with an amino acid sequence as set forth in SEQ ID NO: 53. For the light chain of UU-1093-mod9, a N-to-Q mutation was introduced into the UU-1093 VL CDR1 to reduce or remove deamidation; a I-to-V mutation was introduced into the UU-1093 VL framework region 2 to remove a potential T-cell epitope; a M-to-V mutation was introduced into the UU-1093 VL CDR2 to remove a potential T-cell epitope and to remove an oxidation site; a A-to-G mutation was introduced into the UU-1093 VL CDR2 to remove a potential T-cell epitope; and a W-to-F mutation was introduced into the UU-1093 VL CDR3 to remove an oxidation site.

UU-1093-Mod10

UU-1093-mod anti-hNAMPT antibody UU-1093-mod10 has a heavy chain variable region with an amino acid sequence as set forth in SEQ ID NO: 40, and a light chain variable region with an amino acid sequence as set forth in SEQ ID NO: 51. The heavy chain variable region of UU-1093-mod10 contains a CDR1 domain with an amino acid sequence as set forth in SEQ ID NO: 19, a CDR2 domain with an amino acid sequence as set forth in SEQ ID NO: 39, and a CDR3 domain with an amino acid sequence as set forth in SEQ ID NO: 41. For the heavy chain of UU-1093-mod10, a D-to-E mutation was introduced into the UU-1093 VH CDR2 to remove a potential cleavage or fragmentation site, and a S-to-T mutation was introduced into the UU-1093 VH CDR3 to remove a potential T-cell epitope. The light chain variable region of UU-1093-mod10 contains a CDR1 domain with an amino acid sequence as set forth in SEQ ID NO: 11, a CDR2 domain with an amino acid sequence as set forth in SEQ ID NO: 52, and a CDR3 domain with an amino acid sequence as set forth in SEQ ID NO: 53. For the light chain of UU-1093-mod10, a N-to-Q mutation was introduced into the UU-1093 VL CDR1 to reduce or remove deamidation; a I-to-V mutation was introduced into the UU-1093 VL framework region 2 to remove a potential T-cell epitope; a M-to-V mutation was introduced into the UU-1093 VL CDR2 to remove a potential T-cell epitope and to remove an oxidation site; a A-to-G mutation was introduced into the UU-1093 VL CDR2 to remove a potential T-cell epitope; and a W-to-F mutation was introduced into the UU-1093 VL CDR3 to remove an oxidation site.

UU-1093-Mod11

UU-1093-mod anti-hNAMPT antibody UU-1093-mod11 has a heavy chain variable region with an amino acid sequence as set forth in SEQ ID NO: 42, and a light chain variable region with an amino acid sequence as set forth in SEQ ID NO: 51. The heavy chain variable region of UU-1093-mod11 contains a CDR1 domain with an amino acid sequence as set forth in SEQ ID NO: 43, a CDR2 domain with an amino acid sequence as set forth in SEQ ID NO: 39, and a CDR3 domain with an amino acid sequence as set forth in SEQ ID NO: 44. For the heavy chain of UU-1093-mod11, a M-to-I mutation was introduced into the UU-1093 VH CDR1 to remove an oxidation site; a M-to-V mutation was introduced into the UU-1093 VH framework region 2 to remove an oxidation site and a potential T-cell epitope; a D-to-E mutation was introduced into the UU-1093 VH CDR2 to remove a potential cleavage or fragmentation site; a M-to-V mutation was introduced into the UU-1093 VH framework region 3 to remove an oxidation site; and a K-to-R mutation was introduced into the UU-1093 VH CDR3 to reduce the binding of a potential T-cell epitope. The light chain variable region of UU-1093-mod11 contains a CDR1 domain with an amino acid sequence as set forth in SEQ ID NO: 11, a CDR2 domain with an amino acid sequence as set forth in SEQ ID NO: 52, and a CDR3 domain with an amino acid sequence as set forth in SEQ ID NO: 53. For the light chain of UU-1093-mod11, a N-to-Q mutation was introduced into the UU-1093 VL CDR1 to reduce or remove deamidation; a I-to-V mutation was introduced into the UU-1093 VL framework region 2 to remove a potential T-cell epitope; a M-to-V mutation was introduced into the UU-1093 VL CDR2 to remove a potential T-cell epitope and to remove an oxidation site; a A-to-G mutation was introduced into the UU-1093 VL CDR2 to remove a potential T-cell epitope; and a W-to-F mutation was introduced into the UU-1093 VL CDR3 to remove an oxidation site.

UU-1093-Mod12

UU-1093-mod anti-hNAMPT antibody UU-1093-mod12 has a heavy chain variable region with an amino acid sequence as set forth in SEQ ID NO: 45, and a light chain variable region with an amino acid sequence as set forth in SEQ ID NO: 51. The heavy chain variable region of UU-1093-mod12 contains a CDR1 domain with an amino acid sequence as set forth in SEQ ID NO: 46, a CDR2 domain with an amino acid sequence as set forth in SEQ ID NO: 39, and a CDR3 domain with an amino acid sequence as set forth in SEQ ID NO: 41. For the heavy chain of UU-1093-mod12, a W-to-F mutation and a M-to-I mutation were introduced into the UU-1093 VH CDR1 to remove an oxidation site; a M-to-V mutation was introduced into the UU-1093 VH framework region 2 to remove an oxidation site and a potential T-cell epitope; a D-to-E mutation was introduced into the UU-1093 VH CDR2 to remove a potential cleavage or fragmentation site; a M-to-V mutation was introduced into the UU-1093 VH framework region 3 to remove an oxidation site; and a S-to-T mutation was introduced into the UU-1093 VH CDR3 to remove a potential T-cell epitope. The light chain variable region of UU-1093-mod12 contains a CDR1 domain with an amino acid sequence as set forth in SEQ ID NO: 11, a CDR2 domain with an amino acid sequence as set forth in SEQ ID NO: 52, and a CDR3 domain with an amino acid sequence as set forth in SEQ ID NO: 53. For the light chain of UU-1093-mod12, a N-to-Q mutation was introduced into the UU-1093 VL CDR1 to reduce or remove deamidation; a I-to-V mutation was introduced into the UU-1093 VL framework region 2 to remove a potential T-cell epitope; a M-to-V mutation was introduced into the UU-1093 VL CDR2 to remove a potential T-cell epitope and to remove an oxidation site; a A-to-G mutation was introduced into the UU-1093 VL CDR2 to remove a potential T-cell epitope; and a W-to-F mutation was introduced into the UU-1093 VL CDR3 to remove an oxidation site.

UU-1093-Mod13

UU-1093-mod anti-hNAMPT antibody UU-1093-mod13 has a heavy chain variable region with an amino acid sequence as set forth in SEQ ID NO: 38, and a light chain variable region with an amino acid sequence as set forth in SEQ ID NO: 18. The heavy chain variable region of UU-1093-mod13 contains a CDR1 domain with an amino acid sequence as set forth in SEQ ID NO: 19, a CDR2 domain with an amino acid sequence as set forth in SEQ ID NO: 39, and a CDR3 domain with an amino acid sequence as set forth in SEQ ID NO: 21. For the heavy chain of UU-1093-mod13, a D-to-E mutation was introduced into the UU-1093 VH CDR2 to remove a potential cleavage or fragmentation site. The light chain variable region of UU-1093-mod13 contains a CDR1 domain with an amino acid sequence as set forth in SEQ ID NO: 6, a CDR2 domain with an amino acid sequence as set forth in SEQ ID NO: 7, and a CDR3 domain with an amino acid sequence as set forth in SEQ ID NO: 22. The light chain of UU-1093-mod13 is identical to UU-1093 VL.

UU-1093-Mod14

UU-1093-mod anti-hNAMPT antibody UU-1093-mod14 has a heavy chain variable region with an amino acid sequence as set forth in SEQ ID NO: 40, and a light chain variable region with an amino acid sequence as set forth in SEQ ID NO: 18. The heavy chain variable region of UU-1093-mod14 contains a CDR1 domain with an amino acid sequence as set forth in SEQ ID NO: 19, a CDR2 domain with an amino acid sequence as set forth in SEQ ID NO: 39, and a CDR3 domain with an amino acid sequence as set forth in SEQ ID NO: 41. For the heavy chain of UU-1093-mod14, a D-to-E mutation was introduced into the UU-1093 VH CDR2 to remove a potential cleavage or fragmentation site, and a S-to-T mutation was introduced into the UU-1093 VH CDR3 to remove a potential T-cell epitope. The light chain variable region of UU-1093-mod14 contains a CDR1 domain with an amino acid sequence as set forth in SEQ ID NO: 6, a CDR2 domain with an amino acid sequence as set forth in SEQ ID NO: 7, and a CDR3 domain with an amino acid sequence as set forth in SEQ ID NO: 22. The light chain of UU-1093-mod14 is identical to UU-1093 VL.

UU-1093-Mod15

UU-1093-mod anti-hNAMPT antibody UU-1093-mod15 has a heavy chain variable region with an amino acid sequence as set forth in SEQ ID NO: 42, and a light chain variable region with an amino acid sequence as set forth in SEQ ID NO: 18. The heavy chain variable region of UU-1093-mod15 contains a CDR1 domain with an amino acid sequence as set forth in SEQ ID NO: 43, a CDR2 domain with an amino acid sequence as set forth in SEQ ID NO: 39, and a CDR3 domain with an amino acid sequence as set forth in SEQ ID NO: 44. For the heavy chain of UU-1093-mod15, a M-to-I mutation was introduced into the UU-1093 VH CDR1 to remove an oxidation site; a M-to-V mutation was introduced into the UU-1093 VH framework region 2 to remove an oxidation site and a potential T-cell epitope; a D-to-E mutation was introduced into the UU-1093 VH CDR2 to remove a potential cleavage or fragmentation site; a M-to-V mutation was introduced into the UU-1093 VH framework region 3 to remove an oxidation site; and a K-to-R mutation was introduced into the UU-1093 VH CDR3 to reduce the binding of a potential T-cell epitope. The light chain variable region of UU-1093-mod15 contains a CDR1 domain with an amino acid sequence as set forth in SEQ ID NO: 6, a CDR2 domain with an amino acid sequence as set forth in SEQ ID NO: 7, and a CDR3 domain with an amino acid sequence as set forth in SEQ ID NO: 22. The light chain of UU-1093-mod15 is identical to UU-1093 VL.

UU-1093-Mod16

UU-1093-mod anti-hNAMPT antibody U-1093-mod16 has a heavy chain variable region with an amino acid sequence as set forth in SEQ ID NO: 45, and a light chain variable region with an amino acid sequence as set forth in SEQ ID NO: 18. The heavy chain variable region of UU-1093-mod16 contains a CDR1 domain with an amino acid sequence as set forth in SEQ ID NO: 46, a CDR2 domain with an amino acid sequence as set forth in SEQ ID NO: 39, and a CDR3 domain with an amino acid sequence as set forth in SEQ ID NO: 41. For the heavy chain of UU-1093-mod16, a W-to-F mutation and a M-to-I mutation were introduced into the UU-1093 VH CDR1 to remove an oxidation site; a M-to-V mutation was introduced into the UU-1093 VH framework region 2 to remove an oxidation site and a potential T-cell epitope; a D-to-E mutation was introduced into the UU-1093 VH CDR2 to remove a potential cleavage or fragmentation site; a M-to-V mutation was introduced into the UU-1093 VH framework region 3 to remove an oxidation site; and a S-to-T mutation was introduced into the UU-1093 VH CDR3 to remove a potential T-cell epitope. The light chain variable region of UU-1093-mod16 contains a CDR1 domain with an amino acid sequence as set forth in SEQ ID NO: 6, a CDR2 domain with an amino acid sequence as set forth in SEQ ID NO: 7, and a CDR3 domain with an amino acid sequence as set forth in SEQ ID NO: 22. The light chain of UU-1093-mod16 is identical to UU-1093 VL.

UU-1093-Mod17

UU-1093-mod anti-hNAMPT antibody UU-1093-mod17 has a heavy chain variable region with an amino acid sequence as set forth in SEQ ID NO: 26, and a light chain variable region with an amino acid sequence as set forth in SEQ ID NO: 47. The heavy chain variable region of UU-1093-mod17 contains a CDR1 domain with an amino acid sequence as set forth in SEQ ID NO: 19, a CDR2 domain with an amino acid sequence as set forth in SEQ ID NO: 20, and a CDR3 domain with an amino acid sequence as set forth in SEQ ID NO: 21. The heavy chain of UU-1093-mod17 is identical to UU-1093 VH. The light chain variable region of UU-1093-mod17 contains a CDR1 domain with an amino acid sequence as set forth in SEQ ID NO: 11, a CDR2 domain with an amino acid sequence as set forth in SEQ ID NO: 7, and a CDR3 domain with an amino acid sequence as set forth in SEQ ID NO: 22. For the light chain of UU-1093-mod17, a N-to-Q mutation was introduced into the UU-1093 VL CDR1 to reduce or remove deamidation.

UU-1093-Mod18

UU-1093-mod anti-hNAMPT antibody UU-1093-mod18 has a heavy chain variable region with an amino acid sequence as set forth in SEQ ID NO: 26, and a light chain variable region with an amino acid sequence as set forth in SEQ ID NO: 48. The heavy chain variable region of UU-1093-mod18 contains a CDR1 domain with an amino acid sequence as set forth in SEQ ID NO: 19, a CDR2 domain with an amino acid sequence as set forth in SEQ ID NO: 20, and a CDR3 domain with an amino acid sequence as set forth in SEQ ID NO: 21. The heavy chain of UU-1093-mod18 is identical to UU-1093 VH. The light chain variable region of UU-1093-mod18 contains a CDR1 domain with an amino acid sequence as set forth in SEQ ID NO: 49, a CDR2 domain with an amino acid sequence as set forth in SEQ ID NO: 50, and a CDR3 domain with an amino acid sequence as set forth in SEQ ID NO: 22. For the light chain of UU-1093-mod18, a G-to-A mutation was introduced into the UU-1093 VL CDR1 to reduce or remove deamidation; a I-to-V mutation was introduced into the UU-1093 VL framework region 2 to reduce the binding of a potential T-cell epitope; a M-to-V mutation was introduced into the UU-1093 VL CDR2 to reduce the binding of a potential T-cell epitope and to remove an oxidation site; and a I-to-V mutation was introduced into the UU-1093 VH framework region 3 to reduce the binding of a potential T-cell epitope.

UU-1093-Mod19

UU-1093-mod anti-hNAMPT antibody UU-1093-mod19 has a heavy chain variable region with an amino acid sequence as set forth in SEQ ID NO: 26, and a light chain variable region with an amino acid sequence as set forth in SEQ ID NO: 51. The heavy chain variable region of UU-1093-mod19 contains a CDR1 domain with an amino acid sequence as set forth in SEQ ID NO: 19, a CDR2 domain with an amino acid sequence as set forth in SEQ ID NO: 20, and a CDR3 domain with an amino acid sequence as set forth in SEQ ID NO: 21. The heavy chain of UU-1093-mod17 is identical to UU-1093 VH. The light chain variable region of UU-1093-mod19 contains a CDR1 domain with an amino acid sequence as set forth in SEQ ID NO: 11, a CDR2 domain with an amino acid sequence as set forth in SEQ ID NO: 52, and a CDR3 domain with an amino acid sequence as set forth in SEQ ID NO: 53. For the light chain of UU-1093-mod19, a N-to-Q mutation was introduced into the UU-1093 VL CDR1 to reduce or remove deamidation; a I-to-V mutation was introduced into the UU-1093 VL framework region 2 to remove a potential T-cell epitope; a M-to-V mutation was introduced into the UU-1093 VL CDR2 to remove a potential T-cell epitope and to remove an oxidation site; a A-to-G mutation was introduced into the UU-1093 VL CDR2 to remove a potential T-cell epitope; and a W-to-F mutation was introduced into the UU-1093 VL CDR3 to remove an oxidation site.

TABLE 14

Amino acid sequences of improved UU-1093-mod anti-hNAMPT antibodies

| Antibody | Description | Amino Acid Sequence | Sequence Identifier |
|---|---|---|---|
| UU-1093-mod1 | UU-1093-mod1 heavy chain variable region (VH) (CDRs underlined) | EVQLVQSGAEVKKPGESLRISCKA<br>SGYTFTSYWMHWVRQMPGKGLE<br>WMGEIEPSDSYTNYNQKFKGHVT<br>ISADKSISTAYLQWSSLKASDTAM<br>YYCAKSNYVVPWYFDVWGQGTL<br>VTVSS | SEQ ID NO: 38 |
| | UU-1093-mod1 light chain variable region (VL) (CDRs underlined) | EIVLTQSPGTLSLSPGERATLSCRS<br>SKSLLHSQGITYLYWYQQKPGQA<br>PRLLIYQMSNLASGIPDRFSGSGSG<br>TDFTLTISRLEPEDFAVYYCAQNL<br>ELPWTFGGGTKLEIK | SEQ ID NO: 47 |
| | UU-1093-mod1 CDR-H1 | GYTFTSYWMH | SEQ ID NO: 19 |
| | UU-1093-mod1 CDR-H2 | EIEPSDSYTNYNQKFKG | SEQ ID NO: 39 |
| | UU-1093-mod1 CDR-H3 | AKSNYVVPWYFDV | SEQ ID NO: 21 |
| | UU-1093-mod1 CDR-L1 | RSSKSLLHSQGITYLY | SEQ ID NO: 11 |
| | UU-1093-mod1 CDR-L2 | QMSNLAS | SEQ ID NO: 7 |
| | UU-1093-mod1 CDR-L3 | AQNLELPWT | SEQ ID NO: 22 |

TABLE 14-continued

Amino acid sequences of improved UU-1093-mod anti-hNAMPT antibodies

| Antibody | Description | Amino Acid Sequence | Sequence Identifier |
|---|---|---|---|
| UU-1093-mod2 | UU-1093-mod2 heavy chain variable region (VH) (CDRs underlined) | EVQLVQSGAEVKKPGESLRISCKASGYTFTSYWMHWVRQMPGKGLEWMGEIEPSDSYTNYNQKFKGHVTISADKSISTAYLQWSSLKASDTAMYYCAKTNYVVPWYFDVWGQGTLVTVSS | SEQ ID NO: 40 |
| | UU-1093-mod2 light chain variable region (VL) (CDRs underlined) | EIVLTQSPGTLSLSPGERATLSCRSSKSLLHSQGITYLYWYQQKPGQAPRLLIYQMSNLASGIPDRFSGSGSGTDFTLTISRLEPEDFAVYYCAQNLELPWTFGGGTKLEIK | SEQ ID NO: 47 |
| | UU-1093-mod2 CDR-H1 | GYTFTSYWMH | SEQ ID NO: 19 |
| | UU-1093-mod2 CDR-H2 | EI**E**PSDSYTNYNQKFKG | SEQ ID NO: 39 |
| | UU-1093-mod2 CDR-H3 | AK**T**NYVVPWYFDV | SEQ ID NO: 41 |
| | UU-1093-mod2 CDR-L1 | RSSKSLLHS**Q**GITYLY | SEQ ID NO: 11 |
| | UU-1093-mod2 CDR-L2 | QMSNLAS | SEQ ID NO: 7 |
| | UU-1093-mod2 CDR-L3 | AQNLELPWT | SEQ ID NO: 22 |
| UU-1093-mod3 | UU-1093-mod3 heavy chain variable region (VH) (CDRs underlined) | EVQLVQSGAEVKKPGESLRISCKASGYTFTSYWIHWVRQVPGKGLEWMGEIEPSDSYTNYNQKFKGHVTISADKSISTAYLQWSSLKASDTAVYYCARSNYVVPWYFDVWGQGTLVTVSS | SEQ ID NO: 42 |
| | UU-1093-mod3 light chain variable region (VL) (CDRs underlined) | EIVLTQSPGTLSLSPGERATLSCRSSKSLLHSQGITYLYWYQQKPGQAPRLLIYQMSNLASGIPDRFSGSGSGTDFTLTISRLEPEDFAVYYCAQNLELPWTFGGGTKLEIK | SEQ ID NO: 47 |
| | UU-1093-mod3 CDR-H1 | GYTFTSYW**I**H | SEQ ID NO: 43 |
| | UU-1093-mod3 CDR-H2 | EI**E**PSDSYTNYNQKFKG | SEQ ID NO: 39 |
| | UU-1093-mod3 CDR-H3 | A**R**SNYVVPWYFDV | SEQ ID NO: 44 |
| | UU-1093-mod3 CDR-L1 | RSSKSLLHS**Q**GITYLY | SEQ ID NO: 11 |
| | UU-1093-mod3 CDR-L2 | QMSNLAS | SEQ ID NO: 7 |
| | UU-1093-mod3 CDR-L3 | AQNLELPWT | SEQ ID NO: 22 |
| UU-1093-mod4 | UU-1093-mod4 heavy chain variable region (VH) (CDRs underlined) | EVQLVQSGAEVKKPGESLRISCKASGYTFTSYFIHWVRQVPGKGLEWMGEIEPSDSYTNYNQKFKGHVTISADKSISTAYLQWSSLKASDTAVYYCAKTNYVVPWYFDVWGQGTLVTVSS | SEQ ID NO: 45 |
| | UU-1093-mod4 light chain variable region (VL) (CDRs underlined) | EIVLTQSPGTLSLSPGERATLSCRSSKSLLHSQGITYLYWYQQKPGQAPRLLIYQMSNLASGIPDRFSGSGSGTDFTLTISRLEPEDFAVYYCAQNLELPWTFGGGTKLEIK | SEQ ID NO: 47 |
| | UU-1093-mod4 CDR-H1 | GYTFTSY**FI**H | SEQ ID NO: 46 |
| | UU-1093-mod4 CDR-H2 | EI**E**PSDSYTNYNQKFKG | SEQ ID NO: 39 |
| | UU-1093-mod4 CDR-H3 | AK**T**NYVVPWYFDV | SEQ ID NO: 41 |
| | UU-1093-mod4CDR-L1 | RSSKSLLHS**Q**GITYLY | SEQ ID NO: 11 |
| | UU-1093-mod4 CDR-L2 | QMSNLAS | SEQ ID NO: 7 |
| | UU-1093-mod4 CDR-L3 | AQNLELPWT | SEQ ID NO: 22 |

TABLE 14-continued

Amino acid sequences of improved UU-1093-mod anti-hNAMPT antibodies

| Antibody | Description | Amino Acid Sequence | Sequence Identifier |
|---|---|---|---|
| UU-1093-mod5 | UU-1093-mod5 heavy chain variable region (VH) (CDRs underlined) | EVQLVQSGAEVKKPGESLRISCKASGYTFTSYWMHWVRQMPGKGLEWMGEIEPSDSYTNYNQKFKGHVTISADKSISTAYLQWSSLKASDTAMYYCAKSNYVVPWYFDVWGQGTLVTVSS | SEQ ID NO: 38 |
| | UU-1093-mod5 light chain variable region (VL) (CDRs underlined) | EIVLTQSPGTLSLSPGERATLSCRSSKSLLHSNAITYLYWYQQKPGQAPRLLVYQVSNLASGVPDRFSGSGSGTDFTLTISRLEPEDFAVYYCAQNLELPWTFGGGTKLEIK | SEQ ID NO: 48 |
| | UU-1093-mod5 CDR-H1 | GYTFTSYWMH | SEQ ID NO: 19 |
| | UU-1093-mod5 CDR-H2 | EIEPSDSYTNYNQKFKG | SEQ ID NO: 39 |
| | UU-1093-mod5 CDR-H3 | AKSNYVVPWYFDV | SEQ ID NO: 21 |
| | UU-1093-mod5 CDR-L1 | RSSKSLLHSNAITYLY | SEQ ID NO: 49 |
| | UU-1093-mod5 CDR-L2 | QVSNLAS | SEQ ID NO: 50 |
| | UU-1093-mod5 CDR-L3 | AQNLELPWT | SEQ ID NO: 22 |
| UU-1093-mod6 | UU-1093-mod6 heavy chain variable region (VH) (CDRs underlined) | EVQLVQSGAEVKKPGESLRISCKASGYTFTSYWMHWVRQMPGKGLEWMGEIEPSDSYTNYNQKFKGHVTISADKSISTAYLQWSSLKASDTAMYYCAKTNYVVPWYFDVWGQGTLVTVSS | SEQ ID NO: 40 |
| | UU-1093-mod6 light chain variable region (VL) (CDRs underlined) | EIVLTQSPGTLSLSPGERATLSCRSSKSLLHSNAITYLYWYQQKPGQAPRLLVYQVSNLASGVPDRFSGSGSGTDFTLTISRLEPEDFAVYYCAQNLELPWTFGGGTKLEIK | SEQ ID NO: 48 |
| | UU-1093-mod6 CDR-H1 | GYTFTSYWMH | SEQ ID NO: 19 |
| | UU-1093-mod6 CDR-H2 | EIEPSDSYTNYNQKFKG | SEQ ID NO: 39 |
| | UU-1093-mod6 CDR-H3 | AKTNYVVPWYFDV | SEQ ID NO: 41 |
| | UU-1093-mod6 CDR-L1 | RSSKSLLHSNAITYLY | SEQ ID NO: 49 |
| | UU-1093-mod6 CDR-L2 | QVSNLAS | SEQ ID NO: 50 |
| | UU-1093-mod6 CDR-L3 | AQNLELPWT | SEQ ID NO: 22 |
| UU-1093-mod7 | UU-1093-mod7 heavy chain variable region (VH) (CDRs underlined) | EVQLVQSGAEVKKPGESLRISCKASGYTFTSYWIHWVRQVPGKGLEWMGEIEPSDSYTNYNQKFKGHVTISADKSISTAYLQWSSLKASDTAVYYCARSNYVVPWYFDVWGQGTLVTVSS | SEQ ID NO: 42 |
| | UU-1093-mod7 light chain variable region (VL) (CDRs underlined) | EIVLTQSPGTLSLSPGERATLSCRSSKSLLHSNAITYLYWYQQKPGQAPRLLVYQVSNLASGVPDRFSGSGSGTDFTLTISRLEPEDFAVYYCAQNLELPWTFGGGTKLEIK | SEQ ID NO: 48 |
| | UU-1093-mod7 CDR-H1 | GYTFTSYWIH | SEQ ID NO: 43 |
| | UU-1093-mod7 CDR-H2 | EIEPSDSYTNYNQKFKG | SEQ ID NO: 39 |
| | UU-1093-mod7 CDR-H3 | ARSNYVVPWYFDV | SEQ ID NO: 44 |
| | UU-1093-mod7 CDR-L1 | RSSKSLLHSNAITYLY | SEQ ID NO: 49 |
| | UU-1093-mod7 CDR-L2 | QVSNLAS | SEQ ID NO: 50 |
| | UU-1093-mod7 CDR-L3 | AQNLELPWT | SEQ ID NO: 22 |
| UU-1093-mod8 | UU-1093-mod8 heavy chain variable region | EVQLVQSGAEVKKPGESLRISCKASGYTFTSYFIHWVRQVPGKGLEWMGEIEPSDSYTNYNQKFKGHVTIS | SEQ ID NO: 45 |

TABLE 14-continued

Amino acid sequences of improved UU-1093-mod anti-hNAMPT antibodies

| Antibody | Description | Amino Acid Sequence | Sequence Identifier |
|---|---|---|---|
| | (VH) (CDRs underlined) | ADKSISTAYLQWSSLKASDTAVY YCAKTNYVVPWYFDVWGQGTLV TVSS | |
| | UU-1093-mod8 light chain variable region (VL) (CDRs underlined) | EIVLTQSPGTLSLSPGERATLSCRS SKSLLHSNAITYLYWYQQKPGQA PRLLVYQVSNLASGVPDRFSGSGS GTDFTLTISRLEPEDFAVYYCAQN LELPWTFGGGTKLEIK | SEQ ID NO: 48 |
| | UU-1093-mod8 CDR-H1 | GYTFTSY**FI**H | SEQ ID NO: 46 |
| | UU-1093-mod8 CDR-H2 | EI**E**PSDSYTNYNQKFKG | SEQ ID NO: 39 |
| | UU-1093-mod8 CDR-H3 | AK**T**NYVVPWYFDV | SEQ ID NO: 41 |
| | UU-1093-mod8CDR-L1 | RSSKSLLHSN**A**ITYLY | SEQ ID NO: 49 |
| | UU-1093-mod8 CDR-L2 | Q**V**SNLAS | SEQ ID NO: 50 |
| | UU-1093-mod8 CDR-L3 | AQNLELPWT | SEQ ID NO: 22 |
| UU-1093-mod9 | UU-1093-mod9 heavy chain variable region (VH) (CDRs underlined) | EVQLVQSGAEVKKPGESLRISCKA SGYTFTSYWMHWVRQMPGKGLE WMGEIEPSDSYTNYNQKFKGHVT ISADKSISTAYLQWSSLKASDTAM YYCAKSNYVVPWYFDVWGQGTL VTVSS | SEQ ID NO: 38 |
| | UU-1093-mod9 light chain variable region (VL) (CDRs underlined) | EIVLTQSPGTLSLSPGERATLSCRS SKSLLHSQGITYLYWYQQKPGQA PRLLVYQVSNLGSGIPDRFSGSGS GTDFTLTISRLEPEDFAVYYCAQN LELPFTFGGGTKLEIK | SEQ ID NO: 51 |
| | UU-1093-mod9 CDR-H1 | GYTFTSYWMH | SEQ ID NO: 19 |
| | UU-1093-mod9 CDR-H2 | EI**E**PSDSYTNYNQKFKG | SEQ ID NO: 39 |
| | UU-1093-mod9 CDR-H3 | AKSNYVVPWYFDV | SEQ ID NO: 21 |
| | UU-1093-mod9 CDR-L1 | RSSKSLLHS**Q**GITYLY | SEQ ID NO: 11 |
| | UU-1093-mod9 CDR-L2 | Q**V**SNL**G**S | SEQ ID NO: 52 |
| | UU-1093-mod9 CDR-L3 | AQNLELP**F**T | SEQ ID NO: 53 |
| UU-1093-mod10 | UU-1093-mod10 heavy chain variable region (VH) (CDRs underlined) | EVQLVQSGAEVKKPGESLRISCKA SGYTFTSYWMHWVRQMPGKGLE WMGEIEPSDSYTNYNQKFKGHVT ISADKSISTAYLQWSSLKASDTAM YYCAKTNYVVPWYFDVWGQGTL VTVSS | SEQ ID NO: 40 |
| | UU-1093-mod10 light chain variable region (VL) (CDRs underlined) | EIVLTQSPGTLSLSPGERATLSCRS SKSLLHSQGITYLYWYQQKPGQA PRLLVYQVSNLGSGIPDRFSGSGS GTDFTLTISRLEPEDFAVYYCAQN LELPFTFGGGTKLEIK | SEQ ID NO: 51 |
| | UU-1093-mod10 CDR-H1 | GYTFTSYWMH | SEQ ID NO: 19 |
| | UU-1093-mod10 CDR-H2 | EI**E**PSDSYTNYNQKFKG | SEQ ID NO: 39 |
| | UU-1093-mod10 CDR-H3 | AK**T**NYVVPWYFDV | SEQ ID NO: 41 |
| | UU-1093-mod10 CDR-L1 | RSSKSLLHS**Q**GITYLY | SEQ ID NO: 11 |
| | UU-1093-mod10 CDR-L2 | Q**V**SNL**G**S | SEQ ID NO: 52 |
| | UU-1093-mod10 CDR-L3 | AQNLELP**F**T | SEQ ID NO: 53 |
| UU-1093-mod11 | UU-1093-mod11 heavy chain variable region (VH) (CDRs underlined) | EVQLVQSGAEVKKPGESLRISCKA SGYTFTSYWIHWVRQVPGKGLEW MGEIEPSDSYTNYNQKFKGHVTIS ADKSISTAYLQWSSLKASDTAVY YCARSNYVVPWYFDVWGQGTLV TVSS | SEQ ID NO: 42 |

TABLE 14-continued

Amino acid sequences of improved UU-1093-mod anti-hNAMPT antibodies

| Antibody | Description | Amino Acid Sequence | Sequence Identifier |
|---|---|---|---|
| | UU-1093-mod11 light chain variable region (VL) (CDRs underlined) | EIVLTQSPGTLSLSPGERATLSCRS<br>SKSLLHSQGITYLYWYQQKPGQA<br>PRLLVYQVSNLGSGIPDRFSGSGS<br>GTDFTLTISRLEPEDFAVYYCAQN<br>LELPFTFGGGTKLEIK | SEQ ID NO: 51 |
| | UU-1093-mod11 CDR-H1 | GYTFTSYWIH | SEQ ID NO: 43 |
| | UU-1093-mod11 CDR-H2 | EIEPSDSYTNYNQKFKG | SEQ ID NO: 39 |
| | UU-1093-mod11 CDR-H3 | ARSNYVVPWYFDV | SEQ ID NO: 44 |
| | UU-1093-mod11 CDR-L1 | RSSKSLLHSQGITYLY | SEQ ID NO: 11 |
| | UU-1093-mod11 CDR-L2 | QVSNLGS | SEQ ID NO: 52 |
| | UU-1093-mod11 CDR-L3 | AQNLELPFT | SEQ ID NO: 53 |
| UU-1093-mod12 | UU-1093-mod12 heavy chain variable region (VH) (CDRs underlined) | EVQLVQSGAEVKKPGESLRISCKA<br>SGYTFTSYFIHWVRQVPGKGLEW<br>MGEIEPSDSYTNYNQKFKGHVTIS<br>ADKSISTAYLQWSSLKASDTAVY<br>YCAKTNYVVPWYFDVWGQGTLV<br>TVSS | SEQ ID NO: 45 |
| | UU-1093-mod12 light chain variable region (VL) (CDRs underlined) | EIVLTQSPGTLSLSPGERATLSCRS<br>SKSLLHSQGITYLYWYQQKPGQA<br>PRLLVYQVSNLGSGIPDRFSGSGS<br>GTDFTLTISRLEPEDFAVYYCAQN<br>LELPFTFGGGTKLEIK | SEQ ID NO: 51 |
| | UU-1093-mod12 CDR-H1 | GYTFTSYFIH | SEQ ID NO: 46 |
| | UU-1093-mod12 CDR-H2 | EIEPSDSYTNYNQKFKG | SEQ ID NO: 39 |
| | UU-1093-mod12 CDR-H3 | AKTNYVVPWYFDV | SEQ ID NO: 41 |
| | UU-1093-mod12 CDR-L1 | RSSKSLLHSQGITYLY | SEQ ID NO: 11 |
| | UU-1093-mod12 CDR-L2 | QVSNLGS | SEQ ID NO: 52 |
| | UU-1093-mod12 CDR-L3 | AQNLELPFT | SEQ ID NO: 53 |
| UU-1093-mod13 | UU-1093-mod13 heavy chain variable region (VH) (CDRs underlined) | EVQLVQSGAEVKKPGESLRISCKA<br>SGYTFTSYWMHWVRQMPGKGLE<br>WMGEIEPSDSYTNYNQKFKGHVT<br>ISADKSISTAYLQWSSLKASDTAM<br>YYCAKSNYVVPWYFDVWGQGTL<br>VTVSS | SEQ ID NO: 38 |
| | UU-1093-mod13 light chain variable region (VL) (CDRs underlined) | EIVLTQSPGTLSLSPGERATLSCRS<br>SKSLLHSNGITYLYWYQQKPGQA<br>PRLLIYQMSNLASGIPDRFSGSGSG<br>TDFTLTISRLEPEDFAVYYCAQNL<br>ELPWTFGGGTKLEIK | SEQ ID NO: 18 |
| | UU-1093-mod13 CDR-H1 | GYTFTSYWMH | SEQ ID NO: 19 |
| | UU-1093-mod13 CDR-H2 | EIEPSDSYTNYNQKFKG | SEQ ID NO: 39 |
| | UU-1093-mod13 CDR-H3 | AKSNYVVPWYFDV | SEQ ID NO: 21 |
| | UU-1093-mod13 CDR-L1 | RSSKSLLHSNGITYLY | SEQ ID NO: 6 |
| | UU-1093-mod13 CDR-L2 | QMSNLAS | SEQ ID NO: 7 |
| | UU-1093-mod13 CDR-L3 | AQNLELPWT | SEQ ID NO: 22 |
| UU-1093-mod14 | UU-1093-mod14 heavy chain variable region (VH) (CDRs underlined) | EVQLVQSGAEVKKPGESLRISCKA<br>SGYTFTSYWMHWVRQMPGKGLE<br>WMGEIEPSDSYTNYNQKFKGHVT<br>ISADKSISTAYLQWSSLKASDTAM<br>YYCAKTNYVVPWYFDVWGQGTL<br>VTVSS | SEQ ID NO: 40 |
| | UU-1093-mod14 light chain variable region (VL) | EIVLTQSPGTLSLSPGERATLSCRS<br>SKSLLHSNGITYLYWYQQKPGQA<br>PRLLIYQMSNLASGIPDRFSGSGSG | SEQ ID NO: 18 |

TABLE 14-continued

| Amino acid sequences of improved UU-1093-mod anti-hNAMPT antibodies | | | |
|---|---|---|---|
| Antibody | Description | Amino Acid Sequence | Sequence Identifier |
| | (CDRs underlined) | TDFTLTISRLEPEDFAVYYCAQNL ELPWTFGGGTKLEIK | |
| | UU-1093-mod14 CDR-H1 | GYTFTSYWMH | SEQ ID NO: 19 |
| | UU-1093-mod14 CDR-H2 | EI**E**PSDSYTNYNQKFKG | SEQ ID NO: 39 |
| | UU-1093-mod14 CDR-H3 | AK**T**NYVVPWYFDV | SEQ ID NO: 41 |
| | UU-1093-mod14 CDR-L1 | RSSKSLLHSNGITYLY | SEQ ID NO: 6 |
| | UU-1093-mod14 CDR-L2 | QMSNLAS | SEQ ID NO: 7 |
| | UU-1093-mod14 CDR-L3 | AQNLELPWT | SEQ ID NO: 22 |
| UU-1093-mod15 | UU-1093-mod15 heavy chain variable region (VH) (CDRs underlined) | EVQLVQSGAEVKKPGESLRISCKA SGYTFTSYW**I**HWVRQ**V**PGKGLEW MGEI**E**PSDSYTNYNQKFKGHVTIS ADKSISTAYLQWSSLKASDTA**V**Y YCA**R**SNYVVPWYFDVWGQGTLV TVSS | SEQ ID NO: 42 |
| | UU-1093-mod15 light chain variable region (VL) (CDRs underlined) | EIVLTQSPGTLSLSPGERATLSCRS SKSLLHSNGITYLYWYQQKPGQA PRLLIYQMSNLASGIPDRFSGSGSG TDFTLTISRLEPEDFAVYYCAQNL ELPWTFGGGTKLEIK | SEQ ID NO: 18 |
| | UU-1093-mod15 CDR-H1 | GYTFTSYW**I**H | SEQ ID NO: 43 |
| | UU-1093-mod15 CDR-H2 | EI**E**PSDSYTNYNQKFKG | SEQ ID NO: 39 |
| | UU-1093-mod15 CDR-H3 | A**R**SNYVVPWYFDV | SEQ ID NO: 44 |
| | UU-1093-mod15 CDR-L1 | RSSKSLLHSNGITYLY | SEQ ID NO: 6 |
| | UU-1093-mod15 CDR-L2 | QMSNLAS | SEQ ID NO: 7 |
| | UU-1093-mod15 CDR-L3 | AQNLELPWT | SEQ ID NO: 22 |
| UU-1093-mod16 | UU-1093-mod16 heavy chain variable region (VH) (CDRs underlined) | EVQLVQSGAEVKKPGESLRISCKA SGYTFTSY**FI**HWVRQ**V**PGKGLEW MGEI**E**PSDSYTNYNQKFKGHVTIS ADKSISTAYLQWSSLKASDTA**V**Y YCAK**T**NYVVPWYFDVWGQGTLV TVSS | SEQ ID NO: 45 |
| | UU-1093-mod16 light chain variable region (VL) (CDRs underlined) | EIVLTQSPGTLSLSPGERATLSCRS SKSLLHSNGITYLYWYQQKPGQA PRLLIYQMSNLASGIPDRFSGSGSG TDFTLTISRLEPEDFAVYYCAQNL ELPWTFGGGTKLEIK | SEQ ID NO: 18 |
| | UU-1093-mod16 CDR-H1 | GYTFTSY**FI**H | SEQ ID NO: 46 |
| | UU-1093-mod16 CDR-H2 | EI**E**PSDSYTNYNQKFKG | SEQ ID NO: 39 |
| | UU-1093-mod16 CDR-H3 | AK**T**NYVVPWYFDV | SEQ ID NO: 41 |
| | UU-1093-mod16 CDR-L1 | RSSKSLLHSNGITYLY | SEQ ID NO: 6 |
| | UU-1093-mod16 CDR-L2 | QMSNLAS | SEQ ID NO: 7 |
| | UU-1093-mod16 CDR-L3 | AQNLELPWT | SEQ ID NO: 22 |
| UU-1093-mod17 | UU-1093-mod17 heavy chain variable region (VH) (CDRs underlined) | EVQLVQSGAEVKKPGESLRISCKA SGYTFTSYWMHWVRQMPGKGLE WMGEIDPSDSYTNYNQKFKGHVT ISADKSISTAYLQWSSLKASDTAM YYCAKSNYVVPWYFDVWGQGTL VTVSS | SEQ ID NO: 26 |
| | UU-1093-mod17 light chain variable region (VL) (CDRs underlined) | EIVLTQSPGTLSLSPGERATLSCRS SKSLLHS**Q**GITYLYWYQQKPGQA PRLLIYQMSNLASGIPDRFSGSGSG TDFTLTISRLEPEDFAVYYCAQNL ELPWTFGGGTKLEIK | SEQ ID NO: 47 |

TABLE 14-continued

| Amino acid sequences of improved UU-1093-mod anti-hNAMPT antibodies | | | |
|---|---|---|---|
| Antibody | Description | Amino Acid Sequence | Sequence Identifier |
| | UU-1093-mod17 CDR-H1 | GYTFTSYWMH | SEQ ID NO: 19 |
| | UU-1093-mod17 CDR-H2 | EIDPSDSYTNYNQKFKG | SEQ ID NO: 20 |
| | UU-1093-mod17 CDR-H3 | AKSNYVVPWYFDV | SEQ ID NO: 21 |
| | UU-1093-mod17 CDR-LI | RSSKSLLHS**Q**GITYLY | SEQ ID NO: 11 |
| | UU-1093-mod17 CDR-L2 | QMSNLAS | SEQ ID NO: 7 |
| | UU-1093-mod17 CDR-L3 | AQNLELPWT | SEQ ID NO: 22 |
| UU-1093-mod18 | UU-1093-mod18 heavy chain variable region (VH) (CDRs underlined) | EVQLVQSGAEVKKPGESLRISCKASGYTFTSYWMHWVRQMPGKGLEWMGEIDPSDSYTNYNQKFKGHVTISADKSISTAYLQWSSLKASDTAMYYCAKSNYVVPWYFDVWGQGTLVTVSS | SEQ ID NO: 26 |
| | UU-1093-mod18 light chain variable region (VL) (CDRs underlined) | EIVLTQSPGTLSLSPGERATLSCRSSKSLLHSN**A**ITYLYWYQQKPGQAPRLL**V**YQ**V**SNLASG**V**PDRFSGSGSGTDFTLTISRLEPEDFAVYYCAQNLELPWTFGGGTKLEIK | SEQ ID NO: 48 |
| | UU-1093-mod18 CDR-H1 | GYTFTSYWMH | SEQ ID NO: 19 |
| | UU-1093-mod18 CDR-H2 | EIDPSDSYTNYNQKFKG | SEQ ID NO: 20 |
| | UU-1093-mod18 CDR-H3 | AKSNYVVPWYFDV | SEQ ID NO: 21 |
| | UU-1093-mod18 CDR-L1 | RSSKSLLHSN**A**ITYLY | SEQ ID NO: 49 |
| | UU-1093-mod18 CDR-L2 | Q**V**SNLAS | SEQ ID NO: 50 |
| | UU-1093-mod18 CDR-L3 | AQNLELPWT | SEQ ID NO: 22 |
| UU-1093-mod19 | UU-1093-mod19 heavy chain variable region (VH) (CDRs underlined) | EVQLVQSGAEVKKPGESLRISCKASGYTFTSYWMHWVRQMPGKGLEWMGEIDPSDSYTNYNQKFKGHVTISADKSISTAYLQWSSLKASDTAMYYCAKSNYVVPWYFDVWGQGTLVTVSS | SEQ ID NO: 26 |
| | UU-1093-mod19 light chain variable region (VL) (CDRs underlined) | EIVLTQSPGTLSLSPGERATLSCRSSKSLLHS**Q**GITYLYWYQQKPGQAPRLL**V**YQ**V**SNL**G**SGIPDRFSGSGSGTDFTLTISRLEPEDFAVYYCAQNLELP**F**TFGGGTKLEIK | SEQ ID NO: 51 |
| | UU-1093-mod19 CDR-H1 | GYTFTSYWMH | SEQ ID NO: 19 |
| | UU-1093-mod19 CDR-H2 | EIDPSDSYTNYNQKFKG | SEQ ID NO: 20 |
| | UU-1093-mod19 CDR-H3 | AKSNYVVPWYFDV | SEQ ID NO: 21 |
| | UU-1093-mod19 CDR-L1 | RSSKSLLHS**Q**GITYLY | SEQ ID NO: 11 |

TABLE 14-continued

| Amino acid sequences of improved UU-1093-mod anti-hNAMPT antibodies | | | |
|---|---|---|---|
| Antibody | Description | Amino Acid Sequence | Sequence Identifier |
| | UU-1093-mod19 CDR-L2 | Q**V**SNL**G**S | SEQ ID NO: 52 |
| | UU-1093-mod19 CDR-L3 | AQNLELP**F**T | SEQ ID NO: 53 |

In Table 14, mutated residues are in bold font.

TABLE 15

Comparison of HC CDRs of UU-1093-mod anti-hNAMPT antibodies with HC CDRs of UU-1093

| | Heavy Chain (HC) CDR1 | | | | | | | | | | SEQ ID NO: | HC CDR2 | | | | | | | | | | |
|---|---|---|---|---|---|---|---|---|---|---|---|---|---|---|---|---|---|---|---|---|---|---|
| UU-1093 | G | Y | T | F | T | S | Y | W | M | H | 19 | E | I | D | P | S | D | S | Y | T | N | Y |
| UU-1093-mod1 | | | | | | | | | | | 19 | | | E | | | | | | | | |
| UU-1093-mod2 | | | | | | | | | | | 19 | | | E | | | | | | | | |
| UU-1093-mod3 | | | | | | | | | I | | 43 | | | E | | | | | | | | |
| UU-1093-mod4 | | | | | | | | F | I | | 46 | | | E | | | | | | | | |
| UU-1093-mod5 | | | | | | | | | | | 19 | | | E | | | | | | | | |
| UU-1093-mod6 | | | | | | | | | | | 19 | | | E | | | | | | | | |
| UU-1093-mod7 | | | | | | | | | I | | 43 | | | E | | | | | | | | |
| UU-1093-mod8 | | | | | | | | F | I | | 46 | | | E | | | | | | | | |
| UU-1093-mod9 | | | | | | | | | | | 19 | | | E | | | | | | | | |
| UU-1093-mod10 | | | | | | | | | | | 19 | | | E | | | | | | | | |
| UU-1093-mod11 | | | | | | | | | I | | 43 | | | E | | | | | | | | |
| UU-1093-mod12 | | | | | | | | F | I | | 46 | | | E | | | | | | | | |
| UU-1093-mod13 | | | | | | | | | | | 19 | | | E | | | | | | | | |
| UU-1093-mod14 | | | | | | | | | | | 19 | | | E | | | | | | | | |
| UU-1093-mod15 | | | | | | | | | I | | 43 | | | E | | | | | | | | |
| UU-1093-mod16 | | | | | | | | F | I | | 46 | | | E | | | | | | | | |
| UU-1093-mod17 | | | | | | | | | | | 19 | | | | | | | | | | | |

TABLE 15-continued

| Comparison of HC CDRs of UU-1093-mod anti-hNAMPT antibodies with HC CDRs of UU-1093 | |
|---|---|
| UU-1093-mod18 | 19 |
| UU-1093-mod19 | 19 |

| | HC CD2 | | | | | | SEQ ID NO: | HC CDR3 | | | | | | | | | | | | SEQ ID NO: |
|---|---|---|---|---|---|---|---|---|---|---|---|---|---|---|---|---|---|---|---|---|
| UU-1093 | N | Q | K | F | K | G | 20 | A | K | S | N | Y | V | V | P | W | Y | F | D | V | 21 |
| UU-1093-mod1 | | | | | | | 39 | | | | | | | | | | | | | | 21 |
| UU-1093-mod2 | | | | | | | 39 | | | T | | | | | | | | | | | 41 |
| UU-1093-mod3 | | | | | | | 39 | | R | | | | | | | | | | | | 44 |
| UU-1093-mod4 | | | | | | | 39 | | | T | | | | | | | | | | | 41 |
| UU-1093-mod5 | | | | | | | 39 | | | | | | | | | | | | | | 21 |
| UU-1093-mod6 | | | | | | | 39 | | | T | | | | | | | | | | | 41 |
| UU-1093-mod7 | | | | | | | 39 | | R | | | | | | | | | | | | 44 |
| UU-1093-mod8 | | | | | | | 39 | | | T | | | | | | | | | | | 41 |
| UU-1093-mod9 | | | | | | | 39 | | | | | | | | | | | | | | 21 |
| UU-1093-mod10 | | | | | | | 39 | | | T | | | | | | | | | | | 41 |
| UU-1093-mod11 | | | | | | | 39 | | R | | | | | | | | | | | | 44 |
| UU-1093-mod12 | | | | | | | 39 | | | T | | | | | | | | | | | 41 |
| UU-1093-mod13 | | | | | | | 39 | | | | | | | | | | | | | | 21 |
| UU-1093-mod14 | | | | | | | 39 | | | T | | | | | | | | | | | 41 |
| UU-1093-mod15 | | | | | | | 39 | | R | | | | | | | | | | | | 44 |
| UU-1093-mod16 | | | | | | | 39 | | | T | | | | | | | | | | | 41 |
| UU-1093-mod17 | | | | | | | 20 | | | | | | | | | | | | | | 21 |
| UU-1093-mod18 | | | | | | | 20 | | | | | | | | | | | | | | 21 |
| UU-1093-mod19 | | | | | | | 20 | | | | | | | | | | | | | | 21 |

TABLE 16

Comparison of LC CDRs of UU-1093-mod anti-hNAMPT antibodies with LC CDRs of UU-1093

| | Light Chain (LC) CDR1 | | | | | | | | | | | | | | | | SEQ ID NO: | LC CDR2 | | | | | | | SEQ ID NO: | LC CDR3 | | | | | | | | | SEQ ID NO: |
|---|---|---|---|---|---|---|---|---|---|---|---|---|---|---|---|---|---|---|---|---|---|---|---|---|---|---|---|---|---|---|---|---|---|---|---|
| UU-1093 | R | S | S | K | S | L | L | H | S | N | G | I | T | Y | L | Y | 6 | Q | M | S | N | L | A | S | 7 | A | Q | N | L | E | L | P | W | T | 22 |
| UU-1093-mod1 | | | | | | | | | | Q | | | | | | | 11 | | | | | | | | 7 | | | | | | | | | | 22 |
| UU-1093-mod2 | | | | | | | | | | Q | | | | | | | 11 | | | | | | | | 7 | | | | | | | | | | 22 |
| UU-1093-mod3 | | | | | | | | | | Q | | | | | | | 11 | | | | | | | | 7 | | | | | | | | | | 22 |
| UU-1093-mod4 | | | | | | | | | | Q | | | | | | | 11 | | | | | | | | 7 | | | | | | | | | | 22 |
| UU-1093-mod5 | | | | | | | | | | | A | | | | | | 49 | | V | | | | | | 50 | | | | | | | | | | 22 |
| UU-1093-mod6 | | | | | | | | | | | A | | | | | | 49 | | V | | | | | | 50 | | | | | | | | | | 22 |
| UU-1093-mod7 | | | | | | | | | | | A | | | | | | 49 | | V | | | | | | 50 | | | | | | | | | | 22 |
| UU-1093-mod8 | | | | | | | | | | | A | | | | | | 49 | | V | | | | | | 50 | | | | | | | | | | 22 |
| UU-1093-mod9 | | | | | | | | | | Q | | | | | | | 11 | | V | | | | G | | 52 | | | | | | | | F | | 53 |
| UU-1093-mod10 | | | | | | | | | | Q | | | | | | | 11 | | V | | | | G | | 52 | | | | | | | | F | | 53 |
| UU-1093-mod11 | | | | | | | | | | Q | | | | | | | 11 | | V | | | | G | | 52 | | | | | | | | F | | 53 |
| UU-1093-mod12 | | | | | | | | | | Q | | | | | | | 11 | | V | | | | G | | 52 | | | | | | | | F | | 53 |
| UU-1093-mod13 | | | | | | | | | | | | | | | | | 6 | | | | | | | | 7 | | | | | | | | | | 22 |
| UU-1093-mod14 | | | | | | | | | | | | | | | | | 6 | | | | | | | | 7 | | | | | | | | | | 22 |
| UU-1093-mod15 | | | | | | | | | | | | | | | | | 6 | | | | | | | | 7 | | | | | | | | | | 22 |

TABLE 16-continued

| Comparison of LC CDRs of UU-1093-mod anti-hNAMPT antibodies with LC CDRs of UU-1093 | | | | | | |
|---|---|---|---|---|---|---|
| | Light Chain (LC) CDR1 | SEQ ID NO: | LC CDR2 | SEQ ID NO: | LC CDR3 | SEQ ID NO: |
| UU-1093-mod16 | | 6 | | 7 | | 22 |
| UU-1093-mod17 | Q | 11 | | 7 | | 22 |
| UU-1093-mod18 | A | 49 | V | 50 | | 22 |
| UU-1093-mod19 | Q | 11 | V G | 52 | F | 53 |

Example 12. Tissue Expression of NAMPT in Human Invasive PCa

To assess the role of NAMPT in prostate cancer (PCa) invasiveness and progression, the NAMPT expression was studied in PCa tissue.

Figure 9A:
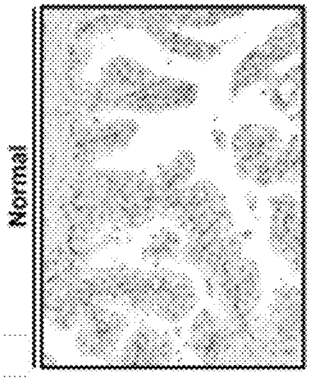
FIGS. 9A-9D show immunohistochemical (IHC) staining for NAMPT in normal, minimally invasive and highly invasive prostate cancer (PCa).

Expression of NAMPT was assessed by immunohistochemical (IHC) staining in normal prostate tissue, in prostatic adenocarcinoma confined to the prostate and without capsular invasion, and in prostatic adenocarcinomas with capsular invasion into peri-prostatic adipose tissues. Representative micrographs are provided in FIGS. 9A-9C. Additionally, NAMPT expression was evaluated by IHC staining in benign prostate tissues, tissues from PCa patients with organ-confined disease (T2 disease; n=12), and tissues from PCa patients with capsule invasive disease (T3 disease; n=14); a cumulative analysis is provided in FIG. 9D.

Figure 9B:
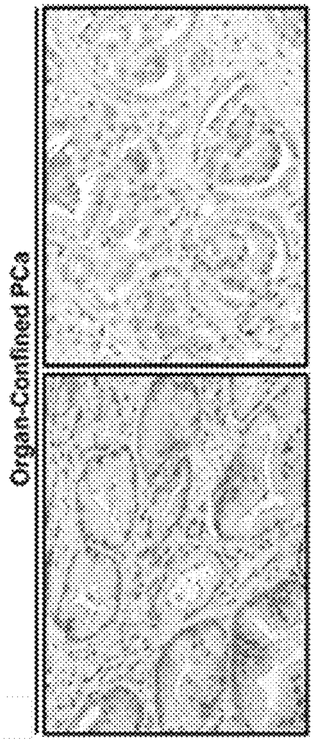
Figure 9C:
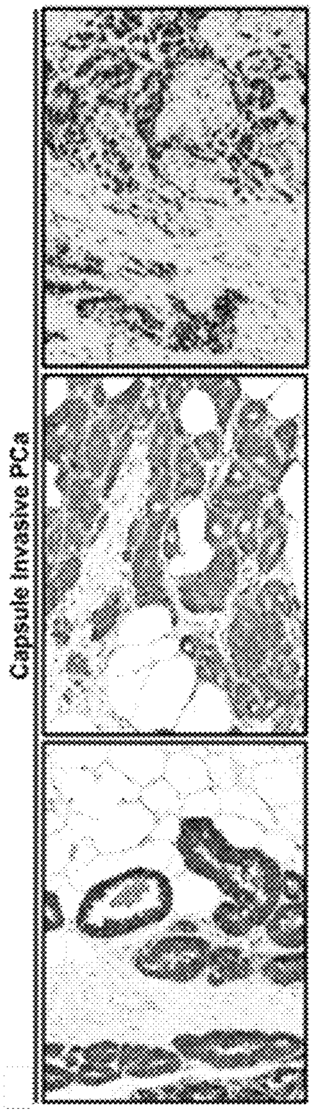
Figure 9D:
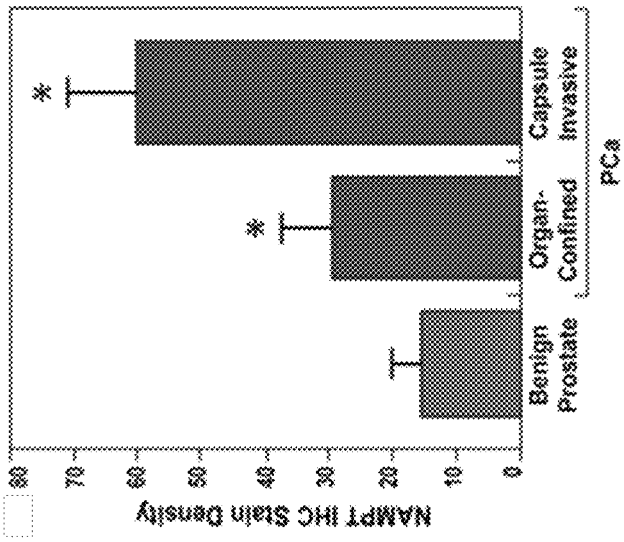

As depicted in FIG. 9, IHC analysis of the normal and PCa tissues showed virtual absence of NAMPT expression in normal prostate tissue (FIG. 9A), and minimal expression of NAMPT in prostatic adenocarcinoma confined to the prostate and without capsular invasion (FIG. 9B). In contrast, prostatic adenocarcinomas with capsular invasion into peri-prostatic adipose tissues show significantly robust NAMPT staining (FIG. 9C). Moreover, comparative analysis of benign prostate tissues and tissues from 26 PCa patients with T2 and T3 disease showed increased expression of NAMPT with increased PCa invasiveness (FIG. 9D). Thus, increased expression of NAMPT was observed in invasive PCa in human.

Example 13. Effect of Radiation Exposure on NAMPT Expression

Radiation therapy is a mainstay of PCa therapy. As extracellular NAMPT (eNAMPT) functions as a damage-associated molecular pattern protein (DAMP) in innate immunity, effect of radiation on NAMPT expression was assessed by evaluating the expression of NAMPT in radiation-exposed murine and human tissues.

To assess the effect of radiation-induced tissue injury and damage on NAMPT expression in murine tissues, C57/B6 mice were exposed to a single dose of thoracic radiation (20 Gy) for 1 week. Effect of radiation on inflammation, vascular leak and inflammatory lung injury was assessed by H&E staining of the murine lung tissues following radiation exposure. Representative micrographs are provided in FIG. 10A. NAMPT expression was evaluated in the lung tissues before and after radiation by IHC staining. Representative micrographs are provided in FIGS. 10B and 10C. To assess the effect of radiation on NAMPT expression in human tissues, normal human epithelial tissues (tonsil) were exposed to radiation (8 Gy) for 24 hours, and NAMPT expression was evaluated by IHC staining. Representative micrographs are provided in FIG. 10D.

Figures 10A, 10B, 10C, 10D:
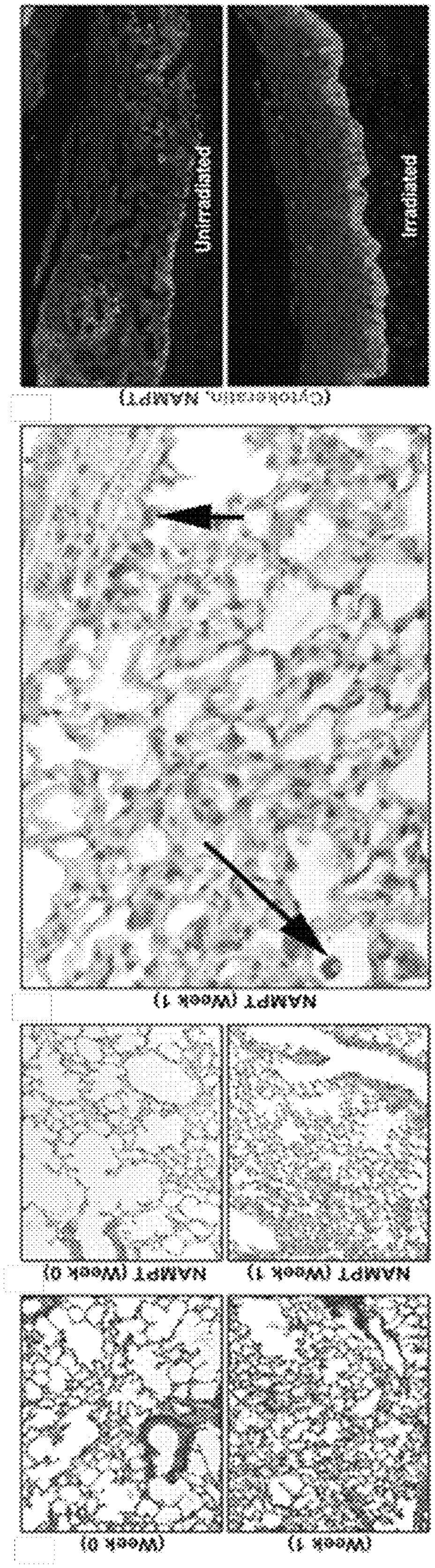
FIGS. 10A-10D depict results from analysis of murine and human tissues following acute and subacute radiation.

As depicted in FIG. 10, after 1 week of radiation exposure, an increase in inflammation, vascular leak and inflammatory injury was observed in murine lung tissues (FIG. 10A). The radiation-induced lung injury was accompanied by prominent NAMPT expression (FIG. 10B), especially in alveolar macrophages and epithelial cells (FIG. 10C). Consistent with radiation as a stimulus for NAMPT tissue expression in mouse, marked increase in NAMPT expression was observed in normal human epithelial tissues (tonsil) 24 hours after radiation exposure (FIG. 10D). Thus, radiation-induced tissue injury significantly induced NAMPT expression.

Example 14. Role of NAMPT in PCa Cell Migration

An in vitro assay of PCa cell migration through human smooth muscle cells was used to assess the role of NAMPT on migration of PCa cells.

Figure 11B:
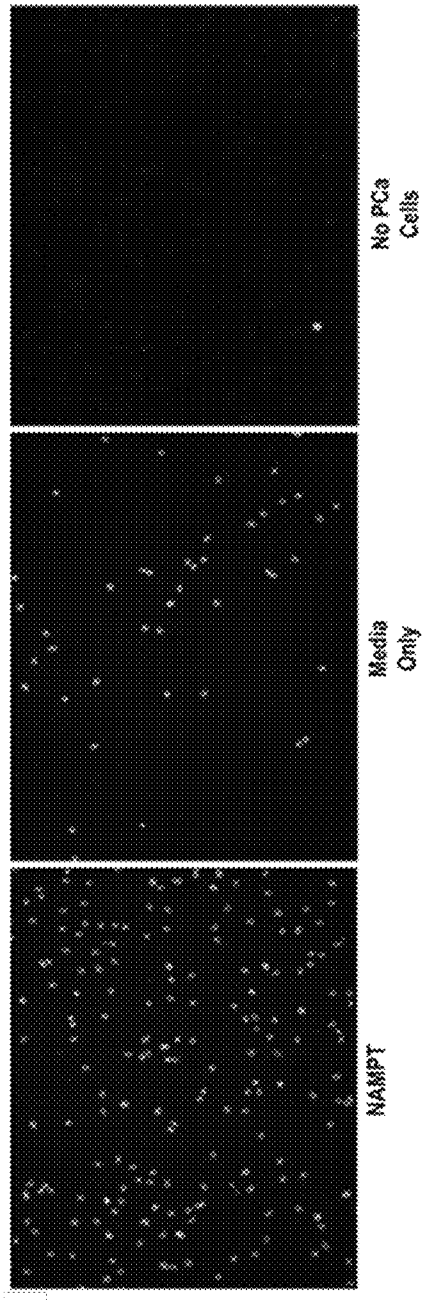
FIGS. 11A-11B depict results from in vitro assay of human DU-145 PCa cell migration through human smooth muscle cells.
Figure 11A:
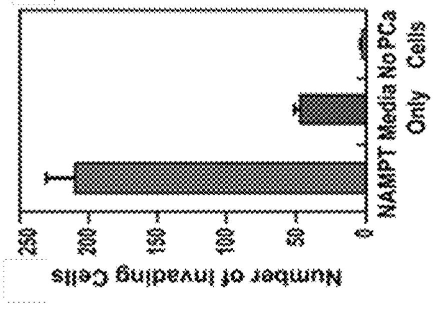

To assess the role of NAMPT in PCa cell migration, NAMPT (100 ng/mL) was added to a culture of human DU-145 PCa cells. Following 24 hours of NAMPT exposure, migration of the PCa cells was assessed. A summary of the observation is provided in FIG. 11A, and representative micrographs are provided in FIG. 11B.

As observed in FIG. 11, NAMPT served as a potent chemoattractant for human DU-145 PCa cells and induced PCa cell migration over a 24-hour period.

Example 15. Characterization of Humanized Anti-hNAMPT Antibody

Figure 12C:
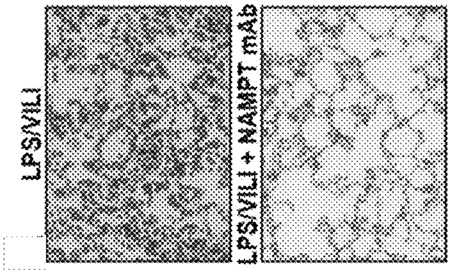
FIGS. 12A-12C depict results from in vivo testing of 1076 humanized anti-hNAMPT antibodies (N-1076, K-1076, and P-1076) and 1093 humanized anti-hNAMPT antibodies (SS-1093, XX-1093, and UU-1093) on inflammation and injury in murine lung injury models.
Figure 12B:
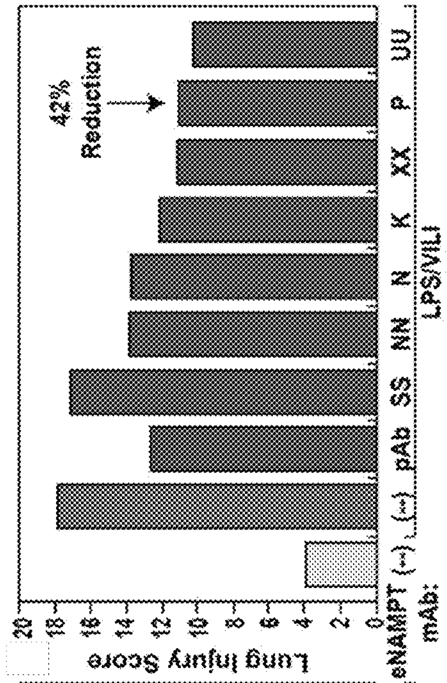

Ability of 1076 humanized anti-hNAMPT antibodies (N-1076, K-1076, and P-1076) and 1093 humanized anti-hNAMPT antibodies (SS-1093, XX-1093, and UU-1093) to treat lung injury was tested in vivo, using two murine lung injury models: a "one hit" model of lung injury that was developed by intratracheal delivery of LPS into mice, and a "two hit" model of lung injury that was developed by exposing mice to LPS and mechanical VILI. Either of the humanized anti-hNAMPT antibodies was administered to these mice in order to assess the capacity of the antibodies to attenuate acute inflammation and injury. Results from the testing is provided in FIG. 12.

Figure 12A:
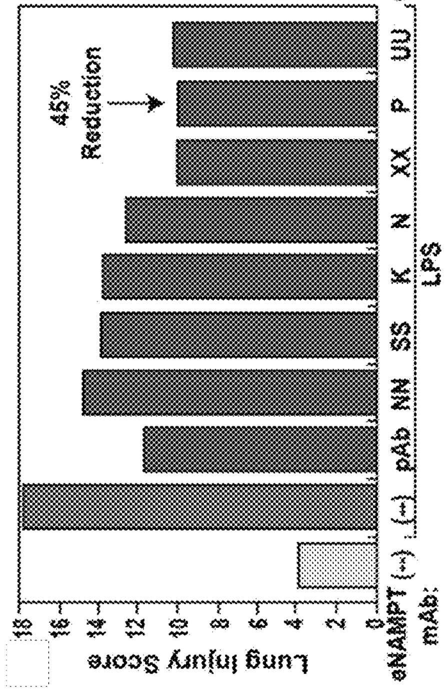

As depicted in FIG. 12A, analysis of integrated lung injury score showed that all of the tested anti-hNAMPT antibodies were effective in reducing lung injury in the LPS-induced "one hit" model. However, the most substantial effect was observed with anti-hNAMPT antibody P-1076. As described in FIG. 12B, analysis of integrated lung injury score showed that all of the tested anti-hNAMPT antibodies were effective in reducing lung injury in the LPS/VILI-induced "two hit" model. However, the most substantial effect was observed with anti-hNAMPT antibody P-1076. As described in FIG. 12C, anti-hNAMPT antibody P-1076 was effective in reducing histologic injury indices in the LPS/VILI-induced "two hit" model of acute inflammatory injury.

Example 16. Effect of Humanized Anti-hNAMPT Antibody P-1076 on PCa Cell Invasion To assess the effect of humanized anti-hNAMPT antibody P-1076 on PCa cell invasion, peritoneal invasion of human PCa cells was evaluated in severe combined immunodeficient (SCID) mice.

To assess the role of humanized anti-hNAMPT antibody P-1076 on PCa cell invasion, metastatic human PCa cells, PC3, were injected intraperitoneally (I. P.) into SCID mice. The mice were injected two times a week with 2 μg of humanized anti-hNAMPT antibody P-1076 or vehicle alone. Peritoneal invasion of the PC3 cells was evaluated 6 weeks after the PC3 cell injection. Representative micrographs and a summary of the results are provided in FIG. 13.

Figures 13A, 13B, 13C:
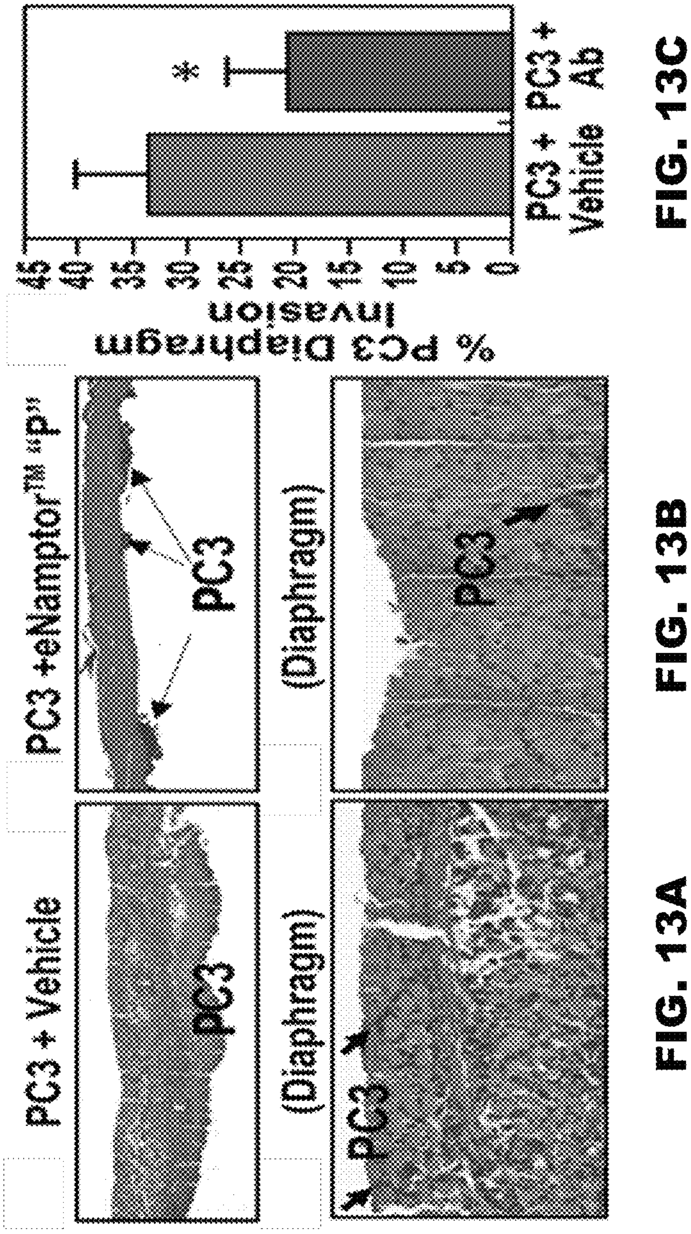
FIGS. 13A-13C depict results from in vivo assay of PCa cell invasiveness through diaphragmatic smooth muscle.

As depicted in FIG. 13, injection of human PCa cell line caused substantial peritoneal muscle invasion (FIG. 13A), while PC3-challenged SCID mice receiving humanized anti-hNAMPT antibody P-1076 exhibited marked reductions in PC3 invasion of the smooth muscle peritoneum (FIG. 13B).

Thus, as summarized in FIG. 13C, observations from this study strongly implicate a role for NAMPT in PCa cell invasiveness and a critical potential for humanized anti-hNAMPT antibody P-1076 to temporize this invasive behavior.

Example 17. In Vivo Treatment of RILI Using Anti-NAMPT Antibodies

The ability impact of anti-NAMPT administration on RILI was assessed using in vivo experiments in C57/B6 mice. The mice were divided into four groups: mice that received 20Gy thoracic radiation and were injected intraperitoneally with a polyclonal NAMPT-neutralizing antibody (pAb); mice that received 20Gy thoracic radiation and were injected intraperitoneally with a monoclonal anti-NAMPT antibody (mAb) (P-1076-mod1); and non-irradiated mice injected with vehicle alone ("Ctrl"); and irradiated mice injected with vehicle alone ("Ctrl"). Amount of BAL protein was measured and count of BAL-expressing cells was obtained. Lung tissues were also subjected to H&E staining to assess lung inflammation. Moreover, acute lung injury (ALI) severity score was assessed based on BAL indices and H&E staining. Results from the corresponding analyses are provided in FIGS. 14A-E.

Figures 14A, 14B, 14C, 14D, 14E:
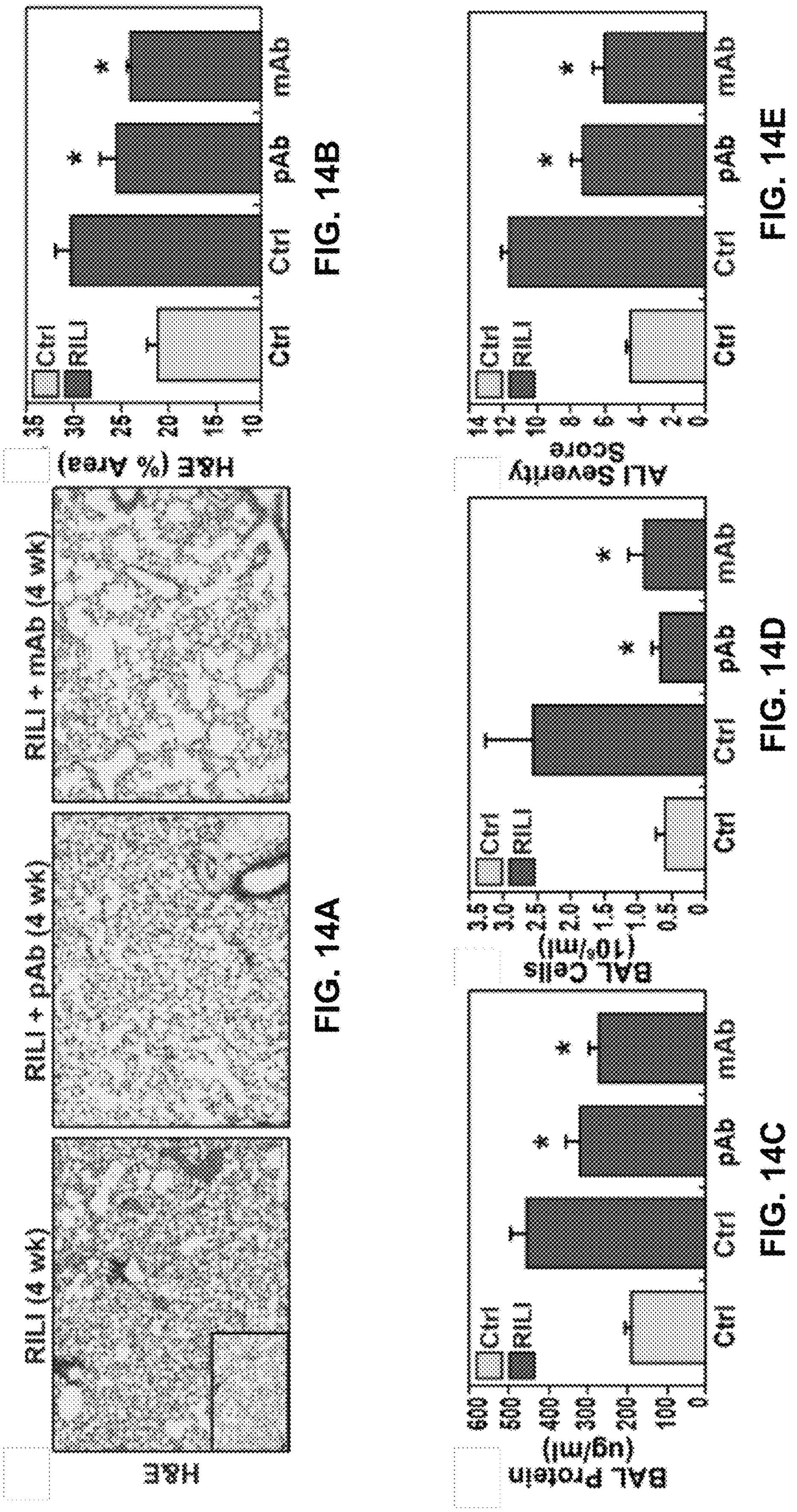
FIGS. 14A-14E depict the effects of NAMPT-neutralizing antibodies on lung inflammation (assessed by H&E staining), amount of BAL protein and count of BAL-expressing cells, as evaluated in a murine model of RILI.

As shown in FIG. 14A, H&E staining of lung tissues from irradiated control mice (injected with vehicle alone) displayed diffuse alveolar damage 4 weeks after radiation exposure (FIG. 14A, left panel), compared to lung tissues from non-irradiated control mice (inset of FIG. 14A, left panel). In contrast, lung tissues from mice that were injected with anti-NAMPT pAb (FIG. 14A, middle panel) or anti-NAMPT mAb (FIG. 14A, right panel) demonstrated reduced H&E staining, indicating less alveolar damage in anti-NAMPT Ab treated mice following radiation exposure. FIG. 14B summarizes H&E staining in lung tissues of non-irradiated control mice, irradiated control mice, and irradiated mice that were injected with anti-NAMPT pAb or mAb. As shown in FIG. 14B, H&E stained area was increased in lung tissues from irradiated control mice compared to that from non-irradiated control mice. However, compared to irradiated control mice, a significant reduction in H&E stained area was observed in lung tissues from mice that were injected with anti-NAMPT pAb or mAb ($p<0.05$), suggesting a role of NAMPT in development of RILI. FIG. 14C shows BAL protein levels in lung tissues of non-irradiated control mice, irradiated control mice, and irradiated mice that were injected with anti-NAMPT pAb or mAb. As shown in FIG. 14C, compared to non-irradiated control mice, mice that were exposed to radiation displayed increased BAL protein levels. However, irradiated mice that were injected with anti-NAMPT pAb or mAb demonstrated significantly reduced BAL protein level compared to the irradiated control mice ($p<0.05$), with more pronounced reduction observed in irradiated mice that were treated with anti-NAMPT mAb. Similarly, count of BAL cells increased in mice that were exposed to irradiation, although irradiated mice that were injected with anti-NAMPT pAb or mAb demonstrated markedly reduced BAL cell count compared to the irradiated control mice ($p<0.05$), with more pronounced reduction observed in irradiated mice that were treated with anti-NAMPT mAb. Furthermore, as shown in FIG. 14E, compared to control mice, mice that were exposed to radiation displayed increased ALI severity score; however, irradiated mice that were injected with anti-NAMPT pAb or mAb demonstrated significantly reduced ALI severity score compared to the irradiated control mice, with more pronounced reduction observed in irradiated mice that were treated with anti-NAMPT mAb. Thus, the results show attenuation of RILI following treatment with anti-NAMPT Abs, underscoring NAMPT as a potential therapeutic target in RILI.

Example 18. Radiolabeled Anti-NAMPT Antibody Identifies Increased NAMPT Expression in Inflamed Lung Tissues Radiolabeled anti-NAMPT antibodies were developed with the goal of non-invasively detecting NAMPT signaling pathway and NAMPT expression in different tissues in vivo. Imaging the mouse models with RILI using radiolabeled anti-NAMPT mAb (P-1076-mod1) would enable defining the optimal time for deploying anti-NAMPT mAb as a therapeutic intervention and to survey the major organs for inflammation and cellular apoptosis, employing other specific radiolabels, following total body irradiation (TBI) or partial body irradiation (PBI), such as in a nuclear incident. To test the detection of NAMPT expression by the radiolabeled anti-NAMPT antibody, $^{99m}$Tc-labeled anti-NAMPT mAb probe was injected into control mice and mice that were exposed to 8Gy PBI, and rapid autoradiograph imaging was performed. Results from the analysis are described in FIGS. 15A-D.

Figure 15A:
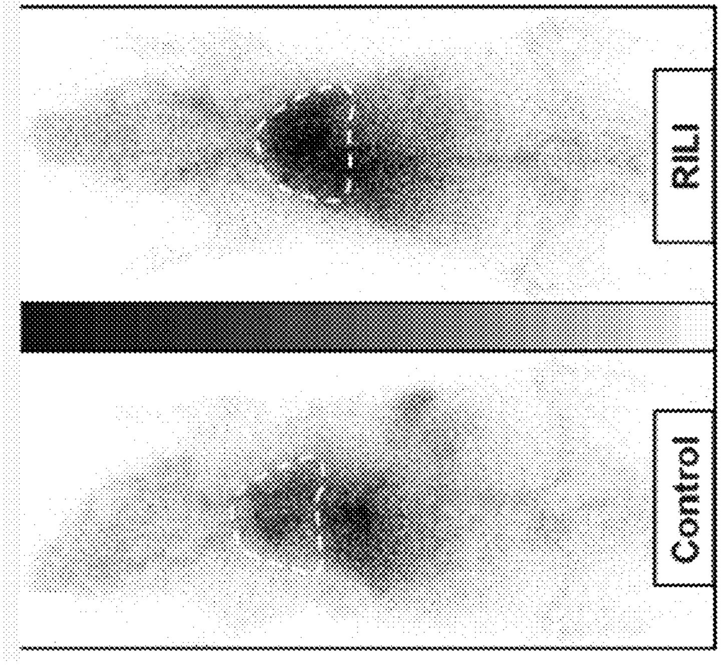
FIGS. 15A-15D depict detection of NAMPT expression by $^{99m}$Tc-labeled anti-NAMPT mAb probe.
Figure 15B:
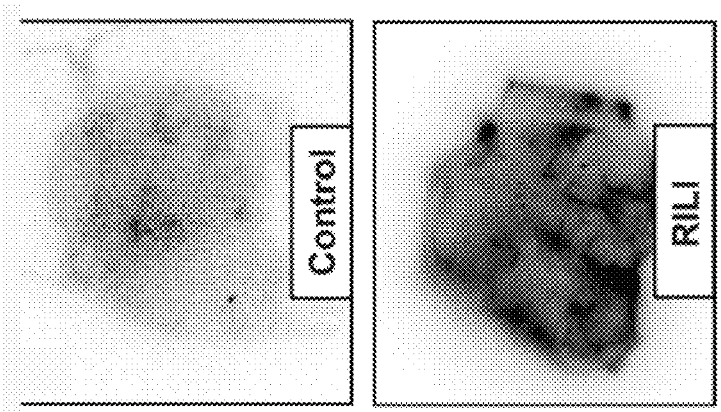
Figure 15C:
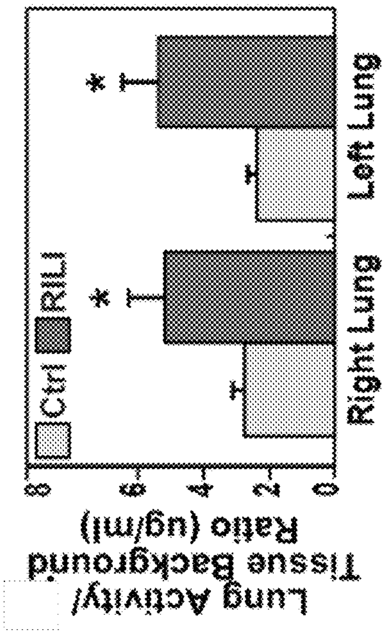
Figure 15D:
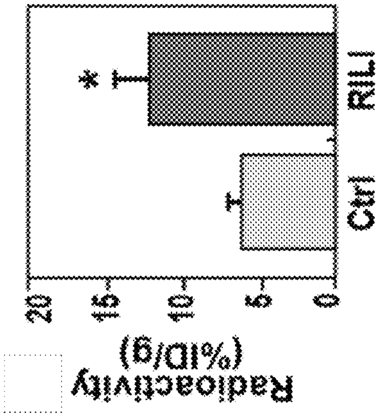

As shown in FIGS. 15A-B, higher radioactive uptake was observed in lungs of irradiated mice compared to non-irradiated control mice, indicating higher NAMPT expression induced by RILI. Furthermore, uptake of radiolabeled anti-NAMPT antibody was used as a measure of lung activity in irradiated mice or non-irradiated control mice. As shown in FIG. 15C, a significant increase in lung activity over tissue background was observed in both right and left lungs from irradiated mice compared to those from non-irradiated control mice ($p<0.05$). Moreover, level of radioactivity in irradiated mice or non-irradiated control mice was determined to assess uptake of the radiolabeled anti-NAMPT mAb. As shown in FIG. 15D, a significant increase in radioactivity was observed in irradiated mice compared to non-irradiated control mice ($p<0.05$), thus confirming increased uptake of the radiolabeled anti-NAMPT mAb in irradiated mice.

Thus, the radiolabeled anti-NAMPT antibody was effective in detecting increased NAMPT expression in inflamed lung tissues. This underscores the potentials of utilizing the radiolabeled anti-NAMPT antibody as a tool for detection of NAMPT, which could be pivotal in using NAMPT as a biomarker in RILI.

Example 19. Validating NAMPT as a Therapeutic Target in RILI Using an In Vivo Model of Radiation-Induced Lung Fibrosis To further validate NAMPT as a therapeutic target in RILI, WT C57/B6 mice were exposed to 20Gy WTLI. The irradiated mice were intraperitoneally injected with 10 μg of an anti-NAMPT mAb (P-1076-mod1) or vehicle control. The mice were evaluated for radiation-induced lung fibrosis (RILF) 18 weeks post radiation exposure by assessing BAL cell count, collagen deposition, and expression of lung tissue smooth muscle actin (SMA), which is a reflection of myofibroblast transition and fibrosis. The results are shown in FIGS. 16A-C.

Figure 16C:
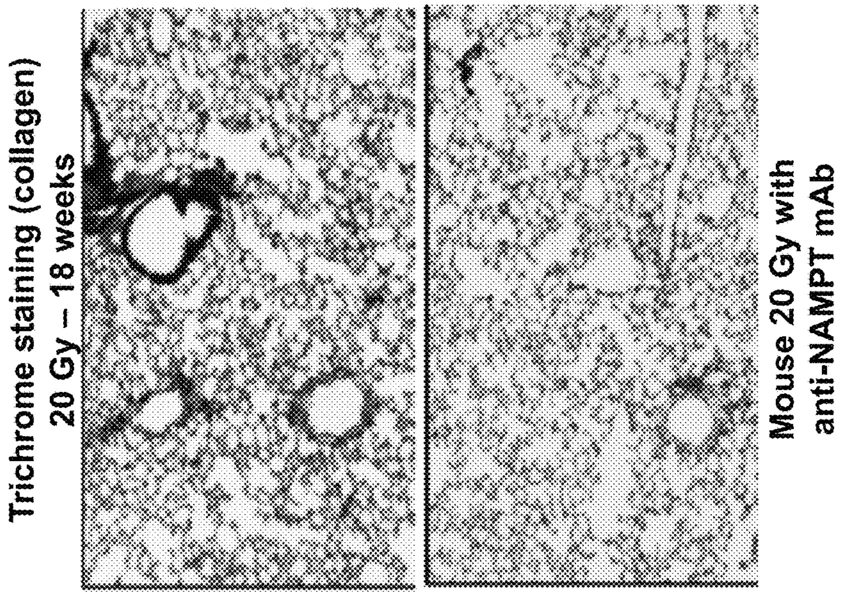
FIGS. 16A-16C depict the effects of a humanized anti-NAMPT mAb on BAL cell count, collagen deposition, and expression of lung tissue smooth muscle actin (SMA), as evaluated in a murine model of RILI 18 weeks after 20Gy radiation exposure.
Figure 16B:
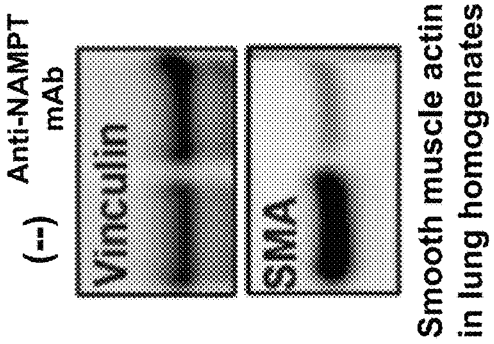
Figure 16A:
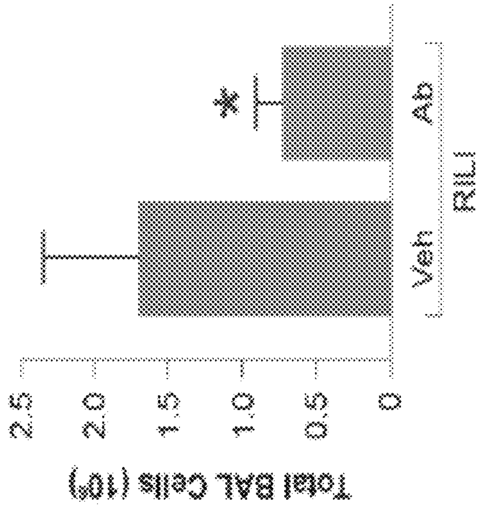

As shown in FIGS. 16A-C, the anti-NAMPT mAb significantly reduced IR-induced RILI, which was reflected by decreased BAL cell count (FIG. 16A), decreased expression of lung tissue SMA (detected by western blot analyses, shown in FIG. 16B), and decreased collagen deposition (detected by Trichrome staining of lung tissues, shown in FIG. 16C) in Ab-treated mice compared to vehicle-treated control mice.

Thus, the results underscore the role of an anti-NAMPT Ab in attenuating RILF, further validating NAMPT as a therapeutic target in RILI.

Example 20. Evaluating the Efficacy of an Anti-NAMPT mAb in Pre-Clinical Models of Lung Injury The efficacy of an anti-NAMPT mAb was validated in a rat model of trauma (blast)/ventilator-induced lung injury (VILI). Sprague Dawley rats were challenged with trauma (blast) followed by 4 hours of mechanical ventilation. Rats were injected with an anti-NAMPT mAb (P-1076-mod1, 100 μg, intravenously (IV)) 30 minute following the blast. Rats, which were exposed to trauma (blast)/VILI and injected with vehicle, served as control. Lungs were removed from the rats ~5 hours after onset of blast and evaluated for injury. Also, edema and inflammatory cell infiltration in lung tissue were assessed by hematoxylin and eosin (H&E) staining, as readout of lung injury. Results from this trauma (blast)/VILI lung injury model are provided in FIGS. 17A-C.

Figures 17A, 17B, 17C:
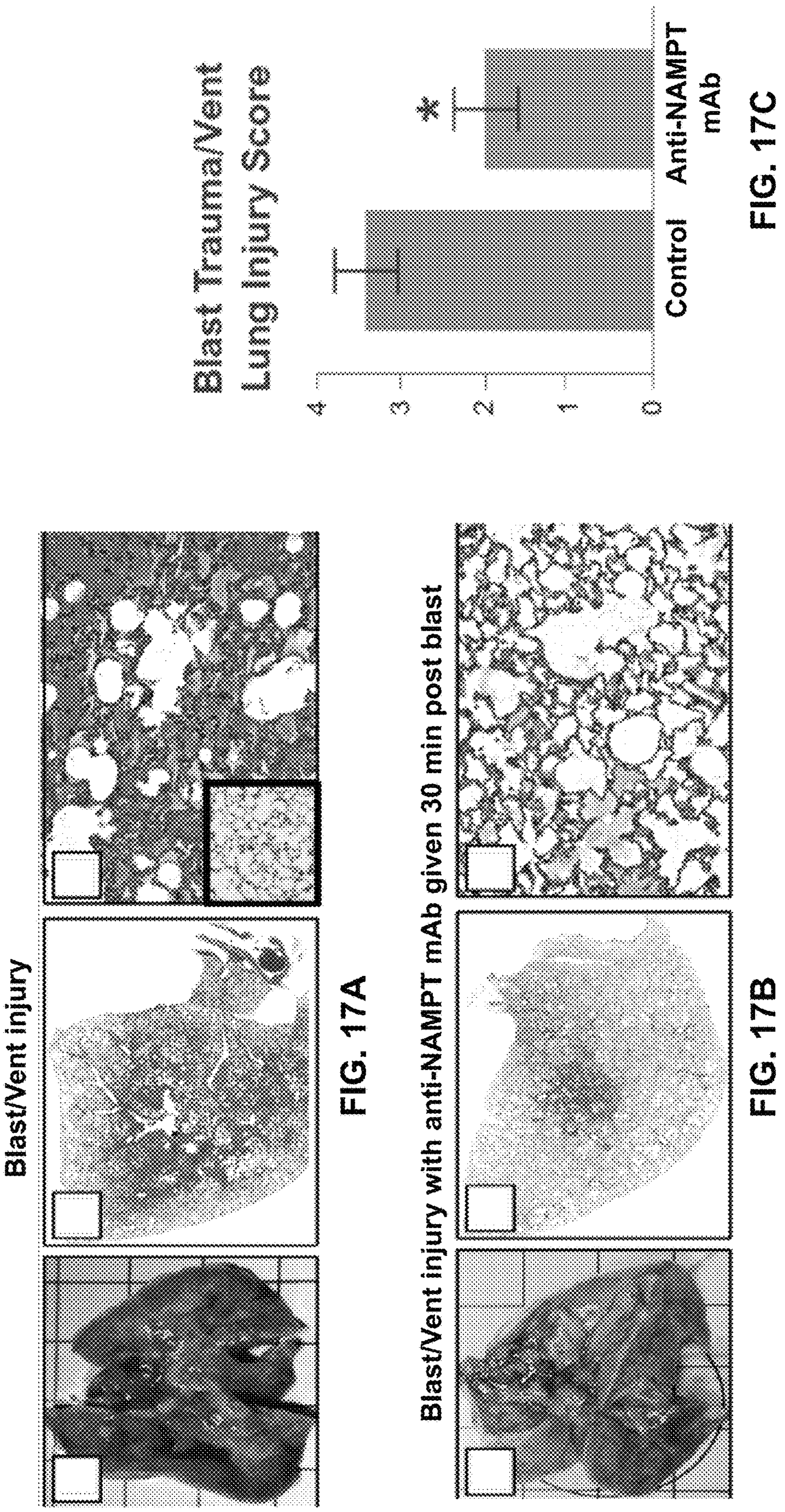
FIGS. 17A-17C depict the effects of a humanized anti-NAMPT mAb on inflammatory cell infiltration, edema and lung injury score, as evaluated in a rat model of trauma (blast)/ventilation-induced lung injury (VILI).

As shown in FIG. 17A, compared to non-challenged rats (FIG. 17A, inset in rightmost box), lung tissues from vehicle injected control trauma/VILI rats showed inflammatory cell infiltration and edema, which was indicative of trauma/VILI induced lung injury. In contrast, as shown in FIG. 17B, lung tissues from anti-NAMPT mAb treated trauma/VILI rats showed marked reduction in inflammatory cell infiltration and edema, thus indicating attenuation of trauma/VILI-induced lung injury by the anti-NAMPT mAb. The effect of the anti-NAMPT mAb on trauma/VILI-induced lung injury is summarized in FIG. 17C, which shows lung injury score of the rats, as assessed from the H&E staining indices. As shown in FIG. 17C, lung injury score was significantly reduced in rats that were treated with anti-NAMPT mAb compared to rats that were injected with vehicle control ($p<0.05$). Thus, the results outlined in FIGS. 17A-C show the efficacy of a NAMPT neutralizing mAb in attenuating trauma/VILI-induced lung injury.

Next, the efficacy of the anti-NAMPT mAb was validated in a murine model of LPS/VILI. Mice were challenged with LPS for 18 hours followed by 4 hours of mechanical ventilation. Mice were injected with an anti-NAMPT mAb (P-1076-mod1, 10 μg, IV), an anti-NAMPT polyclonal antibody (pAb), or vehicle control (PBS). Mice, which were not exposed to LPS/VILI, served as control. Edema and inflammatory cell infiltration in lung tissue from the mice were then assessed by H&E staining, as readout of lung injury. Results from this LPS/VILI lung injury model are provided in FIGS. 18A-C.

Figure 18A:
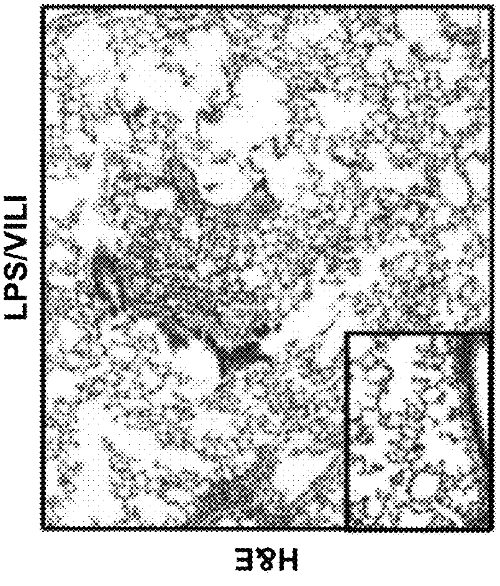
FIGS. 18A-18C depict the effects of NAMPT-neutralizing antibodies on inflammatory cell infiltration, edema and lung injury score, as evaluated in a murine LPS/VILI lung injury model.
Figure 18B:
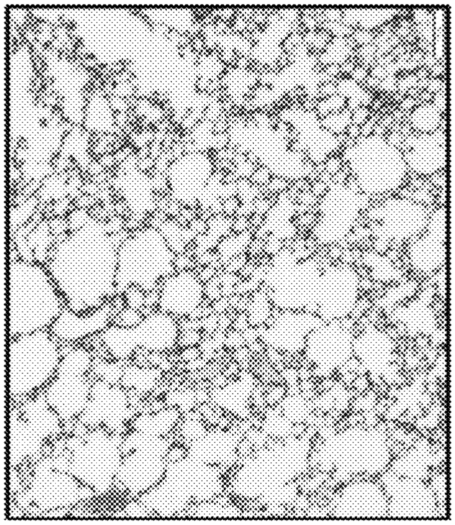
Figure 18C:
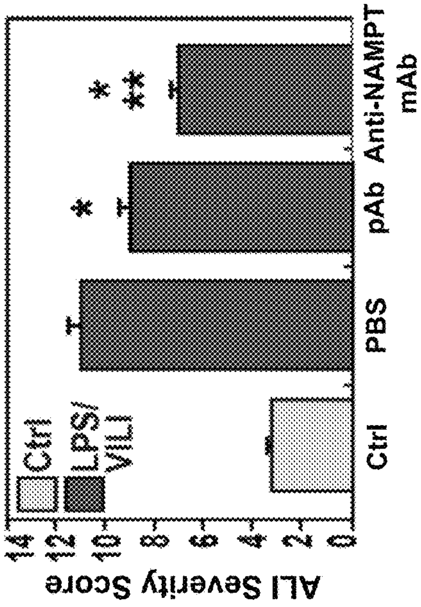

As shown in FIG. 18A, compared to non-challenged mice (FIG. 18A, inset), lung tissues from vehicle injected control mice showed inflammatory cell infiltration and edema, which was indicative of LPS/VILI induced lung injury. In contrast, as shown in FIG. 18B, lung tissues from anti-NAMPT mAb treated mice showed marked reduction in inflammatory cell infiltration and edema, thus indicating attenuation of LPS/VILI-induced lung injury by the anti-NAMPT mAb. The effect of the anti-NAMPT mAb on trauma/VILI-induced lung injury is summarized in FIG. 18C, which shows acute lung injury (ALI) severity score of the mice, as assessed from the H&E staining indices. As shown in FIG. 18C, ALI was markedly reduced in mice treated with anti-NAMPT pAb or mAb compared to vehicle injected mice, with most robust reduction in ALI severity score observed in mice that were treated with the anti-NAMPT mAb ($p<0.001$). Thus, the results outlined in FIGS. 18A-C show the efficacy of a NAMPT neutralizing mAb in attenuating trauma/VILI-induced lung injury.

Accordingly, the results demonstrate the effectiveness of the anti-NAMPT mAb in reducing lung injury in pre-clinical in vivo lung injury models.

Example 21. Radiolabeled Anti-NAMPT Antibody Identifies Increased NAMPT Expression in Inflamed Lung Tissues A humanized anti-NAMPT mAb (K-1076) was radiolabeled to develop an imaging probe that would be capable of non-invasively detecting NAMPT signaling pathway and NAMPT expression in different tissues in vivo. Considering the potentials of NAMPT as a diagnostic and/or prognostic biomarker in acute inflammatory conditions (e.g., COVID-19, ARDS and lung injury), the radiolabeled anti-NAMPT mAb could be used as a diagnostic tool in subjects who are at risk of developing such conditions, or for selecting subjects likely to respond to treatment of such inflammatory conditions with an anti-NAMPT mAb. The present example describes detection of NAMPT expression in inflamed tissues, such as LPS-challenged and ionizing radiation-exposed lungs, using the radiolabeled anti-NAMPT mAb.

First, to test the detection of NAMPT expression by the radiolabeled anti-NAMPT antibody, $^{99m}$Tc-labeled anti-NAMPT mAb probe or radiolabeled IgG control Ab was injected into mice that were exposed to 20Gy whole thoracic lung irradiation (WTLI), and rapid autoradiograph imaging were performed.

Figure 19A:
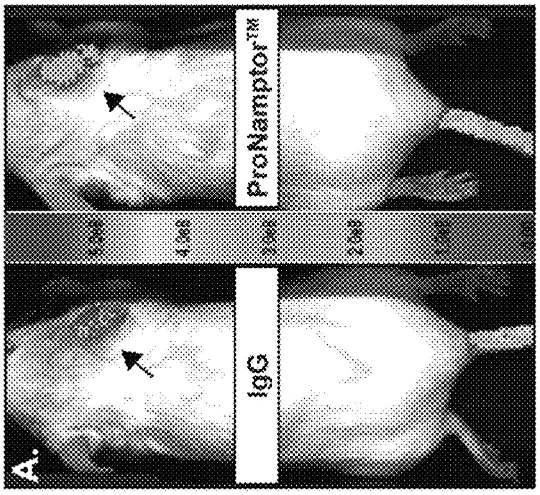
FIGS. 19A-19D depict detection of NAMPT expression by $^{99m}$Tc-labeled anti-NAMPT mAb probe.

As shown in FIG. 19A, markedly higher radioactive uptake was observed in irradiated mice injected with radiolabeled anti-NAMPT mAb (PRONAMPTOR) (FIG. 19A, right panel) compared to irradiated mice injected with the radiolabeled IgG control (FIG. 19A, left panel). Thus, the results shown in FIG. 19A demonstrate the ability of the radiolabeled anti-NAMPT imaging probe in detecting radiation-induced NAMPT expression.

To further assess the detection of NAMPT expression by radiolabeled anti-NAMPT imaging probe, $^{99m}$Tc-labeled anti-NAMPT mAb was injected into vehicle challenged control mice or LPS challenged mice 3 hours or 18 hours after LPS challenge, and rapid autoradiograph imaging was performed. Results from the analysis are shown in FIGS. 19B-D.

Figure 19B:
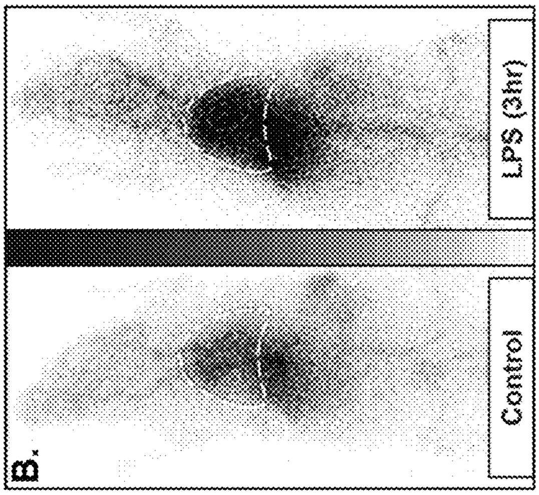
Figure 19C:
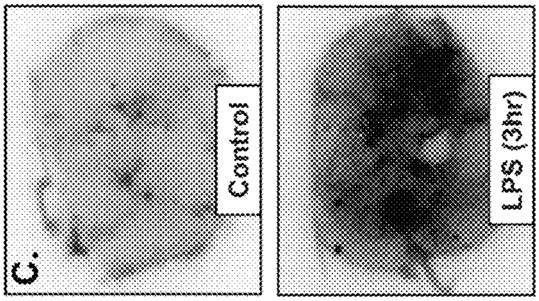
Figure 19D:
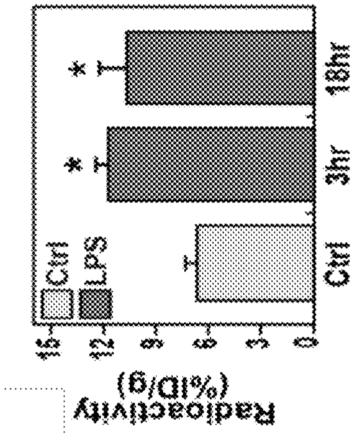

As shown in FIG. 19B, compared to control mice (FIG. 19B, left panel), LPS challenged mice showed markedly higher uptake of the radiolabeled anti-NAMPT imaging probe 3 hours after LPS challenge (FIG. 19B, right panel). Autoradiograph imaging of lungs from LPS challenged mice or control mice further confirmed this observation; compared to control mice (FIG. 19C, left panel), lungs of LPS challenged mice showed markedly higher uptake of the radiolabeled anti-NAMPT imaging probe 3 hour after LPS challenge (FIG. 19C, right panel). Moreover, as shown in FIG. 19D, compared to control mice, LPS challenged mice showed significantly higher radioactivity 3 hours and 18 hours after LPS challenge ($p<0.05$), indicating higher uptake of the radiolabeled anti-NAMPT imaging probe. Thus, the results described in FIGS. 19B-D demonstrate the ability of the radiolabeled anti-NAMPT imaging probe in detecting LPS-induced NAMPT expression.

Accordingly, the radiolabeled anti-NAMPT antibody was effective in detecting increased NAMPT expression in inflamed tissues. This underscores the potentials of utilizing the radiolabeled anti-NAMPT antibody as a tool for detection of NAMPT, which could be pivotal in using NAMPT as a diagnostic and/or prognostic biomarker in acute inflammatory conditions. Moreover, by virtue of detecting increased NAMPT expression in inflamed tissues, this radiolabeled anti-NAMPT imaging probe could be useful for selecting subjects who are likely to respond to treatment of acute inflammatory conditions with a neutralizing anti-NAMPT mAb.

Example 22. Anti-NAMPT Antibody Reduces PAH Manifestation in a Rat Model

Figure 20B:
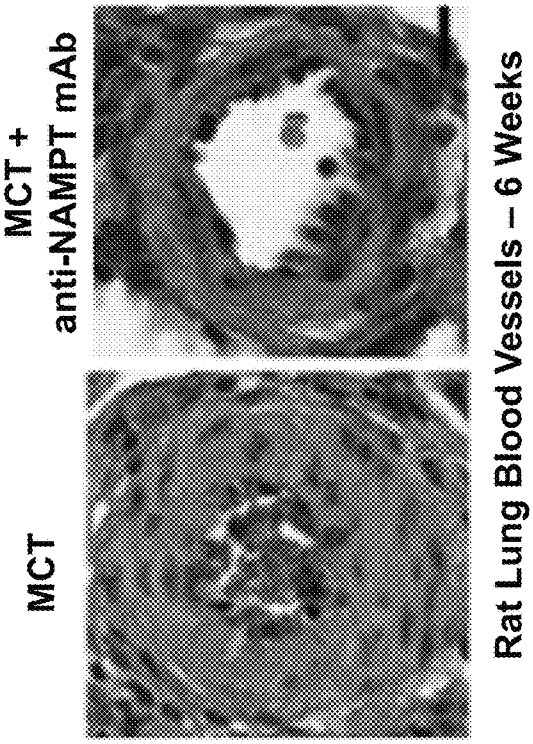
FIGS. 20A-20B depict effects of a humanized anti-NAMPT mAb on right ventricular systolic pressure (RVSP) and pulmonary artery thickness, as evaluated in a rat monocrotaline (MCT) model of PAH.
Figure 20A:
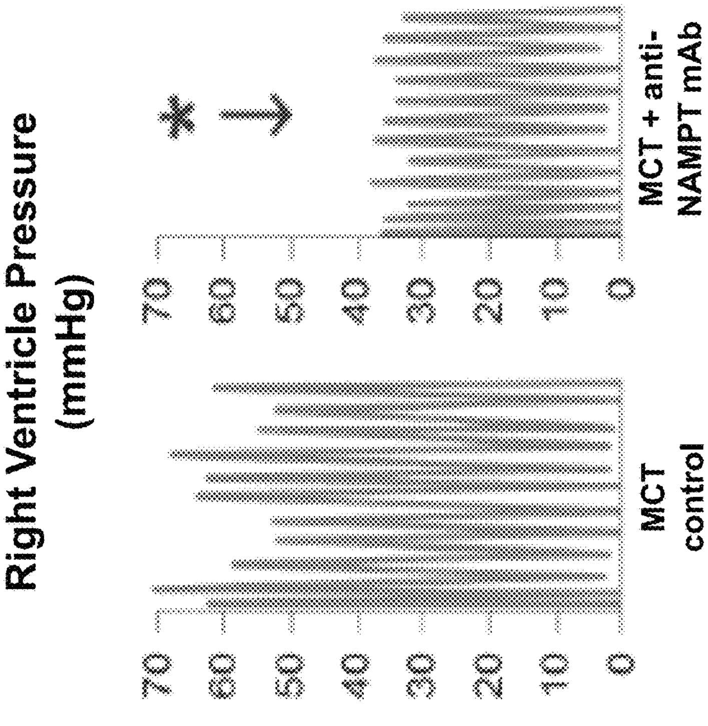

To explore the potentials of NAMPT as a therapeutic target in PAH, a rat monocrotaline (MCT) model of PAH was used. One dose of MCT (60 mg/kg body weight) was subcutaneously injected to Sprague-Dawley rats (190-200 g). The MCT-challenged rats were then injected twice weekly with either an anti-NAMPT mAb (P-1076-mod1, i. p., 100 μg/rat) or vehicle control (control MCT rats). The rats were then assessed for right ventricular systolic pressure (RVSP) and pulmonary artery remodeling. The results are shown in FIGS. 20A and 20B.

RVSP was determined in anti-NAMPT Ab treated MCT rats or control MCT rats by right heart catheterization using a Millar pressure transducer catheter. As shown in FIG. 20A, a significant decrease in RVSP was observed in MCT rats that were treated with anti-NAMPT mAb compared to control MCT rats ($p<0.05$).

Pulmonary artery remodeling was assessed using APERIO IMAGESCOPE software after lungs from anti-NAMPT Ab treated MCT rats or control MCT rats were stained with H&E. As shown in FIG. 20B, a marked decrease in pulmonary artery thickness was observed in anti-NAMPT mAb treated MCT rats compared to control MCT rats.

The results demonstrate that neutralization of NAMPT by anti-NAMPT mAb reverses vascular remodeling and RV dysfunction in a rat model of PAH, thus indicating the effectiveness of NAMPT as a therapeutic target in PAH.

Unless otherwise specified, the disclosure of every patent, patent application, and publication cited herein is hereby incorporated herein by reference to the extent the references set forth information relevant to the instant disclosure. While this invention has been disclosed with reference to particular embodiments, it is apparent that some embodiments and variations of this invention can be devised by others skilled in the art without departing from the true spirit and scope of the invention. The appended claims include all such embodiments and equivalent variations.

Sequences disclosed herein and/or relevant to the present invention are listed in the Sequence Summary Table (Table 17) below.

TABLE 17

Sequence Summary Table

| Sequence Identifier | Description | Sequence |
|---|---|---|
| SEQ ID NO: 1 | heavy chain variable region (VH): D-1076 | QVQLVESGAEVKKPGASVKLSCK ASGYTFTSYWMQWVRQAPGQRL EWMGEIDPSNSYTNYNQKFRGRV TITVDKSASTAYMELSSLRSEDTA VYYCARGGYWGPGTTVTVSS |
| SEQ ID NO: 2 | light chain variable region (VL): D-1076, N-1076, X-1076 | DIVMTQTPLSLSVTPGQPASISCRS SKSLLHSNGITYLYWYLQKPGQPP QLLIYQMSNLASGVPDRFSGSGSG TDFTLKISRVEAEDVGVYYCVQNL ELPYTFGPGTKVDIK |
| SEQ ID NO: 3 | CDR-H1: D-1076, G-1076, K-1076, N-1076, P-1076, V-1076, X-1076, P-1076-mod1, P-1076-mod2, P-1076-mod3, P-1076-mod4, P-1076-mod5, P-1076-mod6, P-1076-mod7, P-1076-mod8, P-1076-mod9, P-1076-mod10, P-1076-mod11, AL-303 | GYTFTSYWMQ |
| SEQ ID NO: 4 | CDR-H2: D-1076, G-1076, K-1076, N-1076, P-1076, V-1076, X-1076, P-1076-mod6, P-1076-mod7, P-1076-mod8, P-1076-mod9, P-1076-mod10, AL-303 | EIDPSNSYTNYNQKFRG |
| SEQ ID NO: 5 | CDR-H3: D-1076, G-1076, K-1076, N-1076, P-1076, V-1076, X-1076, P-1076-mod1, P-1076-mod2, P-1076-mod3, P-1076-mod4, P-1076-mod5, P-1076-mod6, P-1076-mod7, P-1076-mod8, P-1076-mod9, P-1076-mod10, P-1076-mod11,, AL-303 | ARGGY |

TABLE 17-continued

Sequence Summary Table

| Sequence Identifier | Description | Sequence |
|---|---|---|
| SEQ ID NO: 6 | CDR-L1: D-1076, N-1076, X-1076, FF-1093, II-1093, NN-1093, PP-1093, SS-1093, UU-1093, XX-1093, ZZ-1093, AL-303, UU-1093-mod13, UU-1093-mod14, UU-1093-mod15, UU-1093-mod16, AL-303, AL-310 | RSSKSLLHSNGITYLY |
| SEQ ID NO: 7 | CDR-L2: D-1076, N-1076, X-1076, FF-1093, II-1093, NN-1093, PP-1093, SS-1093, UU-1093, XX-1093, ZZ-1093, UU-1093-mod1, UU-1093-mod2, UU-1093-mod3, UU-1093-mod4, UU-1093-mod13, UU-1093-mod14, UU-1093-mod15, UU-1093-mod16, UU-1093-mod17,, AL-303, AL-310 | QMSNLAS |
| SEQ ID NO: 8 | CDR-L3: D-1076, G-1076, K-1076, N-1076, P-1076, V-1076, X-1076, P-1076-mod1, P-1076-mod2, P-1076-mod3, P-1076-mod4, P-1076-mod5, P-1076-mod6, P-1076-mod7, P-1076-mod8, P-1076-mod9, P-1076-mod10, P-1076-mod11,, AL-303 | VQNLELPYT |
| SEQ ID NO: 9 | heavy chain variable region (VH): G-1076, K-1076 | QVQLVQSGAEVKKPGASVKVSCKASGYTFTSYWMQWVRQAPGQGLEWMGEIDPSNSYTNYNQKFRGRVTMTTDTSTSTAYMELRSLRSDDTAVYYCARGGYWGQGTTVTVSS |
| SEQ ID NO: 10 | light chain variable region (VL): G-1076, V-1076 | DIQLTQSPLSLPVTPGEPASISCRSSKSLLHSQGITYLYWYLQKPGQSPQLLIYQLSNLASGVPDRFSGSGSGTDFTLKISRVEAEDVGVYYCVQNLELPYTFGGGTKLEIK |
| SEQ ID NO: 11 | CDR-L1: G-1076, K-1076, P-1076, V-1076, P-1076-mod1, P-1076-mod2, P-1076-mod3, P-1076-mod4, P-1076-mod5, P-1076-mod6, P-1076-mod7, P-1076-mod8, P-1076-mod9, P-1076-mod10, P-1076-mod11, UU-1093-mod1, UU-1093-mod2, UU-1093-mod3, UU-1093-mod4, UU-1093-mod9, UU-1093-mod10, UU-1093-mod11, UU-1093-mod12, UU-1093-mod17, UU-1093-mod19, | RSSKSLLHSQGITYLY |
| SEQ ID NO: 12 | CDR-L2: G-1076, V-1076 | QLSNLAS |
| SEQ ID NO: 13 | light chain variable region (VL): K-1076, P-1076, P-1076-mod11 | DIVMTQSPLSLPVTPGEPASISCRSSKSLLHSQGITYLYWYLQKPGQSPQLLIYQLSNRASGVPDRFSGSGSGTDFTLKISRVEAEDVGVYYCVQNLELPYTFGGGTKLEIK |
| SEQ ID NO: 14 | CDR-L2: K-1076, P-1076, P-1076-mod1, P-1076-mod2, P-1076-mod6, P-1076-mod7, P-1076-mod11 | QLSNRAS |
| SEQ ID NO: 15 | heavy chain variable region (VH): N-1076, P-1076, P-1076-mod6, P-1076-mod7, P-1076-mod8, P-1076-mod9, P-1076-mod10 | QVQLVQSGAEVTKPGASVKVSCKASGYTFTSYWMQWVRQAPGQGLEWVGEIDPSNSYTNYNQKFRGRVTLTRDTSTTTVYMELSSLRSEDTAVYYCARGGYWGQGTTVTVSS |

TABLE 17-continued

| Sequence Summary Table | | |
|---|---|---|
| Sequence Identifier | Description | Sequence |
| SEQ ID NO: 16 | heavy chain variable region (VH): V-1076, X-1076 | QVQLVQSGAEVKKPGASVKVSCK ASGYTFTSYWMQWVRQAPGQGL EWMGEIDPSNSYTNYNQKFRGRV TMTRDTSTSTVYMELSSLRSEDTA VYYCARGGYWGQGTTVTVSS |
| SEQ ID NO: 17 | heavy chain variable region (VH): FF-1093 | QVQLVESGAEVKKPGASVKLSCK ASGYTFTSYWMHWVRQAPGQRL EWMGEIDPSDSYTNYNQKFKGRV TITVDKSASTAYMELSSLRSEDTA VYYCAKSNYVVPWYFDVWGPGT TVTVSS |
| SEQ ID NO: 18 | light chain variable region (VL): FF-1093, PP-1093, UU-1093, ZZ-1093, UU-1093-mod13, UU-1093-mod14, UU-1093-mod15, UU-1093-mod16 | EIVLTQSPGTLSLSPGERATLSCRSS KSLLHSNGITYLYWYQQKPGQAP RLLIYQMSNLASGIPDRFSGSGSGT DFTLTISRLEPEDFAVYYCAQNLEL PWTFGGGTKLEIK |
| SEQ ID NO: 19 | CDR-H1: FF-1093, II-1093, NN-1093, PP-1093, SS-1093, UU-1093, XX-1093, ZZ-1093, UU-1093-mod1, UU-1093-mod2, UU-1093-mod5, UU-1093-mod6, UU-1093-mod9, UU-1093-mod10, UU-1093-mod13, UU-1093-mod14, UU-1093-mod17, UU-1093-mod18, UU-1093-mod19,, AL-310 | GYTFTSYWMH |
| SEQ ID NO: 20 | CDR-H2: FF-1093, II-1093, NN-1093, PP-1093, SS-1093, UU-1093, XX-1093, ZZ-1093, UU-1093-mod17, UU-1093-mod18, UU-1093-mod19, AL-310 | EIDPSDSYTNYNQKFKG |
| SEQ ID NO: 21 | CDR-H3: FF-1093, II-1093, NN-1093, PP-1093, SS-1093, UU-1093, XX-1093, ZZ-1093, UU-1093-mod1, UU-1093-mod5, UU-1093-mod9, UU-1093-mod13, UU-1093-mod17, UU-1093-mod18, UU-1093-mod19,, AL-310 | AKSNYVVPWYFDV |
| SEQ ID NO: 22 | CDR-L3: FF-1093, II-1093, NN-1093, PP-1093, SS-1093, UU-1093, XX-1093, ZZ-1093, UU-1093-mod1, UU-1093-mod2, UU-1093-mod3, UU-1093-mod4, UU-1093-mod5, UU-1093-mod6, UU-1093-mod7, UU-1093-mod8, UU-1093-mod13, UU-1093-mod14, UU-1093-mod15, UU-1093-mod16, UU-1093-mod17, UU-1093-mod18,, AL-310 | AQNLELPWT |
| SEQ ID NO: 23 | heavy chain variable region (VH): II-1093 | QVQLVQSGAEVRKPGASVKVSCK ASGYTFTSYWMHWVRQAPGQGL EWVGEIDPSDSYTNYNQKFKGRV TITADKSTSTAYMELSSLRSEDTD VYYCAKSNYVVPWYFDVWGQGT TVTVSS |
| SEQ ID NO: 24 | light chain variable region (VL): II-1093, NN-1093, SS-1093, XX-1093 | EIVLTQSPATLSLSPGERATLSCRSS KSLLHSNGITYLYWYQQKPGQAP RLLIYQMSNLASGIPARFSGSGSGT DFTLTISSLEPEDFAVYYCAQNLEL PWTFGGGTKLEIK |

TABLE 17-continued

Sequence Summary Table

| Sequence Identifier | Description | Sequence |
|---|---|---|
| SEQ ID NO: 25 | heavy chain variable region (VH): NN-1093 , PP-1093 | QVQLVQSGAEVTKPGASVKVSCKASGYTFTSYWMHWVRQAPGQGLEWVGEIDPSDSYTNYNQKFKGRVTLTRDTSTTTVYMELSSLRSEDTAVYYCAKSNYVVPWYFDVWGQGTTVTVSS |
| SEQ ID NO: 26 | heavy chain variable region (VH): SS-1093, UU-1093, UU-1093-mod17, UU-1093-mod18, UU-1093-mod19 | EVQLVQSGAEVKKPGESLRISCKASGYTFTSYWMHWVRQMPGKGLEWMGEIDPSDSYTNYNQKFKGHVTISADKSISTAYLQWSSLKASDTAMYYCAKSNYVVPWYFDVWGQGTLVTVSS |
| SEQ ID NO: 27 | heavy chain variable region (VH): XX-1093, ZZ-1093 | QVQLVQSGAEVKKPGASVKVSCKASGYTFTSYWMHWVRQAPGQGLEWMGEIDPSDSYTNYNQKFKGRVTMTRDTSTSTVYMELSSLRSEDTAVYYCAKSNYVVPWYFDVWGTGTTVTVSS |
| SEQ ID NO: 28 | heavy chain variable region (VH): P-1076-mod1, P-1076-mod2, P-1076-mod3, P-1076-mod4, P-1076-mod5, P-1076-mod11 | QVQLVQSGAEVTKPGASVKVSCKASGYTFTSYWMQWVRQAPGQGLEWVGEIEPSNSYTNYNQKFRGRVTLTRDTSTTTVYMELSSLRSEDTAVYYCARGGYWGQGTTVTVSS |
| SEQ ID NO: 29 | CDR-H2: P-1076-mod1, P-1076-mod2, P-1076-mod3, P-1076-mod4, P-1076-mod5, P-1076-mod11 | EIEPSNSYTNYNQKFRG |
| SEQ ID NO: 30 | light chain variable region (VL): P-1076-mod1, P-1076-mod6 | DIVMTQSPLSLPVTPGEPASISCRSSKSLLHSQGITYLYWYVQKPGQSPQLLIYQLSNRASGVPDRFSGSGSGTDFTLKISRVEAEDVGVYYCVQNLELPYTFGGGTKLEIK |
| SEQ ID NO: 31 | light chain variable region (VL): P-1076-mod2, P-1076-mod7 | DIVMTQSPLSLPVTPGEPASISCRSSKSLLHSQGITYLYWYIQKPGQSPQLLIYQLSNRASGVPDRFSGSGSGTDFTLKISRVEAEDVGVYYCVQNLELPYTFGGGTKLEIK |
| SEQ ID NO: 32 | light chain variable region (VL): P-1076-mod3, P-1076-mod8 | DIVMTQSPLSLPVTPGEPASISCRSSKSLLHSQGITYLYWYVQKPGQSPQLLIYQGSNRASGVPDRFSGSGSGTDFTLKISRVEAEDVGVYYCVQNLELPYTFGGGTKLEIK |
| SEQ ID NO: 33 | CDR-L2: P-1076-mod3, P-1076-mod8 | QGSNRAS |
| SEQ ID NO: 34 | light chain variable region (VL): P-1076-mod4, P-1076-mod9 | DIVMTQSPLSLPVTPGEPASISCRSSKSLLHSQGITYLYWYVQKPGQSPQLLIYQESNRASGVPDRFSGSGSGTDFTLKISRVEAEDVGVYYCVQNLELPYTFGGGTKLEIK |
| SEQ ID NO: 35 | CDR-L2: P-1076-mod4, P-1076-mod9 | QESNRAS |
| SEQ ID NO: 36 | light chain variable region (VL): P-1076-mod5, P-1076-mod10 | DIVMTQSPLSLPVTPGEPASISCRSSKSLLHSQGITYLYWYIQKPGQSPQLLIYQVSNRASGVPDRFSGSGSGTDFTLKISRVEAEDVGVYYCVQNLELPYTFGGGTKLEIK |
| SEQ ID NO: 37 | CDR-L2: P-1076-mod5, P-1076-mod10 | QVSNRAS |

TABLE 17-continued

Sequence Summary Table

| Sequence Identifier | Description | Sequence |
|---|---|---|
| SEQ ID NO: 38 | heavy chain variable region (VH): UU-1093-mod1, UU-1093-mod5, UU-1093-mod9, UU-1093-mod13 | EVQLVQSGAEVKKPGESLRISCKASGYTFTSYWMHWVRQMPGKGLEWMGEIEPSDSYTNYNQKFKGHVTISADKSISTAYLQWSSLKASDTAMYYCAKSNYVVPWYFDVWGQGTLVTVSS |
| SEQ ID NO: 39 | CDR-H2: UU-1093-mod1, UU-1093-mod2, UU-1093-mod3, UU-1093-mod4, UU-1093-mod5, UU-1093-mod6, UU-1093-mod7, UU-1093-mod8, UU-1093-mod9, UU-1093-mod10, UU-1093-mod11, UU-1093-mod12, UU-1093-mod13, UU-1093-mod14, UU-1093-mod15, UU-1093-mod16 | EIEPSDSYTNYNQKFKG |
| SEQ ID NO: 40 | heavy chain variable region (VH): UU-1093-mod2, UU-1093-mod6, UU-1093-mod10, UU-1093-mod14 | EVQLVQSGAEVKKPGESLRISCKASGYTFTSYWMHWVRQMPGKGLEWMGEIEPSDSYTNYNQKFKGHVTISADKSISTAYLQWSSLKASDTAMYYCAKTNYVVPWYFDVWGQGTLVTVSS |
| SEQ ID NO: 41 | CDR-H3: UU-1093-mod2, UU-1093-mod4, UU-1093-mod6, UU-1093-mod8, UU-1093-mod10, UU-1093-mod12, UU-1093-mod14, UU-1093-mod16 | AKTNYVVPWYFDV |
| SEQ ID NO: 42 | heavy chain variable region (VH): UU-1093-mod3, UU-1093-mod7, UU-1093-mod11, UU-1093-mod15 | EVQLVQSGAEVKKPGESLRISCKASGYTFTSYWIHWVRQVPGKGLEWMGEIEPSDSYTNYNQKFKGHVTISADKSISTAYLQWSSLKASDTAVYYCARSNYVVPWYFDVWGQGTLVTVSS |
| SEQ ID NO: 43 | CDR-H1: UU-1093-mod3, UU-1093-mod7, UU-1093-mod11, UU-1093-mod15 | GYTFTSYWIH |
| SEQ ID NO: 44 | CDR-H3: UU-1093-mod3, UU-1093-mod7, UU-1093-mod11, UU-1093-mod15 | ARSNYVVPWYFDV |
| SEQ ID NO: 45 | heavy chain variable region (VH): UU-1093-mod4, UU-1093-mod8, UU-1093-mod12, UU-1093-mod16 | EVQLVQSGAEVKKPGESLRISCKASGYTFTSYFIHWVRQVPGKGLEWMGEIEPSDSYTNYNQKFKGHVTISADKSISTAYLQWSSLKASDTAVYYCAKTNYVVPWYFDVWGQGTLVTVSS |
| SEQ ID NO: 46 | CDR-H1: UU-1093-mod4, UU-1093-mod8, UU-1093-mod12, UU-1093-mod16 | GYTFTSYFIH |
| SEQ ID NO: 47 | light chain variable region (VL): UU-1093-mod1, UU-1093-mod2, UU-1093-mod3, UU-1093-mod4, UU-1093-mod17 | EIVLTQSPGTLSLSPGERATLSCRSSKSLLHSQGITYLYWYQQKPGQAPRLLIYQMSNLASGIPDRFSGSGSGTDFTLTISRLEPEDFAVYYCAQNLELPWTFGGGTKLEIK |
| SEQ ID NO: 48 | light chain variable region (VL): UU-1093-mod5, UU-1093-mod6, UU-1093-mod7, UU-1093-mod8, UU-1093-mod18 | EIVLTQSPGTLSLSPGERATLSCRSSKSLLHSNAITYLYWYQQKPGQAPRLLVYQVSNLASGVPDRFSGSGSGTDFTLTISRLEPEDFAVYYCAQNLELPWTFGGGTKLEIK |
| SEQ ID NO: 49 | CDR-L1: UU-1093-mod5, UU-1093-mod6, UU-1093-mod7, UU-1093-mod8, UU-1093-mod18 | RSSKSLLHSNAITYLY |

TABLE 17-continued

Sequence Summary Table

| Sequence Identifier | Description | Sequence |
|---|---|---|
| SEQ ID NO: 50 | CDR-L2: UU-1093-mod5, UU-1093-mod6, UU-1093-mod7, UU-1093-mod8, UU-1093-mod18 | QVSNLAS |
| SEQ ID NO: 51 | light chain variable region (VL): UU-1093-mod9, UU-1093-mod10, UU-1093-mod11, UU-1093-mod12, UU-1093-mod19 | EIVLTQSPGTLSLSPGERATLSCRSS KSLLHSQGITYLYWYQQKPGQAP RLLVYQVSNLGSGIPDRFSGSGSG TDFTLTISRLEPEDFAVYYCAQNLE LPFTFGGGTKLEIK |
| SEQ ID NO: 52 | CDR-L2: UU-1093-mod9, UU-1093-mod10, UU-1093-mod11, UU-1093-mod12, UU-1093-mod19 | QVSNLGS |
| SEQ ID NO: 53 | CDR-L3: UU-1093-mod9, UU-1093-mod10, UU-1093-mod11, UU-1093-mod12, UU-1093-mod19 | AQNLELPFT |
| SEQ ID NO: 54 | heavy chain variable region (VH): AL-303 | QVQLQQPGADLVKPGASVKLSCK ASGYTFTSYWMQWVKQRPGQGL EWIGEIDPSNSYTNYNQKFRGKAT LTVDPSSSTAYMQLSSLTSEDSAV YYCARGGYWGQGTTLTVSS |
| SEQ ID NO: 55 | light chain variable region (VL): AL-303 | DIVMTQAAFSNPVTLGTSASISCRS SKSLLHSNGITYLYWYLQKPGQSP QLLIYQMSNLASGVPDRFSSSGSG TDFTLRISRVEAEDVGVYYCVQNL ELPYTFGGGTKLEIK |
| SEQ ID NO: 56 | heavy chain variable region (VH): AL-310 | QVQLQQSGAESVMPGASVKLSCK ASGYTFTSYWMHWVKQRPGQGL EWIGEIDPSDSYTNYNQKFKGKST LTVDKSSSTAYMQLSSLTSEDSAV YYCAKSNYVVPWYFDVWGTGTT VTVSS |
| SEQ ID NO: 57 | light chain variable region (VL): AL-310 | DIVMTQAAFSNPVTLGTSASISCRS SKSLLHSNGITYLYWYLQKPGQSP QLLIYQMSNLASGVPDRFSSSGSG TDFTLRISRVEAEDVGVYYCAQNL ELPWTFGGGTKLEIK |
| SEQ ID NO: 58 | IgG1 heavy chain constant region | ASTKGPSVFPLAPSSKSTSGGTAAL GCLVKDYFPEPVTVSWNSGALTS GVHTFPAVLQSSGLYSLSSVVTVP SSSLGTQTYICNVNHKPSNTKVDK KVEPKSCDKTHTCPPCPAPELLGG PSVFLFPPKPKDTLMISRTPEVTCV VVDVSHEDPEVKFNWYVDGVEV HNAKTKPREEQYNSTYRVVSVLT VLHQDWLNGKEYKCKVSNKALP APIEKTISKAKGQPREPQVYTLPPS RDELTKNQVSLTCLVKGFYPSDIA VEWESNGQPENNYKTTPPVLDSD GSFFLYSKLTVDKSRWQQGNVFS CSVMHEALHNHYTQKSLSLSPGK |
| SEQ ID NO: 59 | Kappa light chain constant region | RTVAAPSVFIFPPSDEQLKSGTASV VCLLNNFYPREAKVQWKVDNAL QSGNSQESVTEQDSKDSTYSLSST LTLSKADYEKHKVYACEVTHQGL SSPVTKSFNRGEC |
| SEQ ID NO: 60 | NAMPT | MNPAAEAEFNILLATDSYKVTHY KQYPPNTSKVYSYFECREKKTENS KLRKVKYEETVFYGLQYILNKYL KGKVVTKEKIQEAKDVYKEHFQD DVFNEKGWNYILEKYDGHLPIEIK AVPEGFVIPRGNVLFTVENTDPEC YWLTNWIETILVQSWYPITVATNS REQKKILAKYLLETSGNLDGLEYK |

TABLE 17-continued

Sequence Summary Table

| Sequence Identifier | Description | Sequence |
|---|---|---|
| | | LHDFGYRGVSSQETAGIGASAHLV NFKGTDTVAGLALIKKYYGTKDP VPGYSVPAAEHSTITAWGKDHEK DAFEHIVTQFSSVPVSVVSDSYDIY NACEKIWGEDLRHLIVSRSTQAPLI IRPDSGNPLDTVLKVLEILGKKFPV TENSKGYKLLPPYLRVIQGDGVDI NTLQEIVEGMKQKMWSIENIAFGS GGGLLQKLTRDLLNCSFKCSYVVT NGLGINVFKDPVADPNKRSKKGR LSLHRTPAGNFVTLEEGKGDLEEY GQDLLHTVFKNGKVTKSYSFDEIR KNAQLNIELEAAHH |
| SEQ ID NO: 61 | K-1076 epitope (residue 17-44) | SYKVTHYKQYPPNTSKVYSYFECR EKKT |
| SEQ ID NO: 62 | K-1076 epitope (residue 117-127) | KAVPEGFVIPR |
| SEQ ID NO: 63 | K-1076 epitope (residue 162-170) | ATNSREQKK |
| SEQ ID NO: 64 | K-1076 epitope (residue 242-261) | VPAAEHSTITAWGKDHEKDA |
| SEQ ID NO: 65 | K-1076 epitope (residue 262-273) | FEHIVTQFSSVP |
| SEQ ID NO: 66 | K-1076 epitope (residue 289-305) | KIWGEDLRHLIVSRSTQ |
| SEQ ID NO: 67 | K-1076 epitope (residue 332-342) | FPVTENSKGYK |
| SEQ ID NO: 68 | K-1076 epitope (residue 374-389) | SIENIAFGSGGGLLQK |
| SEQ ID NO: 69 | K-1076 epitope (residue 418-425) | VADPNKRS |
| SEQ ID NO: 70 | K-1076 epitope (residue 453-466) | YGQDLLHTVFKNGK |
| SEQ ID NO: 71 | K-1076 epitope (residue 408-417) | GLGINVFKDP |
| SEQ ID NO: 72 | NN-1093 epitope (residue 29-51) | NTSKVYSYFECREKKTENSKLRK |
| SEQ ID NO: 73 | NN-1093 epitope (residue 61-72) | GLQYILNKYLKG |
| SEQ ID NO: 74 | NN-1093 epitope (residue 156-170) | WYPITVATNSREQKK |
| SEQ ID NO: 75 | NN-1093 epitope (residue 216-234) | KGTDTVAGLALIKKYYGTK |
| SEQ ID NO: 76 | NN-1093 epitope (residue 316-331) | NPLDTVLKVLEILGKK |
| SEQ ID NO: 77 | NN-1093 epitope (residue 332-342) | FPVTENSKGYK |
| SEQ ID NO: 78 | NN-1093 epitope (residue 373-389) | WSIENIAFGSGGGLLQK |
| SEQ ID NO: 79 | NN-1093 epitope (residue 417-431) | PVADPNKRSKKGRLS |

TABLE 17-continued

| Sequence Summary Table | | |
|---|---|---|
| Sequence Identifier | Description | Sequence |
| SEQ ID NO: 80 | NN-1093 epitope (residue 454-469) | GQDLLHTVFKNGKVTK |
| SEQ ID NO: 81 | NN-1093 epitope (residue 470-478) | SYSFDEIRK |

What is claimed is:

1. An isolated antibody, or an antigen-binding fragment thereof, that binds to human nicotinamide phosphoribosyltransferase (NAMPT), said antibody or antigen-binding fragment thereof comprising:

(a) a heavy chain variable region comprising a CDR1 domain having an amino acid sequence as set forth in SEQ ID NO: 3; a CDR2 domain having an amino acid sequence as set forth in SEQ ID NOs: 4 or 29; and a CDR3 domain having an amino acid sequence as set forth in SEQ ID NO: 5; and (b) a light chain variable region comprising a CDR1 domain having an amino acid sequence as set forth in SEQ ID NO: 6 or 11; a CDR2 domain having an amino acid sequence as set forth in SEQ ID NO: 7, 12, 14, 33, 35 or 37; and a CDR3 domain having an amino acid sequence as set forth in SEQ ID NO: 8.

2. The isolated antibody, or antigen-binding fragment thereof, according to claim 1, wherein the heavy chain variable region comprises:

(a) a CDR1 domain having an amino acid sequence as set forth in SEQ ID NO: 3, a CDR2 domain having an amino acid sequence as set forth in SEQ ID NO: 4, and a CDR3 domain having an amino acid sequence as set forth in SEQ ID NO: 5; or (b) a CDR1 domain having an amino acid sequence as set forth in SEQ ID NO: 3, a CDR2 domain having an amino acid sequence as set forth in SEQ ID NO: 29, and a CDR3 domain having an amino acid sequence as set forth in SEQ ID NO: 5.

3. The isolated antibody, or antigen-binding fragment thereof, according to claim 1, wherein the light chain variable region comprises:

(a) a CDR1 domain having an amino acid sequence as set forth in SEQ ID NO: 6, a CDR2 domain having an amino acid sequence as set forth in SEQ ID NO: 7, and a CDR3 domain having an amino acid sequence as set forth in SEQ ID NO: 8;

(b) a CDR1 domain having an amino acid sequence as set forth in SEQ ID NO: 6, a CDR2 domain having an amino acid sequence as set forth in SEQ ID NO: 12, and a CDR3 domain having an amino acid sequence as set forth in SEQ ID NO: 8;

(c) a CDR1 domain having an amino acid sequence as set forth in SEQ ID NO: 6, a CDR2 domain having an amino acid sequence as set forth in SEQ ID NO: 14, and a CDR3 domain having an amino acid sequence as set forth in SEQ ID NO: 8;

(d) a CDR1 domain having an amino acid sequence as set forth in SEQ ID NO: 6, a CDR2 domain having an amino acid sequence as set forth in SEQ ID NO: 33, and a CDR3 domain having an amino acid sequence as set forth in SEQ ID NO: 8;

(e) a CDR1 domain having an amino acid sequence as set forth in SEQ ID NO: 6, a CDR2 domain having an amino acid sequence as set forth in SEQ ID NO: 35, and a CDR3 domain having an amino acid sequence as set forth in SEQ ID NO: 8;

(f) a CDR1 domain having an amino acid sequence as set forth in SEQ ID NO: 6, a CDR2 domain having an amino acid sequence as set forth in SEQ ID NO: 37, and a CDR3 domain having an amino acid sequence as set forth in SEQ ID NO: 8;

(g) a CDR1 domain having an amino acid sequence as set forth in SEQ ID NO: 11, a CDR2 domain having an amino acid sequence as set forth in SEQ ID NO: 7, and a CDR3 domain having an amino acid sequence as set forth in SEQ ID NO: 8;

(h) a CDR1 domain having an amino acid sequence as set forth in SEQ ID NO: 11, a CDR2 domain having an amino acid sequence as set forth in SEQ ID NO: 12, and a CDR3 domain having an amino acid sequence as set forth in SEQ ID NO: 8;

(i) a CDR1 domain having an amino acid sequence as set forth in SEQ ID NO: 11; a CDR2 domain having an amino acid sequence as set forth in SEQ ID NO: 14; and a CDR3 domain having an amino acid sequence as set forth in SEQ ID NO: 8;

(j) a CDR1 domain having an amino acid sequence as set forth in SEQ ID NO: 11; a CDR2 domain having an amino acid sequence as set forth in SEQ ID NO: 33; and a CDR3 domain having an amino acid sequence as set forth in SEQ ID NO: 8;

(k) a CDR1 domain having an amino acid sequence as set forth in SEQ ID NO: 11; a CDR2 domain having an amino acid sequence as set forth in SEQ ID NO: 35; and a CDR3 domain having an amino acid sequence as set forth in SEQ ID NO: 8; or (l) a CDR1 domain having an amino acid sequence as set forth in SEQ ID NO: 11; a CDR2 domain having an amino acid sequence as set forth in SEQ ID NO: 37; and a CDR3 domain having an amino acid sequence as set forth in SEQ ID NO: 8.

4. The isolated antibody or antigen-binding fragment thereof according to claim 1, wherein the antibody or antigen-binding fragment thereof comprises:

(a) a heavy chain variable region comprising a CDR1 domain having an amino acid sequence as set forth in SEQ ID NO: 3, a CDR2 domain having an amino acid sequence as set forth in SEQ ID NO: 4, and a CDR3 domain having an amino acid sequence as set forth in SEQ ID NO: 5; and a light chain variable region comprising a CDR1 domain having an amino acid sequence as set forth in SEQ ID NO: 6, a CDR2 domain having an amino acid sequence as set forth in SEQ ID NO: 7, and a CDR3 domain having an amino acid sequence as set forth in SEQ ID NO: 8;

(b) a heavy chain variable region comprising a CDR1 domain having an amino acid sequence as set forth in SEQ ID NO: 3, a CDR2 domain having an amino acid sequence as set forth in SEQ ID NO: 4, and a CDR3 domain having an amino acid sequence as set forth in SEQ ID NO: 5; and a light chain variable region comprising a CDR1 domain having an amino acid sequence as set forth in SEQ ID NO: 11, a CDR2 domain having an amino acid sequence as set forth in SEQ ID NO: 12, and a CDR3 domain having an amino acid sequence as set forth in SEQ ID NO: 8;

(c) a heavy chain variable region comprising a CDR1 domain having an amino acid sequence as set forth in SEQ ID NO: 3, a CDR2 domain having an amino acid sequence as set forth in SEQ ID NO: 4, and a CDR3 domain having an amino acid sequence as set forth in SEQ ID NO: 5; and a light chain variable region comprising a CDR1 domain having an amino acid sequence as set forth in SEQ ID NO: 11, a CDR2 domain having an amino acid sequence as set forth in SEQ ID NO: 14, and a CDR3 domain having an amino acid sequence as set forth in SEQ ID NO: 8;

(d) a heavy chain variable region comprising a CDR1 domain having an amino acid sequence as set forth in SEQ ID NO: 3, a CDR2 domain having an amino acid sequence as set forth in SEQ ID NO: 29, and a CDR3 domain having an amino acid sequence as set forth in SEQ ID NO: 5; and a light chain variable region comprising a CDR1 domain having an amino acid sequence as set forth in SEQ ID NO: 11, a CDR2 domain having an amino acid sequence as set forth in SEQ ID NO: 14, and a CDR3 domain having an amino acid sequence as set forth in SEQ ID NO: 8;

(e) a heavy chain variable region comprising a CDR1 domain having an amino acid sequence as set forth in SEQ ID NO: 3, a CDR2 domain having an amino acid sequence as set forth in SEQ ID NO: 29, and a CDR3 domain having an amino acid sequence as set forth in SEQ ID NO: 5; and a light chain variable region comprising a CDR1 domain having an amino acid sequence as set forth in SEQ ID NO: 11, a CDR2 domain having an amino acid sequence as set forth in SEQ ID NO: 33, and a CDR3 domain having an amino acid sequence as set forth in SEQ ID NO: 8;

(f) a heavy chain variable region comprising a CDR1 domain having an amino acid sequence as set forth in SEQ ID NO: 3, a CDR2 domain having an amino acid sequence as set forth in SEQ ID NO: 29, and a CDR3 domain having an amino acid sequence as set forth in SEQ ID NO: 5; and a light chain variable region comprising a CDR1 domain having an amino acid sequence as set forth in SEQ ID NO: 11, a CDR2 domain having an amino acid sequence as set forth in SEQ ID NO: 35, and a CDR3 domain having an amino acid sequence as set forth in SEQ ID NO: 8;

(g) a heavy chain variable region comprising a CDR1 domain having an amino acid sequence as set forth in SEQ ID NO: 3, a CDR2 domain having an amino acid sequence as set forth in SEQ ID NO: 29, and a CDR3 domain having an amino acid sequence as set forth in SEQ ID NO: 5; and a light chain variable region comprising a CDR1 domain having an amino acid sequence as set forth in SEQ ID NO: 11, a CDR2 domain having an amino acid sequence as set forth in SEQ ID NO: 37, and a CDR3 domain having an amino acid sequence as set forth in SEQ ID NO: 8;

(h) a heavy chain variable region comprising a CDR1 domain having an amino acid sequence as set forth in SEQ ID NO: 3, a CDR2 domain having an amino acid sequence as set forth in SEQ ID NO: 4, and a CDR3 domain having an amino acid sequence as set forth in SEQ ID NO: 5; and a light chain variable region comprising a CDR1 domain having an amino acid sequence as set forth in SEQ ID NO: 11, a CDR2 domain having an amino acid sequence as set forth in SEQ ID NO: 33, and a CDR3 domain having an amino acid sequence as set forth in SEQ ID NO: 8;

(i) a heavy chain variable region comprising a CDR1 domain having an amino acid sequence as set forth in SEQ ID NO: 3, a CDR2 domain having an amino acid sequence as set forth in SEQ ID NO: 4, and a CDR3 domain having an amino acid sequence as set forth in SEQ ID NO: 5; and a light chain variable region comprising a CDR1 domain having an amino acid sequence as set forth in SEQ ID NO: 11; a CDR2 domain having an amino acid sequence as set forth in SEQ ID NO: 35; and a CDR3 domain having an amino acid sequence as set forth in SEQ ID NO: 8; or (j) a heavy chain variable region comprising a CDR1 domain having an amino acid sequence as set forth in SEQ ID NO: 3, a CDR2 domain having an amino acid sequence as set forth in SEQ ID NO: 4, and a CDR3 domain having an amino acid sequence as set forth in SEQ ID NO: 5; and a light chain variable region comprising a CDR1 domain having an amino acid sequence as set forth in SEQ ID NO: 11; a CDR2 domain having an amino acid sequence as set forth in SEQ ID NO: 37; and a CDR3 domain having an amino acid sequence as set forth in SEQ ID NO: 8.

5. The isolated antibody, or antigen-binding fragment thereof, according to claim 1, wherein the antibody or antigen-binding fragment thereof is humanized.

6. The isolated antibody, or antigen-binding fragment thereof, according to claim 1, wherein the light chain variable region has an amino acid sequence as set forth in SEQ ID NO: 2, 10, 13, 30, 31, 32, 34 or 36.

7. The isolated antibody, or antigen-binding fragment thereof, according to claim 1, wherein the heavy chain variable region has an amino acid sequence as set forth in SEQ ID NO: 1, 9, 15, 16 or 28.

8. The isolated antibody, or antigen-binding fragment thereof, according to claim 1, wherein the antibody or antigen-binding fragment thereof comprises a heavy chain comprising a variable region comprising the amino acid sequence as set forth in SEQ ID NO: 15, and a light chain comprising a variable region comprising the amino acid sequence as set forth in SEQ ID NO: 13.

9. The isolated antibody, or antigen-binding fragment thereof, according to claim 1, wherein the antibody or antigen-binding fragment thereof comprises a heavy chain comprising a variable region comprising the amino acid sequence as set forth in SEQ ID NO: 26, and a light chain comprising a variable region comprising the amino acid sequence as set forth in SEQ ID NO: 18.

10. The isolated antibody, or antigen-binding fragment thereof, according to claim 1, wherein the antibody or antigen-binding fragment thereof comprises a heavy chain comprising a variable region as described in Table 17, and a light chain comprising a variable region as described in Table 17.

11. The isolated antibody, or antigen-binding fragment thereof, according to claim 1, wherein the antibody or antigen-binding fragment thereof comprises a heavy chain comprising a heavy chain CDR1, CDR2, and CDR3 as described in Table 17, and a light chain comprising a light chain CDR1, CDR2, and CDR3 as described in Table 17.

12. The isolated antibody, or antigen-binding fragment thereof, according to claim 1, wherein the antibody or antigen-binding fragment thereof comprises a humanized heavy chain variable region derived from murine antibody AL-303 or AL-310, and a humanized light chain variable region derived from murine antibody AL-303 or AL-310.

13. The isolated antibody, or antigen-binding fragment thereof, according to claim 1, wherein the antibody or antigen-binding fragment thereof comprises an Fc domain.

14. The isolated antibody, or antigen-binding fragment thereof, according to claim 1, wherein the antibody or antigen-binding fragment thereof is a monoclonal antibody.

15. The isolated antibody, or antigen-binding fragment thereof, according to claim 1, wherein the antibody is an IgG antibody.

16. The isolated antibody, or antigen-binding fragment thereof, according to claim 15, wherein the antibody is an IgG1 or an IgG4 antibody.

17. A pharmaceutical composition comprising the isolated antibody, or antigen-binding fragment thereof, of claim 1, and a pharmaceutically acceptable carrier.

* * * * *

SEQUENCE LISTING

```
<160> NUMBER OF SEQ ID NOS: 81

<210> SEQ ID NO 1
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Gln Val Gln Leu Val Glu Ser Gly Ala Glu Val Lys Lys Pro Gly Ala
1               5                   10                  15

Ser Val Lys Leu Ser Cys Lys Ala Ser Gly Tyr Thr Phe Thr Ser Tyr
            20                  25                  30

Trp Met Gln Trp Val Arg Gln Ala Pro Gly Gln Arg Leu Glu Trp Met
        35                  40                  45

Gly Glu Ile Asp Pro Ser Asn Ser Tyr Thr Asn Tyr Asn Gln Lys Phe
    50                  55                  60

Arg Gly Arg Val Thr Ile Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Trp Gly Pro Gly Thr Thr Val Thr Val Ser Ser
            100                 105                 110


<210> SEQ ID NO 2
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Asp Ile Val Met Thr Gln Thr Pro Leu Ser Leu Ser Val Thr Pro Gly
1               5                   10                  15

Gln Pro Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Pro
        35                  40                  45

Pro Gln Leu Leu Ile Tyr Gln Met Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Val Gln Asn
                85                  90                  95
```

```
Leu Glu Leu Pro Tyr Thr Phe Gly Pro Gly Thr Lys Val Asp Ile Lys
            100                 105                 110


<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Tyr Thr Phe Thr Ser Tyr Trp Met Gln
1               5                   10


<210> SEQ ID NO 4
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Glu Ile Asp Pro Ser Asn Ser Tyr Thr Asn Tyr Asn Gln Lys Phe Arg
1               5                   10                  15

Gly


<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ala Arg Gly Gly Tyr
1               5


<210> SEQ ID NO 6
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Arg Ser Ser Lys Ser Leu Leu His Ser Asn Gly Ile Thr Tyr Leu Tyr
1               5                   10                  15


<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gln Met Ser Asn Leu Ala Ser
1               5


<210> SEQ ID NO 8
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Val Gln Asn Leu Glu Leu Pro Tyr Thr
1               5


<210> SEQ ID NO 9
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met Gln Trp Val Arg Gln Ala Pro Gly Gln Gly Leu Glu Trp Met
        35                  40                  45

Gly Glu Ile Asp Pro Ser Asn Ser Tyr Thr Asn Tyr Asn Gln Lys Phe
    50                  55                  60

Arg Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Gly Tyr Trp Gly Gln Gly Thr Thr Val Thr Val Ser Ser
            100                 105                 110


<210> SEQ ID NO 10
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Asp Ile Gln Leu Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Gln Gly Ile Thr Tyr Leu Tyr Trp Tyr Leu Gln Lys Pro Gly Gln Ser
        35                  40                  45

Pro Gln Leu Leu Ile Tyr Gln Leu Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Val Gln Asn
                85                  90                  95

Leu Glu Leu Pro Tyr Thr Phe Gly Gly Gly Thr Lys Leu Glu Ile Lys
            100                 105                 110


<210> SEQ ID NO 11
<211> LENGTH: 16
<212> TYPE: PRT
```

<213> ORGANISM: Artificial Sequence
<220> FEATURE:
<223> OTHER INFORMATION: Description of Artificial Sequence: Synthetic
peptide

<400> SEQUENCE: 11

Arg Ser Ser Lys Ser Leu Leu His Ser Gln Gly Ile Thr Tyr Leu Tyr
1 5 10 15

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 12

Gln Leu Ser Asn Leu Ala Ser
1 5

<210> SEQ ID NO 13
<211> LENGTH: 112
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 13

Asp Ile Val Met Thr Gln Ser Pro Leu Ser Leu Pro Val Thr Pro Gly
1 5 10 15

Glu Pro Ala Ser Ile Ser Cys Arg Ser Ser Lys Ser Leu Leu His Ser
20 25 30

Gln Gly Ile Thr Tyr Leu Tyr Trp Tyr Leu Gln Lys Pro Gly Gln Ser
35 40 45

Pro Gln Leu Leu Ile Tyr Gln Leu Ser Asn Arg Ala Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Val Gln Asn
85 90 95

Leu Glu Leu Pro Tyr Thr Phe Gly Gly Gly Thr Lys Leu Glu Ile Lys
100 105 110

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 14

Gln Leu Ser Asn Arg Ala Ser
1 5

<210> SEQ ID NO 15
<211> LENGTH: 112
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 15

```
Gln Val Gln Leu Val Gln Ser Gly Ala Glu Val Thr Lys Pro Gly Ala
1               5                   10                  15

Ser Val Lys Val Ser Cys Lys Ala Ser Gly Tyr Thr Phe Thr Ser Tyr
            20                  25                  30

Trp Met Gln Trp Val Arg Gln Ala Pro Gly Gln Gly Leu Glu Trp Val
        35                  40                  45

Gly Glu Ile Asp Pro Ser Asn Ser Tyr Thr Asn Tyr Asn Gln Lys Phe
    50                  55                  60

Arg Gly Arg Val Thr Leu Thr Arg Asp Thr Ser Thr Thr Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Trp Gly Gln Gly Thr Thr Val Thr Val Ser Ser
            100                 105                 110
```

<210> SEQ ID NO 16
<211> LENGTH: 112
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 16

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met Gln Trp Val Arg Gln Ala Pro Gly Gln Gly Leu Glu Trp Met
        35                  40                  45

Gly Glu Ile Asp Pro Ser Asn Ser Tyr Thr Asn Tyr Asn Gln Lys Phe
    50                  55                  60

Arg Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Trp Gly Gln Gly Thr Thr Val Thr Val Ser Ser
            100                 105                 110
```

<210> SEQ ID NO 17
<211> LENGTH: 120
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 17

```
Gln Val Gln Leu Val Glu Ser Gly Ala Glu Val Lys Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Arg Gln Ala Pro Gly Gln Arg Leu Glu Trp Met
        35                  40                  45

Gly Glu Ile Asp Pro Ser Asp Ser Tyr Thr Asn Tyr Asn Gln Lys Phe
    50                  55                  60

Lys Gly Arg Val Thr Ile Thr Val Asp Lys Ser Ala Ser Thr Ala Tyr
```

65 70 75 80

Met Glu Leu Ser Ser Leu Arg Ser Glu Asp Thr Ala Val Tyr Tyr Cys
85 90 95

Ala Lys Ser Asn Tyr Val Val Pro Trp Tyr Phe Asp Val Trp Gly Pro
100 105 110

Gly Thr Thr Val Thr Val Ser Ser
115 120

<210> SEQ ID NO 18
<211> LENGTH: 112
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 18

Glu Ile Val Leu Thr Gln Ser Pro Gly Thr Leu Ser Leu Ser Pro Gly
1 5 10 15

Glu Arg Ala Thr Leu Ser Cys Arg Ser Ser Lys Ser Leu Leu His Ser
20 25 30

Asn Gly Ile Thr Tyr Leu Tyr Trp Tyr Gln Gln Lys Pro Gly Gln Ala
35 40 45

Pro Arg Leu Leu Ile Tyr Gln Met Ser Asn Leu Ala Ser Gly Ile Pro
50 55 60

Asp Arg Phe Ser Gly Ser Gly Ser Gly Thr Asp Phe Thr Leu Thr Ile
65 70 75 80

Ser Arg Leu Glu Pro Glu Asp Phe Ala Val Tyr Tyr Cys Ala Gln Asn
85 90 95

Leu Glu Leu Pro Trp Thr Phe Gly Gly Gly Thr Lys Leu Glu Ile Lys
100 105 110

<210> SEQ ID NO 19
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 19

Gly Tyr Thr Phe Thr Ser Tyr Trp Met His
1 5 10

<210> SEQ ID NO 20
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 20

Glu Ile Asp Pro Ser Asp Ser Tyr Thr Asn Tyr Asn Gln Lys Phe Lys
1 5 10 15

Gly

<210> SEQ ID NO 21
<211> LENGTH: 13
<212> TYPE: PRT
<213> ORGANISM: Artificial Sequence
<220> FEATURE:

<223> OTHER INFORMATION: Description of Artificial Sequence: Synthetic peptide

<400> SEQUENCE: 21

Ala Lys Ser Asn Tyr Val Val Pro Trp Tyr Phe Asp Val
1               5                   10

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 22

Ala Gln Asn Leu Glu Leu Pro Trp Thr
1               5

<210> SEQ ID NO 23
<211> LENGTH: 120
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 23

Gln Val Gln Leu Val Gln Ser Gly Ala Glu Val Arg Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Val
        35                  40                  45

Gly Glu Ile Asp Pro Ser Asp Ser Tyr Thr Asn Tyr Asn Gln Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Asp Val Tyr Tyr Cys
                85                  90                  95

Ala Lys Ser Asn Tyr Val Val Pro Trp Tyr Phe Asp Val Trp Gly Gln
            100                 105                 110

Gly Thr Thr Val Thr Val Ser Ser
        115                 120

<210> SEQ ID NO 24
<211> LENGTH: 112
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 24

Glu Ile Val Leu Thr Gln Ser Pro Ala Thr Leu Ser Leu Ser Pro Gly
1               5                   10                  15

Glu Arg Ala Thr Leu Ser Cys Arg Ser Ser Lys Ser Leu Leu His Ser
            20                  25                  30

Asn Gly Ile Thr Tyr Leu Tyr Trp Tyr Gln Gln Lys Pro Gly Gln Ala
        35                  40                  45

Pro Arg Leu Leu Ile Tyr Gln Met Ser Asn Leu Ala Ser Gly Ile Pro
    50                  55                  60

```
Ala Arg Phe Ser Gly Ser Gly Ser Gly Thr Asp Phe Thr Leu Thr Ile
65                  70                  75                  80

Ser Ser Leu Glu Pro Glu Asp Phe Ala Val Tyr Tyr Cys Ala Gln Asn
                85                  90                  95

Leu Glu Leu Pro Trp Thr Phe Gly Gly Gly Thr Lys Leu Glu Ile Lys
            100                 105                 110


<210> SEQ ID NO 25
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Gln Val Gln Leu Val Gln Ser Gly Ala Glu Val Thr Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Val
        35                  40                  45

Gly Glu Ile Asp Pro Ser Asp Ser Tyr Thr Asn Tyr Asn Gln Lys Phe
    50                  55                  60

Lys Gly Arg Val Thr Leu Thr Arg Asp Thr Ser Thr Thr Thr Val Tyr
65                  70                  75                  80

Met Glu Leu Ser Ser Leu Arg Ser Glu Asp Thr Ala Val Tyr Tyr Cys
                85                  90                  95

Ala Lys Ser Asn Tyr Val Val Pro Trp Tyr Phe Asp Val Trp Gly Gln
            100                 105                 110

Gly Thr Thr Val Thr Val Ser Ser
        115                 120


<210> SEQ ID NO 26
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Glu Val Gln Leu Val Gln Ser Gly Ala Glu Val Lys Lys Pro Gly Glu
1               5                   10                  15

Ser Leu Arg Ile Ser Cys Lys Ala Ser Gly Tyr Thr Phe Thr Ser Tyr
            20                  25                  30

Trp Met His Trp Val Arg Gln Met Pro Gly Lys Gly Leu Glu Trp Met
        35                  40                  45

Gly Glu Ile Asp Pro Ser Asp Ser Tyr Thr Asn Tyr Asn Gln Lys Phe
    50                  55                  60

Lys Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Lys Ser Asn Tyr Val Val Pro Trp Tyr Phe Asp Val Trp Gly Gln
            100                 105                 110

Gly Thr Leu Val Thr Val Ser Ser
        115                 120
```

<210> SEQ ID NO 27
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
        35                  40                  45

Gly Glu Ile Asp Pro Ser Asp Ser Tyr Thr Asn Tyr Asn Gln Lys Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Lys Ser Asn Tyr Val Val Pro Trp Tyr Phe Asp Val Trp Gly Thr
            100                 105                 110

Gly Thr Thr Val Thr Val Ser Ser
        115                 120
```

<210> SEQ ID NO 28
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

```
Gln Val Gln Leu Val Gln Ser Gly Ala Glu Val Thr Lys Pro Gly Ala
1               5                   10                  15

Ser Val Lys Val Ser Cys Lys Ala Ser Gly Tyr Thr Phe Thr Ser Tyr
            20                  25                  30

Trp Met Gln Trp Val Arg Gln Ala Pro Gly Gln Gly Leu Glu Trp Val
        35                  40                  45

Gly Glu Ile Glu Pro Ser Asn Ser Tyr Thr Asn Tyr Asn Gln Lys Phe
    50                  55                  60

Arg Gly Arg Val Thr Leu Thr Arg Asp Thr Ser Thr Thr Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Trp Gly Gln Gly Thr Thr Val Thr Val Ser Ser
            100                 105                 110
```

<210> SEQ ID NO 29
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

```
Glu Ile Glu Pro Ser Asn Ser Tyr Thr Asn Tyr Asn Gln Lys Phe Arg
1               5                   10                  15

Gly


<210> SEQ ID NO 30
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Gln Gly Ile Thr Tyr Leu Tyr Trp Tyr Val Gln Lys Pro Gly Gln Ser
        35                  40                  45

Pro Gln Leu Leu Ile Tyr Gln Leu Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Val Gln Asn
                85                  90                  95

Leu Glu Leu Pro Tyr Thr Phe Gly Gly Gly Thr Lys Leu Glu Ile Lys
            100                 105                 110


<210> SEQ ID NO 31
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Gln Gly Ile Thr Tyr Leu Tyr Trp Tyr Ile Gln Lys Pro Gly Gln Ser
        35                  40                  45

Pro Gln Leu Leu Ile Tyr Gln Leu Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Val Gln Asn
                85                  90                  95

Leu Glu Leu Pro Tyr Thr Phe Gly Gly Gly Thr Lys Leu Glu Ile Lys
            100                 105                 110


<210> SEQ ID NO 32
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32
```

Asp Ile Val Met Thr Gln Ser Pro Leu Ser Leu Pro Val Thr Pro Gly
1 5 10 15

Glu Pro Ala Ser Ile Ser Cys Arg Ser Ser Lys Ser Leu Leu His Ser
20 25 30

Gln Gly Ile Thr Tyr Leu Tyr Trp Tyr Val Gln Lys Pro Gly Gln Ser
35 40 45

Pro Gln Leu Leu Ile Tyr Gln Gly Ser Asn Arg Ala Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Val Gln Asn
85 90 95

Leu Glu Leu Pro Tyr Thr Phe Gly Gly Gly Thr Lys Leu Glu Ile Lys
100 105 110

<210> SEQ ID NO 33
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 33

Gln Gly Ser Asn Arg Ala Ser
1 5

<210> SEQ ID NO 34
<211> LENGTH: 112
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 34

Asp Ile Val Met Thr Gln Ser Pro Leu Ser Leu Pro Val Thr Pro Gly
1 5 10 15

Glu Pro Ala Ser Ile Ser Cys Arg Ser Ser Lys Ser Leu Leu His Ser
20 25 30

Gln Gly Ile Thr Tyr Leu Tyr Trp Tyr Val Gln Lys Pro Gly Gln Ser
35 40 45

Pro Gln Leu Leu Ile Tyr Gln Glu Ser Asn Arg Ala Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Val Gln Asn
85 90 95

Leu Glu Leu Pro Tyr Thr Phe Gly Gly Gly Thr Lys Leu Glu Ile Lys
100 105 110

<210> SEQ ID NO 35
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 35

Gln Glu Ser Asn Arg Ala Ser
1 5

<210> SEQ ID NO 36
<211> LENGTH: 112
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 36

Asp Ile Val Met Thr Gln Ser Pro Leu Ser Leu Pro Val Thr Pro Gly
1 5 10 15

Glu Pro Ala Ser Ile Ser Cys Arg Ser Ser Lys Ser Leu Leu His Ser
20 25 30

Gln Gly Ile Thr Tyr Leu Tyr Trp Tyr Ile Gln Lys Pro Gly Gln Ser
35 40 45

Pro Gln Leu Leu Ile Tyr Gln Val Ser Asn Arg Ala Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Val Gln Asn
85 90 95

Leu Glu Leu Pro Tyr Thr Phe Gly Gly Gly Thr Lys Leu Glu Ile Lys
100 105 110

<210> SEQ ID NO 37
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 37

Gln Val Ser Asn Arg Ala Ser
1 5

<210> SEQ ID NO 38
<211> LENGTH: 120
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 38

Glu Val Gln Leu Val Gln Ser Gly Ala Glu Val Lys Lys Pro Gly Glu
1 5 10 15

Ser Leu Arg Ile Ser Cys Lys Ala Ser Gly Tyr Thr Phe Thr Ser Tyr
20 25 30

Trp Met His Trp Val Arg Gln Met Pro Gly Lys Gly Leu Glu Trp Met
35 40 45

Gly Glu Ile Glu Pro Ser Asp Ser Tyr Thr Asn Tyr Asn Gln Lys Phe
50 55 60

Lys Gly His Val Thr Ile Ser Ala Asp Lys Ser Ile Ser Thr Ala Tyr
65 70 75 80

Leu Gln Trp Ser Ser Leu Lys Ala Ser Asp Thr Ala Met Tyr Tyr Cys
85 90 95

Ala Lys Ser Asn Tyr Val Val Pro Trp Tyr Phe Asp Val Trp Gly Gln

```
            100                 105                 110

Gly Thr Leu Val Thr Val Ser Ser
        115                 120


<210> SEQ ID NO 39
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Glu Ile Glu Pro Ser Asp Ser Tyr Thr Asn Tyr Asn Gln Lys Phe Lys
1               5                   10                  15

Gly


<210> SEQ ID NO 40
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Glu Val Gln Leu Val Gln Ser Gly Ala Glu Val Lys Lys Pro Gly Glu
1               5                   10                  15

Ser Leu Arg Ile Ser Cys Lys Ala Ser Gly Tyr Thr Phe Thr Ser Tyr
            20                  25                  30

Trp Met His Trp Val Arg Gln Met Pro Gly Lys Gly Leu Glu Trp Met
        35                  40                  45

Gly Glu Ile Glu Pro Ser Asp Ser Tyr Thr Asn Tyr Asn Gln Lys Phe
    50                  55                  60

Lys Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Lys Thr Asn Tyr Val Val Pro Trp Tyr Phe Asp Val Trp Gly Gln
            100                 105                 110

Gly Thr Leu Val Thr Val Ser Ser
        115                 120


<210> SEQ ID NO 41
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Ala Lys Thr Asn Tyr Val Val Pro Trp Tyr Phe Asp Val
1               5                   10


<210> SEQ ID NO 42
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 42

Glu Val Gln Leu Val Gln Ser Gly Ala Glu Val Lys Lys Pro Gly Glu
1 5 10 15

Ser Leu Arg Ile Ser Cys Lys Ala Ser Gly Tyr Thr Phe Thr Ser Tyr
20 25 30

Trp Ile His Trp Val Arg Gln Val Pro Gly Lys Gly Leu Glu Trp Met
35 40 45

Gly Glu Ile Glu Pro Ser Asp Ser Tyr Thr Asn Tyr Asn Gln Lys Phe
50 55 60

Lys Gly His Val Thr Ile Ser Ala Asp Lys Ser Ile Ser Thr Ala Tyr
65 70 75 80

Leu Gln Trp Ser Ser Leu Lys Ala Ser Asp Thr Ala Val Tyr Tyr Cys
85 90 95

Ala Arg Ser Asn Tyr Val Val Pro Trp Tyr Phe Asp Val Trp Gly Gln
100 105 110

Gly Thr Leu Val Thr Val Ser Ser
115 120

<210> SEQ ID NO 43
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 43

Gly Tyr Thr Phe Thr Ser Tyr Trp Ile His
1 5 10

<210> SEQ ID NO 44
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 44

Ala Arg Ser Asn Tyr Val Val Pro Trp Tyr Phe Asp Val
1 5 10

<210> SEQ ID NO 45
<211> LENGTH: 120
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 45

Glu Val Gln Leu Val Gln Ser Gly Ala Glu Val Lys Lys Pro Gly Glu
1 5 10 15

Ser Leu Arg Ile Ser Cys Lys Ala Ser Gly Tyr Thr Phe Thr Ser Tyr
20 25 30

Phe Ile His Trp Val Arg Gln Val Pro Gly Lys Gly Leu Glu Trp Met
35 40 45

Gly Glu Ile Glu Pro Ser Asp Ser Tyr Thr Asn Tyr Asn Gln Lys Phe
50 55 60

Lys Gly His Val Thr Ile Ser Ala Asp Lys Ser Ile Ser Thr Ala Tyr
65 70 75 80

```
Leu Gln Trp Ser Ser Leu Lys Ala Ser Asp Thr Ala Val Tyr Tyr Cys
                85                  90                  95

Ala Lys Thr Asn Tyr Val Val Pro Trp Tyr Phe Asp Val Trp Gly Gln
            100                 105                 110

Gly Thr Leu Val Thr Val Ser Ser
        115                 120


<210> SEQ ID NO 46
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Gly Tyr Thr Phe Thr Ser Tyr Phe Ile His
1               5                   10


<210> SEQ ID NO 47
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Glu Ile Val Leu Thr Gln Ser Pro Gly Thr Leu Ser Leu Ser Pro Gly
1               5                   10                  15

Glu Arg Ala Thr Leu Ser Cys Arg Ser Ser Lys Ser Leu Leu His Ser
            20                  25                  30

Gln Gly Ile Thr Tyr Leu Tyr Trp Tyr Gln Gln Lys Pro Gly Gln Ala
        35                  40                  45

Pro Arg Leu Leu Ile Tyr Gln Met Ser Asn Leu Ala Ser Gly Ile Pro
    50                  55                  60

Asp Arg Phe Ser Gly Ser Gly Ser Gly Thr Asp Phe Thr Leu Thr Ile
65                  70                  75                  80

Ser Arg Leu Glu Pro Glu Asp Phe Ala Val Tyr Tyr Cys Ala Gln Asn
                85                  90                  95

Leu Glu Leu Pro Trp Thr Phe Gly Gly Gly Thr Lys Leu Glu Ile Lys
            100                 105                 110


<210> SEQ ID NO 48
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Glu Ile Val Leu Thr Gln Ser Pro Gly Thr Leu Ser Leu Ser Pro Gly
1               5                   10                  15

Glu Arg Ala Thr Leu Ser Cys Arg Ser Ser Lys Ser Leu Leu His Ser
            20                  25                  30

Asn Ala Ile Thr Tyr Leu Tyr Trp Tyr Gln Gln Lys Pro Gly Gln Ala
        35                  40                  45

Pro Arg Leu Leu Val Tyr Gln Val Ser Asn Leu Ala Ser Gly Val Pro
    50                  55                  60
```

-continued

```
Asp Arg Phe Ser Gly Ser Gly Ser Gly Thr Asp Phe Thr Leu Thr Ile
65                  70                  75                  80

Ser Arg Leu Glu Pro Glu Asp Phe Ala Val Tyr Tyr Cys Ala Gln Asn
                85                  90                  95

Leu Glu Leu Pro Trp Thr Phe Gly Gly Gly Thr Lys Leu Glu Ile Lys
            100                 105                 110


<210> SEQ ID NO 49
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Arg Ser Ser Lys Ser Leu Leu His Ser Asn Ala Ile Thr Tyr Leu Tyr
1               5                   10                  15


<210> SEQ ID NO 50
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Gln Val Ser Asn Leu Ala Ser
1               5


<210> SEQ ID NO 51
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Glu Ile Val Leu Thr Gln Ser Pro Gly Thr Leu Ser Leu Ser Pro Gly
1               5                   10                  15

Glu Arg Ala Thr Leu Ser Cys Arg Ser Ser Lys Ser Leu Leu His Ser
            20                  25                  30

Gln Gly Ile Thr Tyr Leu Tyr Trp Tyr Gln Gln Lys Pro Gly Gln Ala
        35                  40                  45

Pro Arg Leu Leu Val Tyr Gln Val Ser Asn Leu Gly Ser Gly Ile Pro
    50                  55                  60

Asp Arg Phe Ser Gly Ser Gly Ser Gly Thr Asp Phe Thr Leu Thr Ile
65                  70                  75                  80

Ser Arg Leu Glu Pro Glu Asp Phe Ala Val Tyr Tyr Cys Ala Gln Asn
                85                  90                  95

Leu Glu Leu Pro Phe Thr Phe Gly Gly Gly Thr Lys Leu Glu Ile Lys
            100                 105                 110


<210> SEQ ID NO 52
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52
```

```
Gln Val Ser Asn Leu Gly Ser
1               5


<210> SEQ ID NO 53
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Ala Gln Asn Leu Glu Leu Pro Phe Thr
1               5


<210> SEQ ID NO 54
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Gln Val Gln Leu Gln Gln Pro Gly Ala Asp Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met Gln Trp Val Lys Gln Arg Pro Gly Gln Gly Leu Glu Trp Ile
        35                  40                  45

Gly Glu Ile Asp Pro Ser Asn Ser Tyr Thr Asn Tyr Asn Gln Lys Phe
    50                  55                  60

Arg Gly Lys Ala Thr Leu Thr Val Asp Pro Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Gly Gly Tyr Trp Gly Gln Gly Thr Thr Leu Thr Val Ser Ser
            100                 105                 110


<210> SEQ ID NO 55
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Asp Ile Val Met Thr Gln Ala Ala Phe Ser Asn Pro Val Thr Leu Gly
1               5                   10                  15

Thr Ser Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Ala Ser Gly Val Pro
    50                  55                  60

Asp Arg Phe Ser Ser Ser Gly Ser Gly Thr Asp Phe Thr Leu Arg Ile
65                  70                  75                  80

Ser Arg Val Glu Ala Glu Asp Val Gly Val Tyr Tyr Cys Val Gln Asn
                85                  90                  95
```

Leu Glu Leu Pro Tyr Thr Phe Gly Gly Gly Thr Lys Leu Glu Ile Lys
100 105 110

<210> SEQ ID NO 56
<211> LENGTH: 120
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 56

Gln Val Gln Leu Gln Gln Ser Gly Ala Glu Ser Val Met Pro Gly Ala
1 5 10 15

Ser Val Lys Leu Ser Cys Lys Ala Ser Gly Tyr Thr Phe Thr Ser Tyr
20 25 30

Trp Met His Trp Val Lys Gln Arg Pro Gly Gln Gly Leu Glu Trp Ile
35 40 45

Gly Glu Ile Asp Pro Ser Asp Ser Tyr Thr Asn Tyr Asn Gln Lys Phe
50 55 60

Lys Gly Lys Ser Thr Leu Thr Val Asp Lys Ser Ser Ser Thr Ala Tyr
65 70 75 80

Met Gln Leu Ser Ser Leu Thr Ser Glu Asp Ser Ala Val Tyr Tyr Cys
85 90 95

Ala Lys Ser Asn Tyr Val Val Pro Trp Tyr Phe Asp Val Trp Gly Thr
100 105 110

Gly Thr Thr Val Thr Val Ser Ser
115 120

<210> SEQ ID NO 57
<211> LENGTH: 112
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 57

Asp Ile Val Met Thr Gln Ala Ala Phe Ser Asn Pro Val Thr Leu Gly
1 5 10 15

Thr Ser Ala Ser Ile Ser Cys Arg Ser Ser Lys Ser Leu Leu His Ser
20 25 30

Asn Gly Ile Thr Tyr Leu Tyr Trp Tyr Leu Gln Lys Pro Gly Gln Ser
35 40 45

Pro Gln Leu Leu Ile Tyr Gln Met Ser Asn Leu Ala Ser Gly Val Pro
50 55 60

Asp Arg Phe Ser Ser Ser Gly Ser Gly Thr Asp Phe Thr Leu Arg Ile
65 70 75 80

Ser Arg Val Glu Ala Glu Asp Val Gly Val Tyr Tyr Cys Ala Gln Asn
85 90 95

Leu Glu Leu Pro Trp Thr Phe Gly Gly Gly Thr Lys Leu Glu Ile Lys
100 105 110

<210> SEQ ID NO 58
<211> LENGTH: 330
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 58

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Lys Val Glu Pro Lys Ser Cys Asp Lys Thr His Thr Cys Pro Pro Cys
100 105 110

Pro Ala Pro Glu Leu Leu Gly Gly Pro Ser Val Phe Leu Phe Pro Pro
115 120 125

Lys Pro Lys Asp Thr Leu Met Ile Ser Arg Thr Pro Glu Val Thr Cys
130 135 140

Val Val Val Asp Val Ser His Glu Asp Pro Glu Val Lys Phe Asn Trp
145 150 155 160

Tyr Val Asp Gly Val Glu Val His Asn Ala Lys Thr Lys Pro Arg Glu
165 170 175

Glu Gln Tyr Asn Ser Thr Tyr Arg Val Val Ser Val Leu Thr Val Leu
180 185 190

His Gln Asp Trp Leu Asn Gly Lys Glu Tyr Lys Cys Lys Val Ser Asn
195 200 205

Lys Ala Leu Pro Ala Pro Ile Glu Lys Thr Ile Ser Lys Ala Lys Gly
210 215 220

Gln Pro Arg Glu Pro Gln Val Tyr Thr Leu Pro Pro Ser Arg Asp Glu
225 230 235 240

Leu Thr Lys Asn Gln Val Ser Leu Thr Cys Leu Val Lys Gly Phe Tyr
245 250 255

Pro Ser Asp Ile Ala Val Glu Trp Glu Ser Asn Gly Gln Pro Glu Asn
260 265 270

Asn Tyr Lys Thr Thr Pro Pro Val Leu Asp Ser Asp Gly Ser Phe Phe
275 280 285

Leu Tyr Ser Lys Leu Thr Val Asp Lys Ser Arg Trp Gln Gln Gly Asn
290 295 300

Val Phe Ser Cys Ser Val Met His Glu Ala Leu His Asn His Tyr Thr
305 310 315 320

Gln Lys Ser Leu Ser Leu Ser Pro Gly Lys
325 330

<210> SEQ ID NO 59
<211> LENGTH: 107
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 59

Arg Thr Val Ala Ala Pro Ser Val Phe Ile Phe Pro Pro Ser Asp Glu
1 5 10 15

-continued

```
Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105


<210> SEQ ID NO 60
<211> LENGTH: 491
<212> TYPE: PRT
<213> ORGANISM: Homo sapiens

<400> SEQUENCE: 60

Met Asn Pro Ala Ala Glu Ala Glu Phe Asn Ile Leu Leu Ala Thr Asp
1               5                   10                  15

Ser Tyr Lys Val Thr His Tyr Lys Gln Tyr Pro Pro Asn Thr Ser Lys
            20                  25                  30

Val Tyr Ser Tyr Phe Glu Cys Arg Glu Lys Lys Thr Glu Asn Ser Lys
        35                  40                  45

Leu Arg Lys Val Lys Tyr Glu Glu Thr Val Phe Tyr Gly Leu Gln Tyr
    50                  55                  60

Ile Leu Asn Lys Tyr Leu Lys Gly Lys Val Val Thr Lys Glu Lys Ile
65                  70                  75                  80

Gln Glu Ala Lys Asp Val Tyr Lys Glu His Phe Gln Asp Asp Val Phe
                85                  90                  95

Asn Glu Lys Gly Trp Asn Tyr Ile Leu Glu Lys Tyr Asp Gly His Leu
            100                 105                 110

Pro Ile Glu Ile Lys Ala Val Pro Glu Gly Phe Val Ile Pro Arg Gly
        115                 120                 125

Asn Val Leu Phe Thr Val Glu Asn Thr Asp Pro Glu Cys Tyr Trp Leu
    130                 135                 140

Thr Asn Trp Ile Glu Thr Ile Leu Val Gln Ser Trp Tyr Pro Ile Thr
145                 150                 155                 160

Val Ala Thr Asn Ser Arg Glu Gln Lys Lys Ile Leu Ala Lys Tyr Leu
                165                 170                 175

Leu Glu Thr Ser Gly Asn Leu Asp Gly Leu Glu Tyr Lys Leu His Asp
            180                 185                 190

Phe Gly Tyr Arg Gly Val Ser Ser Gln Glu Thr Ala Gly Ile Gly Ala
        195                 200                 205

Ser Ala His Leu Val Asn Phe Lys Gly Thr Asp Thr Val Ala Gly Leu
    210                 215                 220

Ala Leu Ile Lys Lys Tyr Tyr Gly Thr Lys Asp Pro Val Pro Gly Tyr
225                 230                 235                 240

Ser Val Pro Ala Ala Glu His Ser Thr Ile Thr Ala Trp Gly Lys Asp
                245                 250                 255

His Glu Lys Asp Ala Phe Glu His Ile Val Thr Gln Phe Ser Ser Val
            260                 265                 270

Pro Val Ser Val Val Ser Asp Ser Tyr Asp Ile Tyr Asn Ala Cys Glu
        275                 280                 285
```

```
Lys Ile Trp Gly Glu Asp Leu Arg His Leu Ile Val Ser Arg Ser Thr
    290                 295                 300

Gln Ala Pro Leu Ile Ile Arg Pro Asp Ser Gly Asn Pro Leu Asp Thr
305                 310                 315                 320

Val Leu Lys Val Leu Glu Ile Leu Gly Lys Lys Phe Pro Val Thr Glu
                325                 330                 335

Asn Ser Lys Gly Tyr Lys Leu Leu Pro Pro Tyr Leu Arg Val Ile Gln
            340                 345                 350

Gly Asp Gly Val Asp Ile Asn Thr Leu Gln Glu Ile Val Glu Gly Met
        355                 360                 365

Lys Gln Lys Met Trp Ser Ile Glu Asn Ile Ala Phe Gly Ser Gly Gly
    370                 375                 380

Gly Leu Leu Gln Lys Leu Thr Arg Asp Leu Leu Asn Cys Ser Phe Lys
385                 390                 395                 400

Cys Ser Tyr Val Val Thr Asn Gly Leu Gly Ile Asn Val Phe Lys Asp
                405                 410                 415

Pro Val Ala Asp Pro Asn Lys Arg Ser Lys Lys Gly Arg Leu Ser Leu
            420                 425                 430

His Arg Thr Pro Ala Gly Asn Phe Val Thr Leu Glu Glu Gly Lys Gly
        435                 440                 445

Asp Leu Glu Glu Tyr Gly Gln Asp Leu Leu His Thr Val Phe Lys Asn
    450                 455                 460

Gly Lys Val Thr Lys Ser Tyr Ser Phe Asp Glu Ile Arg Lys Asn Ala
465                 470                 475                 480

Gln Leu Asn Ile Glu Leu Glu Ala Ala His His
                485                 490


<210> SEQ ID NO 61
<211> LENGTH: 28
<212> TYPE: PRT
<213> ORGANISM: Homo sapiens

<400> SEQUENCE: 61

Ser Tyr Lys Val Thr His Tyr Lys Gln Tyr Pro Pro Asn Thr Ser Lys
1               5                   10                  15

Val Tyr Ser Tyr Phe Glu Cys Arg Glu Lys Lys Thr
            20                  25


<210> SEQ ID NO 62
<211> LENGTH: 11
<212> TYPE: PRT
<213> ORGANISM: Homo sapiens

<400> SEQUENCE: 62

Lys Ala Val Pro Glu Gly Phe Val Ile Pro Arg
1               5                   10


<210> SEQ ID NO 63
<211> LENGTH: 9
<212> TYPE: PRT
<213> ORGANISM: Homo sapiens

<400> SEQUENCE: 63

Ala Thr Asn Ser Arg Glu Gln Lys Lys
1               5


<210> SEQ ID NO 64
<211> LENGTH: 20
```

```
<212> TYPE: PRT
<213> ORGANISM: Homo sapiens

<400> SEQUENCE: 64

Val Pro Ala Ala Glu His Ser Thr Ile Thr Ala Trp Gly Lys Asp His
1               5                   10                  15

Glu Lys Asp Ala
            20


<210> SEQ ID NO 65
<211> LENGTH: 12
<212> TYPE: PRT
<213> ORGANISM: Homo sapiens

<400> SEQUENCE: 65

Phe Glu His Ile Val Thr Gln Phe Ser Ser Val Pro
1               5                   10


<210> SEQ ID NO 66
<211> LENGTH: 17
<212> TYPE: PRT
<213> ORGANISM: Homo sapiens

<400> SEQUENCE: 66

Lys Ile Trp Gly Glu Asp Leu Arg His Leu Ile Val Ser Arg Ser Thr
1               5                   10                  15

Gln


<210> SEQ ID NO 67
<211> LENGTH: 11
<212> TYPE: PRT
<213> ORGANISM: Homo sapiens

<400> SEQUENCE: 67

Phe Pro Val Thr Glu Asn Ser Lys Gly Tyr Lys
1               5                   10


<210> SEQ ID NO 68
<211> LENGTH: 16
<212> TYPE: PRT
<213> ORGANISM: Homo sapiens

<400> SEQUENCE: 68

Ser Ile Glu Asn Ile Ala Phe Gly Ser Gly Gly Gly Leu Leu Gln Lys
1               5                   10                  15


<210> SEQ ID NO 69
<211> LENGTH: 8
<212> TYPE: PRT
<213> ORGANISM: Homo sapiens

<400> SEQUENCE: 69

Val Ala Asp Pro Asn Lys Arg Ser
1               5


<210> SEQ ID NO 70
<211> LENGTH: 14
<212> TYPE: PRT
<213> ORGANISM: Homo sapiens

<400> SEQUENCE: 70

Tyr Gly Gln Asp Leu Leu His Thr Val Phe Lys Asn Gly Lys
1               5                   10
```

<210> SEQ ID NO 71
<211> LENGTH: 10
<212> TYPE: PRT
<213> ORGANISM: Homo sapiens

<400> SEQUENCE: 71

Gly Leu Gly Ile Asn Val Phe Lys Asp Pro
1 5 10

<210> SEQ ID NO 72
<211> LENGTH: 23
<212> TYPE: PRT
<213> ORGANISM: Homo sapiens

<400> SEQUENCE: 72

Asn Thr Ser Lys Val Tyr Ser Tyr Phe Glu Cys Arg Glu Lys Lys Thr
1 5 10 15

Glu Asn Ser Lys Leu Arg Lys
20

<210> SEQ ID NO 73
<211> LENGTH: 12
<212> TYPE: PRT
<213> ORGANISM: Homo sapiens

<400> SEQUENCE: 73

Gly Leu Gln Tyr Ile Leu Asn Lys Tyr Leu Lys Gly
1 5 10

<210> SEQ ID NO 74
<211> LENGTH: 15
<212> TYPE: PRT
<213> ORGANISM: Homo sapiens

<400> SEQUENCE: 74

Trp Tyr Pro Ile Thr Val Ala Thr Asn Ser Arg Glu Gln Lys Lys
1 5 10 15

<210> SEQ ID NO 75
<211> LENGTH: 19
<212> TYPE: PRT
<213> ORGANISM: Homo sapiens

<400> SEQUENCE: 75

Lys Gly Thr Asp Thr Val Ala Gly Leu Ala Leu Ile Lys Lys Tyr Tyr
1 5 10 15

Gly Thr Lys

<210> SEQ ID NO 76
<211> LENGTH: 16
<212> TYPE: PRT
<213> ORGANISM: Homo sapiens

<400> SEQUENCE: 76

Asn Pro Leu Asp Thr Val Leu Lys Val Leu Glu Ile Leu Gly Lys Lys
1 5 10 15

<210> SEQ ID NO 77
<211> LENGTH: 11
<212> TYPE: PRT
<213> ORGANISM: Homo sapiens

<400> SEQUENCE: 77

-continued

```
Phe Pro Val Thr Glu Asn Ser Lys Gly Tyr Lys
1               5                   10


<210> SEQ ID NO 78
<211> LENGTH: 17
<212> TYPE: PRT
<213> ORGANISM: Homo sapiens

<400> SEQUENCE: 78

Trp Ser Ile Glu Asn Ile Ala Phe Gly Ser Gly Gly Gly Leu Leu Gln
1               5                   10                  15

Lys


<210> SEQ ID NO 79
<211> LENGTH: 15
<212> TYPE: PRT
<213> ORGANISM: Homo sapiens

<400> SEQUENCE: 79

Pro Val Ala Asp Pro Asn Lys Arg Ser Lys Lys Gly Arg Leu Ser
1               5                   10                  15


<210> SEQ ID NO 80
<211> LENGTH: 16
<212> TYPE: PRT
<213> ORGANISM: Homo sapiens

<400> SEQUENCE: 80

Gly Gln Asp Leu Leu His Thr Val Phe Lys Asn Gly Lys Val Thr Lys
1               5                   10                  15


<210> SEQ ID NO 81
<211> LENGTH: 9
<212> TYPE: PRT
<213> ORGANISM: Homo sapiens

<400> SEQUENCE: 81

Ser Tyr Ser Phe Asp Glu Ile Arg Lys
1               5
```